United States Patent
Danishefsky et al.

(10) Patent No.: US 8,859,615 B2
(45) Date of Patent: Oct. 14, 2014

(54) COMPOUNDS, COMPOSITIONS AND METHODS FOR REDUCING TOXICITY AND TREATING OR PREVENTING DISEASES

(76) Inventors: Samuel J. Danishefsky, Englewood, NJ (US); Ting-Chao Chou, Paramus, NJ (US); Xiaoguang Lei, Chao Yang (CN); Heedong Yun, Tenafly, NJ (US); Fay Ng, New York, NY (US); John Hartung, New York, NY (US); Dalibor Sames, New York, NY (US)

( * ) Notice: Subject to any disclaimer, the term of this patent is extended or adjusted under 35 U.S.C. 154(b) by 407 days.

(21) Appl. No.: 13/061,508

(22) PCT Filed: Aug. 27, 2009

(86) PCT No.: PCT/US2009/055221
§ 371 (c)(1),
(2), (4) Date: Aug. 12, 2011

(87) PCT Pub. No.: WO2010/025272
PCT Pub. Date: Mar. 4, 2010

(65) Prior Publication Data
US 2011/0312904 A1    Dec. 22, 2011

Related U.S. Application Data

(63) Continuation-in-part of application No. PCT/US2008/074444, filed on Aug. 27, 2008.

(60) Provisional application No. 61/092,291, filed on Aug. 27, 2008, provisional application No. 61/122,268, filed on Dec. 12, 2008, provisional application No. 61/228,083, filed on Jul. 23, 2009.

(51) Int. Cl.
| | | |
|---|---|---|
| A61K 31/191 | (2006.01) |
| A61K 31/357 | (2006.01) |
| C07C 31/22 | (2006.01) |
| C07D 317/12 | (2006.01) |
| C07C 33/048 | (2006.01) |
| A61K 31/047 | (2006.01) |
| A61K 31/075 | (2006.01) |
| A61K 31/165 | (2006.01) |
| A61K 31/196 | (2006.01) |
| A61K 31/337 | (2006.01) |
| A61K 31/343 | (2006.01) |
| A61K 31/4192 | (2006.01) |
| A61K 31/427 | (2006.01) |
| A61K 31/661 | (2006.01) |
| A61K 31/675 | (2006.01) |
| A61K 31/7048 | (2006.01) |
| A61K 45/06 | (2006.01) |

(Continued)

(52) U.S. Cl.
CPC ............ *C07C 33/048* (2013.01); *A61K 31/047* (2013.01); *A61K 31/075* (2013.01); *A61K 31/165* (2013.01); *A61K 31/196* (2013.01); *A61K 31/337* (2013.01); *A61K 31/343* (2013.01); *A61K 31/357* (2013.01); *A61K 31/4192* (2013.01); *A61K 31/427* (2013.01); *A61K 31/661* (2013.01); *A61K 31/675* (2013.01); *A61K 31/7048* (2013.01); *A61K 45/06* (2013.01); *C07C 33/05* (2013.01); *C07C 33/14* (2013.01); *C07C 33/30* (2013.01); *C07C 43/315* (2013.01); *C07C 49/24* (2013.01); *C07D 249/04* (2013.01); *C07D 317/16* (2013.01); *C07D 317/18* (2013.01); *C07D 317/20* (2013.01); *C07D 317/22* (2013.01); *C07D 317/24* (2013.01); *C07D 317/26* (2013.01); *C07D 317/28* (2013.01); *C07D 317/30* (2013.01); *C07B 2200/07* (2013.01); *C07C 2101/02* (2013.01); *C07C 2101/14* (2013.01)

USPC ............ 514/463; 514/578; 549/448; 568/855

(58) Field of Classification Search
USPC ............. 424/728; 435/375; 514/26, 130, 567, 514/463, 578; 568/592, 855; 549/448
See application file for complete search history.

(56) References Cited

U.S. PATENT DOCUMENTS

| 2003/0092638 A1 | 5/2003 | Huang et al. |
| 2007/0110831 A1 | 5/2007 | Ikonte et al. |

OTHER PUBLICATIONS

Yun, et al., J. Org. Chem., 2005, 70, 10375-10380.*

(Continued)

*Primary Examiner* — Rebecca Anderson
*Assistant Examiner* — Karen Cheng
(74) *Attorney, Agent, or Firm* — Ostrolenk Faber LLP

(57) ABSTRACT

The present invention provides compounds of Formula (I), compositions comprising an effective amount of a compound of Formula (I), optionally with chemotherapeutic drugs such as a tubulin-binding drug, and methods of their use for reducing the toxicity of cytotoxic agents, treating or preventing cancer or a neuropathic disorder, inducing a chemoprotective phase II enzyme, DNA, or protein synthesis, enhancing the immune system, treating inflammation, improving and enhancing general health or well-being, and methods for making compounds of Formula (I).

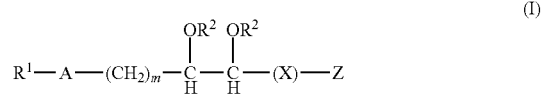

18 Claims, 40 Drawing Sheets

(51) Int. Cl.
*C07C 33/05* (2006.01)
*C07C 33/14* (2006.01)
*C07C 33/30* (2006.01)
*C07C 43/315* (2006.01)
*C07C 49/24* (2006.01)
*C07D 249/04* (2006.01)
*C07D 317/16* (2006.01)
*C07D 317/18* (2006.01)
*C07D 317/20* (2006.01)
*C07D 317/22* (2006.01)
*C07D 317/24* (2006.01)
*C07D 317/26* (2006.01)
*C07D 317/28* (2006.01)
*C07D 317/30* (2006.01)

(56) References Cited

OTHER PUBLICATIONS

Mizumaki, et al., Brain Res., 950 (2002), pp. 254-260.*
Patani et al., Chem Rev, 1996, vol. 96 (8), especially p. 3147.*
Cho, 2008, Organic Letters, vol. 20, No. 2, p. 257-259.*
Yun et al. Total Synthesis as a Resource in Drug Discovery: The First in Vivo Evaluation of Panaxytriol and its Derivatives. Journal of Organic Chemistry 2005, 70:10375-10380.
Chong et al. Ginseng, is there a Use in Clinical Medicine. Postgraduate Medical Journal 1988, 64: 841-846.

* cited by examiner

FIG. 9A.
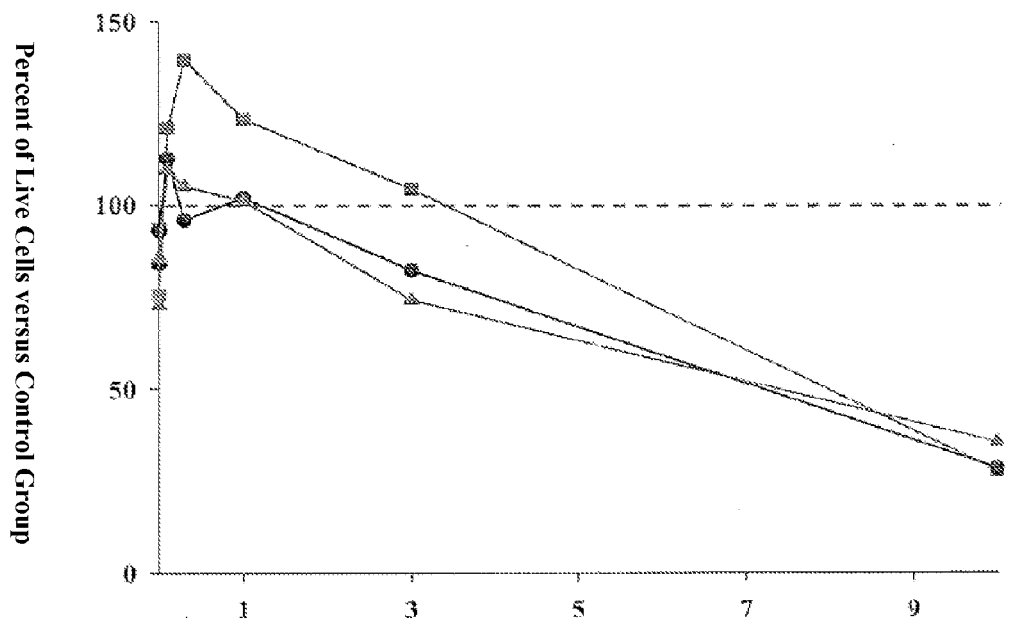
Panaxytriol (μM)
FIG. 9B.
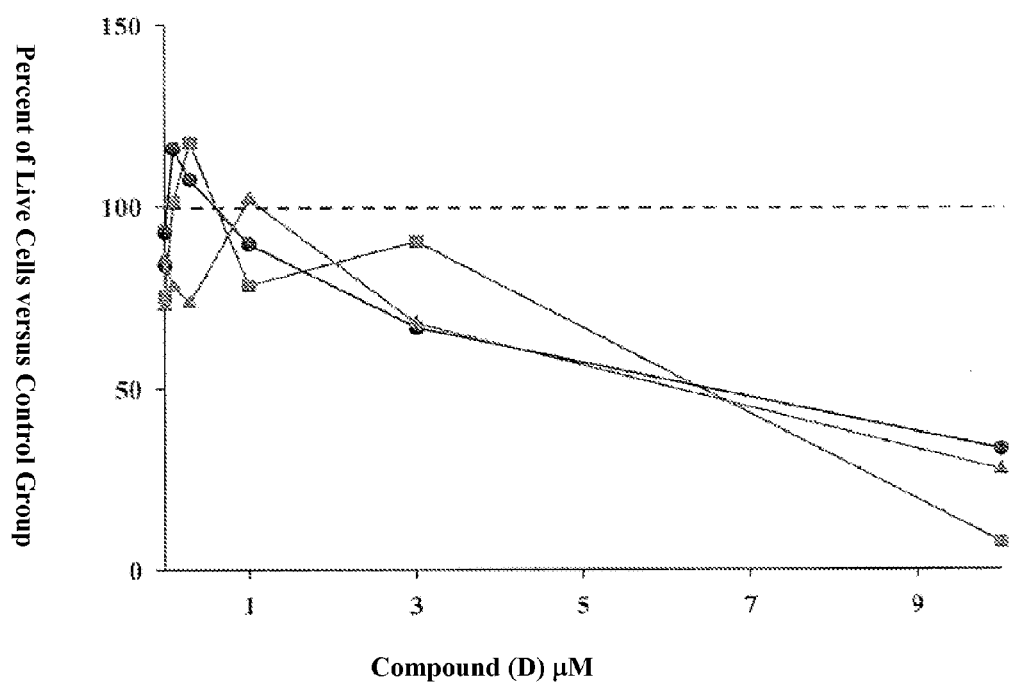
Compound (D) μM
FIGS. 9A & 9B

COMPOUNDS, COMPOSITIONS AND METHODS FOR REDUCING TOXICITY AND TREATING OR PREVENTING DISEASES

This invention was made with government support under Grant No. HL 25848 awarded by the National Institutes of Health. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entireties.

1. BACKGROUND OF THE INVENTION

Cancer is second only to cardiovascular disease as the leading cause of death in the United States. The American Cancer Society estimated that 1.4 million new cancer cases would be diagnosed and 565,000 people would die of cancer in 2006 (American Cancer Society, *Cancer Facts and Figures 2006*, Atlanta, Ga.). The National Cancer Institute estimated that in January 2002, approximately 10.1 million living Americans had a history of cancer. The National Institutes of Health estimate direct medical costs of cancer as over $100 billion per year with an additional $100 billion in indirect costs due to lost productivity—the largest such costs of any major disease.

Cancer is a process by which the controlling mechanisms that regulate cell growth and differentiation are impaired, resulting in a failure to control cell turnover and growth. This lack of control can cause a tumor to grow progressively, enlarging and occupying space in vital areas of the body. If the tumor invades surrounding tissue and is transported to distant sites, death of the individual can result.

The selective killing of cancer cells, while minimizing deleterious effects on normal cells, is a desired goal in cancer therapy. Modalities commonly used in the treatment of cancer include chemotherapy, radiation therapy, surgery and biological therapy (a broad category that includes gene-, protein- or cell-based treatments and immunotherapy). Despite the availability of a variety of anticancer agents, traditional chemotherapy has drawbacks. Many anticancer agents are toxic, and chemotherapy can cause significant, and often dangerous, side effects, including severe nausea, bone marrow depression, liver, heart and kidney damage, and immunosuppression. Additionally, many tumor cells eventually develop multi-drug resistance after being exposed to one or more anticancer agents. As such, single-agent chemotherapy is effective for only a very limited number of cancers. Many chemotherapeutic drugs are anti-proliferative agents, acting at different stages of the cell cycle. Since it is difficult to predict the pattern of sensitivity of a neoplastic cell population to anticancer drugs, or the current stage of the cell cycle that a cell happens to be in, it is common to use multi-drug regimens in the treatment of cancer.

Despite the significant research efforts and resources that have been directed towards the development of novel anticancer agents and improved methods for treating cancer there remains a need in the art for novel compounds, compositions, or methods that are useful for treating cancer with improved therapeutic indices and for preventing cancer, including non-toxic anticancer agents and anticancer agents that avoid multi-drug resistance, are therefore beneficial.

The immune system is the body's primary means of defense. The cells of the immune system work powerfully in concert to recognize and eliminate disease agents. Enhancing the immune system could improve the body's ability to defend itself from diseases such as those caused by pathogens and cancer. Critical steps in the growth and production of cells including those of the immune system are DNA and protein synthesis.

Citation of any reference in this application is not an admission that the reference is prior art.

2. SUMMARY OF THE INVENTION

The present application provides Compounds, compositions, and methods for reducing or preventing the side effects of drugs, reducing the toxic effect of cytotoxic agents, for example cancer chemotherapeutic agents, treating or preventing cancer or a neurotrophic disorder, enhancing the immune system, treating inflammation, and inducing chemoprotective phase II enzymes or the synthesis of DNA or RNA.

In one aspect the invention provides compounds and compositions of Formula (I):

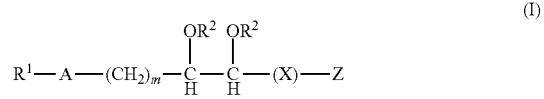

or a pharmaceutically acceptable salt, solvate or hydrate thereof, wherein:

$R^1$ is $(R^3)(R^4)C(R^4)$—, $R^5C(O)$—, $R^5OC(O)$—, $R^5NHC(O)$—, —$C(R^3)$=$C(R^3)(R^4)$, —$OC(R^3)(R^4)(R^4)$ or an oxygen-containing -3 to -7-membered monocyclic heterocycle;

each $R^2$ is independently —H, —$C_1$-$C_6$ alkyl, or —C(O)—$C_1$-$C_6$ alkyl, or both $R^2$ groups combine to form —C(O)— or —$C(R^a)(R^a)$—, wherein each $R^a$ is independently —H, —$C_1$-$C_6$ alkyl or phenyl;

$R^3$ is —H, —OH, —O—$C_1$-$C_6$ alkyl, $R^5C(O)$—, $R^5OC(O)$—, or $R^5NHC(O)$—, —SH, —$NH_2$, —Cl, —F, —CN, —$NO_2$, —$CF_3$ or —$CCl_3$;

each $R^4$ is independently —H, —$C_1$-$C_6$ alkyl, —$C_2$-$C_6$ alkenyl, —$C_2$-$C_6$ alkynyl, -aryl, $R^5C(O)$—, $R^5OC(O)$—, or $R^5NHC(O)$—, wherein the —$C_1$-$C_6$ alkyl, —$C_2$-$C_6$ alkenyl or —$C_2$-$C_6$ alkynyl is unsubstituted or substituted with one or more of a halogen, aryl, —CN, —$N(R^5)_2$, —$OR^5$, or —C(O)$R^5$;

$R^5$ is —H, —$C_1$-$C_6$ alkyl, —$C_2$-$C_6$ alkenyl, —$C_2$-$C_6$ alkynyl, ($C_3$-$C_8$ monocyclic cycloalkyl)-, ($C_3$-$C_8$ monocyclic cycloalkenyl)-, (5 or -6-membered monocyclic heteroaryl)- or (7 to -10-membered bicyclic heteroaryl)-;

A is —C≡C—, —C≡C—C≡C—, —C≡C—C≡C—C($R^3$)($R^4$)—,

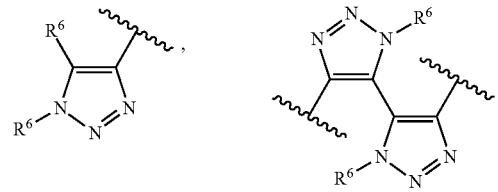

-continued

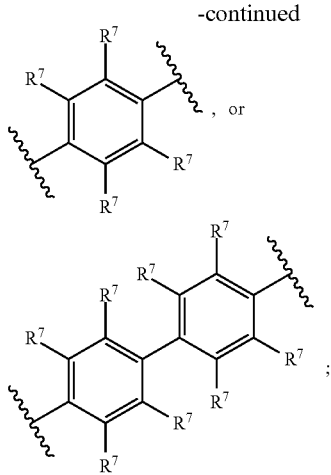

each R⁶ is independently —H, -aryl, —C₁-C₆ alkyl, ZC(O)—, ZOC(O)—, —X—Z, or —SO₂Z;
each R⁷ is independently —H, -aryl, or —YR⁴;
each Y is independently —NR⁴—, —O—, or —SO₂—;

each X is independently —C₁-C₆ alkylene-, —C₂-C₆ alkenylene- or —C₂-C₆ alkynylene-, wherein the C₁-C₆ alkylene, —C₂-C₆ alkenylene- or —C₂-C₆ alkynylene- may be substituted with one or more C₃-C₈ monocyclic cycloalkyl, C₃-C₈ monocyclic cycloalkenyl, 5- or -6-membered monocyclic heteroaryl, 7- to 10-membered bicyclic heteroaryl, oxygen-containing 3- to 7-membered monocyclic heterocycle, aryl, —C₁-C₆ alkyl, -halo, —O—(C₁-C₆ alkyl), —OH, —CN, —COOR', —OC(O)R', —N(R')₂, —NHC(O)R' or —C(O)NHR' groups wherein each R' is independently —H or unsubstituted —C₁-C₆ alkyl;

Z is —H, -aryl, —C₁-C₆ alkyl, —C₂-C₆ alkenyl, —C₂-C₆ alkynyl, —C₃-C₈ monocyclic cycloalkyl, —C₃-C₈ monocyclic cycloalkenyl, -(5 or -6-membered monocyclic heteroaryl) -(7 to -10-membered bicyclic heteroaryl), or —C₁-C₆ alkyl- substituted with -aryl, —C₃-C₈ monocyclic cycloalkyl, —C₃-C₈ monocyclic cycloalkenyl, -(5 or -6-membered monocyclic heteroaryl) -(7 to -10-membered bicyclic heteroaryl);

m is an integer ranging from 1 to 6; and
n is 0, 1, or 2.

In one embodiment, at least one of R³ and R⁴ is not —H.

In one embodiment, the invention provides the following compounds of Formula I:

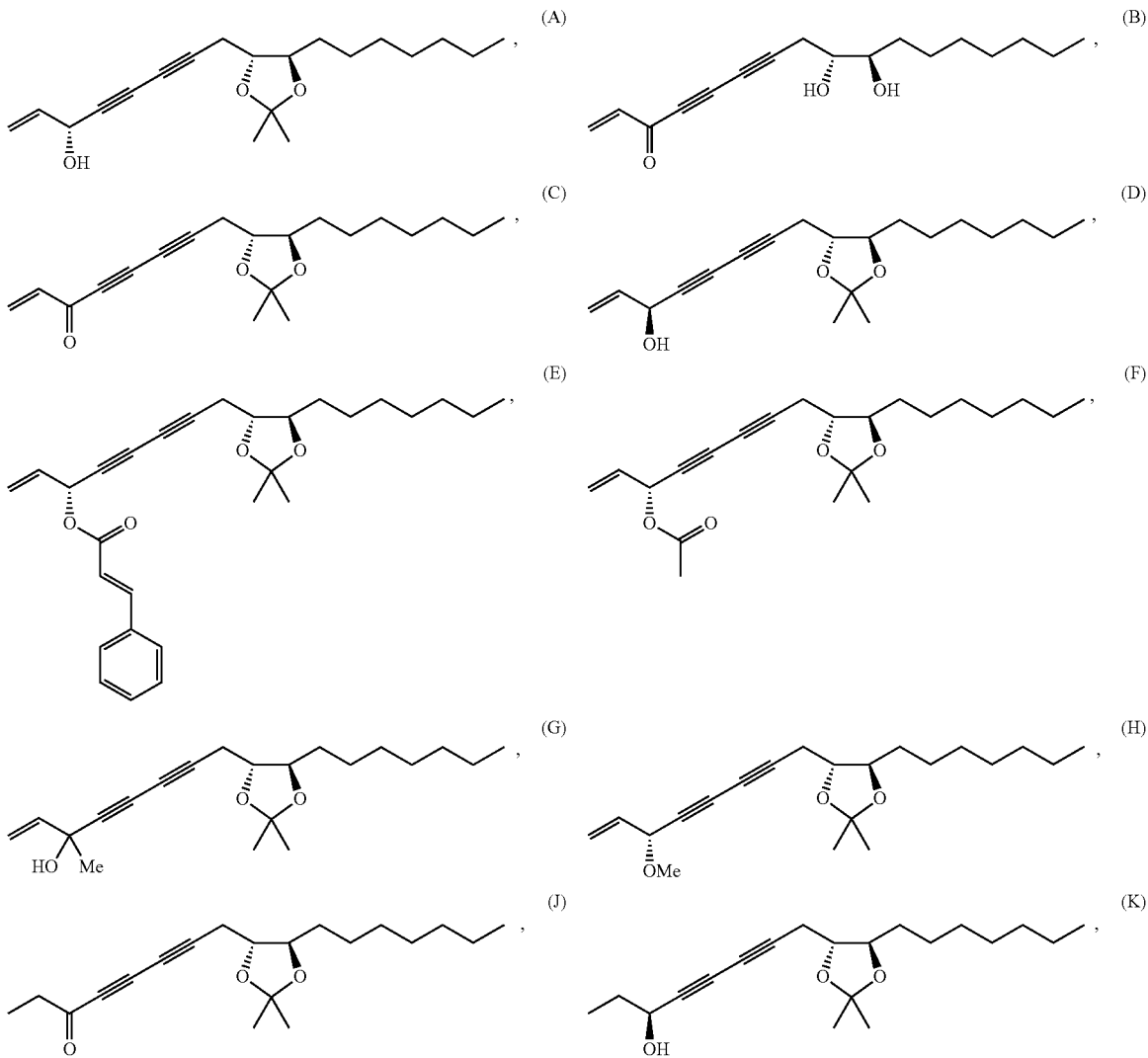

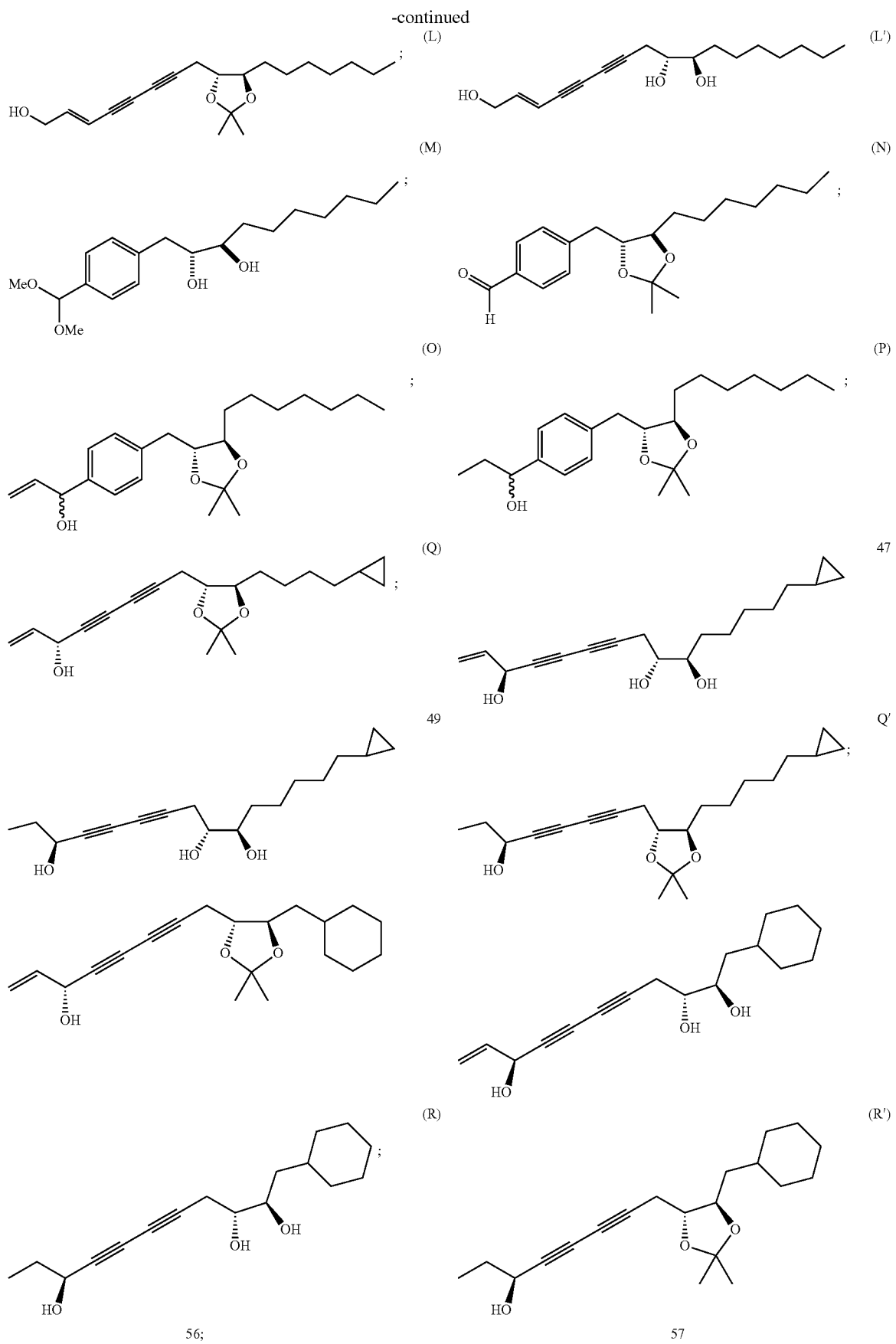

-continued
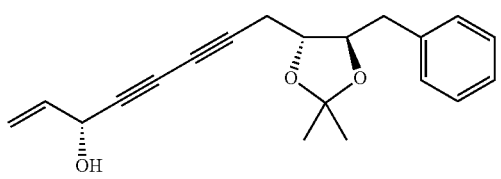 (S)
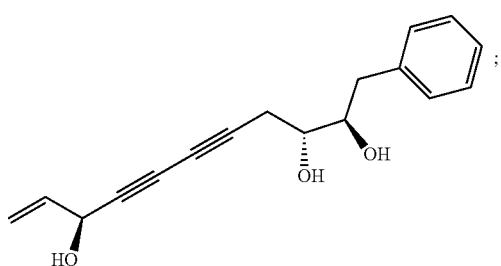 61
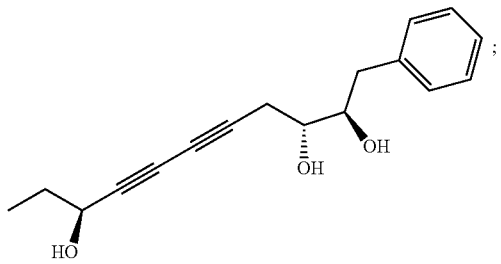 62
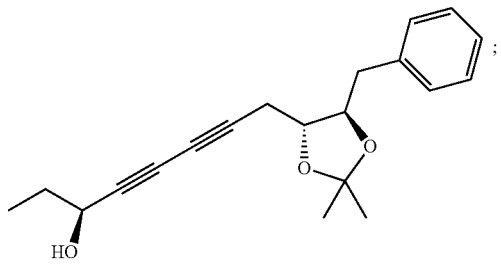 S'
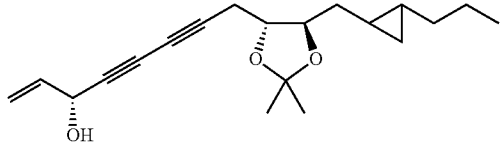 (T)
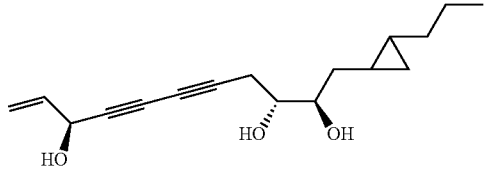 72
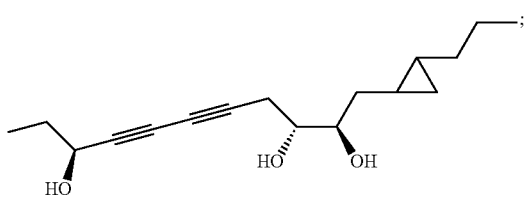 73
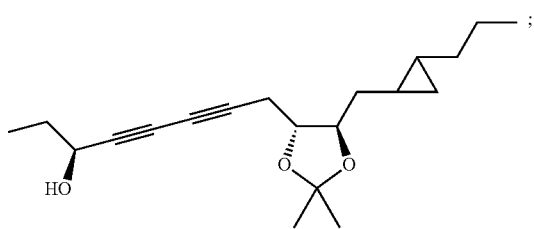 (T')
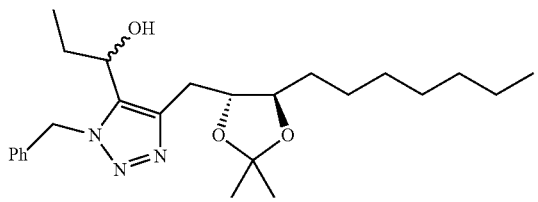 (U)
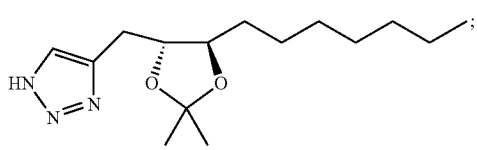 (V)
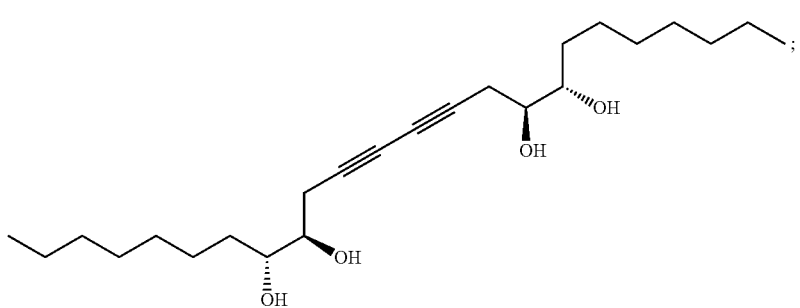 (W)

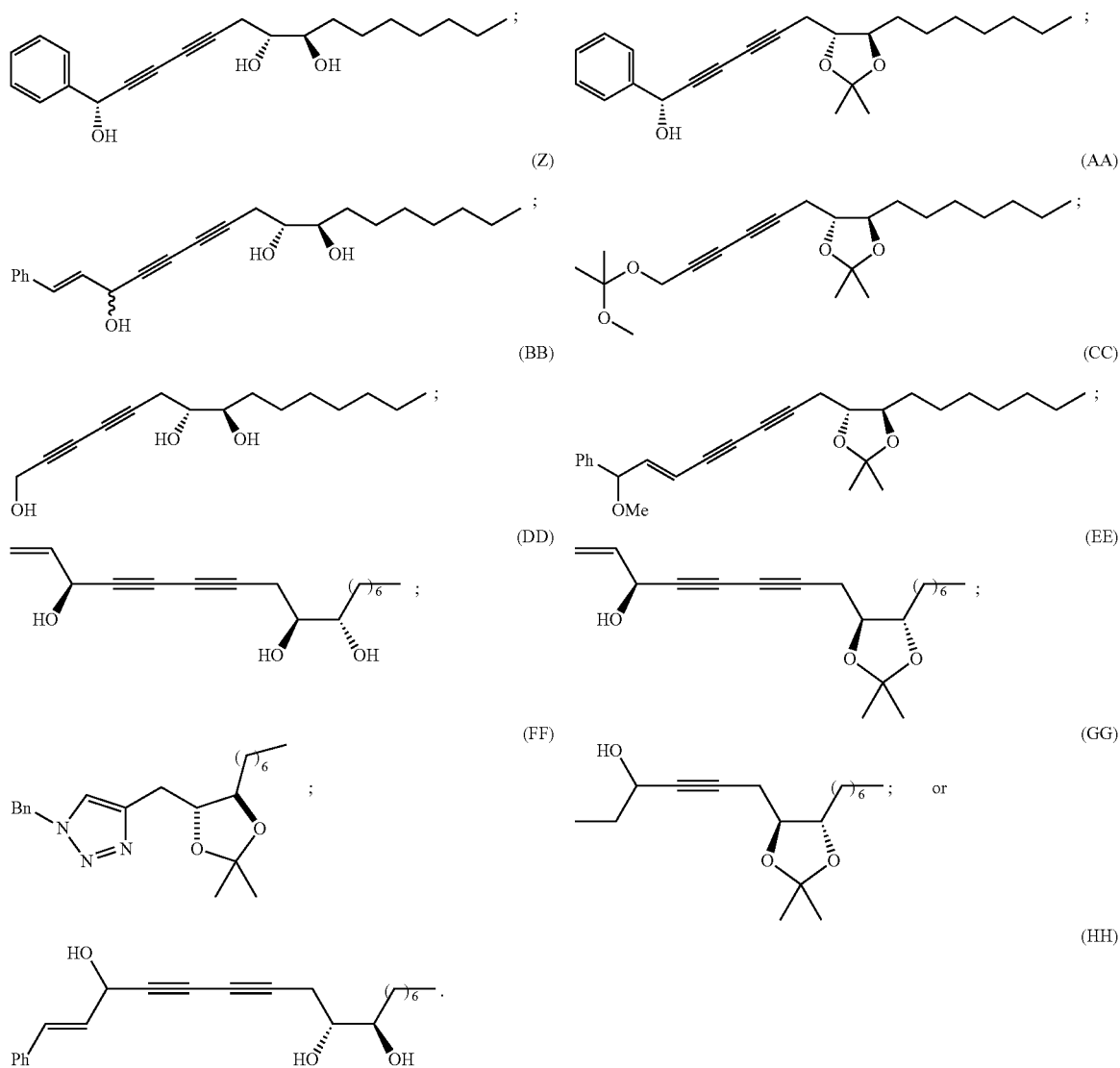

In one aspect, a compound useful in the methods of the invention is panaxytriol.

In another aspect, the invention provides a composition comprising a compound of Formula (I) and a physiologically acceptable carrier or vehicle.

In another aspect, the invention provides a composition comprising 1) a compound of Formula (I); and 2) a tubulin-binding drug.

In another aspect, the invention provides a composition comprising 1) a compound of Formula (I); and 2) a toxic agent, such as a cytotoxic agent, including a neurotoxic agent, or a chemotherapeutic drug.

In another aspect, the invention provides a method for reducing the side effects of a drug, comprising administering a compound of claim 1 to a subject in need thereof. In one embodiment, the drug is an anti-cancer agent. In another embodiment, the drug is a tubulin-binding drug. In still another embodiment, the drug is fludelone, iso-fludelone, or paclitaxel.

In another aspect, the invention provides a method for treating or preventing cancer comprising administering to a subject in need thereof an effective amount of a compound of Formula (I); or a composition comprising 1) a compound of Formula (I) and 2) a chemotherapeutic agent, such as a tubulin-binding drug.

In yet another aspect, the invention provides a method for treating a neurotrophic disorder comprising administering to a subject in need thereof an effective amount of a compound of Formula (I).

In still another aspect, the invention provides a method for inducing a chemoprotective phase II enzyme in a subject comprising administering to a subject in need thereof an effective amount of a compound of Formula (I). In one embodiment, the induction of a chemoprotective phase II enzyme prevents cancer or reduces the risk of its onset.

In another aspect the invention provides a method for inducing DNA synthesis in a cell comprising contacting the cell with an effective amount of a compound of Formula (I). In some embodiments, the cell is in vitro or in vivo.

In another aspect the invention provides a method for inducing protein synthesis in a cell comprising contacting the cell with an effective amount of a compound of Formula (I). In some embodiments, the cell is in vitro or in vivo.

In another aspect, the invention provides a method for reducing or preventing a toxic effect of a toxic agent, comprising administering a compound of Formula (I) to subject in need thereof. In one embodiment, the toxicity is cytotoxicity and the toxic agent is a cytotoxic agent, for example a cancer chemotherapeutic agent. In another embodiment, the toxicity is neurotoxicity and the toxic agent is a neurotoxic agent, for example a cancer chemotherapeutic agent.

In another aspect, the invention provides for improving or enhancing the general health or well-being of a subject by administering a compound of Formula (I) to the subject. The subject can be in need of an improvement in their general health or well-being.

In another aspect, the invention provides for reducing physico-chemical stress or promoting the healing of injuries in a subject by administering an effective amount of a compound of claim Formula (I) to a subject in need thereof.

In yet another aspect, the invention provides for enhancing the immune system of a subject comprising administering an effective amount of a compound of Formula (I) to a subject in need thereof.

In one aspect, the invention provides for enhancing the immune system of a subject by administering an effective amount of a compound of Formula (I) to a subject in need thereof. In one embodiment, the immune system is enhanced by induction of a chemoprotective phase II enzyme. In one aspect, the compound of Formula (I) induces a chemoprotective phase II enzyme in the subject.

In another aspect the invention provides a method for making Compound (G):

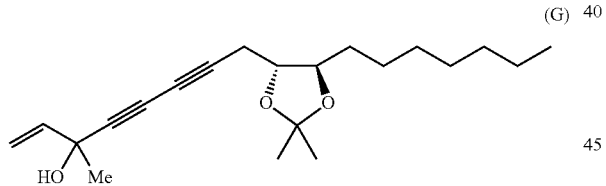

comprising allowing compound (C)

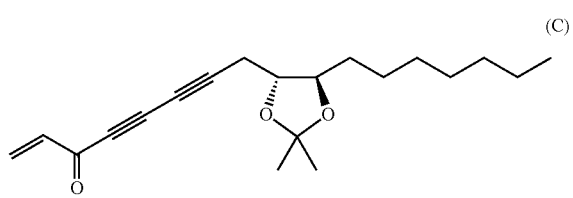 [SMILES: C=CC(=O)C#CC#CC[C@H]1OC(C)(C)O[C@@H]1CCCCCCC]

to react with a methyl nucleophile under conditions sufficient to produce compound (G). In some embodiments, the methyl nucleophile is MeLi; ZnMe$_2$, CuMe$_2$, or a methyl Grignard reagent such as MeMgCl, MeMgBr, or MeMgI. In other embodiments, the conditions comprise a chiral ligand.

In another aspect the invention provides a method for making Compound (H):

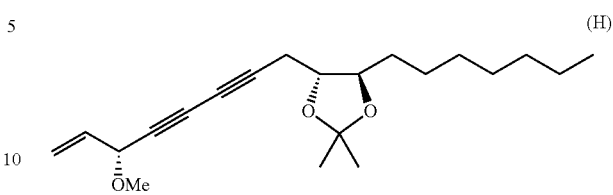

comprising allowing compound (A)

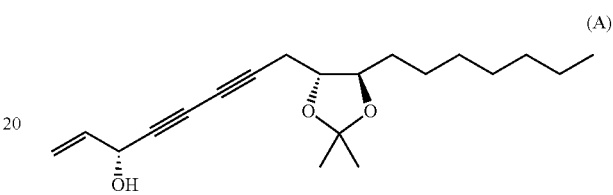

to react with an electrophilic methyl under conditions sufficient to produce compound (H). In some embodiments, the electrophilic methyl is Me$_3$OBF$_4$, MeBr, MeI, MeOTf, SO$_4$Me$_2$, or CO$_3$Me$_2$.

In another aspect, the invention provides a method for making Compound (J):

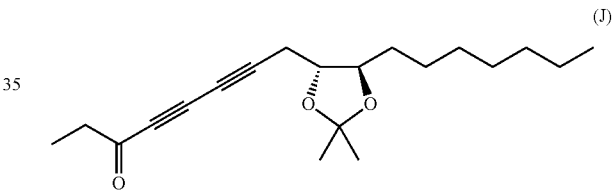

comprising oxidizing a compound having the formula

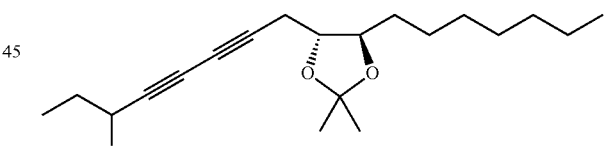

with an oxidant under conditions sufficient to produce compound (J).

In some embodiments, the oxidant is TPAP, and the conditions include NMO.

In another aspect, the invention provides a method for making Compound (K):

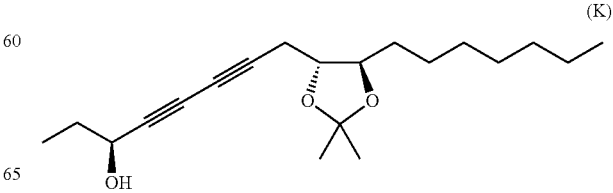

comprising allowing a compound having the structure

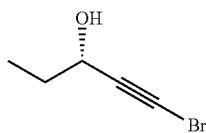

to react with compound 6"

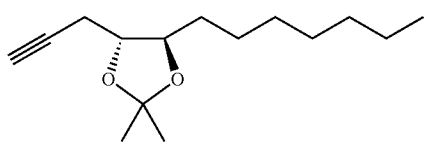

in the presence of Cu(I) under conditions sufficient to produce compound (K).

In one embodiment, Cu(I) is from a copper salt, for example a halide salt such as CuCl. In another embodiment, Cu(I) is generated in situ from a Cu(II) salt, such as copper(II) sulfate and a reducing agent, for example ascorbate or ascorbic acid.

In another aspect, the invention provides a method for making Compound (L):

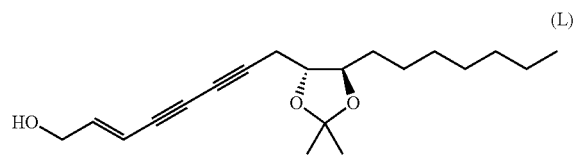 [SMILES: CCCCCCC[C@H]1OC(C)(C)O[C@@H]1CC#CC#C/C=C/CO]

comprising reacting a compound having the structure

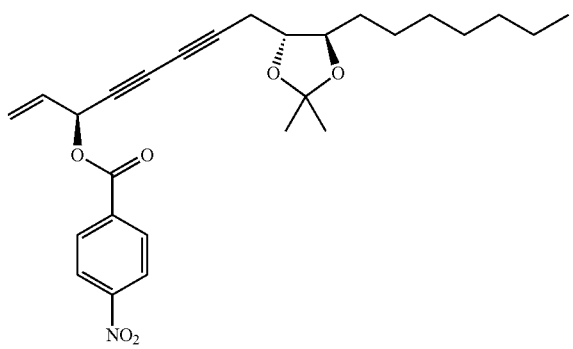 [SMILES: C=C[C@@H](C#CC#CC[C@H]1OC(C)(C)O[C@@H]1CCCCCCC)OC(=O)c1ccc([N+](=O)[O-])cc1]

with a hydroxide ion, under conditions sufficient to produce Compound (L).

In one embodiment, the hydroxide ion is from an aqueous base. In another embodiment, the aqueous base is NaOMe in wet methanol.

A Compound of Formula (I) or a pharmaceutically acceptable salt thereof (a "Compound"), and compositions comprising it, are useful for treating or preventing diseases, including cancer, chemotherapy-induced toxicity or the side effects thereof e.g. body weight loss, inflammation, and a neurotrophic disorder (a "Condition") in a subject in need thereof. Compounds of Formula (I-a)-(I-o) and examples herein are also considered "Compounds" of the invention. In one embodiment Compounds act synergistically with tubulin-binding drugs and other anticancer drugs to treat or prevent cancer. Thus, the invention also provides compositions comprising Compounds and drugs, for example cytotoxic agents such as anticancer agents including tubulin-binding drugs. A Compound of Formula (I) is also useful for inducing phase II chemoprotective enzymes, for example enzymes having an antioxidant effect, and for inducing DNA and/or protein synthesis.

The invention further provides compositions comprising an effective amount of a Compound and a physiologically acceptable carrier or vehicle.

The invention further provides compositions comprising an effective amount of a Compound and a tubulin-binding drug, and a physiologically acceptable carrier or vehicle.

The details of the invention are set forth in the accompanying description below. All references cited in this specification are incorporated herein by reference in their entireties.

3. BRIEF DESCRIPTION OF THE DRAWINGS

FIGS. 1A and 1B show the therapeutic, anti-cancer effects of various dosage regimens of panaxytriol and Compound (A), respectively, given by i.v. injection in nude mice bearing human mammary carcinoma MX-1 xenograft tumors, which is an in vivo model for breast cancer. Different dosages under the X axis indicate that the dose of the corresponding compound was increased to the indicated level for the indicated time period. The compounds were administered starting on day 8. In these experiments, the effect appears to be not very dose-dependent at high dosages. FIGS. 1A and 1C are the same experiment. FIG. 1A shows the results on the tumor size, while FIG. 1C shows the results as body weight change. FIGS. 1B and 1D are related in the same manner as FIGS. 1A and 1C.

In FIG. 1A, on Day 24, tumor suppression by panaxytriol was 52.3% compared to the control tumor size on Day 24 (tumor size change is the final tumor size minus the initial tumor size). ● represents a control (sacrificed on, n=4); □ represents panaxytriol in escalating doses: 30 mg/kg Q2D×3 (days 8-12), 50 mg/kg Q2D×3 (days 14-18), 75 mg/kg Q2D×5 (days 20-28), n=3; and Δ represents panaxytriol in escalating doses: 50 mg/kg Q2D×3, 75 mg/kg Q2D×3, 100 mg/kg Q2D×5, n=3. All animals were sacrificed on Day 28.

In FIG. 1B, on Day 24, tumor suppression by Compound (A) was 47.7% compared to the control tumor size. ● represents Control (sacrificed on Day No.); □ represents Compound A 10 mg/kg Q2D×3 (days 8-12), 30 mg/kg Q2D×3 (days 14-18), 50 mg/kgQ2D×5 (days 20-28), n=3; and Δ represents Compound A 20 mg/kgQ2D×3 (days 8-12), 50 mg/kg Q2D×3 (days 14-18), 100 mg/kg Q2D×5 (days 20-28), n=3.

FIGS. 1C and 1D show the effects of various dosages of panaxytriol and Compound (D), respectively, given by i.v. injections on the body weight of nude mice bearing human mammary carcinoma MX-1 xenografts, an in vivo model for breast cancer. There was no evidence of panaxytriol or Compound A toxicity. The compounds were administered starting on day 8. In FIGS. 1C and 1D, body weight is calculated as the total weight of the mouse minus the weight of the tumor.

In FIG. 1C, ● represents a control (sacrificed on Day 28, n=4); □ represents Panaxytriol 30 mg/kg Q2D×3 (days 8-12), 50 mg/kg Q2D×3 (days 14-18), 75 mg/kg Q2D×5 (days 20-28), n=3; and Δ is Panaxytriol 50 mg/kg Q2D×3 (days 8-12), 75 mg/kg Q2D×3 (days 14-18), 100 mg/kg Q2D×5 (days 20-28), n=3.

In FIG. 1D, ● represents a control (sacrificed on Day 28, n=4); □ represents Compound A 10 mg/kg Q2D×3 (days 8-12), 30 mg/kg Q2D×3 (days 14-18), 50 mg/kg Q2D×5 (days 20-28), n=3; and Δ represents Compound A 20 mg/kgQ2D×3 (days 8-12), 50 mg/kg Q2D×3 (days 14-18), 100 mg/kg Q2D×5 (days 20-28), n=3.

FIG. 2 shows the therapeutic effects of panaxytriol and Compound (D) at various dosages in an in vivo model of breast cancer using nude mice bearing human mammary carcinoma MX-1 xenograft tumors (i.v. injection, n=5): ● represents a control; □ represents Compound D at 5 mg/kg Q2D×6 iv.inj.; Δ represents Compound D at 15 mg/kg Q2D× 2, then 20 mg/kg Q2D×4 iv.inj.; and X represents panaxytriol at 60 mg/kg Q2D×5 iv.inj. The compounds were administered starting on day 8.

FIG. 3 shows the therapeutic effect of Compound (D) at various dosages in an in vivo model for breast cancer using nude mice bearing human mammary carcinoma MX-1 xenograft tumors (iv. Infusion, n=5): ○ represents a control; Δ represents Compound D at 30 mg/kg Q2D×5 iv.inf.; and □ represents Compound D at 15 mg/kg Q2D×1, then 45 mg/kg Q2D×4 iv.inf. The compounds were administered starting on day 8.

FIGS. 4A and 4B show the therapeutic effect of an anticancer drug, Iso-Oxazole-Fludelone (i.v. infusion.), alone and in combination with Compound (D) (i.v. injection), in an in vivo assay for colon cancer using nude mice bearing human colon carcinoma HCT-116 xenografts (n=6). FIG. 4B is an approximately 20-fold enlargement of the vertical scale of the data depicted in FIG. 4A. Iso-oxazole-fludelone is an illustrative tubulin-binding anticancer agent, sharing a mechanism of action with epothilones.

In FIG. 4A, ● represents a control (Untreated Sacrificed on D27); ○ represents Compound D 10 mg/kg (iv.inj.) Q3D×3, Q6D×3; ▲ represents Compound D 10 mg/kg (iv.inj.) Q3D× 3, Q6D×7+Iso-Flu 25 mg/kg (iv.infu.) Q12D×4, 6/6 CR on D23,36,43,45,51,57; and Δ represents Iso-Flu 25 mg/kg (iv.infu.) Q12D×4, 6/6 CR on D36,43,45,51,57. The compounds were administered starting on day 9.

In FIG. 4B (a 20-fold enlargement of the Y axis in FIG. 4A), ▲ represents Compound D 10 mg/kg (iv.inj.) Q3D×3, Q6D×3+Iso-Flu 25 mg/kg (iv.infu.) Q12D×3, 2/6 CR on D23, 36; and Δ represents Iso-Flu 25 mg/kg (iv.infu.) Q12D×3, 1/6 CR on D36. The compounds were administered starting on day 9. CR means complete remission, thus 2/6CR means the treatment resulted in 2 out of 6 complete tumor remissions occurring on the given day(s). The results show that Compound D significantly enhances the therapeutic effect of Iso-oxazole-fludelone.

FIG. 4C compares the effect of the combination of Compound (D) and Iso-Oxazole-Fludelone on body weight of nude mice bearing human colon carcinoma HCT-116 xenografts against the effect of each molecule alone (n=6). ● represents a control (Untreated Sacrificed on D27); ○ represents Compound D 10 mg/kg (iv.inj.) Q3D×3, Q6D×3; ▲ represents Compound D 10 mg/kg (iv.inj.) Q3D×3, Q6D×7+ Iso-Flu 25 mg/kg (iv.infu.) Q12D×4, 6/6 CR on D23,36,43, 45,51,57; and Δ represents Iso-Flu 25 mg/kg (iv.infu.) Q12D× 4, 6/6 CR on D36,43,45,51,57. Iso-Flu and Compound D were administered starting on day 9. CR means complete remission, thus 6/6CR means the treatment resulted in 6 out of 6 complete tumor remissions occurring on the given day(s). The results show that co-administration with Compound D significantly reduces iso-oxazole-fludelone toxicity.

FIG. 5A shows the therapeutic effect of the anticancer drug, Cyclophosphamide (an illustrative DNA-alkylating anticancer agent), in combination with Compound (D) in an in vivo assay for breast cancer using nude mice bearing human mammary carcinoma MX-1 xenografts. ● represents a control (Untreated, Sacrificed on D21, n=6); ○ represents Compound D 10 mg/kg (iv.inj.) Q4D×3, n=6; ▲ represents Compound D 10 mg/kg (iv.inj.) Q4D×3, Q6D×2+Cyclophosphamide 120 mg/kg (oral) Q2D×8, 120 mg (ip) Q2D×4, 8/8 CR on D21,21,21,23,23,23,25,27, (n=8); and Δ represents Cyclophosphamide 120 mg/kg (oral) Q2D×8, 120 mg (ip) Q2D×4, 8/8 CR on D21,21,21,23,23,23,25,27, (n=8). The compounds were administered starting on day 9.

FIG. 5B shows the effect of the combination of Compound (D) and Cyclophosphamide on body weight of nude mice bearing human colon carcinoma HCT-116 xenografts versus each molecule alone. ● represents a control (Untreated, Sacrificed on D21, n=6); ○ represents Compound D 10 mg/kg (iv.inj.) Q4D×3, n=6; ▲ represents Compound D 10 mg/kg (iv.inj.) Q4D×3, Q6D×2+Cyclophosphamide 120 mg/kg (oral) Q2D×8, 120 mg (ip) Q2D×4, 8/8 CR on D21,21,21,23, 23,23,25,27, (n=8); and Δ represents Cyclophosphamide 120 mg/kg (oral) Q2D×8, 120 mg (ip) Q2D×4, 8/8 CR on D21, 21,21,23,23,23,25,27, (n=8). The compounds were administered starting on day 9.

FIG. 6A shows the therapeutic effects of Compound D and 5-fluoro-uracil (5FU, an illustrative antimetabolite cancer drug), alone and in combination, in an in vivo assay for breast cancer using nude mice bearing human mammary carcinoma MX-1 xenografts. ● represents a control (Untreated, Sacrificed on D22, n=6); ○ represents Compound D 10 mg/kg (iv.inj.) Q4D×4, n=6; ▲ represents Compound D 10 mg/kg (iv.inj.) Q4D×4, +5FU 50 mg/kg (iv.inj.) QD×5, 2/8 died on D19,20 (n=8); and Δ represents 5FU 50 mg/kg (iv.inj.) QD×5, 5/8 died on D18,18,19,20,21 (n=8). Each * represents a mouse death. The compounds were administered starting on day 9.

FIG. 6B shows the effect of the combination of Compound (D) and 5-fluoro-uracil (5FU) on body weight changes in an in vivo assay for breast cancer using nude mice bearing human mammary carcinoma MX-1 xenografts. ● represents a control (Untreated, Sacrificed on D22, n=6); ○ represents Compound D 10 mg/kg (iv.inj.) Q4D×4, n=6; ▲ represents Compound D 10 mg/kg (iv.inj.) Q4D×4, +5FU 50 mg/kg (iv.inj.) QD×5, 2/8 died on D19,20 (n=8); and Δ represents 5FU 50 mg/kg (iv.inj.) QD×5, 5/8 died on D18,18,19,20,21 (n=8). Each * represents a mouse death. 5 The compounds were administered starting on day 9.

FIG. 7A shows the therapeutic effects of Compound (D) and Iso-Oxazole-Fludelone in an in vivo model for colon cancer using nude mice bearing human colon carcinoma HCT-116 xenograft (n=6). ● represents a control; ○ represents Compound D 10 mg/kg (iv.inj.) Q3D×2; ■ represents Compound D 10 mg/kg (iv.inj.) Q3D×2+Iso-Flu 10 mg/kg (iv.inj.) Q4D×1; □ represents Iso-Flu 10 mg/kg (iv.inj.) Q4D×1; ▲ represents Compound D 10 mg/kg (iv.inj.) Q3D× 2+Iso-Flu 25 mg/kg (iv.infu.) Q12D×1; and Δ represents Iso-Flu 25 mg/kg (iv.infu.) Q12D×1.

FIG. 7B shows body weight changes following treatment with Compound (D) and Iso-Oxazole-Fludelone in in an in vivo model for colon cancer using nude mice bearing human colon carcinoma HCT-116 xenograft (n=6). ● represents a control; ○ represents Compound D 10 mg/kg (iv.inj.) Q3D× 2; ■ represents Compound D 10 mg/kg (iv.inj.) Q3D×2+Iso-Flu 10 mg/kg (iv.inj.) Q4D×1; □ represents Iso-Flu 10 mg/kg (iv.inj.) Q4D×1; ▲ represents Compound D 10 mg/kg (iv.inj.) Q3D×2+Iso-Flu 25 mg/kg (iv.infu.) Q12D×1; and Δ represents Iso-Flu 25 mg/kg (iv.infu.) Q12D×1. * means P<0.05 and ** means P<0.01, as compared with Compound D 10 mg/kg+Iso-fludelone 25 mg/kg (Δ vs. ▲).

FIG. 8 show the effects of PHA and different concentrations of compounds of the invention, at different time points, on the proliferation of a culture of human lymphocytes as measured by DNA synthesis through incorporation of radiolabeled thymidine into the DNA.

FIG. 8A shows the stimulation by Phytohemagglutinin-M (PHA) of the proliferation of the cultured, human PBMC lymphocytes used in the radiolabeled thymidine DNA synthesis assays depicted in FIG. 8. Cells from the tested cell culture were used to generate the experimental results shown in FIGS. 8A-8E. The data show that the cells were healthy and in good condition for over 120 hours during incubation. ○ represents —PHA (control); □ represents +PHA (10 ug); Δ represents +DMSO; and ◊ represents +PHA+DMSO.

FIGS. 9A & 9B show effects of panaxytriol and Compound D, respectively, in varying doses at 24 (■), 72 (●), and 120 (▲) hours on human PBMC lymphocyte survival based on actual cell counts. In both cases, lower amounts of the compounds increase cell proliferation. FIG. 9A shows that panaxytriol has a maximal activation effect at 24 hours, while FIG. 9B shows Compound (D) has a maximal activation at 24 and 72 hours. Cell counts in controls without active agent were: at 24 hrs: 75.4%; at 72 hrs: 93.0%; and at 120 hrs: 85.7%. FIG. 9 parallel the experiments in FIG. 8 but used a different method to determine cell survival; the method used in FIG. 9 was actual cell counting using a hemocytometer and microscope. Cell samples were split and analyzed using either the method of FIG. 8 or 9, with the corresponding results displayed in the corresponding figures.

FIG. 10 show controls and the effects of different concentrations of compounds of the invention, at different time points, on the proliferation of cultured mouse splenocytes as measured by DNA synthesis through incorporation of radiolabeled thymidine into the cells' DNA.

Figure 10A:
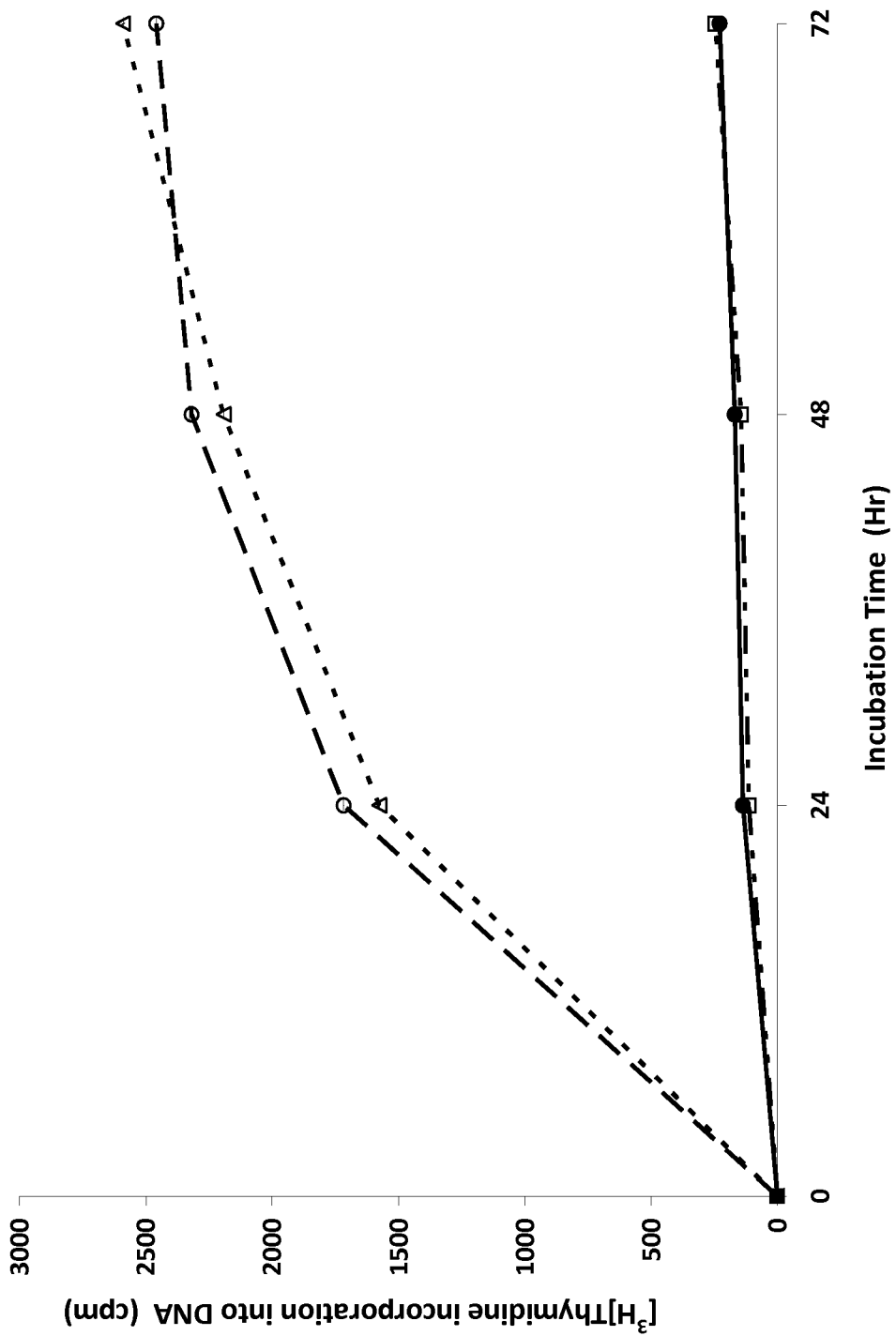

FIG. 10A shows the stimulation by Phytohemagglutinin-M (PHA) of the proliferation of cultured CD-1 mouse splenocytes. Cells of the same cell culture were used in the assays of FIG. 10. The assay shows that the cell culture of CD-1 mouse splenocytes used in the assays in FIG. 10 were in good condition for at least 72 hours during incubation. ● represents Control; ○ represents +PHA (3 ug) in a final volume of 200 μl; □ represents +DMSO; and Δ represents +PHA+DMSO.

Figure 10B:
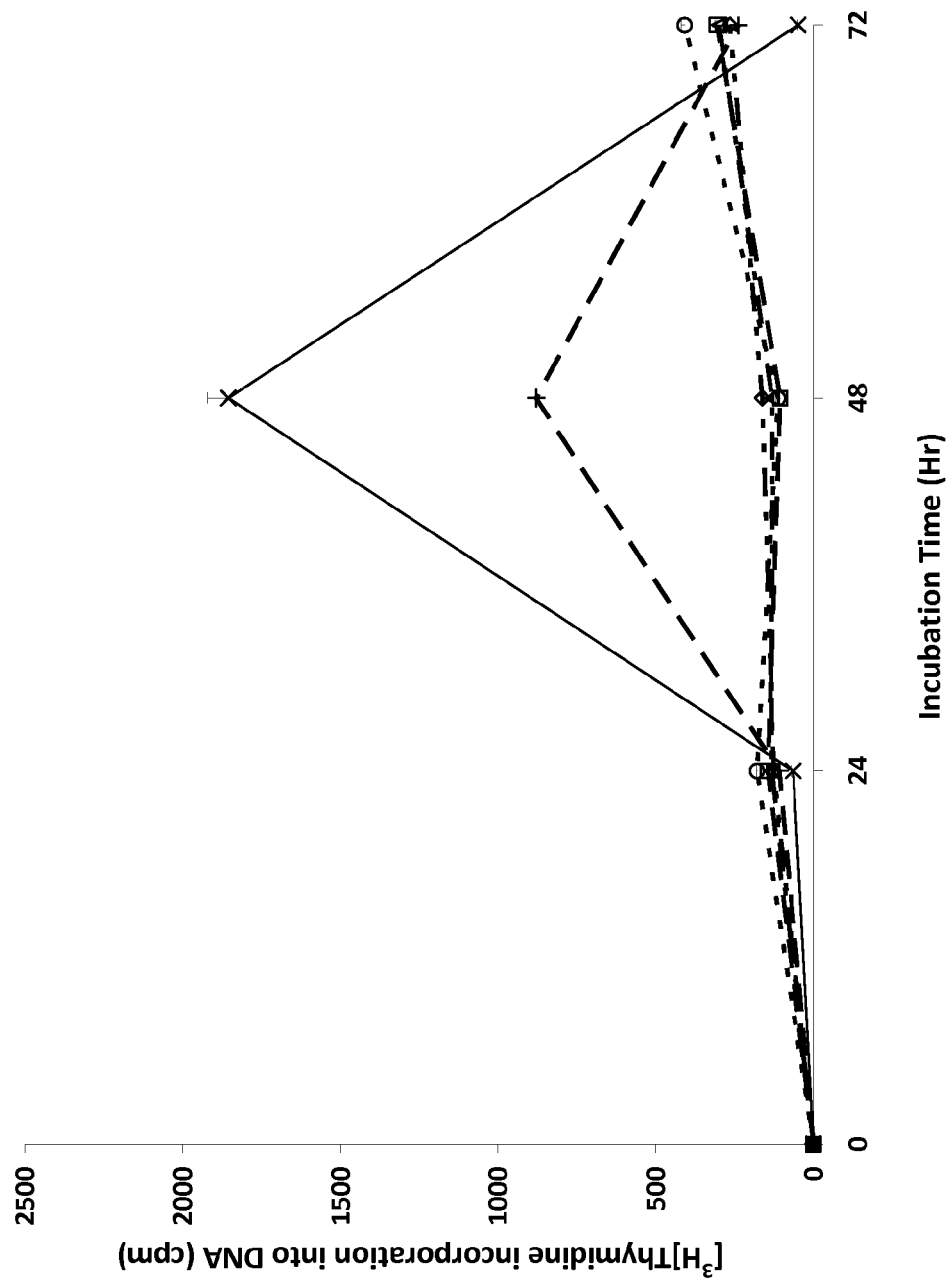

FIG. 10B shows effects of different concentrations of panaxytriol at various time points on the proliferation of cultured CD-1 mouse splenocytes as measured by radiolabeled thymidine incorporation into DNA. ○ represents 0.01 uM Panaxytriol; □ represents 0.03 uM Panaxytriol; Δ represents 0.1 uM Panaxytriol; ◊ represents 0.3 uM Panaxytriol; + represents 1 uM Panaxytriol; and X represents 3 uM Panaxytriol.

Figure 10C:
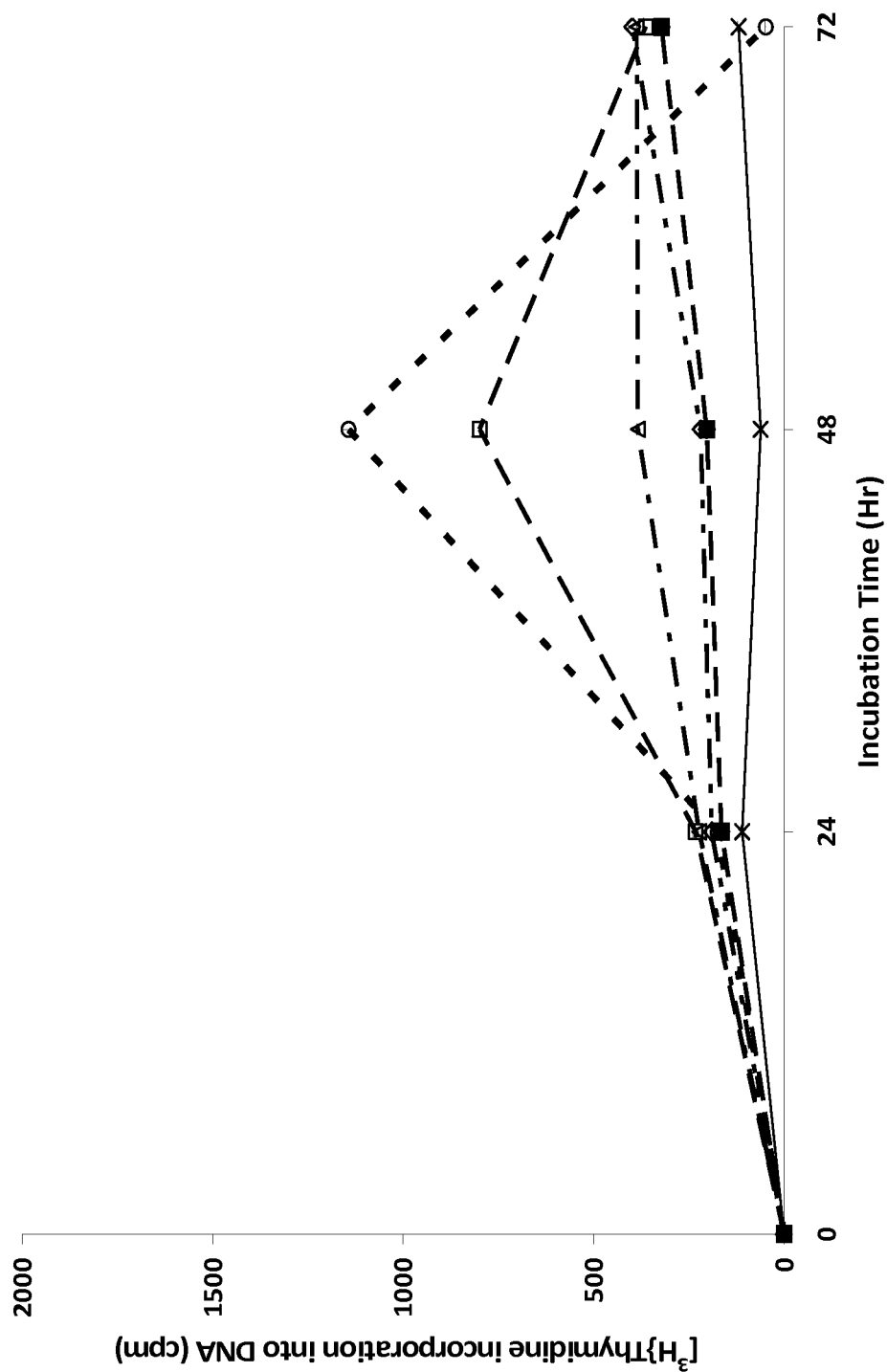

FIG. 10C shows effects of different concentrations of Compound D at various time points on the proliferation of cultured CD-1 mouse splenocytes as measured by radiolabeled thymidine incorporation into DNA. ○ represents 0.01 uM Compound D; □ represents 0.03 uM Compound D; Δ represents 0.1 uM Compound D; ◊ represents 0.3 uM Compound D; ■ represents 1 uM Compound D; and X represents 3 uM Compound D.

Figure 10D:
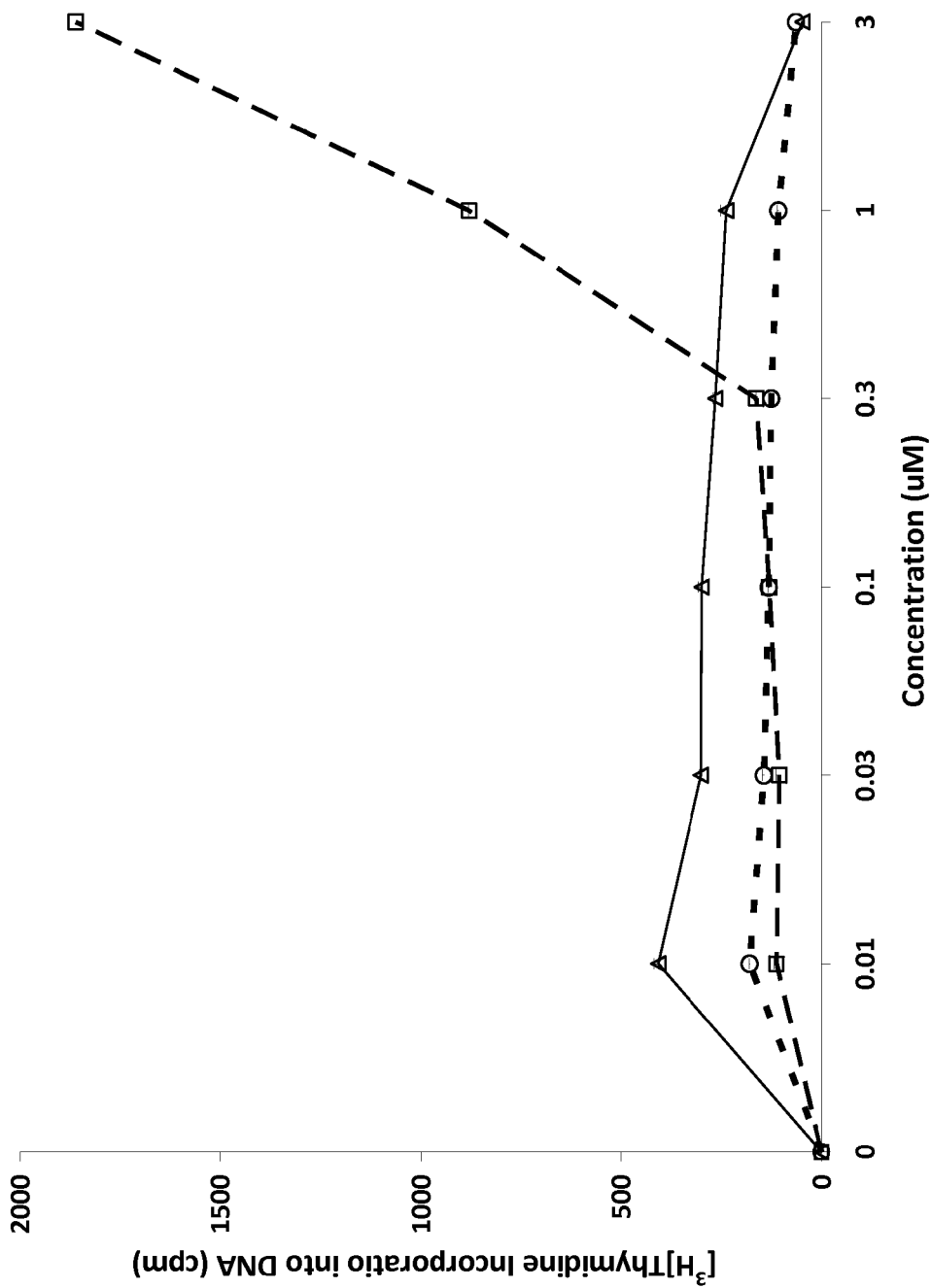

FIG. 10D is a reverse plot of FIG. 10B showing the dose-response curve for panaxytriol on stimulation of DNA synthesis (i.e. cell proliferation) of cultured CD-1 mouse splenocytes using panaxytriol in varying doses at 24 (○), 48 (□), and 72 (Δ) hours.

Figure 10E:
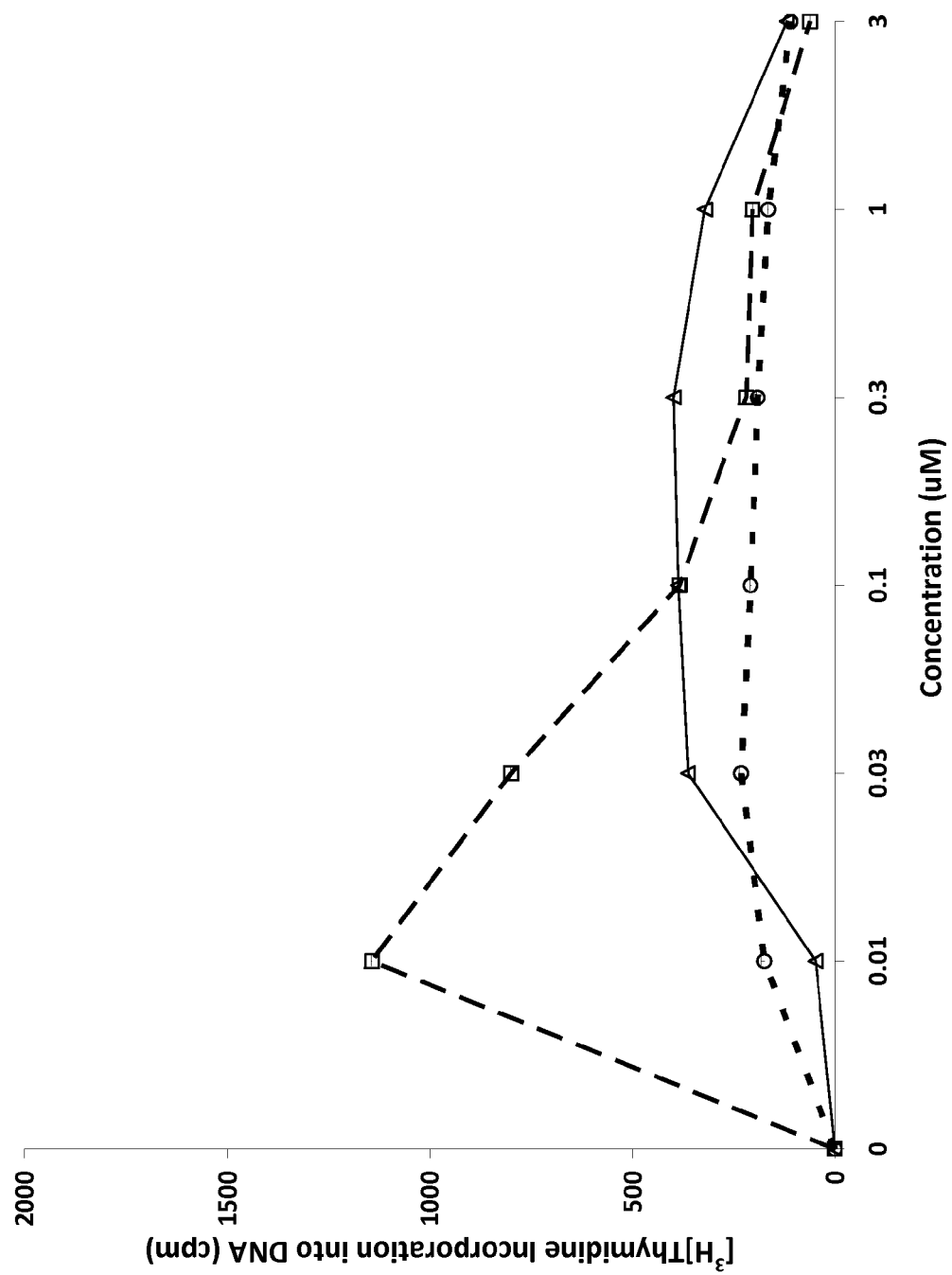

FIG. 10E is a reverse plot of FIG. 10C showing the dose-response curve for Compound D on stimulation of DNA synthesis (i.e. cell proliferation) of cultured CD-1 mouse splenocytes using Compound D in varying doses at 24 (○), 48 (□), and 72 (Δ) hours.

Figure 10F:
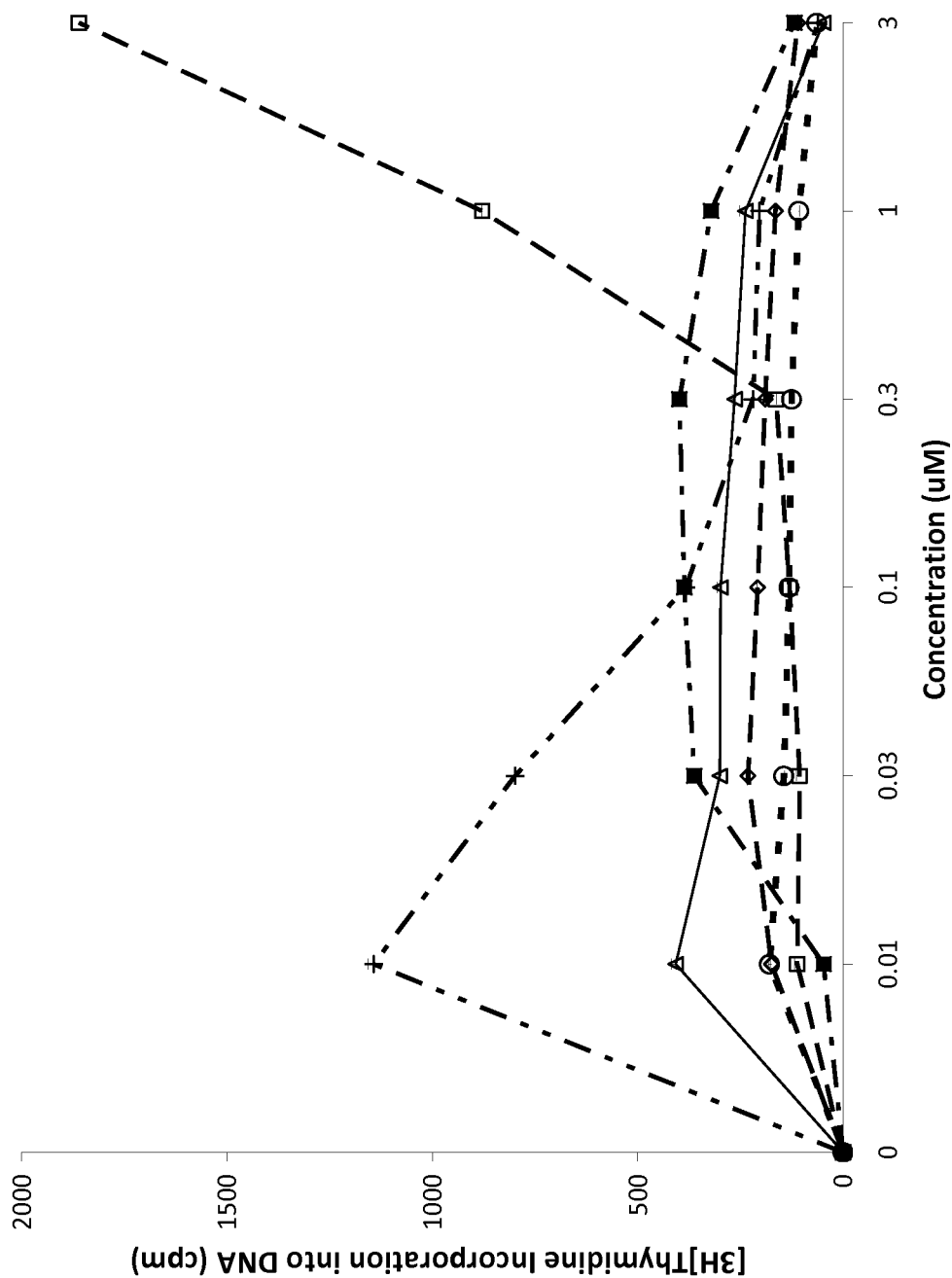

FIG. 10F is an overlay of FIGS. 10D and 10E using panaxytriol in varying doses at 24 (○), 48 (□), and 72 (Δ) hours and Compound D in varying doses at 24 (◊), 48 (+), and 72 (■) hours.

FIG. 11 show controls and the effects of different concentrations of compounds of the invention, at different time points, on the proliferation of cultured mouse splenocytes as measured by DNA synthesis through incorporation of radiolabeled thymidine into the DNA.

Figure 11A:
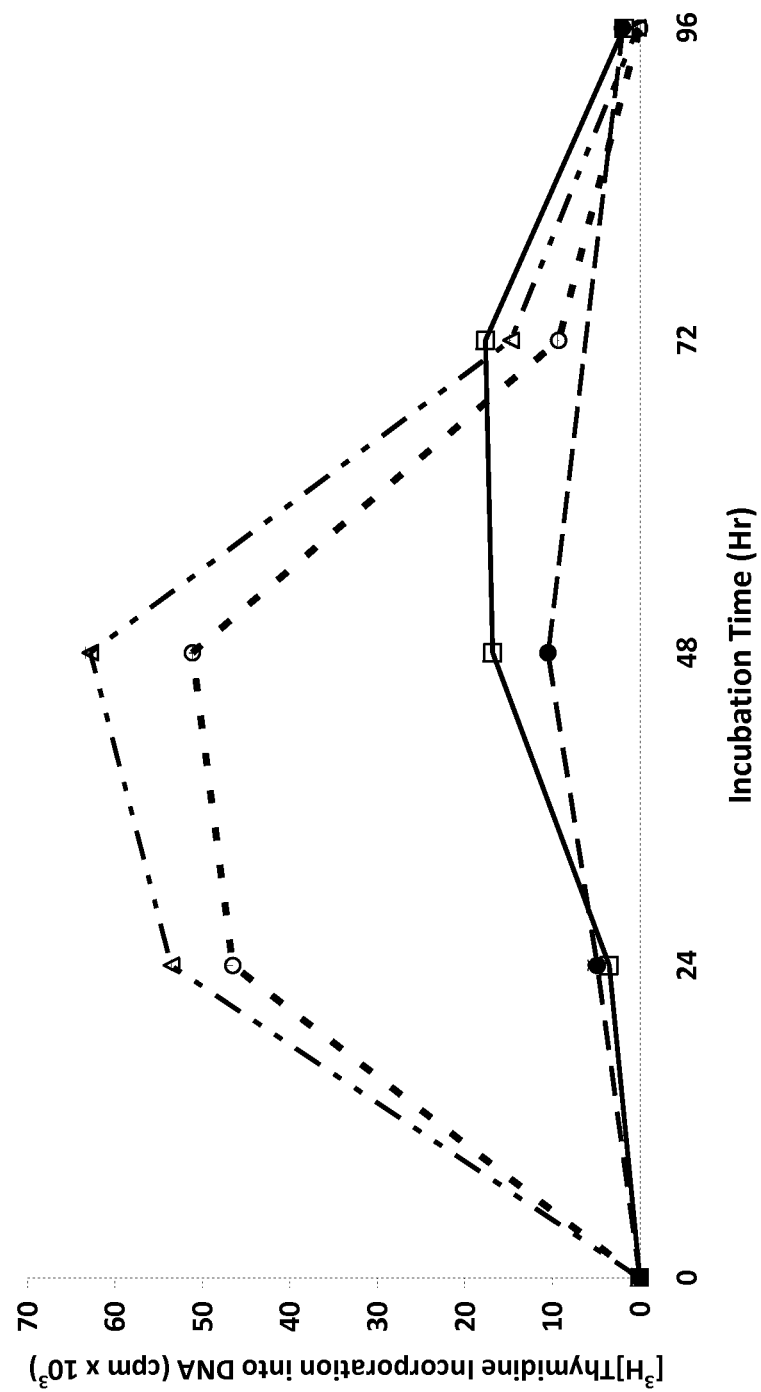

FIG. 11A shows the stimulation of cultured CD-1 mouse splenocyte proliferation by Phytohemagglutinin-M (PHA 3 μg in a final volume of 200 μl). Cells of the same cell culture were used in the assays of FIG. 12. ● represents Control; ○ represents +PHA; □ represents +DMSO; and Δ represents +PHA+DMSO.

Figure 11B:
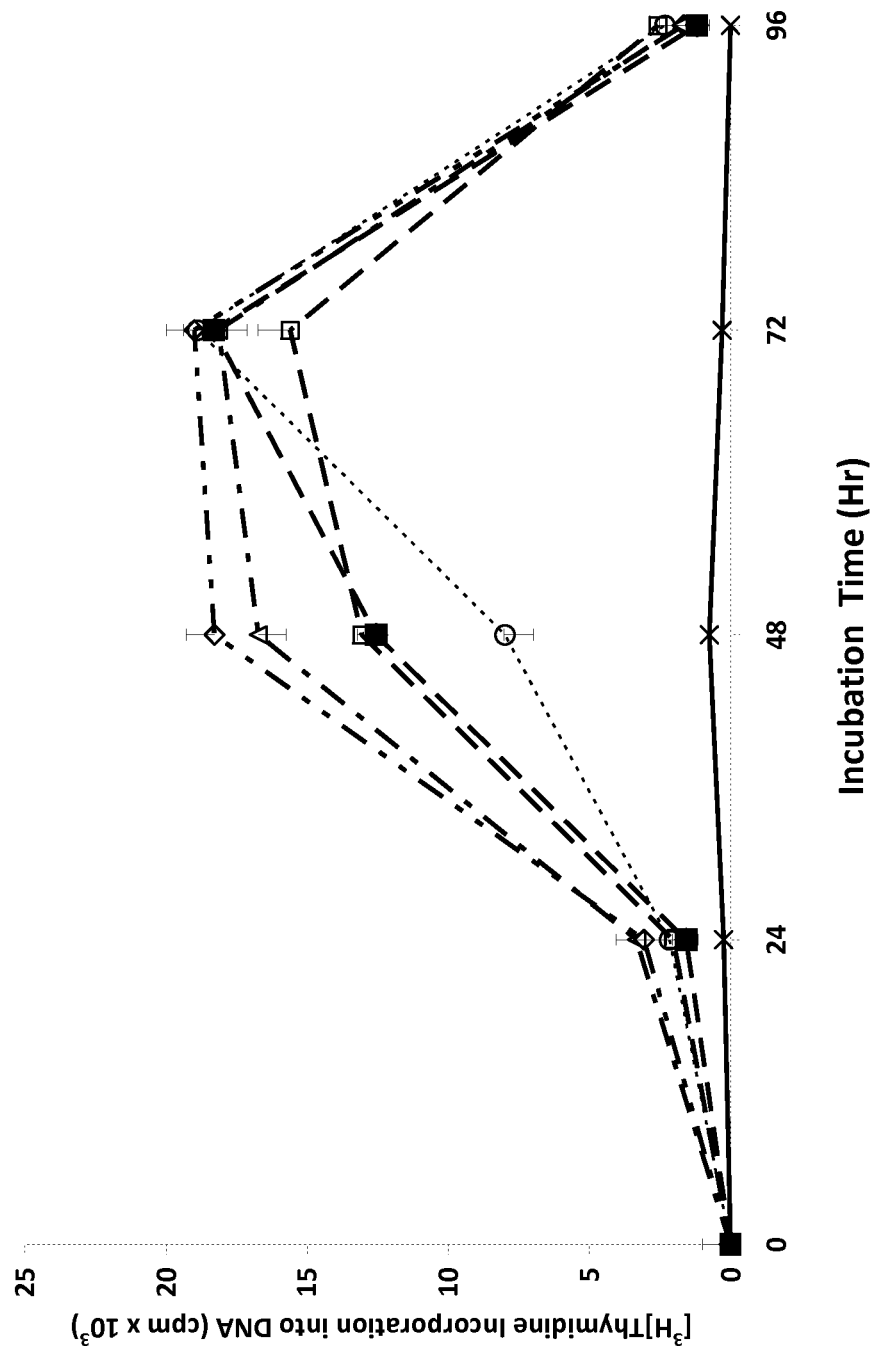

FIG. 11B shows the effects of different concentrations of panaxytriol at various time points on the proliferation of cultured CD-1 mouse splenocytes as measured by radiolabeled thymidine incorporation into DNA. ○ represents Panaxytriol at 0.03 uM; □ represents Panaxytriol at 0.1 uM; Δ represents Panaxytriol at 0.3 uM; ◊ represents Panaxytriol at 1 uM; ■ represents Panaxytriol at 3 uM; and X represents Panaxytriol at 10 uM.

Figure 11C:
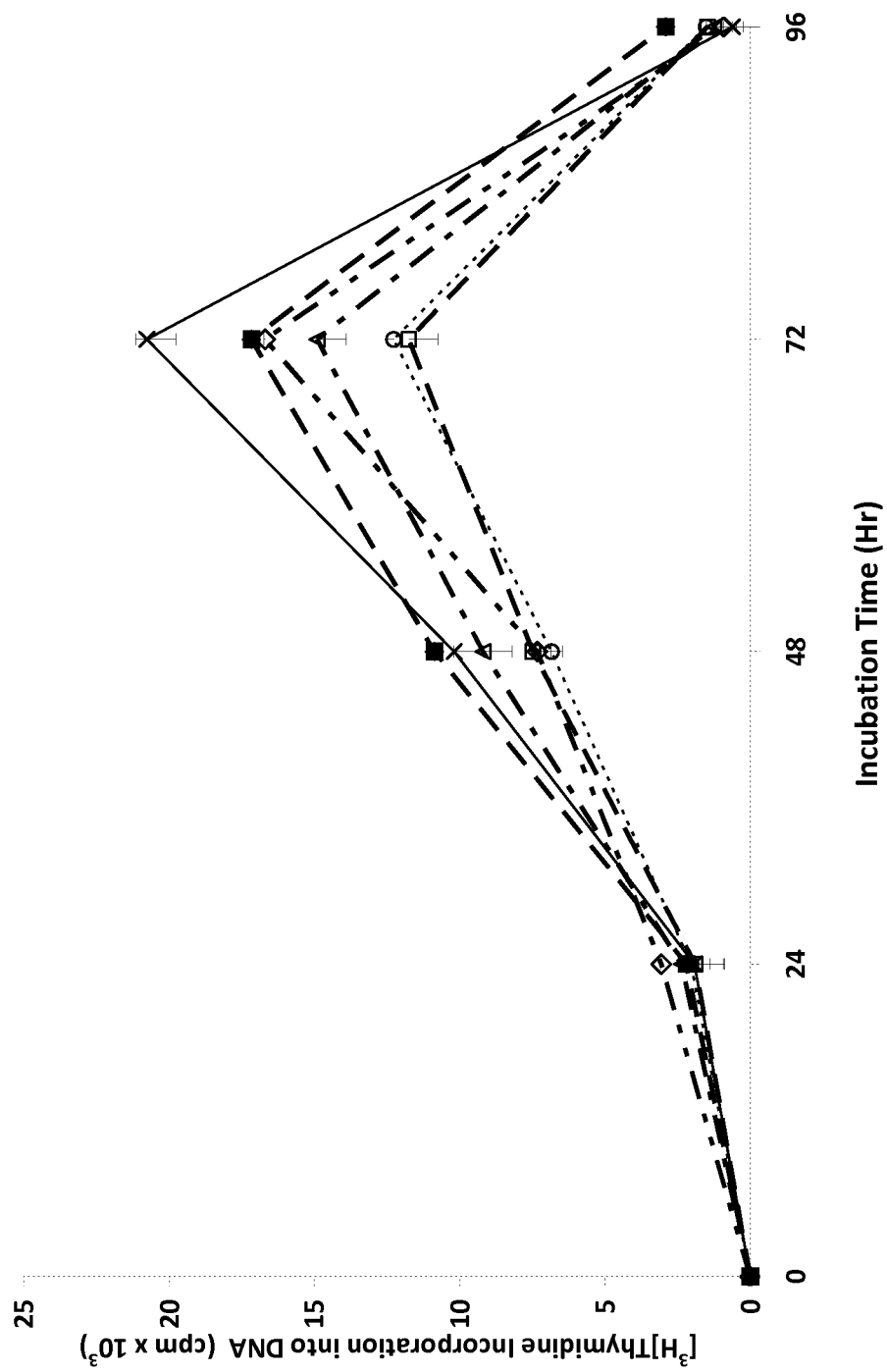

FIG. 11C shows the effects of different concentrations of Compound D at various time points on the proliferation of cultured CD-1 mouse splenocytes as measured by radiolabeled thymidine incorporation into DNA. ○ represents Compound D at 0.001 uM; □ represents Compound D at 0.003 uM; Δ represents Compound D at 0.01 uM; ◇ represents Compound D at 0.03 uM; ■ represents Compound D at 0.1 uM; and X represents Compound D at 0.3 uM.

Figure 11D:
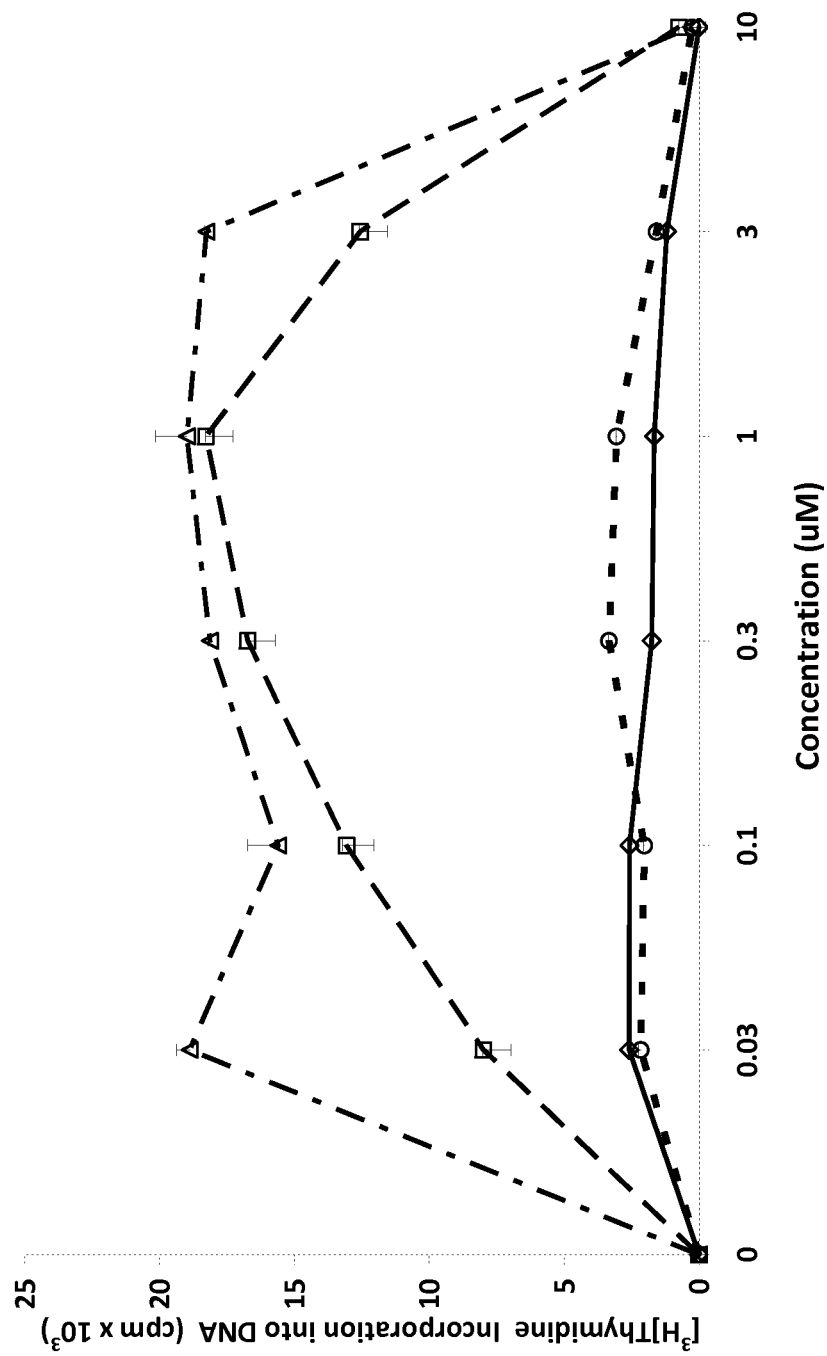

FIG. 11D is a reverse plot of FIG. 11B, showing the dose-response curve for panaxytriol on stimulation of DNA synthesis (i.e. cell proliferation) of cultured CD-1 mouse splenocytes using panaxytriol in varying doses at 24 (○), 48 (□), 72 (Δ), and 96 (◇) hours.

Figure 11E:
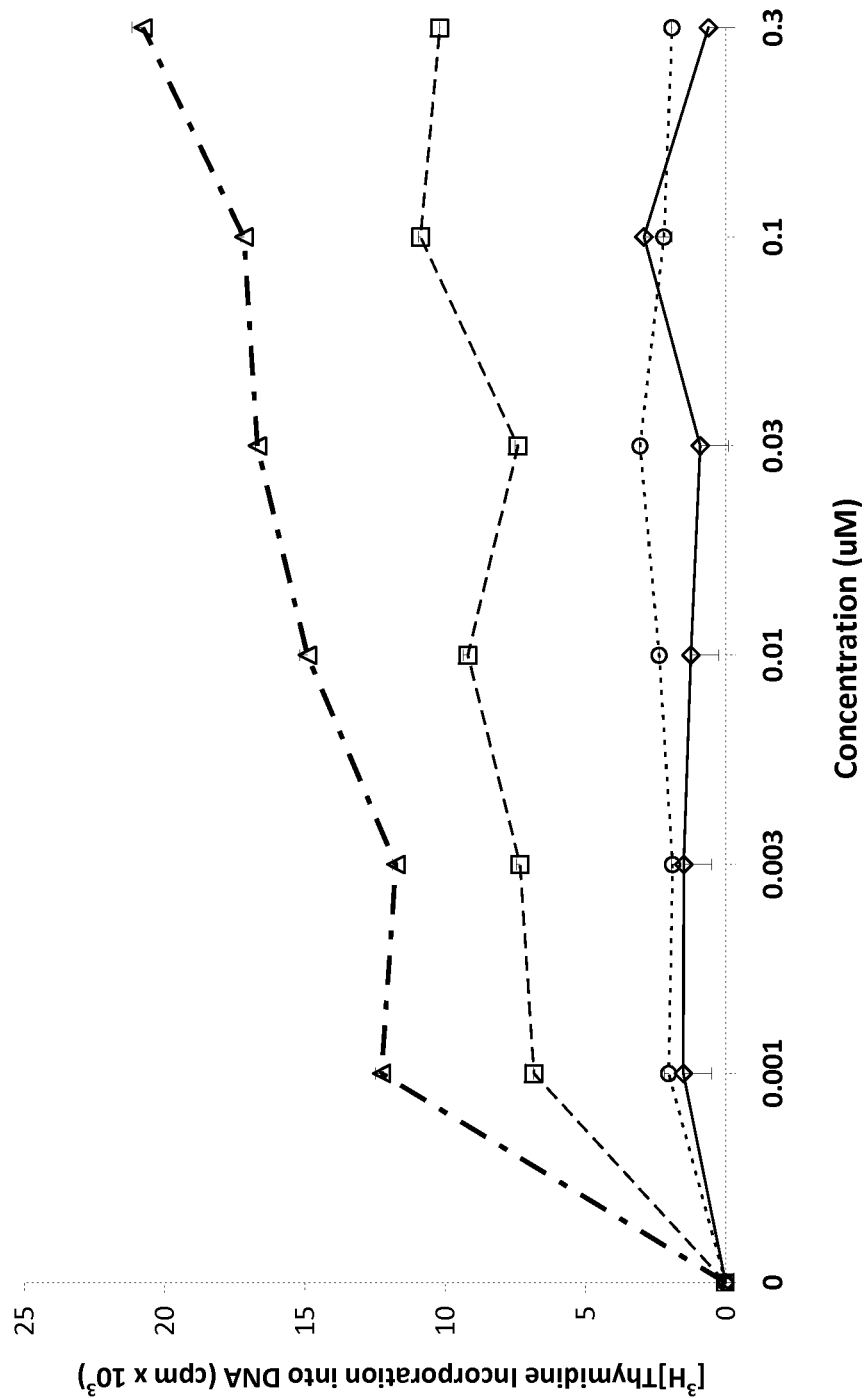

FIG. 11E is a reverse plot of FIG. 11C, showing the dose-response curve for Compound D on stimulation of DNA synthesis (i.e. cell proliferation) of cultured CD-1 mouse splenocytes using Compound D in varying doses at 24 (○), 48 (□), 72 (Δ), and 96 (◇) hours.

Figure 12:
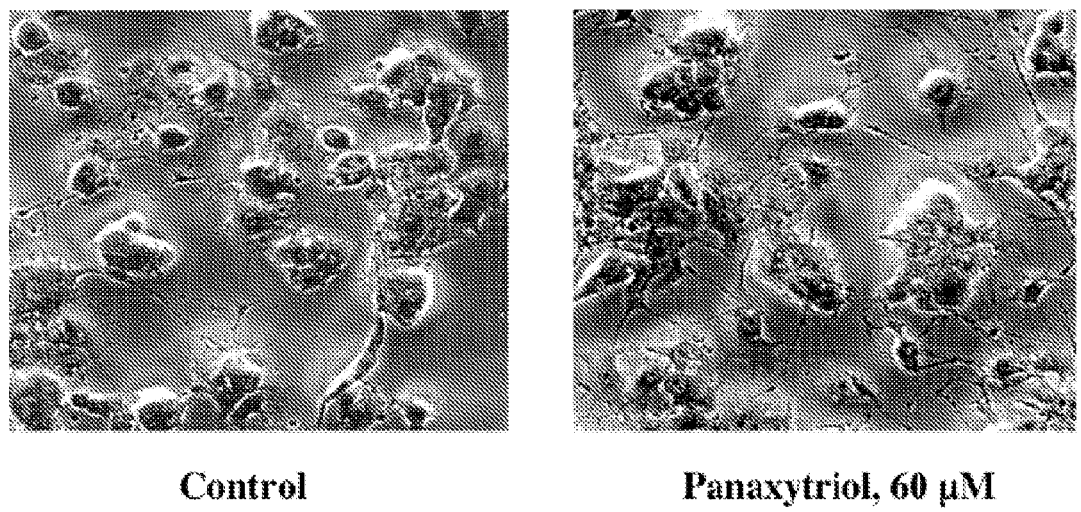

FIG. 12 shows images of neurite outgrowth with or without administration of panaxytriol.

Figure 13:
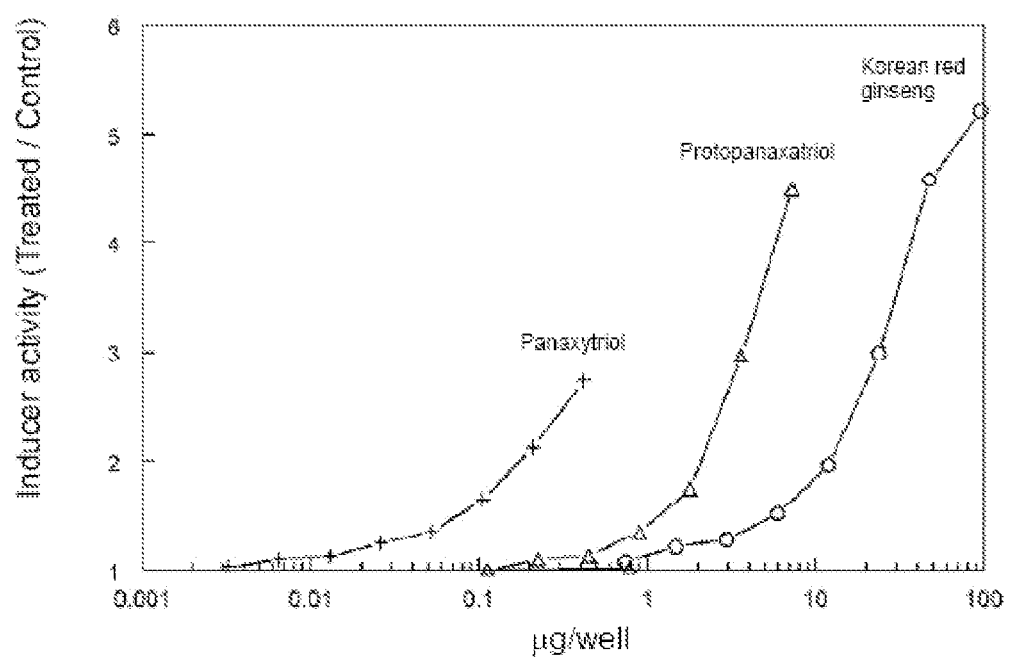

FIG. 13 shows a comparison of the induction of quinone reductase (NQO1) by Korean red ginseng extract, protopanaxatriol and panaxytriol. (+) represents Panaxytriol (molecular weight 267), (Δ) represents Protopanaxatriol (molecular weight 461), and (O) represents Korean red Sun ginseng extract.

Figure 14:
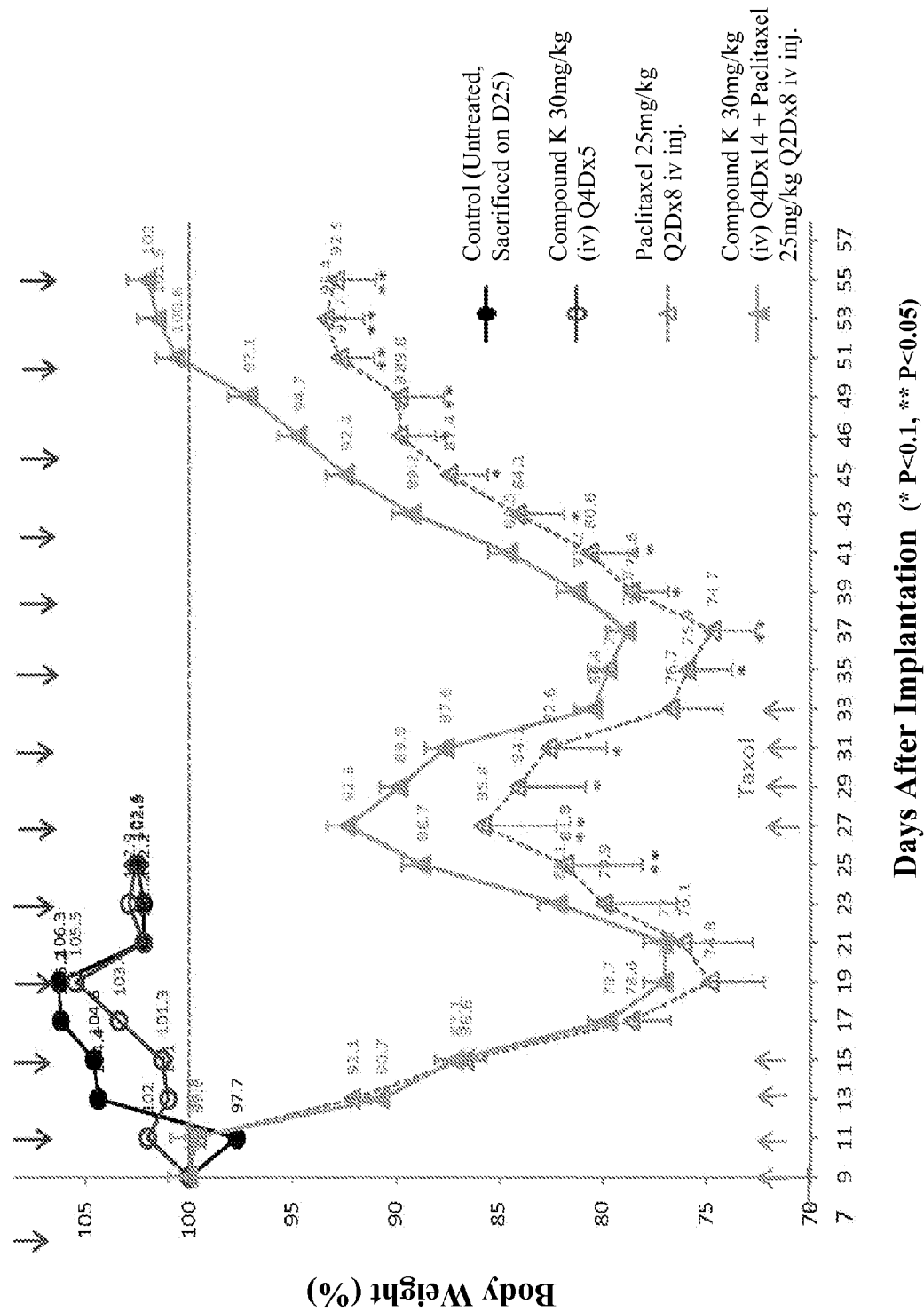

FIG. 14 shows the effects of prolonged high doses of paclitaxel (TAXOL) and Compound K, given by i.v. injections, on the body weight of nude mice bearing human mammary carcinoma MX-1 xenografts, an in vivo model for breast cancer. ● represents a control with untreated mice sacrificed on day 25. ○ represents Compound K 30 mg/kg (iv.inj.) Q4D×5, administered on the days indicated by the arrows at the top of the graph. ▲ represents Compound K 30 mg/kg (iv.inj.) Q4D×14+paclitaxel 25 mg/kg (iv.inj.) Q2D×8 (10/10CR). Δ represents paclitaxel 25 mg/kg (iv.inj.) Q2D×8, administered on the days indicated by the arrows on the bottom of the graph. The mice administered taxol or the combination showed 10/10 CR, which means ten out of ten mice showed complete remission of the tumor. The experimental procedure for FIG. 14 was carried out similarly to that in FIG. 1. * means P<0.1 and ** means P<0.05. Body weight was calculated as described for FIGS. 1 and 4-7.

Figure 15:
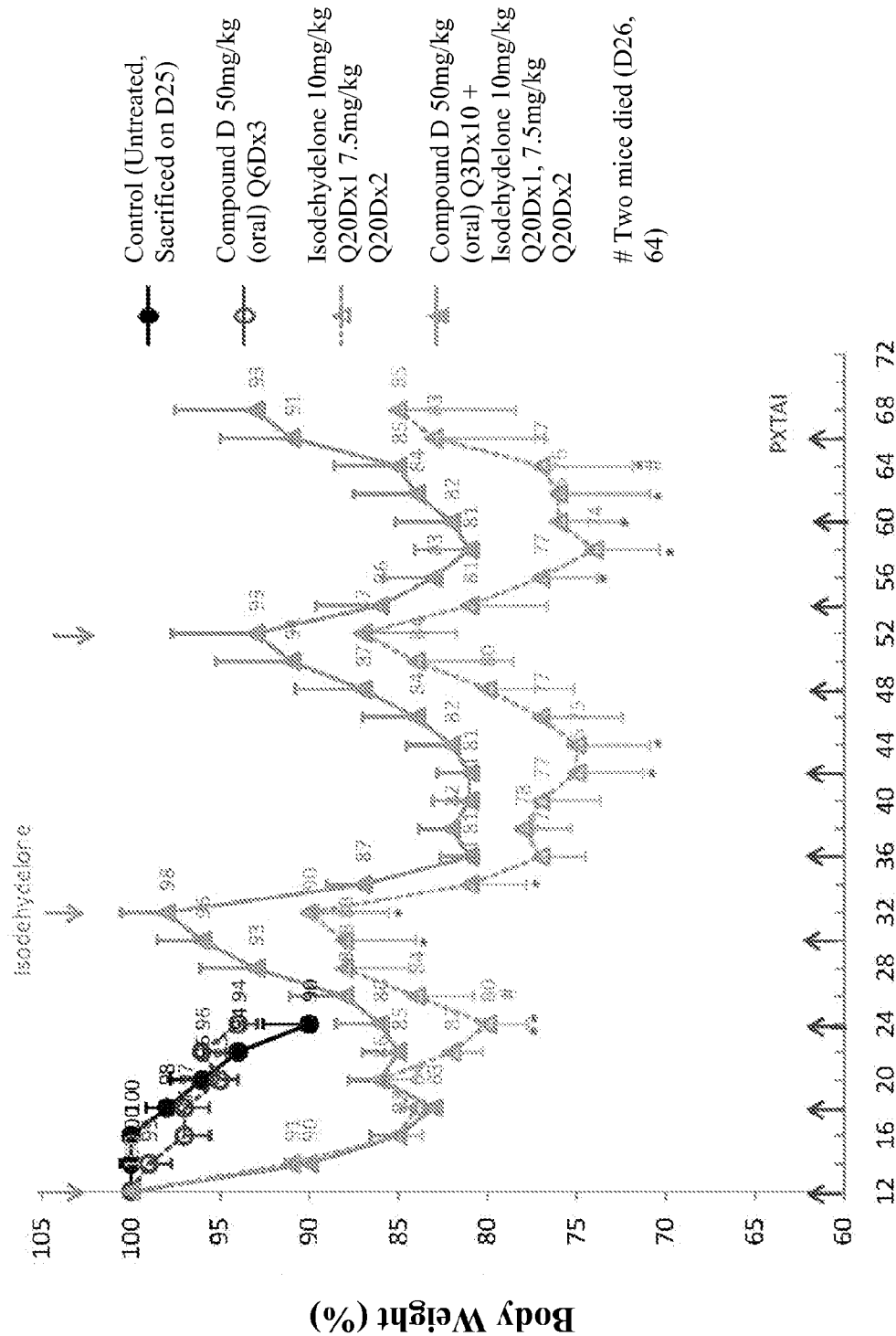

FIG. 15 shows the body weight change in nude mice bearing human colon carcinoma HCT-116 xenograft (n=7), a colon cancer assay, when administered Isodehydelone (i.e. iso-oxazole-dehydelone) (6 hr-iv. Infusion), Compound (D) (PXTAI) (orally), or a combination of orally administered Compound (D) and Isodehydelone (6 hr-iv. Infusion). Body weight was calculated as described for FIGS. 1, 4-7, and 14. The results show that Compound (D) administered oral reduces the toxicity of isodehydelone alone. * means P<0.1 and ** means P<0.05. The experiment was carried out similar to that described for FIGS. 4 and 7 except Compound (D) was administered orally.

Figure 16:
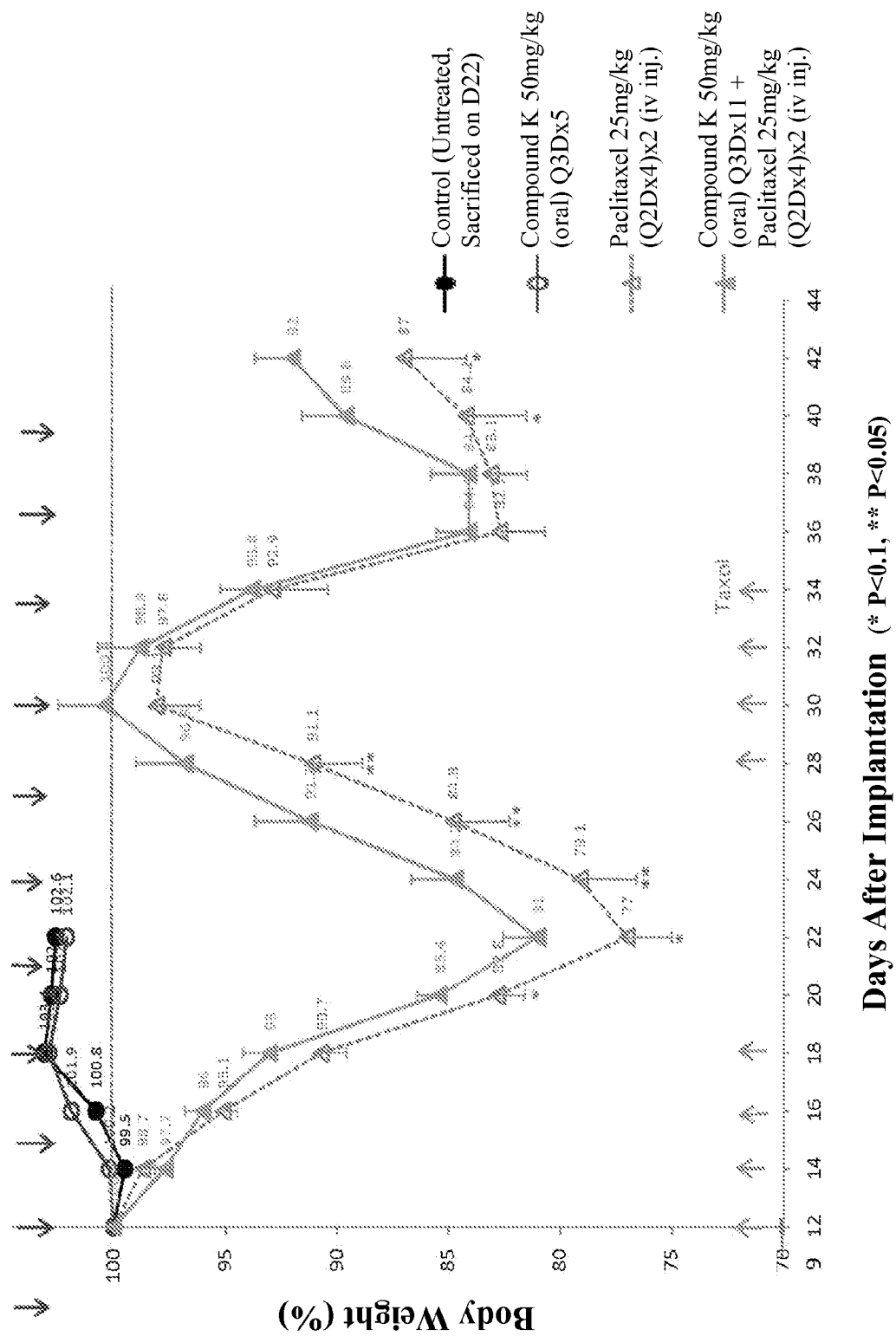

FIG. 16 shows the effects of prolonged high doses of paclitaxel (TAXOL) and orally administered Compound K on the body weight of nude mice bearing human mammary carcinoma MX-1 xenografts, an in vivo model for breast cancer. The results show that Compound K is orally effective in Reducing the Toxicity of paclitaxel and improving recovery after treatment. The experiments were performed as indicated for FIG. 14, with Compound (K) being administered orally. Compound K was administered on the days indicated by the arrows at the top of the graph, and paclitaxel was administered on the days indicated by the arrows on the bottom of the graph. Body weight was calculated as described for FIGS. 1, 4-7, 14 and 15. * means P<0.1 and ** means P<0.05.

Figure 17:
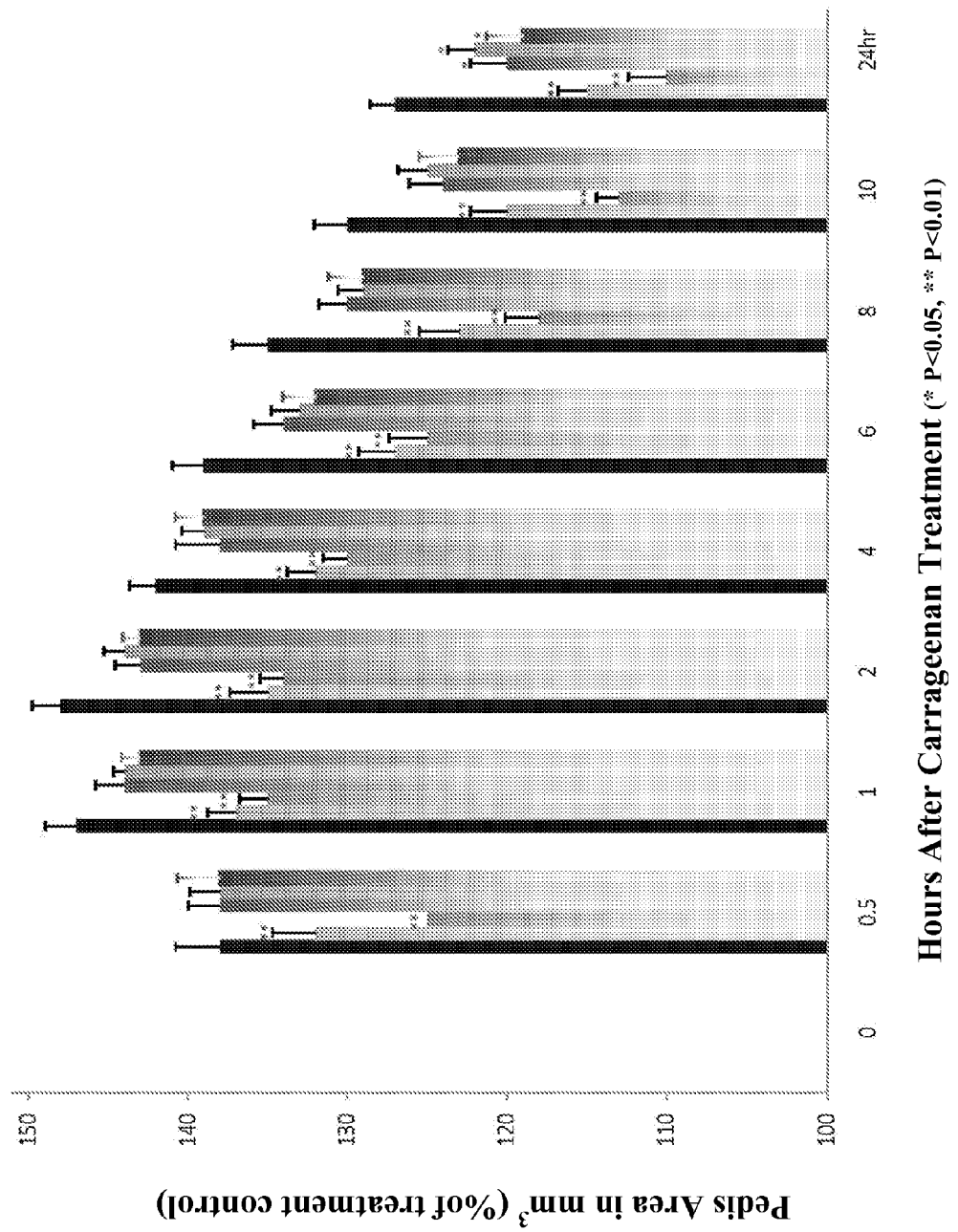

FIG. 17 compares the anti-inflammatory effect of Compound (D), acetylsalicylic acid (aspirin), and LIDEX against carrageenan-induced paw edema in CD mice. Compound (D) shows a mild, slow on-set, anti-inflammatory effect. The first vertical bar in each set is the control. The second vertical bar in each set is acetylsalicylic acid (200 mg/kg, oral). The third vertical bar in each set is LIDEX cream administered locally, the fourth vertical bar in each set is Compound (D) (10 mg/kg iv injection), the fifth vertical bar in each set is Compound (D) (15 mg/kg iv injection), and the sixth vertical bar in each set is Compound (D) (20 mg/kg iv injection). 1% Carrageenan (20 μL, i.m., injected directly into the paw of CD mice to produce paw edema) was administered at time=0. Compound (D) was administered at 24 hours prior to the carrageenan injection, 1 hour prior to the carrageenan injection, and 6 hours after the carrageenan injection. Acetylsalicylic acid was administered at 1 hour prior to the carrageenan injection, and 6 hours after the carrageenan injection. LIDEX cream was administered at 1 hour prior to the carrageenan injection, and 6 hours after the carrageenan injection. * means P<0.05 and ** means P<0.01.

The experimental procedures used to generate the figures are described herein, e.g. in the Examples.

4. DETAILED DESCRIPTION OF THE INVENTION

4.1 Definitions and Abbreviations

The following definitions are used herein:

A "tubulin-binding drug" refers to a ligand of tubulin or to a compound capable of binding α or β-tubulin monomers or oligomers thereof, αβ-tubulin heterodimers or oligomers thereof, or polymerized microtubules.

Illustrative tubulin-binding drugs include, but are not limited to:

a) Combretastatins or other stilbene analogs (Pettit et al, Can. J. Chem., 1982; Pettit et al, J. Org. Chem., 1985; Pettit et al, J. Nat. Prod., 1987; Lin et al, Biochemistry, 1989; Singh et al, J. Org. Chem., 1989; Cushman et al, J. Med. Chem., 1991; Getahun et al, J. Med. Chem., 1992; Andres et al, Bioorg. Med. Chem. Lett., 1993; Mannila, Liebigs. Ann. Chem., 1993; Shirai et al, Bioorg. Med. Chem. Lett., 1994; Medarde et al., Bioorg. Med. Chem. Lett., 1995; Pettit et al, J. Med. Chem., 1995; Wood et al, Br. J. Cancer., 1995; Bedford et al, Bioorg. Med. Chem. Lett., 1996; Dorr et al, Invest. New Drugs, 1996; Jonnalagadda et al., Bioorg. Med. Chem. Lett., 1996; Shirai et al, Heterocycles, 1997; Aleksandrzak K, Anticancer Drugs, 1998; Chen et al, Biochem. Pharmacol., 1998; Ducki et al, Bioorg. Med. Chem. Lett., 1998; Hatanaka et al, Bioorg. Med. Chem. Lett., 1998; Medarde, Eur. J. Med. Chem., 1998; Medina et al, Bioorg. Med. Chem. Lett., 1998; Ohsumi et al, Bioorg. Med. Chem. Lett., 1998; Ohsumi et al., J. Med. Chem., 1998; Pettit G R et al., J. Med. Chem., 1998; Shirai et al, Bioorg. Med. Chem. Lett., 1998; Banwell et al, Aust. J. Chem., 1999; Medarde et al, Bioorg. Med. Chem. Lett., 1999; Shan et al, PNAS, 1999; Combeau et al, Mol. Pharmacol, 2000; Pettit et al, J. Med Chem, 2000; Pettit et al, Anticancer Drug Design, 2000; Pinney et al, Bioorg. Med. Chem. Lett., 2000; Flynn et al., Bioorg. Med. Chem. Lett., 2001; Gwaltney et al, Bioorg. Med. Chem. Lett., 2001; Lawrence et al, 2001; Nguyen-Hai et al, Bioorg. Med. Chem. Lett., 2001; Xia et al, J. Med. Chem., 2001; Tahir et al., Cancer Res., 2001; Wu-Wong et al., Cancer Res., 2001; Janik et al, Biooorg. Med. Chem. Lett., 2002; Kim et al., Bioorg Med Chem. Lett., 2002; Li et al, Biooorg. Med. Chem. Lett., 2002; Nam et al, Bioorg. Med. Chem. Lett., 2002; Wang et al, J. Med. Chem. 2002; Hsieh et al, Bioorg. Med. Chem. Lett., 2003; Hadimani et al., Bioorg. Med. Chem. Lett., 2003; Mu et al, J. Med. Chem, 2003; Nam, Curr. Med. Chem., 2003; Pettit et al, J. Med. Chem., 2003; WO 02/50007, WO 02/22626, WO 02/14329, WO 01/81355, WO 01/12579, WO 01/09103, WO 01/81288, WO 01/84929, WO 00/48591, WO 00/48590, WO 00/73264, WO 00/06556, WO 00/35865, WO 00/48590, WO 99/51246, WO 99/34788, WO 99/35150, WO 99/48495, WO 92/16486, U.S. Pat. Nos. 6,433,012, 6,201,001, 6,150,407, 6,169,104, 5,731,353, 5,674,906, 5,569,786, 5,561,122, 5,430,062, 5,409,953, 5,525,632, 4,996,237 and 4,940,726 and U.S. patent application Ser. No. 10/281,528);

b) 2,3-substituted Benzo[b]thiophenes (Pinney et al, Bioorg. Med. Chem. Lett., 1999; Chen et al, J. Org. Chem., 2000; U.S. Pat. Nos. 5,886,025; 6,162,930, and 6,350,777; WO 98/39323);

c) 2,3-disubstituted Benzo[b]furans (WO 98/39323, WO 02/060872);

d) Disubstituted Indoles (Gastpar R, J. Med. Chem., 1998; Bacher et al, Cancer Res., 2001; Flynn et al, Bioorg. Med. Chem. Lett, 2001; WO 99/51224, WO 01/19794, WO 01/92224, WO 01/22954; WO 02/060872, WO 02/12228, WO 02/22576, and U.S. Pat. No. 6,232,327);

e) 2-Aroylindoles (Mahboobi et al, J. Med. Chem., 2001; Gastpar et al., J. Med. Chem., 1998; WO 01/82909)

f) 2,3-disubstituted Dihydronaphthalenes (WO 01/68654, WO 02/060872);

g) Benzamidazoles (WO 00/41669);

h) Chalcones (Lawrence et al, Anti-Cancer Drug Des, 2000; WO 02/47604)

i) Colchicine, Allocolchicine, Thiocolcichine, Halichondrin B, and Colchicine derivatives (WO 99/02166, WO 00/40529, WO 02/04434, WO 02/08213, U.S. Pat. Nos. 5,423,753. 6,423,753) in particular the N-acetyl colchinol prodrug, ZD-6126;

j) Curacin A and its derivatives (Gerwick et al, J. Org. Chem., 1994, Blokhin et al, Mol. Pharnacol., 1995; Verdier-Pinard, Arch. Biochem. Biophys., 1999; WO 02/06267);

k) Dolastatins such as Dolastatin-10, Dolastatin-15, and their analogs (Pettit et al, J. Am. Chem. Soc., 1987; Bai et al, Mol. Pharmacol, 1995; Pettit et al, Anti-Cancer Drug Des., 1998; Poncet, Curr. Pharm. Design, 1999; WO 99/35164; WO 01/40268; U.S. Pat. No. 5,985,837);

l) Epothilones such as Epothilones A, B, C, D, and Desoxyepothilones A and B, Fludelone (Chou et al. Cancer Res. 65:9445-9454, 2005), 9,10-dehydro-desoxyepothilone B (dehydelone), iso-oxazole-dehydelone (17-isooxazole-dehydelone), fludelone, iso-oxazole-fludelone (17-isooxazole-fludelone), (Danishefsky, et al., PNAS, v. 105, 35:13157-62, 2008; WO 99/02514, U.S. Pat. No. 6,262,094, Nicolau et al., Nature, 1997, Pub. No. US2005/0143429);

m) Inadones (Leoni et al., J. Natl. Cancer Inst., 2000; U.S. Pat. No. 6,162,810);

n) Lavendustin A and its derivatives (Mu F et al, J. Med. Chem., 2003);

o) 2-Methoxyestradiol and its derivatives (Fotsis et al, Nature, 1994; Schumacher et al, Clin. Cancer Res., 1999; Cushman et al, J. Med. Chem., 1997; Verdier-Pinard et al, Mol. Pharmacol, 2000; Wang et al, J. Med. Chem., 2000; WO 95/04535, WO 01/30803, WO 00/26229, WO 02/42319 and U.S. Pat. Nos. 6,528,676, 6,271,220, 5,892,069, 5,661,143, and 5,504,074);

p) Monotetrahydrofurans ("COBRAs"; Uckun, Bioorg. Med. Chem. Lett., 2000; U.S. Pat. No. 6,329,420);

q) Phenylhistin and its derivatives (Kanoh et al, J. Antibiot., 1999; Kano et al, Bioorg. Med. Chem., 1999; U.S. Pat. No. 6,358,957);

r) Podophyllotoxins such as Epidophyllotoxin (Hammonds et al, J. Med. Microbiol, 1996; Coretese et al, J. Biol. Chem., 1977);

s) Rhizoxins (Nakada et al, Tetrahedron Lett., 1993; Boger et al, J. Org. Chem., 1992; Rao, et al, Tetrahedron Lett., 1992; Kobayashi et al, Pure Appl. Chem., 1992; Kobayashi et al, Indian J. Chem., 1993; Rao et al, Tetrahedron Lett., 1993);

t) 2-strylquinazolin-4(3H)-ones ("SQOs", Jiang et al, J. Med. Chem., 1990);

u) Spongistatin and Synthetic spiroketal pyrans ("SPIKETs"; Pettit et al, J. Org. Chem., 1993; Uckun et al, Bioorgn. Med. Chem. Lett., 2000; U.S. Pat. No. 6,335,364, WO 00/00514);

v) Taxanes such as Paclitaxel (TAXOL™), Docetaxel (TAXOTERE™), and Paclitaxel derivatives (U.S. Pat. No. 5,646,176, WIPO Publication No. WO 94/14787, Kingston, J. Nat. Prod., 1990; Schiff et al, Nature, 1979; Swindell et al, J. Cell Biol., 1981);

x) Vinca Alkaloids such as Vinblastine, Vincristine, Vindesine, Vinflunine, Vinorelbine (NAVELBINE™) (Owellen et al, Cancer Res., 1976; Lavielle et al, J. Med. Chem., 1991; Holwell et al, Br. J. Cancer., 2001); and y) Welwistatin (Zhang et al, Molecular Pharmacology, 1996).

Specific examples of tubulin-binding drugs include, but are not limited to, allocolchicine, amphethinile, chelidonine, colchicide, colchicine, combrestatin A1, combrestatin A4, combretastain A4 phosphate, combrestatin 3, combrestatin 4, cryptophycin, curacin A, deo-dolastatin 10, desoxyepothilone A, desoxyepothilone B, dihydroxy-pentamethoxy-flananone, docetaxel, dolastatin 10, dolastatin 15, epidophyllotoxin, epothilone A, epothilone B, epothilone C, epothilone D, etoposide, 9,10-dehydro-desoxyepothilone B (dehydelone), iso-oxazole-dehydelone (17-isooxazole-dehydelone), fludelone, iso-oxazole-fludelone (17-isooxazole-fludelone), griseofulvin, halichondrin B, isocolchicine, lavendustin A, methyl-3,5-diiodo-4-(4'-methoxyphenoxy)benzoate, N-acetylcolchinol, N-acetylcolchinol-O-phosphate, N-[2-[(4-hydroxyphenyl)amino]-3-pyridyl]-4-methoxybenzenesulfonamide, nocodazole, paclitaxel, phenstatin, phenylhistin, piceid, podophyllotoxin, resveratrol, rhizoxin, sanguinarine, spongistatin 1, steganacin, TAXOL, teniposide, thiocolchicine, vincristine, vinblastine, welwistatin, (Z)-2-methoxy-5-[2-(3,4,5-trimethoxyphenyl)vinyl]phenylamine, (Z)-3,5,4'-trimethoxystilbene (R3), 2-aryl-1,8-naphthyridin-4(1H)-one, 2-(4'-methoxyphenyl)-3-(3',4',5'-trimethoxybenzoyl)-6-methoxybenzo[b]thiophene, 2-methoxy estradiol, 2-strylquinazolin-4(3H)-one, 5,6-dihydroindolo(2,1-a)isoquinoline, and 10-deacetylbaccatin III.

A "subject" is a mammal, e.g., a human, mouse, rat, guinea pig, dog, cat, horse, cow, pig, or non-human primate, such as a monkey, chimpanzee, baboon. In one embodiment, the monkey is a rhesus. In one embodiment, the subject is a human.

The phrase "pharmaceutically acceptable salt," as used herein, is a salt formed from an acid and a base, for example an acidic or a basic salt of a molecule. The molecule in the salt can be a Compound of the invention or a tubulin-binding drug. In one instance, the term "pharmaceutically acceptable salt" refers to a salt of an acid and a basic nitrogen group of a molecule. Illustrative salts formed from an acid and a basic nitrogen group of a molecule include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, besylate, mesylate, camphor sulfonate, and pamoate (i.e., 1,1'-methylene-bis-(2-OH-3-naphthoate)) salts. The term "pharmaceutically acceptable salt" also refers to a salt of a molecule having an acidic functional group, and a pharmaceutically acceptable inorganic or organic base. Illustrative salts formed from a base and an acidic functional group of a molecule include, but are not limited to, sodium, potassium, lithium, calcium, magnesium, aluminum, zinc, ammonium; and salts with organic amines such as quaternary, tertiary, secondary, or primary organic amines, examples of which include unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, tris-(hydroxymethyl)methylamine, or 2-hydroxy-tert-butylamine, or N,N-di-lower alkyl-N-(hydroxy lower alkyl)-amines, such as N,N-dimethyl-N-(2-hydroxyethyl)amine or tri-(2-OH-ethyl)amine; N-methyl-D-glucamine; and amino acids such as arginine, lysine, and the like. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines such as tertiary, secondary, or primary organic amines, examples of which include unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, tris-(hydroxymethyl)methylamine, or 2-hydroxy-tert-butylamine, or N,N-di-lower alkyl-N-(hydroxy lower alkyl)-amines, such as N,N-dimethyl-N-(2-hydroxyethyl)amine or tri-(2-OH-ethyl)amine; N-methyl-D-glucamine; and amino acids such as arginine, lysine, and the like.

The phrase "solvate," as used herein, is a complex of a Compound and an organic solvent. The organic solvent can be a pharmaceutically acceptable organic solvent, for example, ethanol. Non-limiting examples of organic solvents useful in the invention include alcohols, for example, methanol, ethanol, propanol, isopropanol, butanol, or isobutanol; THF; methylene chloride; chloroform; acetonitrile; acetates such as ethyl or isopropyl acetate; ethers such as diethyl ether or MTBE; ketones such as acetone or ethyl methyl ketone; pentanes; hexanes; DMSO and NMP. Other suitable solvents for a given application will be apparent to a person skilled in the art.

An "effective amount" when used in connection with a Compound of the invention or a tubulin-binding drug is an amount of the Compound of the invention or tubulin-binding drug, individually or in combination, that is effective for treating or preventing a Condition individually or in combination with another Compound of the invention.

The language "in combination" includes administration within the same composition and separately. In the latter instance, the tubulin-binding drug is administered during a time when the Compound of the invention exerts its prophylactic or therapeutic effect, or vice versa.

Also when administered separately, in one embodiment, the tubulin-binding drug is administered prior to administering the Compound of the invention. In another embodiment, the tubulin-binding drug is administered subsequent to administering the Compound of the invention. In another embodiment, the tubulin-binding drug and a Compound of the invention are administered concurrently.

The language "coupling agent" as used herein is a reagent that forms amide or ester bonds, such as by coupling acids and amines or alcohols, respectively. In one instance, a "coupling agent" may also be referred to as a peptide coupling agent or reagent. Suitable coupling agents are well known to a person of skill in the art and are commercially available. Illustrative coupling agents include, but are not limited to, DCC, dimethylpropyl-ethylcarbodiimide (EDC), or carbonyl diimidazole (CDI). Other suitable coupling reagents will be apparent to a person of skill in the art. A coupling agent may be used in conjunction with a catalyst, such as 4-dimethylaminopyridine (DMAP)

"$C_1$-$C_6$ alkyl" as used herein is a straight or branched chain saturated hydrocarbon containing 1-6 carbon atoms. Representative $C_1$-$C_6$ alkyl groups include, but are not limited to, methyl, ethyl, propyl, isopropyl, butyl, tert-butyl, sec-butyl, isobutyl, pentyl, isopentyl, neopentyl, hexyl, isohexyl and neohexyl. In one embodiment, the $C_1$-$C_6$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_6$ alkyl group is unsubstituted.

"$C_2$-$C_6$ alkenyl" as used herein is a straight or branched chain hydrocarbon containing 2-6 carbon atoms and at least one double bond. Representative $C_2$-$C_6$ alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene. In one embodiment, the $C_2$-$C_6$ alkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_2$-$C_6$ alkenyl group is unsubstituted.

"$C_2$-$C_6$ alkynyl" as used herein is a straight or branched chain hydrocarbon containing 2-6 carbon atoms and at least one triple bond. Representative $C_2$-$C_6$ alkynyl groups include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne. In one embodiment, the $C_2$-$C_6$ alkynyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_2$-$C_6$ alkynyl group is unsubstituted.

"$C_1$-$C_6$ alkylene" as used herein is a $C_1$-$C_6$ alkyl group, wherein one of the $C_1$-$C_6$ alkyl group's hydrogen atoms has been replaced with a bond. Representative $C_1$-$C_6$ alkylene groups include, but are not limited to, methylene, ethylene, propylene, isopropylene, butylene, tert-butylene, sec-butylene, isobutylene, pentylene, isopentylene, neopentylene, hexylene, isohexylene and neohexylene. In one embodiment, the $C_1$-$C_6$ alkylene group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. In another embodiment, the $C_1$-$C_6$ alkylene group is substituted with a $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl group.

"$C_2$-$C_6$ alkenylene" as used herein is a $C_2$-$C_6$ alkenyl group, wherein one of the $C_2$-$C_6$ alkenyl group's hydrogen atoms has been replaced with a bond. Representative $C_2$-$C_6$ alkenylene groups include, but are not limited to, ethenylene, propenylene, 1-butenylene, 2-butenylene, isobutenylene, sec-butenylene, 1-pentenylene, 2-pentenylene, isopentenylene, 1-hexenylene, 2-hexenylene, 3-hexenylene and isohexenylene. In one embodiment, the $C_1$-$C_6$ alkenylene group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. In another embodiment, the $C_1$-$C_6$ alkylene group is substituted with a $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl group.

"$C_2$-$C_6$ alkynylene" as used herein is a $C_2$-$C_6$ alkynyl group, wherein one of the $C_2$-$C_6$ alkynyl group's hydrogen atoms has been replaced with a bond. Representative $C_2$-$C_6$ alkynylene groups include, but are not limited to, acetylenyl, propynylene, 1-butynylene, 2-butynylene, isobutynylene, sec-butynylene, 1-pentynylene, 2-pentynylene, isopentynylene, 1-hexynylene, 2-hexynylene, 3-hexynylene and isohexynylene. In one embodiment, the $C_1$-$C_6$ alkynyllene group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. In another embodiment, the $C_1$-$C_6$ alkylene group is substituted with a $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl group.

"Halo" refers to —F, —Cl, —Br or —I.

A "$C_3$-$C_8$ monocyclic cycloalkyl" is a non-aromatic, saturated hydrocarbon ring containing 3-8 carbon atoms. Representative $C_3$-$C_8$ monocyclic cycloalkyl groups are cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl group is unsubstituted.

A "$C_3$-$C_8$ monocyclic cycloalkenyl" is a non-aromatic hydrocarbon ring containing 3-8 carbon atoms and having at least one endocyclic double bond. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, 1,3,5-cycloheptatrienyl, cyclooctenyl, 1,3-cyclooctadienyl, 1,4-cyclooctadienyl, 1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl group is unsubstituted.

The term "5- or -6-membered monocyclic heteroaryl" as used herein is a 5- or 6-membered aromatic monocyclic cycloalkyl in which 1-4 of the ring carbon atoms have been independently replaced with a N, O or S atom. The 5 or -6-membered monocyclic heteroaryls are attached via a ring carbon atom. Representative examples of a 5- or -6-membered monocyclic heteroaryl group include, but are not limited to furanyl, imidazolyl, isothiazolyl, isoxazolyl, oxadiazolyl, oxazolidinyl, oxazolyl, oxazolidinyl, pyrimidinyl, pyrazinyl, pyrazolyl, pyridazinyl, pyridinyl, thiazolyl, thiadiazolyl, thiophenyl, triazinyl, and triazolyl. In one embodiment, the 5- or -6-membered monocyclic heteroaryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 5- or -6-membered monocyclic heteroaryl group is unsubstituted.

The term "7- to -10-membered bicyclic heteroaryl" as used herein is a bicyclic 7- to 10-membered aromatic bicyclic cycloalkyl in which one or both of the of the rings of the bicyclic ring system have 1-4 of its ring carbon atoms independently replaced with a N, O or S atom. A 7- to -10-membered bicyclic heteroaryl is attached via a ring carbon atom. Examples of 7- to -10-membered bicyclic heteroaryls include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of the 7- to -10-membered bicyclic heteroaryl group can substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 7- to 10-membered bicyclic heteroaryl group is unsubstituted.

An "oxygen-containing 3- to 7-membered monocyclic heterocycle" as used herein is: (i) a 3- or 4-membered non-aromatic monocyclic cycloalkyl group in which 1 of the ring carbon atoms has been replaced with an oxygen atom; or (ii) a 5-, 6-, or 7-membered aromatic or non-aromatic monocyclic cycloalkyl group in which one of the ring carbon atoms has been replaced with an oxygen atom and up to 2 of the remaining ring carbon atoms have been independently replaced with a N, O or S atom. A non-aromatic oxygen-containing 3- to 7-membered monocyclic heterocycles can be attached via a ring nitrogen, sulfur, or carbon atom. An aromatic oxygen-containing 3- to 7-membered monocyclic heterocycle is attached via a ring carbon atom. Representative examples of oxygen-containing 3- to 7-membered monocyclic heterocycles include, but are not limited to, furanyl, pyranyl, dihydrofuranyl, dihydropyranyl, tetrahydrofuranyl, tetrahydropyranyl, 1,3-dioxolanyl, oxazolyl, isoxazolyl, 1,2,3-oxadiazolyl, 1,4-dioxane and morpholinyl. In one embodiment, the oxygen-containing 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the oxygen-containing 3- to 7-membered monocyclic heterocycle group is unsubstituted.

An "aryl" group is a phenyl or naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl group is unsubstituted.

A "(para)-phenylene" group is depicted below:

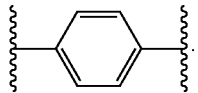 [SMILES: *c1ccc(*)cc1]

A "(para)-biphenylene" group is depicted below:

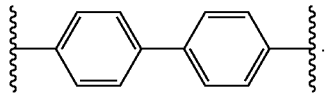

"Conditions sufficient" are reaction conditions under which a given reaction proceeds to a given product. Reaction conditions include solvent, e.g., organic solvent, dry organic solvent, aqueous solvent, or the absence of solvent (i.e. neat); temperature; atmosphere, e.g., a dry or inert atmosphere, for example under positive pressure of argon or nitrogen; ligands; co-catalysts; water scavengers; acid scavengers (i.e. bases); base scavengers (i.e. acids); and radical scavengers. Examples organic solvents include alcohols, for example, methanol, ethanol, propanol, isopropanol, butanol, or isobutanol; THF; methylene chloride; chloroform; acetonitrile; acetates such as ethyl or isopropyl acetate; ethers such as diethyl ether or MTBE; ketones such as acetone or ethyl methyl ketone; pentanes; hexanes; DMSO and NMP. Appropriate reaction conditions sufficient to accomplish a given reaction will be apparent to a person skilled in the art.

The following abbreviations are used herein and have the indicated definitions: CBS is 2-methyl-oxazaborolidine, DCC is dicyclohexyl carbodiimide, DIBAL is diisobutylaluminum hydride, DMAP is N,N-dimethylaminopyridine, EDA is ethylenediamine, $EtNH_2$ is ethylamine, HMPA is hexamethylphosphoramide, Me is methyl, MeOH is methanol, NaH is sodium hydride, NBS is N-bromosuccinimide, TBAF is tetrabutylammonium fluoride, TBDPS is tert-butyldiphenylsilyl, TBDPSCl is tert-butyldiphenylsilyl chloride, MTPA-Cl is Mosher's acid chloride, Tf is trifluoromethanesulfonate, THF is tetrahydrofuran, p-TsOH is para-toluenesulfonic acid, HRMS is High-Resolution Mass Spectroscopy, $R_f$ is Retention Factor, and Q2D×3 means every second day for three doses.

4.2 Sources of Panaxytriol

Ginseng is a deciduous perennial plant that belongs to the Araliaceae family. Ginseng species include *Panax ginseng*, *Panax quinquefolius* L. (American ginseng), *Panax japonicus* (Japanese ginseng), *Panax notoginseng* (Sanchiginseng); *Panax trifolius* L. (Dwarf ginseng), *Panax vietnamensis*, and *Panax pseudoginseng*.

*Panax ginseng* can be harvested after 2 to 6 years of cultivation, and it can be classified in three ways depending on how it is processed: (a) fresh ginseng (less than 4 years old and can be consumed fresh); (b) white ginseng (4-6 years old and then dried after peeling); and (c) red ginseng (harvested when 6 years old and then steamed and dried).

Upon harvesting, ginseng can be used to make various products: for example, fresh sliced ginseng, juice, extract (tincture or boiled extract), powder, tea, tablets, and capsules.

Several components of red ginseng have been isolated and evaluated for their anticancer properties, including panaxytriol:

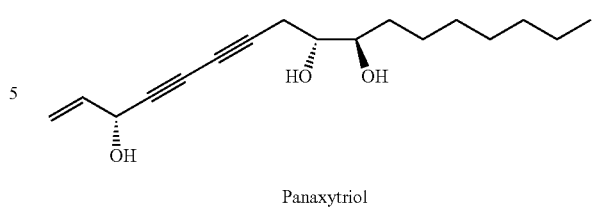

Panaxytriol

4.3 Compounds of Formula (I)

In one embodiment, the invention provides compounds of Formula (I) as defined herein, and pharmaceutically acceptable salts, solvates, and hydrates thereof. In another embodiment, compounds of Formula (I) are compounds of Formula (I-a), (I-b), (I-c), (I-d), (I-e), (I-f), (I-g), (I-h), (I-i), (I-j), (I-k), (I-l), (I-m), (I-n) and (I-o); compound (A), (B), (C), (D), (E), (F), (G), (H), (J), (K), (L), (M), (N), (O), (P), (Q), (R), (S), (T), (U), (V), (W), (X), (Y), (Z), (AA), (BB), (CC), (DD), (EE), (FF), (GG), (HH), (1), (2), (3), (4), and (5); and compounds as otherwise disclosed herein. In a specific embodiment, compounds of the invention do not include panaxytriol.

In one embodiment, a Compound of the invention has the following stereochemistry:

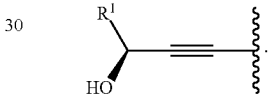

In another embodiment, a Compound of the invention has the following stereochemistry:

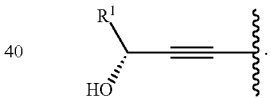

Compounds of Formula (I-a)

In one embodiment, the invention provides compounds of Formula (I-a):

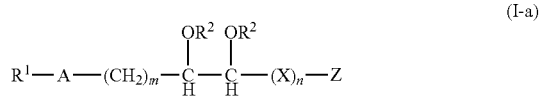

and pharmaceutically acceptable salts, solvates, and hydrates thereof,
wherein:
$R^1$ is $(R^3)(R^4)C(H)$—, $R^5OC(O)$—, $R^5NHC(O)$— or an oxygen-containing -3 to -7-membered monocyclic heterocycle;
each $R^2$ is independently —H, $C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, $C_1$-$C_6$ alkyl or phenyl;
$R^3$ is —SH, —$NH_2$, —Cl, —F, —CN, —$NO_2$, —$CF_3$ or —$CCl_3$;

$R^4$ is —$C_1$-$C_6$ alkyl, —$C_2$-$C_6$ alkenyl or —$C_2$-$C_6$ alkynyl;
$R^5$ is —H, —$C_1$-$C_6$ alkyl, —$C_2$-$C_6$ alkenyl or —$C_2$-$C_6$ alkynyl;
A is —C≡C—C≡C— or -(para)-phenylene-;
each X is independently —$C_1$-$C_6$ alkylene-, —$C_2$-$C_6$ alkenylene- or —$C_2$-$C_6$ alkynylene-;
Z is —H, -aryl, —$C_1$-$C_6$ alkyl, —$C_2$-$C_6$ alkenyl, —$C_2$-$C_6$ alkynyl, —$C_3$-$C_8$ monocyclic cycloalkyl, —$C_3$-$C_8$ monocyclic cycloalkenyl, -(5 or -6-membered monocyclic heteroaryl) or -(7 to -10-membered bicyclic heteroaryl);
m is an integer ranging from 1 to 6; and
n is 0, 1 or 2.

In one embodiment, $R^1$ is $(R^3)(R^4)C(H)$—.
In another embodiment, $R^1$ is $R^5OC(O)$—.
In still another embodiment, $R^1$ is $R^5NHC(O)$—.
In a further embodiment, $R^1$ is -oxygen-containing -3 to -7-membered monocyclic heterocycle.
In one embodiment, $R^2$ is —H.
In another embodiment, $R^2$ is —$C_1$-$C_6$ alkyl.
In still another embodiment, $R^2$ is —$C(O)R^5$.
In another embodiment, both $R^2$ groups combine to form —C(O)—.
In a further embodiment, both $R^2$ groups combine to form —$C(CH_3)_2$
In one embodiment, $R^3$ is —F.
In another embodiment, $R^3$ is —SH.
In still another embodiment, $R^3$ is —$NH_2$.
In another embodiment, $R^3$ is —CN.
In another embodiment, $R^3$ is —$NO_2$.
In still another embodiment, $R^3$ is —$CF_3$.
In a further embodiment, $R^3$ is —$CCl_3$.
In one embodiment, $R^4$ is —$C_1$-$C_6$ alkyl.
In another embodiment, $R^4$ is —$C_2$-$C_6$ alkenyl.
In still another embodiment, $R^4$ is —$C_2$-$C_6$ alkynyl.
In another embodiment, $R^4$ is —CH=$CH_2$.
In one embodiment A is —C≡C—C≡C—.
In another embodiment, A is -(para)-phenylene-.
In one embodiment, each $R^6$ is independently —H or alkyl.
In another embodiment, X is —$C_1$-$C_6$ alkylene-, n is 1 and Z is —H.
In still another embodiment, X is —$(CH_2)_6$—, n is 1 and Z is —H.
In one embodiment, m is 1.
In one embodiment, $R^1$ is $(R^3)(R^4)C(H)$— and each occurrence of $R^2$ is —H.
In another embodiment, $R^1$ is $(R^3)(R^4)C(H)$—, each occurrence of $R^2$ is —H, X is —$C_1$-$C_6$ alkylene-, n is 1 and Z is —H.
In one embodiment, $R^3$ is —F and $R^4$ is —$C_2$-$C_6$ alkenyl.
In another embodiment, $R^3$ is —CN and $R^4$ is —$C_2$-$C_6$ alkenyl.
In another embodiment, $R^3$ is —SH and $R^4$ is —$C_2$-$C_6$ alkenyl.
In still another embodiment, $R^3$ is —$NH_2$ and $R^4$ is —$C_2$-$C_6$ alkenyl.
In another embodiment, $R^3$ is —$NO_2$ and $R^4$ is —$C_2$-$C_6$ alkenyl.
In another embodiment, $R^3$ is —$CF_3$ and $R^4$ is —$C_2$-$C_6$ alkenyl.
In yet another embodiment, $R^3$ is —Cl and $R^4$ is —$C_2$-$C_6$ alkenyl.
In another embodiment, $R^3$ is —$CCl_3$ and $R^4$ is —$C_2$-$C_6$ alkenyl.
In one embodiment, $R^3$ is —F, $R^4$ is —$C_2$-$C_6$ alkenyl, and each $R^2$ is —H.
In another embodiment, $R^3$ is —CN, $R^4$ is —$C_2$-$C_6$ alkenyl, and each $R^2$ is —H.

In another embodiment, $R^3$ is —SH, $R^4$ is —$C_2$-$C_6$ alkenyl, and each $R^2$ is —H.
In still another embodiment, $R^3$ is —$NH_2$, $R^4$ is —$C_2$-$C_6$ alkenyl, and each $R^2$ is —H.
In another embodiment, $R^3$ is —$NO_2$, $R^4$ is —$C_2$-$C_6$ alkenyl, and each $R^2$ is —H.
In another embodiment, $R^3$ is —$CF_3$, $R^4$ is —$C_2$-$C_6$ alkenyl, and each $R^2$ is —H.
In yet another embodiment, $R^3$ is —Cl, $R^4$ is —$C_2$-$C_6$ alkenyl, and each $R^2$ is —H.
In another embodiment, $R^3$ is —$CCl_3$, $R^4$ is —$C_2$-$C_6$ alkenyl, X is —$(CH_2)_6$—, n is 1 and Z is —H.
In one embodiment, $R^3$ is —F, $R^4$ is —$C_2$-$C_6$ alkenyl, X is —$(CH_2)_6$—, n is 1 and Z is —H.
In another embodiment, $R^3$ is —CN, $R^4$ is —$C_2$-$C_6$ alkenyl, X is —$(CH_2)_6$—, n is 1 and Z is —H.
In another embodiment, $R^3$ is —SH, $R^4$ is —$C_2$-$C_6$ alkenyl, X is —$(CH_2)_6$—, n is 1 and Z is —H.
In still another embodiment, $R^3$ is —$NH_2$, $R^4$ is —$C_2$-$C_6$ alkenyl, X is —$(CH_2)_6$—, n is 1 and Z is —H.
In another embodiment, $R^3$ is —$NO_2$, $R^4$ is —$C_2$-$C_6$ alkenyl, X is —$(CH_2)_6$—, n is 1 and Z is —H.
In another embodiment, $R^3$ is —$CF_3$, $R^4$ is —$C_2$-$C_6$ alkenyl, X is —$(CH_2)_6$—, n is 1 and Z is —H.
In yet another embodiment, $R^3$ is —Cl, $R^4$ is —$C_2$-$C_6$ alkenyl, X is —$(CH_2)_6$—, n is 1 and Z is —H.
In another embodiment, $R^3$ is —$CCl_3$, $R^4$ is —$C_2$-$C_6$ alkenyl, X is —$(CH_2)_6$—, n is 1 and Z is —H.

In one embodiment, where $R^1$ is —$C(O)OR^5$, —$C(O)NHR^5$ or oxygen-containing 3 to -7-membered monocyclic heterocycle, the compounds of formula (I-a) exist as a single stereoisomer, for example, that depicted by any of the formulas set forth below:

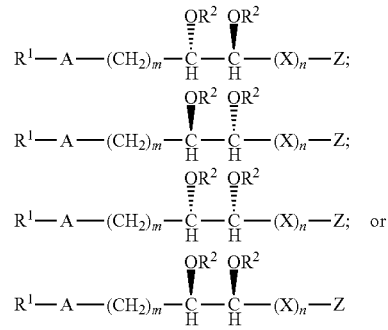

wherein $R^1$, $R^2$, A, X, Z, m and n are as defined above for the compounds of formula (I-a).

In another embodiment, where $R^1$ is $(R^3)(R^4)C(H)$—, the compounds of formula (I-a) can exist as a single stereoisomer, for example, that depicted by any of the formulas set forth below:

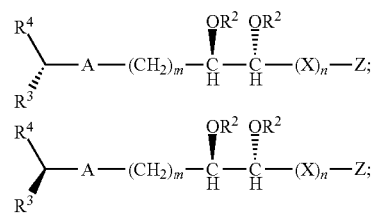

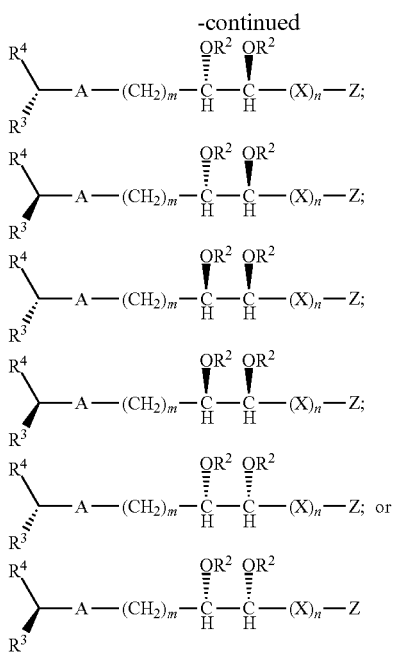

wherein $R^2$, $R^3$, $R^4$, A, X, Z, m and n are as defined above for the compounds of formula (I-a).

Illustrative examples of the Compounds of Formula (I-a) include the compounds of Formula (I-a') as set forth below:

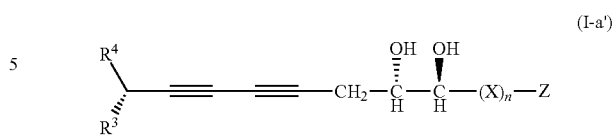

(I-a')

| Compound | $R^3$ | $R^4$ | $(X)_n$ | Z |
|---|---|---|---|---|
| Ia'-1 | —F | —CH=CH₂ | —(CH₂)₆— | —H |
| Ia'-2 | —Cl | —CH=CH₂ | —(CH₂)₆— | —H |
| Ia'-3 | —NH₂ | —CH=CH₂ | —(CH₂)₆— | —H |
| Ia'-4 | —CN | —CH=CH₂ | —(CH₂)₆— | —H |
| Ia'-5 | —SH | —CH=CH₂ | —(CH₂)₆— | —H |
| Ia'-6 | —NO₂ | —CH=CH₂ | —(CH₂)₆— | —H |
| Ia'-7 | —CF₃ | —CH=CH₂ | —(CH₂)₆— | —H |
| Ia'-8 | —CCl₃ | —CH=CH₂ | —(CH₂)₆— | —H | and pharmaceutically acceptable salts, solvates, and hydrates thereof.

Additional illustrative examples of the Compounds of Formula (I-a) include the compounds of Formula (I-a") as set forth below:

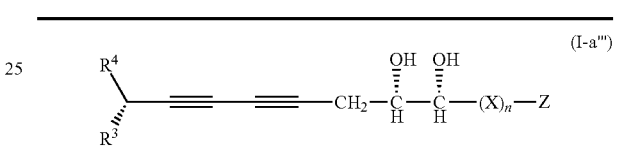

(I-a')

| Compound | $R^3$ | $R^4$ | $(X)_n$ | Z |
|---|---|---|---|---|
| Ia"-1 | —F | —CH=CH₂ | —(CH₂)₆— | —H |
| Ia"-2 | —Cl | —CH=CH₂ | —(CH₂)₆— | —H |
| Ia"-3 | —NH₂ | —CH=CH₂ | —(CH₂)₆— | —H |
| Ia"-4 | —CN | —CH=CH₂ | —(CH₂)₆— | —H |
| Ia"-5 | —SH | —CH=CH₂ | —(CH₂)₆— | —H |
| Ia"-6 | —NO₂ | —CH=CH₂ | —(CH₂)₆— | —H |
| Ia"-7 | —CF₃ | —CH=CH₂ | —(CH₂)₆— | —H |
| Ia"-8 | —CCl₃ | —CH=CH₂ | —(CH₂)₆— | —H | and pharmaceutically acceptable salts, solvates, and hydrates thereof.

Additional illustrative examples of the Compounds of Formula (I-a) include the compounds of Formula (I-a''') as set forth below:

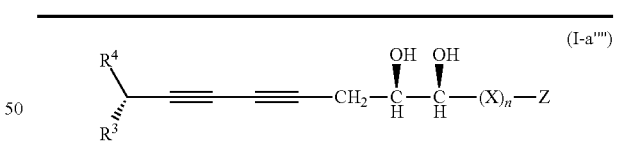

(I-a''')

| Compound | $R^3$ | $R^4$ | $(X)_n$ | Z |
|---|---|---|---|---|
| Ia'''-1 | —F | —CH=CH₂ | —(CH₂)₆— | —H |
| Ia'''-2 | —Cl | —CH=CH₂ | —(CH₂)₆— | —H |
| Ia'''-3 | —NH₂ | —CH=CH₂ | —(CH₂)₆— | —H |
| Ia'''-4 | —CN | —CH=CH₂ | —(CH₂)₆— | —H |
| Ia'''-5 | —SH | —CH=CH₂ | —(CH₂)₆— | —H |
| Ia'''-6 | —NO₂ | —CH=CH₂ | —(CH₂)₆— | —H |
| Ia'''-7 | —CF₃ | —CH=CH₂ | —(CH₂)₆— | —H |
| Ia'''-8 | —CCl₃ | —CH=CH₂ | —(CH₂)₆— | —H | and pharmaceutically acceptable salts, solvates, and hydrates thereof.

Additional illustrative examples of the Compounds of Formula (I-a) include the compounds of Formula (I-a'''') as set forth below:

(I-a'''')

| Compound | $R^3$ | $R^4$ | $(X)_n$ | Z |
|---|---|---|---|---|
| Ia''''-1 | —F | —CH=CH₂ | —(CH₂)₆— | —H |
| Ia''''-2 | —Cl | —CH=CH₂ | —(CH₂)₆— | —H |
| Ia''''-3 | —NH₂ | —CH=CH₂ | —(CH₂)₆— | —H |
| Ia''''-4 | —CN | —CH=CH₂ | —(CH₂)₆— | —H |
| Ia''''-5 | —SH | —CH=CH₂ | —(CH₂)₆— | —H |
| Ia''''-6 | —NO₂ | —CH=CH₂ | —(CH₂)₆— | —H |
| Ia''''-7 | —CF₃ | —CH=CH₂ | —(CH₂)₆— | —H |
| Ia''''-8 | —CCl₃ | —CH=CH₂ | —(CH₂)₆— | —H | and pharmaceutically acceptable salts, solvates, and hydrates thereof.

Additional illustrative examples of the Compounds of Formula (I-a) include the compounds of Formula (I-aa) as set forth below:

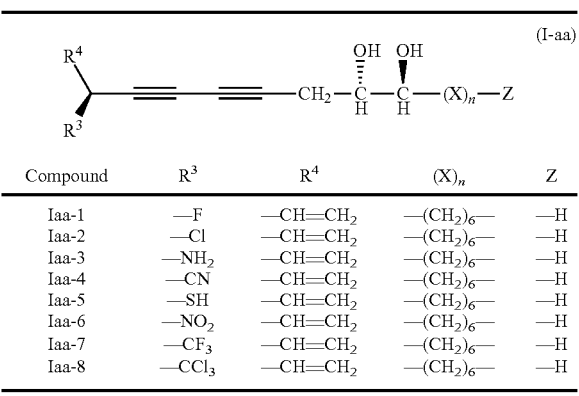

| Compound | $R^3$ | $R^4$ | $(X)_n$ | Z |
|---|---|---|---|---|
| Iaa-1 | —F | —CH=CH$_2$ | —(CH$_2$)$_6$— | —H |
| Iaa-2 | —Cl | —CH=CH$_2$ | —(CH$_2$)$_6$— | —H |
| Iaa-3 | —NH$_2$ | —CH=CH$_2$ | —(CH$_2$)$_6$— | —H |
| Iaa-4 | —CN | —CH=CH$_2$ | —(CH$_2$)$_6$— | —H |
| Iaa-5 | —SH | —CH=CH$_2$ | —(CH$_2$)$_6$— | —H |
| Iaa-6 | —NO$_2$ | —CH=CH$_2$ | —(CH$_2$)$_6$— | —H |
| Iaa-7 | —CF$_3$ | —CH=CH$_2$ | —(CH$_2$)$_6$— | —H |
| Iaa-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-aa') as set forth below:

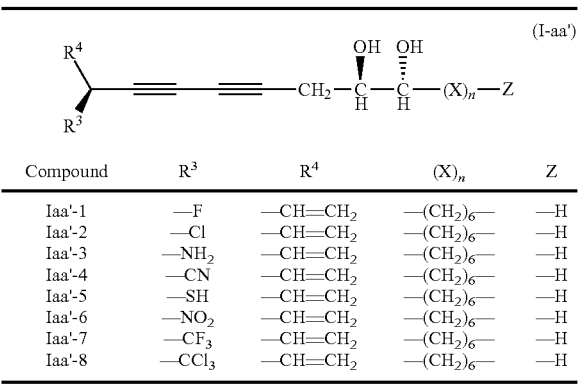

| Compound | $R^3$ | $R^4$ | $(X)_n$ | Z |
|---|---|---|---|---|
| Iaa'-1 | —F | —CH=CH$_2$ | —(CH$_2$)$_6$— | —H |
| Iaa'-2 | —Cl | —CH=CH$_2$ | —(CH$_2$)$_6$— | —H |
| Iaa'-3 | —NH$_2$ | —CH=CH$_2$ | —(CH$_2$)$_6$— | —H |
| Iaa'-4 | —CN | —CH=CH$_2$ | —(CH$_2$)$_6$— | —H |
| Iaa'-5 | —SH | —CH=CH$_2$ | —(CH$_2$)$_6$— | —H |
| Iaa'-6 | —NO$_2$ | —CH=CH$_2$ | —(CH$_2$)$_6$— | —H |
| Iaa'-7 | —CF$_3$ | —CH=CH$_2$ | —(CH$_2$)$_6$— | —H |
| Iaa'-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-aa'') as set forth below:

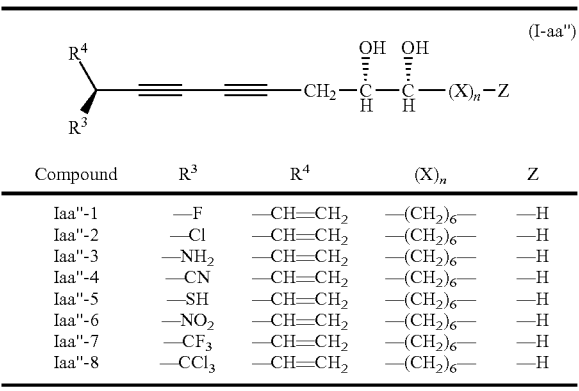

| Compound | $R^3$ | $R^4$ | $(X)_n$ | Z |
|---|---|---|---|---|
| Iaa''-1 | —F | —CH=CH$_2$ | —(CH$_2$)$_6$— | —H |
| Iaa''-2 | —Cl | —CH=CH$_2$ | —(CH$_2$)$_6$— | —H |
| Iaa''-3 | —NH$_2$ | —CH=CH$_2$ | —(CH$_2$)$_6$— | —H |
| Iaa''-4 | —CN | —CH=CH$_2$ | —(CH$_2$)$_6$— | —H |
| Iaa''-5 | —SH | —CH=CH$_2$ | —(CH$_2$)$_6$— | —H |
| Iaa''-6 | —NO$_2$ | —CH=CH$_2$ | —(CH$_2$)$_6$— | —H |
| Iaa''-7 | —CF$_3$ | —CH=CH$_2$ | —(CH$_2$)$_6$— | —H |
| Iaa''-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-aa''') as set forth below:

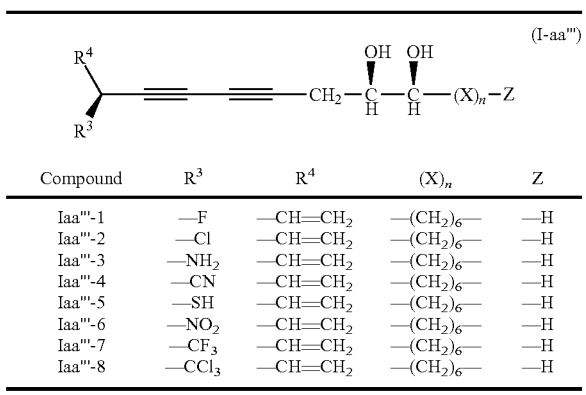

| Compound | $R^3$ | $R^4$ | $(X)_n$ | Z |
|---|---|---|---|---|
| Iaa'''-1 | —F | —CH=CH$_2$ | —(CH$_2$)$_6$— | —H |
| Iaa'''-2 | —Cl | —CH=CH$_2$ | —(CH$_2$)$_6$— | —H |
| Iaa'''-3 | —NH$_2$ | —CH=CH$_2$ | —(CH$_2$)$_6$— | —H |
| Iaa'''-4 | —CN | —CH=CH$_2$ | —(CH$_2$)$_6$— | —H |
| Iaa'''-5 | —SH | —CH=CH$_2$ | —(CH$_2$)$_6$— | —H |
| Iaa'''-6 | —NO$_2$ | —CH=CH$_2$ | —(CH$_2$)$_6$— | —H |
| Iaa'''-7 | —CF$_3$ | —CH=CH$_2$ | —(CH$_2$)$_6$— | —H |
| Iaa'''-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-ab) as set forth below:

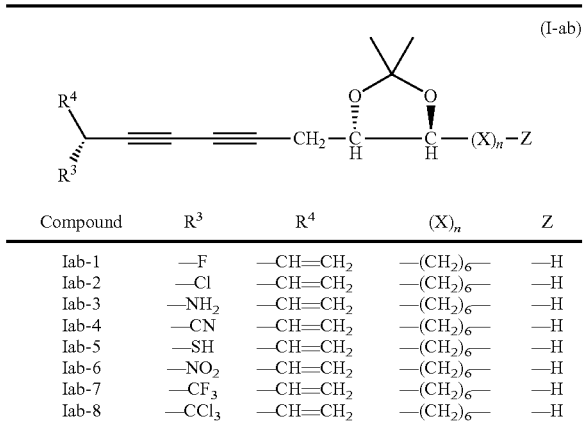

| Compound | $R^3$ | $R^4$ | $(X)_n$ | Z |
|---|---|---|---|---|
| Iab-1 | —F | —CH=CH$_2$ | —(CH$_2$)$_6$— | —H |
| Iab-2 | —Cl | —CH=CH$_2$ | —(CH$_2$)$_6$— | —H |
| Iab-3 | —NH$_2$ | —CH=CH$_2$ | —(CH$_2$)$_6$— | —H |
| Iab-4 | —CN | —CH=CH$_2$ | —(CH$_2$)$_6$— | —H |
| Iab-5 | —SH | —CH=CH$_2$ | —(CH$_2$)$_6$— | —H |
| Iab-6 | —NO$_2$ | —CH=CH$_2$ | —(CH$_2$)$_6$— | —H |
| Iab-7 | —CF$_3$ | —CH=CH$_2$ | —(CH$_2$)$_6$— | —H |
| Iab-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-ab') as set forth below:

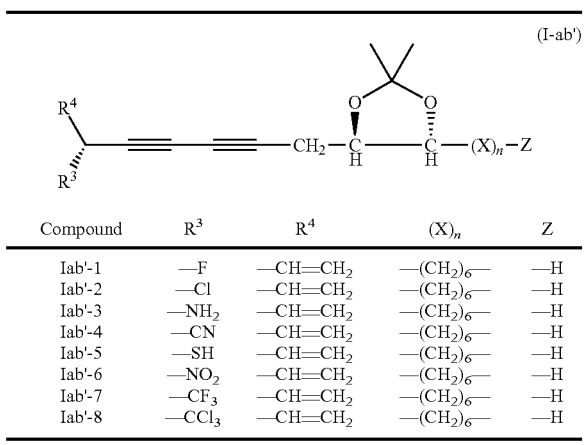

| Compound | $R^3$ | $R^4$ | $(X)_n$ | Z |
|---|---|---|---|---|
| Iab'-1 | —F | —CH=CH$_2$ | —(CH$_2$)$_6$— | —H |
| Iab'-2 | —Cl | —CH=CH$_2$ | —(CH$_2$)$_6$— | —H |
| Iab'-3 | —NH$_2$ | —CH=CH$_2$ | —(CH$_2$)$_6$— | —H |
| Iab'-4 | —CN | —CH=CH$_2$ | —(CH$_2$)$_6$— | —H |
| Iab'-5 | —SH | —CH=CH$_2$ | —(CH$_2$)$_6$— | —H |
| Iab'-6 | —NO$_2$ | —CH=CH$_2$ | —(CH$_2$)$_6$— | —H |
| Iab'-7 | —CF$_3$ | —CH=CH$_2$ | —(CH$_2$)$_6$— | —H |
| Iab'-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-ab″) as set forth below:

(I-ab″)

| Compound | $R^3$ | $R^4$ | $(X)_n$ | Z |
|---|---|---|---|---|
| Iab″-1 | —F | —CH=CH$_2$ | —(CH$_2$)$_6$— | —H |
| Iab″-2 | —Cl | —CH=CH$_2$ | —(CH$_2$)$_6$— | —H |
| Iab″-3 | —NH$_2$ | —CH=CH$_2$ | —(CH$_2$)$_6$— | —H |
| Iab″-4 | —CN | —CH=CH$_2$ | —(CH$_2$)$_6$— | —H |
| Iab″-5 | —SH | —CH=CH$_2$ | —(CH$_2$)$_6$— | —H |
| Iab″-6 | —NO$_2$ | —CH=CH$_2$ | —(CH$_2$)$_6$— | —H |
| Iab″-7 | —CF$_3$ | —CH=CH$_2$ | —(CH$_2$)$_6$— | —H |
| Iab″-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-ab‴) as set forth below:

(I-ab‴)

| Compound | $R^3$ | $R^4$ | $(X)_n$ | Z |
|---|---|---|---|---|
| Iab‴-1 | —F | —CH=CH$_2$ | —(CH$_2$)$_6$— | —H |
| Iab‴-2 | —Cl | —CH=CH$_2$ | —(CH$_2$)$_6$— | —H |
| Iab‴-3 | —NH$_2$ | —CH=CH$_2$ | —(CH$_2$)$_6$— | —H |
| Iab‴-4 | —CN | —CH=CH$_2$ | —(CH$_2$)$_6$— | —H |
| Iab‴-5 | —SH | —CH=CH$_2$ | —(CH$_2$)$_6$— | —H |
| Iab‴-6 | —NO$_2$ | —CH=CH$_2$ | —(CH$_2$)$_6$— | —H |
| Iab‴-7 | —CF$_3$ | —CH=CH$_2$ | —(CH$_2$)$_6$— | —H |
| Iab‴-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-abb) as set forth below:

(I-abb)

| Compound | $R^3$ | $R^4$ | $(X)_n$ | Z |
|---|---|---|---|---|
| Iabb-1 | —F | —CH=CH$_2$ | —(CH$_2$)$_6$— | —H |
| Iabb-2 | —Cl | —CH=CH$_2$ | —(CH$_2$)$_6$— | —H |
| Iabb-3 | —NH$_2$ | —CH=CH$_2$ | —(CH$_2$)$_6$— | —H |
| Iabb-4 | —CN | —CH=CH$_2$ | —(CH$_2$)$_6$— | —H |
| Iabb-5 | —SH | —CH=CH$_2$ | —(CH$_2$)$_6$— | —H |
| Iabb-6 | —NO$_2$ | —CH=CH$_2$ | —(CH$_2$)$_6$— | —H |
| Iabb-7 | —CF$_3$ | —CH=CH$_2$ | —(CH$_2$)$_6$— | —H |
| Iabb-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-abb′) as set forth below:

(I-abb′)

| Compound | $R^3$ | $R^4$ | $(X)_n$ | Z |
|---|---|---|---|---|
| Iabb′-1 | —F | —CH=CH$_2$ | —(CH$_2$)$_6$— | —H |
| Iabb′-2 | —Cl | —CH=CH$_2$ | —(CH$_2$)$_6$— | —H |
| Iabb′-3 | —NH$_2$ | —CH=CH$_2$ | —(CH$_2$)$_6$— | —H |
| Iabb′-4 | —CN | —CH=CH$_2$ | —(CH$_2$)$_6$— | —H |
| Iabb′-5 | —SH | —CH=CH$_2$ | —(CH$_2$)$_6$— | —H |
| Iabb′-6 | —NO$_2$ | —CH=CH$_2$ | —(CH$_2$)$_6$— | —H |
| Iabb′-7 | —CF$_3$ | —CH=CH$_2$ | —(CH$_2$)$_6$— | —H |
| Iabb′-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-abb″) as set forth below:

(I-abb″)

| Compound | $R^3$ | $R^4$ | $(X)_n$ | Z |
|---|---|---|---|---|
| Iabb″-1 | —F | —CH=CH$_2$ | —(CH$_2$)$_6$— | —H |
| Iabb″-2 | —Cl | —CH=CH$_2$ | —(CH$_2$)$_6$— | —H |
| Iabb″-3 | —NH$_2$ | —CH=CH$_2$ | —(CH$_2$)$_6$— | —H |
| Iabb″-4 | —CN | —CH=CH$_2$ | —(CH$_2$)$_6$— | —H |
| Iabb″-5 | —SH | —CH=CH$_2$ | —(CH$_2$)$_6$— | —H |
| Iabb″-6 | —NO$_2$ | —CH=CH$_2$ | —(CH$_2$)$_6$— | —H |
| Iabb″-7 | —CF$_3$ | —CH=CH$_2$ | —(CH$_2$)$_6$— | —H |
| Iabb″-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-a) include the compounds of Formula (I-abb‴) as set forth below:

(I-abb''')

[Structure: R⁴R³CH-C≡C-C≡C-CH₂-CH(O-)-CH(O-)(X)ₙ-Z with acetonide (gem-dimethyl dioxolane) group]

| Compound | R³ | R⁴ | (X)ₙ | Z |
|---|---|---|---|---|
| Iabb'''-1 | —F | —CH=CH₂ | —(CH₂)₆— | —H |
| Iabb'''-2 | —Cl | —CH=CH₂ | —(CH₂)₆— | —H |
| Iabb'''-3 | —NH₂ | —CH=CH₂ | —(CH₂)₆— | —H |
| Iabb'''-4 | —CN | —CH=CH₂ | —(CH₂)₆— | —H |
| Iabb'''-5 | —SH | —CH=CH₂ | —(CH₂)₆— | —H |
| Iabb'''-6 | —NO₂ | —CH=CH₂ | —(CH₂)₆— | —H |
| Iabb'''-7 | —CF₃ | —CH=CH₂ | —(CH₂)₆— | —H |
| Iabb'''-8 | —CCl₃ | —CH=CH₂ | —(CH₂)₆— | —H | and pharmaceutically acceptable salts, solvates, and hydrates thereof.

Additional illustrative examples of the Compounds of Formula (I-a) include the compounds of Formula (I-ac) as set forth below:

(I-ac)

[Structure: R¹-C≡C-C≡C-CH₂-CH(OH)-CH(OH)-(X)ₙ-Z]

| Compound | R¹ | (X)ₙ | Z |
|---|---|---|---|
| Iac-1 | —C(O)OCH=CH₂ | —(CH₂)₆— | —H |
| Iac-2 | —C(O)OCH₂CH₃ | —(CH₂)₆— | —H |
| Iac-3 | —C(O)NHCH=CH₂ | —(CH₂)₆— | —H |
| Iac-4 | —C(O)NHCH₂CH₃ | —(CH₂)₆— | —H | and pharmaceutically acceptable salts, solvates, and hydrates thereof.

Additional illustrative examples of the Compounds of Formula (I-a) include the compounds of Formula (I-ac') as set forth below:

(I-ac')

[Structure: R¹-C≡C-C≡C-CH₂-CH(OH)-CH(OH)-(X)ₙ-Z with specific stereochemistry]

| Compound | R¹ | (X)ₙ | Z |
|---|---|---|---|
| Iac'-1 | —C(O)OCH=CH₂ | —(CH₂)₆— | —H |
| Iac'-2 | —C(O)OCH₂CH₃ | —(CH₂)₆— | —H |
| Iac'-3 | —C(O)NHCH=CH₂ | —(CH₂)₆— | —H |
| Iac'-4 | —C(O)NHCH₂CH₃ | —(CH₂)₆— | —H | and pharmaceutically acceptable salts, solvates, and hydrates thereof.

Additional illustrative examples of the Compounds of Formula (I-a) include the compounds of Formula (I-ac'') as set forth below:

(I-ac'')

[Structure: R¹-C≡C-C≡C-CH₂-CH(OH)-CH(OH)-(X)ₙ-Z with specific stereochemistry]

| Compound | R¹ | (X)ₙ | Z |
|---|---|---|---|
| Iac''-1 | —C(O)OCH=CH₂ | —(CH₂)₆— | —H |
| Iac''-2 | —C(O)OCH₂CH₃ | —(CH₂)₆— | —H |
| Iac''-3 | —C(O)NHCH=CH₂ | —(CH₂)₆— | —H |
| Iac''-4 | —C(O)NHCH₂CH₃ | —(CH₂)₆— | —H | and pharmaceutically acceptable salts, solvates, and hydrates thereof.

Additional illustrative examples of the Compounds of Formula (I-a) include the compounds of Formula (I-ac''') as set forth below:

(I-ac''')

[Structure: R¹-C≡C-C≡C-CH₂-CH(OH)-CH(OH)-(X)ₙ-Z with specific stereochemistry]

| Compound | R¹ | (X)ₙ | Z |
|---|---|---|---|
| Iac'''-1 | —C(O)OCH=CH₂ | —(CH₂)₆— | —H |
| Iac'''-2 | —C(O)OCH₂CH₃ | —(CH₂)₆— | —H |
| Iac'''-3 | —C(O)NHCH=CH₂ | —(CH₂)₆— | —H |
| Iac'''-4 | —C(O)NHCH₂CH₃ | —(CH₂)₆— | —H | and pharmaceutically acceptable salts, solvates, and hydrates thereof.

Additional illustrative examples of the Compounds of Formula (I-a) include the compounds of Formula (I-ad) as set forth below:

(I-ad)

[Structure: R¹-C≡C-C≡C-CH₂-CH-CH-(X)ₙ-Z with acetonide group]

| Compound | R¹ | (X)ₙ | Z |
|---|---|---|---|
| Iad-1 | —C(O)OCH=CH₂ | —(CH₂)₆— | —H |
| Iad-2 | —C(O)OCH₂CH₃ | —(CH₂)₆— | —H |
| Iad-3 | —C(O)NHCH=CH₂ | —(CH₂)₆— | —H |
| Iad-4 | —C(O)NHCH₂CH₃ | —(CH₂)₆— | —H | and pharmaceutically acceptable salts, solvates, and hydrates thereof.

Additional illustrative examples of the Compounds of Formula (I-a) include the compounds of Formula (I-ad') as set forth below:

(I-ad')

[Structure: R¹-C≡C-C≡C-CH₂-CH-CH-(X)ₙ-Z with acetonide group]

| Compound | R¹ | (X)ₙ | Z |
|---|---|---|---|
| Iad'-1 | —C(O)OCH=CH₂ | —(CH₂)₆— | —H |
| Iad'-2 | —C(O)OCH₂CH₃ | —(CH₂)₆— | —H |

| | | | |
|---|---|---|---|
| Iad'-3 | —C(O)NHCH=CH$_2$ | —(CH$_2$)$_6$— | —H |
| Iad'-4 | —C(O)NHCH$_2$CH$_3$ | —(CH$_2$)$_6$— | —H | and pharmaceutically acceptable salts, solvates, and hydrates thereof.

Additional illustrative examples of the Compounds of Formula (I-a) include the compounds of Formula (I-ad″) as set forth below:

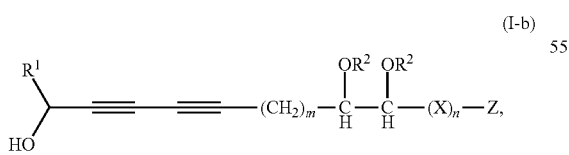

(I-ad″)

| Compound | R$^1$ | (X)$_n$ | Z |
|---|---|---|---|
| Iad″-1 | —C(O)OCH=CH$_2$ | —(CH$_2$)$_6$— | —H |
| Iad″-2 | —C(O)OCH$_2$CH$_3$ | —(CH$_2$)$_6$— | —H |
| Iad″-3 | —C(O)NHCH=CH$_2$ | —(CH$_2$)$_6$— | —H |
| Iad″-4 | —C(O)NHCH$_2$CH$_3$ | —(CH$_2$)$_6$— | —H | and pharmaceutically acceptable salts, solvates, and hydrates thereof.

Additional illustrative examples of the Compounds of Formula (I-a) include the compounds of Formula (I-ad‴) as set forth below:

(I-ad‴)

| Compound | R$^1$ | (X)$_n$ | Z |
|---|---|---|---|
| Iad‴-1 | —C(O)OCH=CH$_2$ | —(CH$_2$)$_6$— | —H |
| Iad‴-2 | —C(O)OCH$_2$CH$_3$ | —(CH$_2$)$_6$— | —H |
| Iad‴-3 | —C(O)NHCH=CH$_2$ | —(CH$_2$)$_6$— | —H |
| Iad‴-4 | —C(O)NHCH$_2$CH$_3$ | —(CH$_2$)$_6$— | —H | and pharmaceutically acceptable salts, solvates, and hydrates thereof.

Compounds of Formula (I-b)

The present invention provides Compounds according to Formula (I-b), below:

(I-b)

wherein:
R$^1$ is (C$_1$-C$_6$ alkyl)-, (C$_2$-C$_6$ alkenyl)- or (C$_2$-C$_6$ alkynyl)-;
each R$^2$ is independently —C$_1$-C$_6$ alkyl, or —C(O)—C$_1$-C$_6$ alkyl, or both R$^2$ groups combine to form —C(O)— or —CH$_2$—;
each X is independently —C$_1$-C$_6$ alkylene-, —C$_2$-C$_6$ alkenylene- or —C$_2$-C$_6$ alkynylene-;

Z is —H, -aryl, —C$_1$-C$_6$ alkyl, —C$_2$-C$_6$ alkenyl, —C$_2$-C$_6$ alkynyl, —C$_3$-C$_8$ monocyclic cycloalkyl, —C$_3$-C$_8$ monocyclic cycloalkenyl, -(5 or -6-membered monocyclic heteroaryl) or -(7 to -10-membered bicyclic heteroaryl);
m is an integer ranging from 1 to 6; and
n is 0, 1 or 2;
and pharmaceutically acceptable salts, solvates, and hydrates thereof.

In one embodiment, R$^1$ is —C$_1$-C$_6$ alkyl.
In another embodiment, R$^1$ is —C$_2$-C$_6$ alkenyl.
In still another embodiment, R$^1$ is —C$_2$-C$_6$ alkynyl.
In another embodiment, R$^1$ is —CH=CH$_2$.
In another embodiment, R$^2$ is —C$_1$-C$_6$ alkyl.
In still another embodiment, R$^2$ is —C(O)—C$_1$-C$_6$ alkyl.
In another embodiment, both R$^2$ groups combine to form —C(O)—.
In a further embodiment, both R$^2$ groups combine to form —CH$_2$—.
In another embodiment, X is —C$_1$-C$_6$ alkylene, n is 1 and Z is —H.
In still another embodiment, X is —(CH$_2$)$_6$—, n is 1 and Z is —H.
In one embodiment, m is 1.
In one embodiment, R$^1$ is —C$_1$-C$_6$ alkyl and R$^2$ is —C$_1$-C$_6$ alkyl.
In another embodiment, R$^1$ is —C$_2$-C$_6$ alkenyl and R$^2$ is —C$_1$-C$_6$ alkyl.
In still another embodiment, R$^1$ is —C$_2$-C$_6$ alkynyl and R$^2$ is —C$_1$-C$_6$ alkyl.
In one embodiment, R$^1$ is —C$_1$-C$_6$ alkyl and both R$^2$ groups combine to form —CH$_2$—.
In another embodiment, R$^1$ is —C$_2$-C$_6$ alkenyl and both R$^2$ groups combine to form —CH$_2$—.
In still another embodiment, R$^1$ is —C$_2$-C$_6$ alkynyl and both R$^2$ groups combine to form —CH$_2$—.
In one embodiment, R$^1$ is —C$_1$-C$_6$ alkyl, X is —C$_1$-C$_6$ alkyl, n is 1 and Z is —H.
In another embodiment, R$^1$ is —C$_2$-C$_6$ alkenyl, X is —C$_1$-C$_6$ alkyl, n is 1 and Z is —H.
In still another embodiment, R$^1$ is —C$_2$-C$_6$ alkynyl, X is —C$_1$-C$_6$ alkyl, n is 1 and Z is —H.

The compounds of formula (I-b) can exist as a single stereoisomer, for example, that depicted by any of the formulas set forth below:

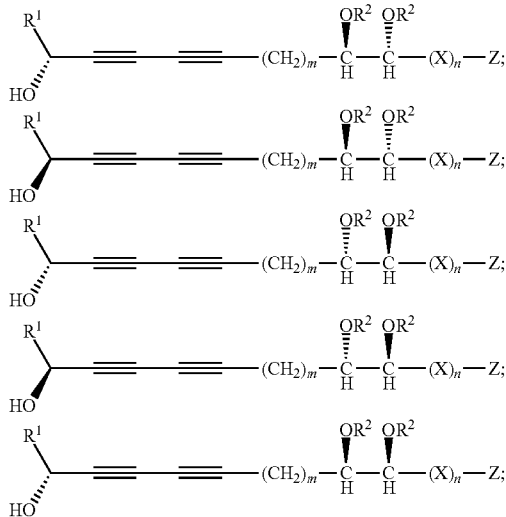

-continued

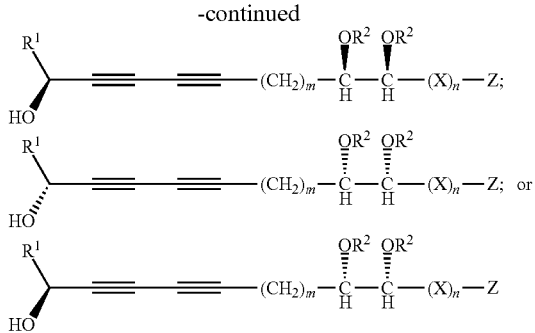

wherein R¹, R², X, Z, m and n are as defined for the Compounds of formula (I-b).

Illustrative examples of the Compounds of Formula (I-b) include the compounds of Formula (I-ba) as set forth below.

(I-ba)

| Compound | R¹ | (X)$_n$ | Z |
|---|---|---|---|
| Iba-1 | —CH=CH$_2$ | —(CH$_2$)$_6$— | —H |
| Iba-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-ba') as set forth below.

(I-ba')

| Compound | R¹ | (X)$_n$ | Z |
|---|---|---|---|
| Iba'-1 | —CH=CH$_2$ | —(CH$_2$)$_6$— | —H |
| Iba'-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-ba") as set forth below.

(I-ba")

| Compound | R¹ | (X)$_n$ | Z |
|---|---|---|---|
| Iba"-1 | —CH=CH$_2$ | —(CH$_2$)$_6$— | —H |
| Iba"-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-ba''') as set forth below.

(I-ba''')

| Compound | R¹ | (X)$_n$ | Z |
|---|---|---|---|
| Iba'''-1 | —CH=CH$_2$ | —(CH$_2$)$_6$— | —H |
| Iba'''-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-baa) as set forth below.

(I-baa)

| Compound | R¹ | (X)$_n$ | Z |
|---|---|---|---|
| Ibaa-1 | —CH=CH$_2$ | —(CH$_2$)$_6$— | —H |
| Ibaa-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-baa') as set forth below.

(I-baa')

| Compound | R¹ | (X)$_n$ | Z |
|---|---|---|---|
| Iba'-1 | —CH=CH$_2$ | —(CH$_2$)$_6$— | —H |
| Iba'-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-baa") as set forth below.

(I-baa")

| Compound | R¹ | (X)$_n$ | Z |
|---|---|---|---|
| Ibaa"-1 | —CH=CH$_2$ | —(CH$_2$)$_6$— | —H |
| Ibaa"-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-baa''') as set forth below.

(I-baa''')

R¹—*—≡—≡—CH₂—HC—HC—(X)ₙ—Z
HO                    O   O
                       \\ //
                        CH

| Compound | R¹ | (X)ₙ | Z |
|---|---|---|---|
| Ibaa'''-1 | —CH=CH₂ | —(CH₂)₆— | —H |
| Ibaa'''-2 | —CH₂CH₃ | —(CH₂)₆— | —H | and pharmaceutically acceptable salts, solvates, and hydrates thereof.

Additional illustrative examples of the Compounds of Formula (I-b) include the compounds of Formula (I-bb) as set forth below.

(I-bb)

| Compound | R¹ | (X)ₙ | Z |
|---|---|---|---|
| Ibb-1 | —CH=CH₂ | —(CH₂)₆— | —H |
| Ibb-2 | —CH₂CH₃ | —(CH₂)₆— | —H | and pharmaceutically acceptable salts, solvates, and hydrates thereof.

Additional illustrative examples of the Compounds of Formula (I-b) include the compounds of Formula (I-bb') as set forth below.

(I-bb')

| Compound | R¹ | (X)ₙ | Z |
|---|---|---|---|
| Ibb'-1 | —CH=CH₂ | —(CH₂)₆— | —H |
| Ibb'-2 | —CH₂CH₃ | —(CH₂)₆— | —H | and pharmaceutically acceptable salts, solvates, and hydrates thereof.

Additional illustrative examples of the Compounds of Formula (I-b) include the compounds of Formula (I-bb'') as set forth below.

(I-bb'')

| Compound | R¹ | (X)ₙ | Z |
|---|---|---|---|
| Ibb''-1 | —CH=CH₂ | —(CH₂)₆— | —H |
| Ibb''-2 | —CH₂CH₃ | —(CH₂)₆— | —H | and pharmaceutically acceptable salts, solvates, and hydrates thereof.

Additional illustrative examples of the Compounds of Formula (I-b) include the compounds of Formula (I-bb''') as set forth below:

(I-bb''')

| Compound | R¹ | (X)ₙ | Z |
|---|---|---|---|
| Ibb'''-1 | —CH=CH₂ | —(CH₂)₆— | —H |
| Ibb'''-2 | —CH₂CH₃ | —(CH₂)₆— | —H | and pharmaceutically acceptable salts, solvates, and hydrates thereof.

Additional illustrative examples of the Compounds of Formula (I-b) include the compounds of Formula (I-bbb) as set forth below:

(I-bbb)

| Compound | R¹ | (X)ₙ | Z |
|---|---|---|---|
| Ibbb-1 | —CH=CH₂ | —(CH₂)₆— | —H |
| Ibbb-2 | —CH₂CH₃ | —(CH₂)₆— | —H | and pharmaceutically acceptable salts, solvates, and hydrates thereof.

Additional illustrative examples of the Compounds of Formula (I-b) include the compounds of Formula (I-bbb') as set forth below:

(I-bbb')

$$\underset{HO}{\overset{R^1}{\triangleleft}}{-}{\equiv}{-}{\equiv}{-}CH_2{-}HC{\overset{O}{\underset{\cdot}{<}}}{\overset{\overset{O}{\parallel}}{\underset{\cdot}{C}}}{\overset{O}{\underset{\cdot}{>}}}HC{-}(X)_n{-}Z$$

| Compound | $R^1$ | $(X)_n$ | Z |
|---|---|---|---|
| Ibbb'-1 | —CH=CH$_2$ | —(CH$_2$)$_6$— | —H |
| Ibbb'-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-bbb″) as set forth below:

(I-bbb″)

| Compound | $R^1$ | $(X)_n$ | Z |
|---|---|---|---|
| Ibbb″-1 | —CH=CH$_2$ | —(CH$_2$)$_6$— | —H |
| Ibbb″-2 | —CH$_2$CH$_3$ | —(CH$_2$)$_6$— | —H | and pharmaceutically acceptable salts, solvates, and hydrates thereof.

Additional illustrative examples of the Compounds of Formula (I-b) include the compounds of Formula (I-bbb‴) as set forth below:

(I-bbb‴)

| Compound | $R^1$ | $(X)_n$ | Z |
|---|---|---|---|
| Ibbb‴-1 | —CH=CH$_2$ | —(CH$_2$)$_6$— | —H |
| Ibbb‴-2 | —CH$_2$CH$_3$ | —(CH$_2$)$_6$— | —H | and pharmaceutically acceptable salts, solvates, and hydrates thereof.

Compounds of Formula (I-c)

The present invention provides Compounds according to Formula (I-c):

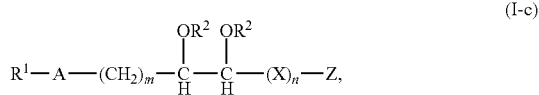

(I-c)

wherein:

$R^1$ is $(R^3)(R^4)C(H)$—, $R^5C(O)$—, $R^5OC(O)$—, $R^5NHC(O)$— or an oxygen-containing -3 to -7-membered monocyclic heterocycle;

each $R^2$ is independently —H, —$C_1$-$C_6$ alkyl, or —C(O)—$C_1$-$C_6$ alkyl, or both $R^2$ groups combine to form —C(O)— or —C($R^a$)(10-, wherein each $R^a$ is independently —H, —$C_1$-$C_6$ alkyl or phenyl;

$R^3$ is —SH, —NH$_2$, —Cl, —F, —CN, —NO$_2$, —CF$_3$ or —CCl$_3$;

$R^4$ is —$C_1$-$C_6$ alkyl, —$C_2$-$C_6$ alkenyl or —$C_2$-$C_6$ alkynyl;

$R^5$ is —H, —$C_1$-$C_6$ alkyl, —$C_2$-$C_6$ alkenyl or —$C_2$-$C_6$ alkynyl;

A is -(para)-biphenylene-;

each X is independently —$C_1$-$C_6$ alkylene-, —$C_2$-$C_6$ alkenylene- or —$C_2$-$C_6$ alkynylene-;

Z is —H, -aryl, —$C_1$-$C_6$ alkyl, —$C_2$-$C_6$ alkenyl, —$C_2$-$C_6$ alkynyl, —$C_3$-$C_8$ monocyclic cycloalkyl, —$C_3$-$C_8$ monocyclic cycloalkenyl, -(5 or -6-membered monocyclic heteroaryl) or -(7 to -10-membered bicyclic heteroaryl);

m is an integer ranging from 1 to 6; and n is 0, 1 or 2;

and pharmaceutically acceptable salts, solvates, and hydrates thereof.

In one embodiment, $R^1$ is $CH(R^3)$—$R^4$.

In another embodiment, $R^1$ is —C(O)—$C_2$-$C_6$ alkynyl.

In still another embodiment, $R^1$ is —C(O)NHR$^5$.

In another embodiment, $R^1$ is —C(O)OR$^5$.

In a further embodiment, $R^1$ is -oxygen-containing -3 to -7-membered monocyclic heterocycle.

In one embodiment, $R^2$ is —H.

In another embodiment, $R^2$ is —$C_1$-$C_6$ alkyl.

In still another embodiment, $R^2$ is —C(O)—$C_1$-$C_6$ alkyl.

In another embodiment, both $R^2$ groups combine to form —C(O)—.

In a further embodiment, both $R^2$ groups combine to form —C(CH$_3$)$_2$—.

In one embodiment, $R^3$ is —F.

In another embodiment, $R^3$ is —SH.

In still another embodiment, $R^3$ is —NH$_2$.

In another embodiment, $R^3$ is —CN.

In one embodiment, $R^4$ is —$C_1$-$C_6$ alkyl.

In another embodiment, $R^4$ is —$C_2$-$C_6$ alkenyl.

In still another embodiment, $R^4$ is —$C_2$-$C_6$ alkynyl.

In another embodiment, $R^4$ is —CH=CH$_2$.

In another embodiment, X is —$C_1$-$C_6$ alkylene, n is 1 and Z is —H.

In still another embodiment, X is —(CH$_2$)$_6$—, n is 1 and Z is —H.

In one embodiment, m is 1.

In one embodiment, $R^3$ is —F and $R^4$ is —$C_2$-$C_6$ alkenyl.

In another embodiment, $R^3$ is —CN and $R^4$ is —$C_2$-$C_6$ alkenyl.

In another embodiment, $R^3$ is —SH and $R^4$ is —$C_2$-$C_6$ alkenyl.

In still another embodiment, $R^3$ is —NH$_2$ and $R^4$ is —$C_2$-$C_6$ alkenyl.

In another embodiment, $R^3$ is —NO$_2$ and $R^4$ is —$C_2$-$C_6$ alkenyl.

In another embodiment, $R^3$ is —CF$_3$ and $R^4$ is —$C_2$-$C_6$ alkenyl.

In yet another embodiment, $R^3$ is —Cl and $R^4$ is —$C_2$-$C_6$ alkenyl.

In another embodiment, $R^3$ is —CCl$_3$ and $R^4$ is —$C_2$-$C_6$ alkenyl.

In another embodiment, where $R^1$ is —C(O)R$^5$, —C(O)OR$^5$, —C(O)NHR$^5$ or oxygen-containing 3 to -7-membered monocyclic heterocycle, the Compounds of formula (I-c) can exist as a single stereoisomer, for example, that depicted by any of the formulas set forth below:

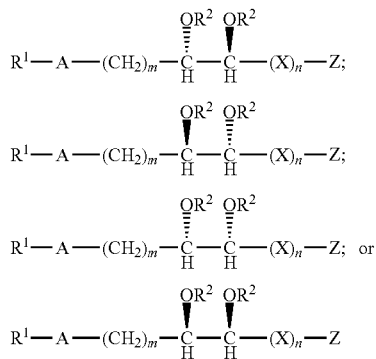

wherein $R^1$, $R^2$, A, X, Z, m and n are as defined above for the Compounds of formula (I-c).

In another embodiment, where $R^1$ is $(R^3)(R^4)C(H)$—, the Compounds of formula (I-c) can exist as a single stereoisomer, for example, that depicted by any of the formulas set forth below:

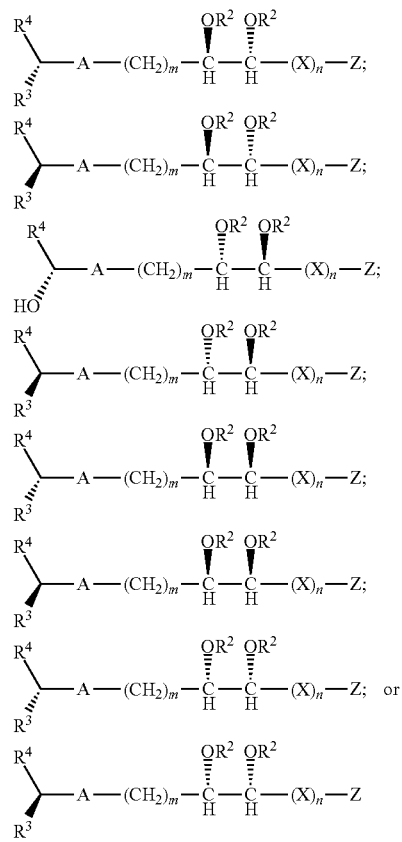

wherein $R^2$, $R^3$, $R^4$, A, X, Z, m and n are as defined above for the Compounds of formula (I-c).

Illustrative examples of the Compounds of Formula (I-c) include the compounds of Formula (I-ca) as set forth below:

(I-ca)

| Compound | $R^3$ | $R^4$ | $(X)_n$ | Z |
|---|---|---|---|---|
| Ica-1 | —F | —CH=CH$_2$ | —(CH$_2$)$_6$— | —H |
| Ica-2 | —Cl | —CH=CH$_2$ | —(CH$_2$)$_6$— | —H |
| Ica-3 | —NH$_2$ | —CH=CH$_2$ | —(CH$_2$)$_6$— | —H |
| Ica-4 | —CN | —CH=CH$_2$ | —(CH$_2$)$_6$— | —H |
| Ica-5 | —SH | —CH=CH$_2$ | —(CH$_2$)$_6$— | —H |
| Ica-6 | —NO$_2$ | —CH=CH$_2$ | —(CH$_2$)$_6$— | —H |
| Ica-7 | —CF$_3$ | —CH=CH$_2$ | —(CH$_2$)$_6$— | —H |
| Ica-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-c) include the compounds of Formula (I-ca') as set forth below:

(I-ca')

| Compound | $R^3$ | $R^4$ | $(X)_n$ | Z |
|---|---|---|---|---|
| Ica'-1 | —F | —CH=CH$_2$ | —(CH$_2$)$_6$— | —H |
| Ica'-2 | —Cl | —CH=CH$_2$ | —(CH$_2$)$_6$— | —H |
| Ica'-3 | —NH$_2$ | —CH=CH$_2$ | —(CH$_2$)$_6$— | —H |
| Ica'-4 | —CN | —CH=CH$_2$ | —(CH$_2$)$_6$— | —H |
| Ica'-5 | —SH | —CH=CH$_2$ | —(CH$_2$)$_6$— | —H |
| Ica'-6 | —NO$_2$ | —CH=CH$_2$ | —(CH$_2$)$_6$— | —H |
| Ica'-7 | —CF$_3$ | —CH=CH$_2$ | —(CH$_2$)$_6$— | —H |
| Ica'-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-c) include the compounds of Formula (I-ca") as set forth below:

(I-ca")

| Compound | $R^3$ | $R^4$ | $(X)_n$ | Z |
|---|---|---|---|---|
| Ica"-1 | —F | —CH=CH$_2$ | —(CH$_2$)$_6$— | —H |
| Ica"-2 | —Cl | —CH=CH$_2$ | —(CH$_2$)$_6$— | —H |
| Ica"-3 | —NH$_2$ | —CH=CH$_2$ | —(CH$_2$)$_6$— | —H |
| Ica"-4 | —CN | —CH=CH$_2$ | —(CH$_2$)$_6$— | —H |
| Ica"-5 | —SH | —CH=CH$_2$ | —(CH$_2$)$_6$— | —H |
| Ica"-6 | —NO$_2$ | —CH=CH$_2$ | —(CH$_2$)$_6$— | —H |
| Ica"-7 | —CF$_3$ | —CH=CH$_2$ | —(CH$_2$)$_6$— | —H |
| Ica"-8 | —CCl$_3$ | —CH=CH$_2$ | —(CH$_2$)$_6$— | —H | and pharmaceutically acceptable salts, solvates, and hydrates thereof.

Additional illustrative examples of the Compounds of Formula (I-c) include the compounds of Formula (I-ca''') as set forth below:

(I-ca''')

[Structure: R⁴R³CH-C₆H₄-C₆H₄-CH₂-C(H)(OH)-C(H)(OH)-(X)ₙ-Z, with wedge bonds on OH groups]

| Compound | R³ | R⁴ | (X)ₙ | Z |
|---|---|---|---|---|
| Ica'''-1 | —F | —CH=CH₂ | —(CH₂)₆— | —H |
| Ica'''-2 | —Cl | —CH=CH₂ | —(CH₂)₆— | —H |
| Ica'''-3 | —NH₂ | —CH=CH₂ | —(CH₂)₆— | —H |
| Ica'''-4 | —CN | —CH=CH₂ | —(CH₂)₆— | —H |
| Ica'''-5 | —SH | —CH=CH₂ | —(CH₂)₆— | —H |
| Ica'''-6 | —NO₂ | —CH=CH₂ | —(CH₂)₆— | —H |
| Ica'''-7 | —CF₃ | —CH=CH₂ | —(CH₂)₆— | —H |
| Ica'''-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-caa) as set forth below:

(I-caa)

[Structure with OH groups, one dashed wedge]

| Compound | R³ | R⁴ | (X)ₙ | Z |
|---|---|---|---|---|
| Icaa-1 | —F | —CH=CH₂ | —(CH₂)₆— | —H |
| Icaa-2 | —Cl | —CH=CH₂ | —(CH₂)₆— | —H |
| Icaa-3 | —NH₂ | —CH=CH₂ | —(CH₂)₆— | —H |
| Icaa-4 | —CN | —CH=CH₂ | —(CH₂)₆— | —H |
| Icaa-5 | —SH | —CH=CH₂ | —(CH₂)₆— | —H |
| Icaa-6 | —NO₂ | —CH=CH₂ | —(CH₂)₆— | —H |
| Icaa-7 | —CF₃ | —CH=CH₂ | —(CH₂)₆— | —H |
| Icaa-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-caa') as set forth below:

(I-caa')

[Structure with OH groups, solid wedges]

| Compound | R³ | R⁴ | (X)ₙ | Z |
|---|---|---|---|---|
| Icaa'-1 | —F | —CH=CH₂ | —(CH₂)₆— | —H |
| Icaa'-2 | —Cl | —CH=CH₂ | —(CH₂)₆— | —H |
| Icaa'-3 | —NH₂ | —CH=CH₂ | —(CH₂)₆— | —H |
| Icaa'-4 | —CN | —CH=CH₂ | —(CH₂)₆— | —H |
| Icaa'-5 | —SH | —CH=CH₂ | —(CH₂)₆— | —H |
| Icaa'-6 | —NO₂ | —CH=CH₂ | —(CH₂)₆— | —H |
| Icaa'-7 | —CF₃ | —CH=CH₂ | —(CH₂)₆— | —H |
| Icaa'-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-caa'') as set forth below:

(I-caa'')

[Structure with OH groups, both dashed wedges]

| Compound | R³ | R⁴ | (X)ₙ | Z |
|---|---|---|---|---|
| Icaa''-1 | —F | —CH=CH₂ | —(CH₂)₆— | —H |
| Icaa''-2 | —Cl | —CH=CH₂ | —(CH₂)₆— | —H |
| Icaa''-3 | —NH₂ | —CH=CH₂ | —(CH₂)₆— | —H |
| Icaa''-4 | —CN | —CH=CH₂ | —(CH₂)₆— | —H |
| Icaa''-5 | —SH | —CH=CH₂ | —(CH₂)₆— | —H |
| Icaa''-6 | —NO₂ | —CH=CH₂ | —(CH₂)₆— | —H |
| Icaa''-7 | —CF₃ | —CH=CH₂ | —(CH₂)₆— | —H |
| Icaa''-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-caa''') as set forth below:

(I-ca''')

[Structure with OH groups]

| Compound | R³ | R⁴ | (X)ₙ | Z |
|---|---|---|---|---|
| Icaa'''-1 | —F | —CH=CH₂ | —(CH₂)₆— | —H |
| Icaa'''-2 | —Cl | —CH=CH₂ | —(CH₂)₆— | —H |
| Icaa'''-3 | —NH₂ | —CH=CH₂ | —(CH₂)₆— | —H |
| Icaa'''-4 | —CN | —CH=CH₂ | —(CH₂)₆— | —H |
| Icaa'''-5 | —SH | —CH=CH₂ | —(CH₂)₆— | —H |
| Icaa'''-6 | —NO₂ | —CH=CH₂ | —(CH₂)₆— | —H |
| Icaa'''-7 | —CF₃ | —CH=CH₂ | —(CH₂)₆— | —H |
| Icaa'''-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cb) as set forth below:

(I-cb)

[Structure with acetonide/dioxolane ring]

| Compound | R³ | R⁴ | (X)ₙ | Z |
|---|---|---|---|---|
| Icb1 | —F | —CH=CH₂ | —(CH₂)₆— | —H |
| Icb-2 | —Cl | —CH=CH₂ | —(CH₂)₆— | —H |
| Icb-3 | —NH₂ | —CH=CH₂ | —(CH₂)₆— | —H |
| Icb-4 | —CN | —CH=CH₂ | —(CH₂)₆— | —H |
| Icb-5 | —SH | —CH=CH₂ | —(CH₂)₆— | —H |
| Icb-6 | —NO₂ | —CH=CH₂ | —(CH₂)₆— | —H |
| Icb-7 | —CF₃ | —CH=CH₂ | —(CH₂)₆— | —H |
| Icb-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cb') as set forth below:

(I-cb')

[Structure: R4/R3-substituted benzyl-biphenyl-CH2-CH-CH-(X)n-Z with dioxolane ring (wedge bonds)]

| Compound | R³ | R⁴ | (X)ₙ | Z |
|---|---|---|---|---|
| Icb'-1 | —F | —CH=CH₂ | —(CH₂)₆— | —H |
| Icb'-2 | —Cl | —CH=CH₂ | —(CH₂)₆— | —H |
| Icb'-3 | —NH₂ | —CH=CH₂ | —(CH₂)₆— | —H |
| Icb'-4 | —CN | —CH=CH₂ | —(CH₂)₆— | —H |
| Icb'-5 | —SH | —CH=CH₂ | —(CH₂)₆— | —H |
| Icb'-6 | —NO₂ | —CH=CH₂ | —(CH₂)₆— | —H |
| Icb'-7 | —CF₃ | —CH=CH₂ | —(CH₂)₆— | —H |
| Icb'-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cb″) as set forth below:

(I-cb″)

| Compound | R³ | R⁴ | (X)ₙ | Z |
|---|---|---|---|---|
| Ic″b1 | —F | —CH=CH₂ | —(CH₂)₆— | —H |
| Icb″-2 | —Cl | —CH=CH₂ | —(CH₂)₆— | —H |
| Icb″-3 | —NH₂ | —CH=CH₂ | —(CH₂)₆— | —H |
| Icb″-4 | —CN | —CH=CH₂ | —(CH₂)₆— | —H |
| Icb″-5 | —SH | —CH=CH₂ | —(CH₂)₆— | —H |
| Icb″-6 | —NO₂ | —CH=CH₂ | —(CH₂)₆— | —H |
| Icb″-7 | —CF₃ | —CH=CH₂ | —(CH₂)₆— | —H |
| Icb″-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cb‴) as set forth below:

(I-cb‴)

| Compound | R³ | R⁴ | (X)ₙ | Z |
|---|---|---|---|---|
| Icb‴-1 | —F | —CH=CH₂ | —(CH₂)₆— | —H |
| Icb‴-2 | —Cl | —CH=CH₂ | —(CH₂)₆— | —H |
| Icb‴-3 | —NH₂ | —CH=CH₂ | —(CH₂)₆— | —H |
| Icb‴-4 | —CN | —CH=CH₂ | —(CH₂)₆— | —H |
| Icb‴-5 | —SH | —CH=CH₂ | —(CH₂)₆— | —H |
| Icb‴-6 | —NO₂ | —CH=CH₂ | —(CH₂)₆— | —H |
| Icb‴-7 | —CF₃ | —CH=CH₂ | —(CH₂)₆— | —H |
| Icb‴-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cbb) as set forth below:

(I-cbb)

| Compound | R³ | R⁴ | (X)ₙ | Z |
|---|---|---|---|---|
| Icbb 1 | —F | —CH=CH₂ | —(CH₂)₆— | —H |
| Icbb-2 | —Cl | —CH=CH₂ | —(CH₂)₆— | —H |
| Icbb-3 | —NH₂ | —CH=CH₂ | —(CH₂)₆— | —H |
| Icbb-4 | —CN | —CH=CH₂ | —(CH₂)₆— | —H |
| Icbb-5 | —SH | —CH=CH₂ | —(CH₂)₆— | —H |
| Icbb-6 | —NO₂ | —CH=CH₂ | —(CH₂)₆— | —H |
| Icbb-7 | —CF₃ | —CH=CH₂ | —(CH₂)₆— | —H |
| Icbb-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cbb') as set forth below:

(I-cbb')

| Compound | R³ | R⁴ | (X)ₙ | Z |
|---|---|---|---|---|
| Icbb'-1 | —F | —CH=CH₂ | —(CH₂)₆— | —H |
| Icbb'-2 | —Cl | —CH=CH₂ | —(CH₂)₆— | —H |
| Icbb'-3 | —NH₂ | —CH=CH₂ | —(CH₂)₆— | —H |
| Icbb'-4 | —CN | —CH=CH₂ | —(CH₂)₆— | —H |
| Icbb'-5 | —SH | —CH=CH₂ | —(CH₂)₆— | —H |
| Icbb'-6 | —NO₂ | —CH=CH₂ | —(CH₂)₆— | —H |
| Icbb'-7 | —CF₃ | —CH=CH₂ | —(CH₂)₆— | —H |
| Icbb'-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cbb″) as set forth below:

(I-cbb″)

| Compound | R³ | R⁴ | (X)ₙ | Z |
|---|---|---|---|---|
| Icbb″-1 | —F | —CH=CH₂ | —(CH₂)₆— | —H |
| Icbb″-2 | —Cl | —CH=CH₂ | —(CH₂)₆— | —H |
| Icbb″-3 | —NH₂ | —CH=CH₂ | —(CH₂)₆— | —H |
| Icbb″-4 | —CN | —CH=CH₂ | —(CH₂)₆— | —H |
| Icbb″-5 | —SH | —CH=CH₂ | —(CH₂)₆— | —H |

-continued

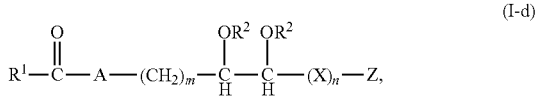

(I-cbb'')

| Compound | R³ | R⁴ | (X)ₙ | Z |
|---|---|---|---|---|
| Icbb''-6 | —NO₂ | —CH=CH₂ | —(CH₂)₆— | —H |
| Icbb''-7 | —CF₃ | —CH=CH₂ | —(CH₂)₆— | —H |
| Icbb''-8 | —CCl₃ | —CH=CH₂ | —(CH₂)₆— | —H | and pharmaceutically acceptable salts, solvates, and hydrates thereof.

Additional illustrative examples of the Compounds of Formula (I-c) include the compounds of Formula (I-cbb''') as set forth below:

(I-cbb''')

| Compound | R³ | R⁴ | (X)ₙ | Z |
|---|---|---|---|---|
| Icbb'''-1 | —F | —CH=CH₂ | —(CH₂)₆— | —H |
| Icbb'''-2 | —Cl | —CH=CH₂ | —(CH₂)₆— | —H |
| Icbb'''-3 | —NH₂ | —CH=CH₂ | —(CH₂)₆— | —H |
| Icbb'''-4 | —CN | —CH=CH₂ | —(CH₂)₆— | —H |
| Icbb'''-5 | —SH | —CH=CH₂ | —(CH₂)₆— | —H |
| Icbb'''-6 | —NO₂ | —CH=CH₂ | —(CH₂)₆— | —H |
| Icbb'''-7 | —CF₃ | —CH=CH₂ | —(CH₂)₆— | —H |
| Icbb'''-8 | —CCl₃ | —CH=CH₂ | —(CH₂)₆— | —H | and pharmaceutically acceptable salts, solvates, and hydrates thereof.

Compounds of Formula (I-d)

The present invention provides Compounds according to Formula (I-d), below:

$$R^1-\overset{O}{\overset{\|}{C}}-A-(CH_2)_m-\overset{OR^2}{\underset{H}{\overset{|}{C}}}-\overset{OR^2}{\underset{H}{\overset{|}{C}}}-(X)_n-Z,$$

(I-d)

wherein:
R¹ is (C₂-C₆ alkynyl)-, (C₃-C₈ monocyclic cycloalkyl)-, (C₃-C₈ monocyclic cycloalkenyl)-, (5 or -6-membered monocyclic heteroaryl)- or (7 to -10-membered bicyclic heteroaryl)-;
each R² is independently —H, —C₁-C₆ alkyl, or —C(O)—C₁-C₆ alkyl, or both R² groups combine to form —C(O)— or —C(Rᵃ)(Rᵃ)—, wherein each Rᵃ is independently —H, —C₁-C₆ alkyl or phenyl;
A is —C≡C—C≡C— or -(para)-phenylene-;
each X is independently —C₁-C₆ alkylene-, —C₂-C₆ alkenylene- or —C₂-C₆ alkynylene-;
Z is —H, -aryl, —C₁-C₆ alkyl, —C₂-C₆ alkenyl, —C₂-C₆ alkynyl, —C₃-C₈ monocyclic cycloalkyl, —C₃-C₈ monocyclic cycloalkenyl, -(5 or -6-membered monocyclic heteroaryl) or -(7 to -10-membered bicyclic heteroaryl);
m is an integer ranging from 1 to 6; and
n is 0, 1 or 2;
and pharmaceutically acceptable salts, solvates, and hydrates thereof.

In one embodiment, R¹ is —C₂-C₆ alkynyl.
In another embodiment, R¹ is —C₃-C₈ monocyclic cycloalkyl.
In another embodiment, R¹ is —C₃-C₈ monocyclic cycloalkenyl.
In still another embodiment, R¹ is -(5 or -6-membered monocyclic heteroaryl).
In a further embodiment, R¹ is -7 to -10-membered bicyclic heteroaryl.
In one embodiment, R² is —H.
In another embodiment, R² is —C₁-C₆ alkyl.
In still another embodiment, R² is —C(O)R⁵.
In another embodiment, both R² groups combine to form —C(O)—.
In a further embodiment, both R² groups combine to form —C(CH₃)₂—.
In one embodiment A is —C≡C—C≡C—.
In another embodiment, A is -(para)-phenylene-.
In another embodiment, X is —C₁-C₆ alkylene, n is 1 and Z is —H.
In still another embodiment, X is —(CH₂)₆—, n is 1 and Z is —H.
In one embodiment, m is 1.
In one embodiment, R¹ is —C₂-C₆ alkynyl and R² is —H.
In another embodiment, R¹ is —C₃-C₈ monocyclic cycloalkyl and R² is —H.
In another embodiment, R¹ is —C₃-C₈ monocyclic cycloalkenyl and R² is —H.
In still another embodiment, R¹ is -(5 or -6-membered monocyclic heteroaryl) and R² is —H.
In a further embodiment, R¹ is -7 to -10-membered bicyclic heteroaryl and R² is —H.
In one embodiment, R¹ is —C₂-C₆ alkynyl, X is —(CH₂)₆—, n is 1 and Z is —H.
In another embodiment, R¹ is —C₃-C₈ monocyclic cycloalkyl, X is —(CH₂)₆—, n is 1 and Z is —H.
In another embodiment, R¹ is —C₃-C₈ monocyclic cycloalkenyl, X is —(CH₂)₆—, n is 1 and Z is —H.
In still another embodiment, R¹ is -(5 or -6-membered monocyclic heteroaryl), X is —(CH₂)₆—, n is 1 and Z is —H.
In a further embodiment, R¹ is -7 to -10-membered bicyclic heteroaryl, X is —(CH₂)—, n is 1 and Z is —H.

In one embodiment, the Compounds of formula (I-d) can exist as a single stereoisomer, for example, that depicted by any of the formulas set forth below:

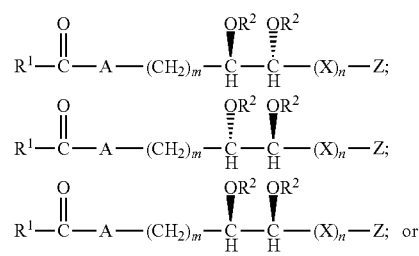

-continued

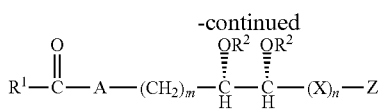

wherein $R^1$, $R^2$, A, X, Z, m and n are as defined above for the Compounds of formula (I-d).

Illustrative examples of the Compounds of Formula (I-d) include the compounds of Formula (I-da) as set forth below:

(I-da)

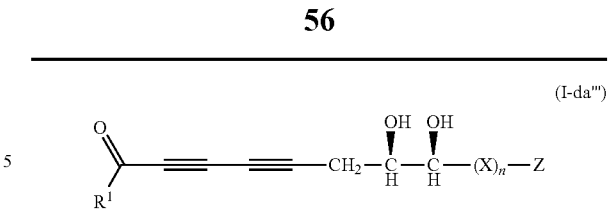

| Compound | $R^1$ | $(X)_n$ | Z |
|---|---|---|---|
| Ida-1 | —C≡CH | —(CH$_2$)$_6$— | —H |
| Ida-2 | -furan-2-yl | —(CH$_2$)$_6$— | —H |
| Ida-3 | -cyclopentyl | —(CH$_2$)$_6$— | —H |
| Ida-4 | -cyclohexyl | —(CH$_2$)$_6$— | —H | and pharmaceutically acceptable salts, solvates, and hydrates thereof.

Additional illustrative examples of the Compounds of Formula (I-d) include the compounds of Formula (I-da') as set forth below:

(I-da')

| Compound | $R^1$ | $(X)_n$ | Z |
|---|---|---|---|
| Ida'-1 | —C≡CH | —(CH$_2$)$_6$— | —H |
| Ida'-2 | -furan-2-yl | —(CH$_2$)$_6$— | —H |
| Ida'-3 | -cyclopentyl | —(CH$_2$)$_6$— | —H |
| Ida'-4 | -cyclohexyl | —(CH$_2$)$_6$— | —H | and pharmaceutically acceptable salts, solvates, and hydrates thereof.

Additional illustrative examples of the Compounds of Formula (I-d) include the compounds of Formula (I-da") as set forth below:

(I-da")

| Compound | $R^1$ | $(X)_n$ | Z |
|---|---|---|---|
| Ida"-1 | —C≡CH | —(CH$_2$)$_6$— | —H |
| Ida"-2 | -furan-2-yl | —(CH$_2$)$_6$— | —H |
| Ida"-3 | -cyclopentyl | —(CH$_2$)$_6$— | —H |
| Ida"-4 | -cyclohexyl | —(CH$_2$)$_6$— | —H | and pharmaceutically acceptable salts, solvates, and hydrates thereof.

Additional illustrative examples of the Compounds of Formula (I-d) include the compounds of Formula (I-da''') as set forth below:

(I-da''')

| Compound | $R^1$ | $(X)_n$ | Z |
|---|---|---|---|
| Ida'''-1 | —C≡CH | —(CH$_2$)$_6$— | —H |
| Ida'''-2 | -furan-2-yl | —(CH$_2$)$_6$— | —H |
| Ida'''-3 | -cyclopentyl | —(CH$_2$)$_6$— | —H |
| Ida'''-4 | -cyclohexyl | —(CH$_2$)$_6$— | —H | and pharmaceutically acceptable salts, solvates, and hydrates thereof.

Additional illustrative examples of the Compounds of Formula (I-d) include the compounds of Formula (I-db) as set forth below:

(I-db)

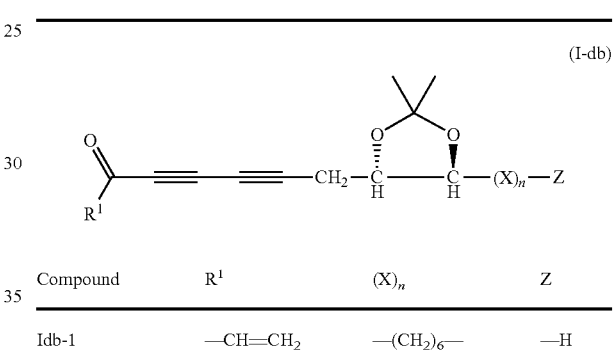

| Compound | $R^1$ | $(X)_n$ | Z |
|---|---|---|---|
| Idb-1 | —CH═CH$_2$ | —(CH$_2$)$_6$— | —H |
| Idb-2 | —CH$_2$CH$_3$ | —(CH$_2$)$_6$— | —H | and pharmaceutically acceptable salts, solvates, and hydrates thereof.

Additional illustrative examples of the Compounds of Formula (I-d) include the compounds of Formula (I-db') as set forth below:

(I-db')

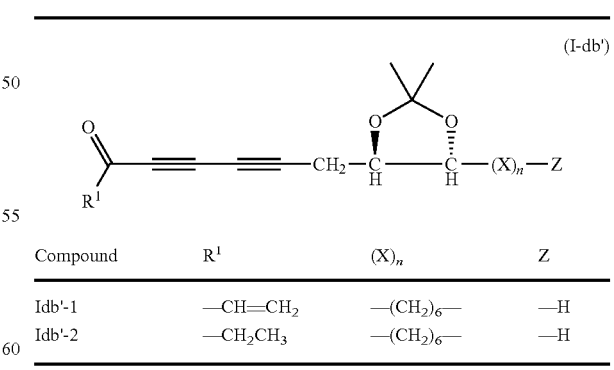

| Compound | $R^1$ | $(X)_n$ | Z |
|---|---|---|---|
| Idb'-1 | —CH═CH$_2$ | —(CH$_2$)$_6$— | —H |
| Idb'-2 | —CH$_2$CH$_3$ | —(CH$_2$)$_6$— | —H | and pharmaceutically acceptable salts, solvates, and hydrates thereof.

Additional illustrative examples of the Compounds of Formula (I-d) include the compounds of Formula (I-db") as set forth below:

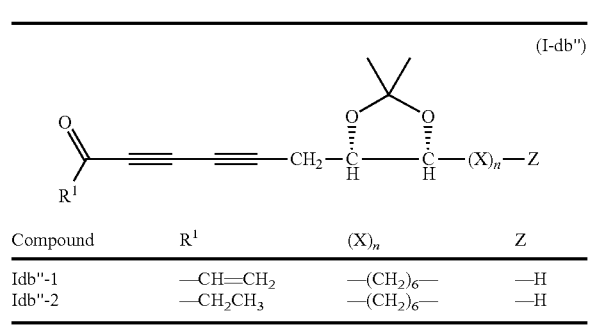

| Compound | R[1] | (X)$_n$ | Z |
|---|---|---|---|
| Idb''-1 | —CH=CH$_2$ | —(CH$_2$)$_6$— | —H |
| Idb''-2 | —CH$_2$CH$_3$ | —(CH$_2$)$_6$— | —H | and pharmaceutically acceptable salts, solvates, and hydrates thereof.

Additional illustrative examples of the Compounds of Formula (I-d) include the compounds of Formula (I-db''') as set forth below:

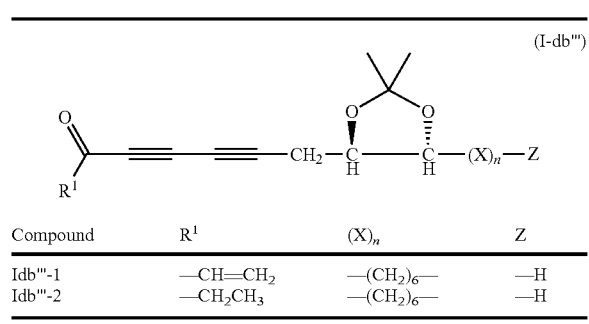

| Compound | R[1] | (X)$_n$ | Z |
|---|---|---|---|
| Idb'''-1 | —CH=CH$_2$ | —(CH$_2$)$_6$— | —H |
| Idb'''-2 | —CH$_2$CH$_3$ | —(CH$_2$)$_6$— | —H | and pharmaceutically acceptable salts, solvates, and hydrates thereof.

Compounds of Formula (I-e)

The present invention provides Compounds according to Formula (I-e), below:

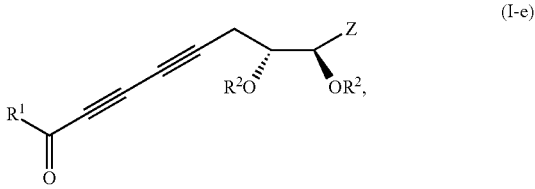

wherein:
R[1] is —C$_1$-C$_6$ alkyl, —C$_2$-C$_6$ alkenyl or —C$_2$-C$_6$ alkynyl;
each R[2] is independently —H, —C$_1$-C$_6$ alkyl, or —C(O)—C$_1$-C$_6$ alkyl, or both R[2] groups combine to form —C(O)— or —C(R$^a$)(R$^a$)—, wherein each R$^a$ is independently —H, —C$_1$-C$_6$ alkyl or phenyl; and
Z is —C$_1$-C$_{10}$ alkyl;
and pharmaceutically acceptable salts, solvates, and hydrates thereof.

In one embodiment, R[1] is —CH=CH$_2$.
In one embodiment, R[1] is —CH$_2$CH$_3$.
In one embodiment, R[2] is —H.
In another embodiment, R[2] is —C$_1$-C$_6$ alkyl.
In still another embodiment, R[2] is —C(O)R[5].
In another embodiment, both R[2] groups combine to form —C(O)—.
In a further embodiment, both R[2] groups combine to form —C(CH$_3$)$_2$—.

In another embodiment, R[5] is —C$_1$-C$_6$ alkyl.
In another embodiment, Z is —C$_7$ alkyl.
In one embodiment, a compound of Formula (I-e) is not panaxacol.
Illustrative examples of compounds of Formula (I-e) are:

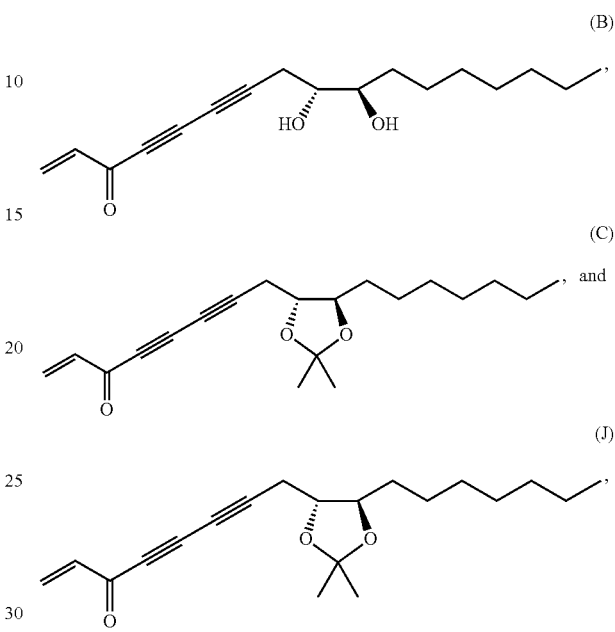

and pharmaceutically acceptable salts, solvates, and hydrates thereof.

Compounds of Formula (I-f)

The present invention provides Compounds according to Formula (I-f), below:

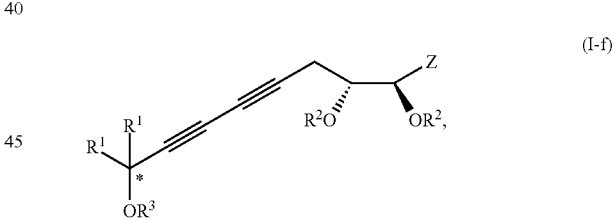

wherein:
each R[1] is independently —H, —C$_1$-C$_6$ alkyl, —C$_2$-C$_6$ alkenyl or —C$_2$-C$_6$ alkynyl, so long as both R[1] are non-identical;
each R[2] is independently —H, —C$_1$-C$_6$ alkyl, or —C(O)—C$_1$-C$_6$ alkyl, or both R[2] groups combine to form —C(O)— or —C(R$^a$)(R$^a$)—, wherein each R$^a$ is independently —H, —C$_1$-C$_6$ alkyl or phenyl;
R[3] is —H, —C$_1$-C$_6$ alkyl, —C$_2$-C$_6$ alkenyl, —C$_2$-C$_6$ alkynyl, -aryl, or —C(O)R[5];
R[5] is —H, —C$_1$-C$_6$ alkyl, —C$_2$-C$_6$ alkenyl, —C$_2$-C$_6$ alkynyl, -aryl, —C$_1$-C$_6$ alkylene-aryl, or —C$_2$-C$_6$ alkenylene-aryl; and
Z is —C$_1$-C$_{10}$ alkyl;
and pharmaceutically acceptable salts, solvates, and hydrates thereof.

In one embodiment, one R[1] is —CH=CH$_2$ and the other R[1] is —H.

In one embodiment, one $R^1$ is —CH=CH$_2$ and the other $R^1$ is —C$_1$-C$_6$ alkyl.

In one embodiment, one $R^1$ is —CH=CH$_2$ and the other $R^1$ is methyl.

In one embodiment, the chirality of the starred carbon is (R).

In another embodiment, the chirality of the starred carbon is (S).

In one embodiment, one $R^1$ is —CH$_2$CH$_3$ and the other $R^1$ is —H.

In one embodiment, $R^2$ is —H.

In another embodiment, $R^2$ is —C$_1$-C$_6$ alkyl.

In still another embodiment, $R^2$ is —C(O)R$^5$.

In one embodiment, $R^2$ is not acetyl or methyl.

In another embodiment, both $R^2$ groups combine to form —C(O)—.

In a further embodiment, both $R^2$ groups combine to form —C(CH$_3$)$_2$—.

In one embodiment, $R^3$ is —H, —C$_1$-C$_6$ alkyl, or —C(O)R$^5$.

In one embodiment, $R^3$ is —H.

In another embodiment, $R^3$ is —C$_1$-C$_6$ alkyl.

In another embodiment, $R^3$ is methyl.

In another embodiment, $R^3$ is —C(O)R$^5$.

In another embodiment, $R^5$ is —C$_1$-C$_6$ alkyl, -aryl, —C$_1$-C$_6$ alkylene-aryl, or —C$_2$-C$_6$ alkenylene-aryl.

In one embodiment, $R^5$ is —C$_1$-C$_6$ alkyl.

In one embodiment, $R^5$ is methyl.

In one embodiment, $R^5$ is -aryl.

In one embodiment, $R^5$ is -phenyl.

In one embodiment, $R^5$ is —C$_1$-C$_6$ alkylene-aryl.

In one embodiment, $R^5$ is —C$_2$-C$_6$ alkenylene-aryl.

In another embodiment, Z is —C$_7$ alkyl.

In one embodiment, a compound of Formula (I-f) is not panaxytriol, dihydropanaxacol or an acetylated or methylated panaxytriol.

In one embodiment, the compound of Formula (I-f) is

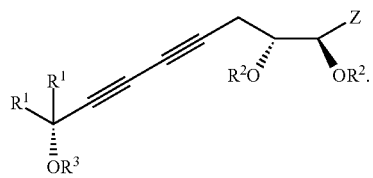

In another embodiment, the compound of Formula (I-f) is

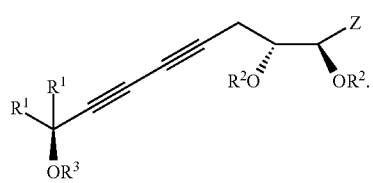

Illustrative examples of compounds of Formula (I-f) are:

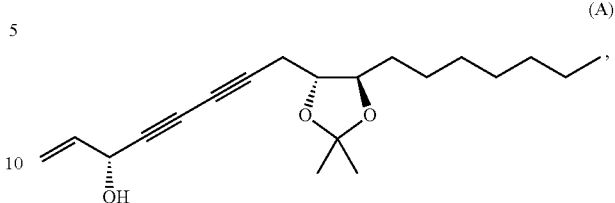
(A)

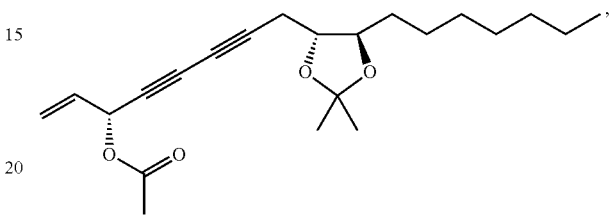
(F)

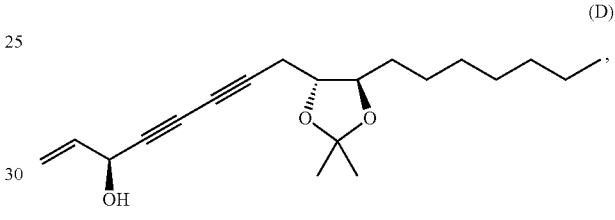
(D)

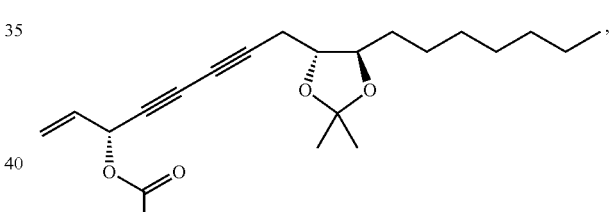
(E)

(G)

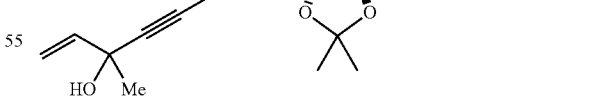
(H)

and

-continued

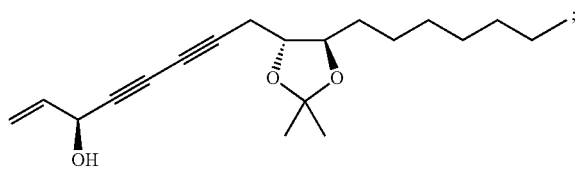
(K)

and pharmaceutically acceptable salts, solvates, and hydrates thereof.

In one embodiment, the stereochemistry of Compound (G) is

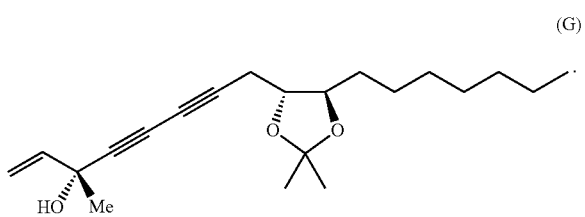 [SMILES: C=C[C@@](C)(O)C#CC#CC[C@H]1OC(C)(C)O[C@@H]1CCCCCCC]
(G)

In another embodiment, the stereochemistry of Compound (G) is

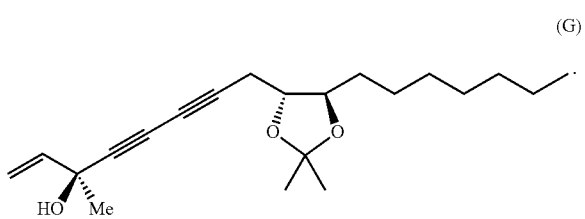 [SMILES: C=C[C@](C)(O)C#CC#CC[C@H]1OC(C)(C)O[C@@H]1CCCCCCC]
(G)

In one embodiment, compounds of formula (I-f) do not include dihydropanaxacol or panaxytriol.

Compounds of Formula (I-g)

The present invention provides Compounds according to Formula (I-g):

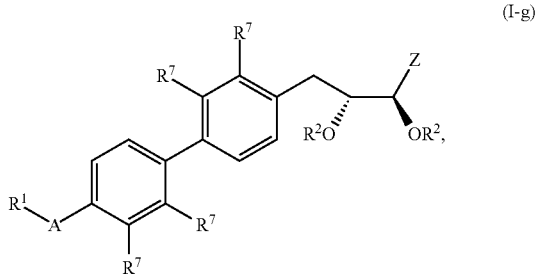
(I-g)

wherein:
$R^1$ is independently —H, —$C_1$-$C_6$ alkyl, —$C_2$-$C_6$ alkenyl or —$C_2$-$C_6$ alkynyl;
each $R^2$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl;

each $R^7$ is independently —H, -aryl, or —$XR^5$;
each X is independently —$NR^5$—, —O—, or —$SO_2$—;
each $R^4$ is —H, —$C_1$-$C_6$ alkyl, —$C_2$-$C_6$ alkenyl or —C(O)—$C_1$-$C_6$ alkyl;
each $R^5$ is independently —H, —$C_1$-$C_6$ alkyl or aryl;
A is —C(O)— or —$CHOR^4$—; and
Z is —$C_1$-$C_{10}$ alkyl;
and pharmaceutically acceptable salts, solvates, and hydrates thereof.

In one embodiment, $R^1$ is —CH=$CH_2$.
In one embodiment, the chirality of the starred carbon is (R).
In another embodiment, the chirality of the starred carbon is (S).
In one embodiment, one $R^1$—$CH_2CH_3$.
In one embodiment, $R^2$ is —H.
In another embodiment, $R^2$ is —$C_1$-$C_6$ alkyl.
In still another embodiment, $R^2$ is —C(O)$R^5$.
In another embodiment, both $R^2$ groups combine to form —C(O)—.
In a further embodiment, both $R^2$ groups combine to form —$(CH_3)_2$—.
In one embodiment, $R^4$ is —H.
In one embodiment, $R^4$ is —$C_1$-$C_6$ alkyl.
In one embodiment, $R^4$ is —C(O)—$C_1$-$C_6$ alkyl.
In one embodiment, $R^5$ is —$C_1$-$C_6$ alkyl.
In one embodiment, $R^7$ is —H.
In one embodiment, A is —C(O)—.
In one embodiment, A is —$CHOR^4$—.
In one embodiment, A is —$CHOR^4$— and $R^4$ is —H.
In another embodiment, Z is —$C_7$ alkyl.
In one embodiment, the compound of Formula (I-g) is

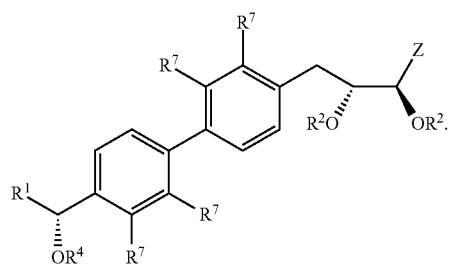

In another embodiment, the compound of Formula (I-g) is

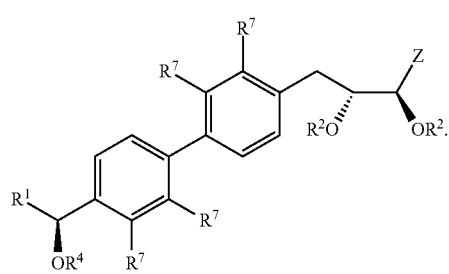

In yet another embodiment, the compound of Formula (I-g) is

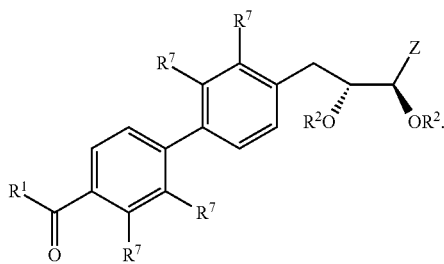

Illustrative examples of compounds of Formula (I-g) are:

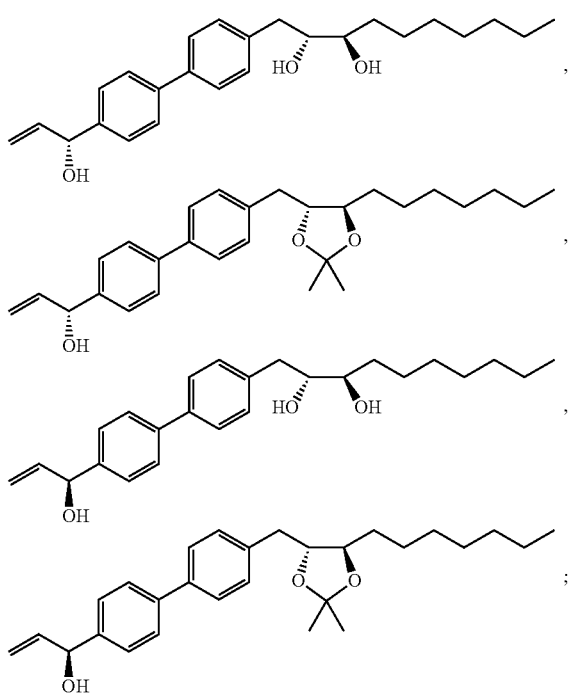

and pharmaceutically acceptable salts, solvates, and hydrates thereof.

Compounds of Formula (I-h)

The present invention provides Compounds according to Formula (I-h):

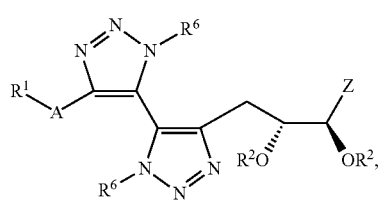

(I-h)

wherein:

$R^1$ is independently —H, —$C_1$-$C_6$ alkyl, —$C_2$-$C_6$ alkenyl or —$C_2$-$C_6$ alkynyl;

each $R^2$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl;

each $R^6$ is independently —H, —$C_1$-$C_6$ alkyl, aryl, or —$SO_2R^5$;

$R^4$ is —H, —$C_1$-$C_6$ alkyl, —$C_2$-$C_6$ alkenyl or —C(O)—$C_1$-$C_6$ alkyl;

each $R^5$ is independently —H, -aryl, —$C_1$-$C_6$ alkyl, —$C_2$-$C_6$ alkenyl, —$C_2$-$C_6$ alkynyl, —$C_3$-$C_8$ monocyclic cycloalkyl, —$C_3$-$C_8$ monocyclic cycloalkenyl, -(5 or -6-membered monocyclic heteroaryl) or -(7 to -10-membered bicyclic heteroaryl);

A is —C(O)— or —$CHOR^4$—; and

Z is —$C_1$-$C_{10}$ alkyl, and pharmaceutically acceptable salts, solvates, and hydrates thereof.

In one embodiment, $R^1$ is —CH=$CH_2$.

In one embodiment, $R^1$ is —$CH_2CH_3$.

In one embodiment, $R^2$ is —H.

In another embodiment, $R^2$ is —$C_1$-$C_6$ alkyl.

In still another embodiment, $R^2$ is —C(O)$R^5$.

In another embodiment, both $R^2$ groups combine to form —C(O)—.

In a further embodiment, both $R^2$ groups combine to form —C($CH_3$)$_2$—.

In one embodiment $R^6$ is —H.

In another embodiment $R^6$ is —$C_1$-$C_6$ alkyl.

In another embodiment $R^6$ is methyl.

In another embodiment, $R^5$ is —$C_1$-$C_6$ alkyl.

In one embodiment, A is —C(O)—.

In one embodiment, A is —$CHOR^4$—.

In one embodiment, A is —$CHOR^4$— and $R^4$ is —H.

In another embodiment, Z is —$C_7$ alkyl.

In another embodiment, $R^5$ is —$C_1$-$C_6$ alkyl.

In another embodiment, Z is —$C_7$ alkyl.

In one embodiment, the compound of Formula (I-h) is

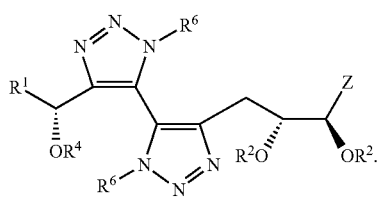

In another embodiment, the compound of Formula (I-h) is

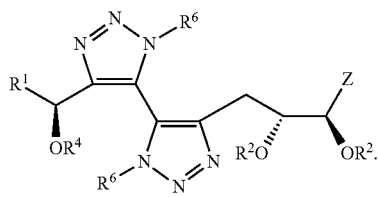

Illustrative examples of compounds of Formula (I-h) are:

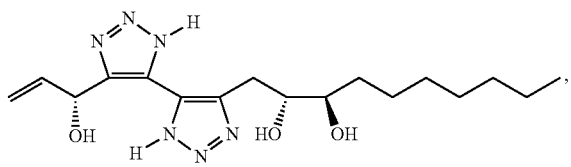

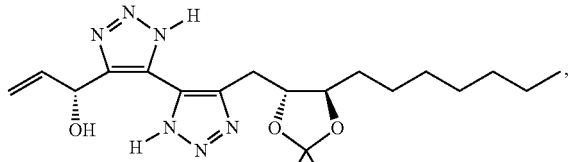

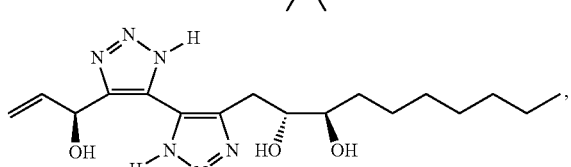

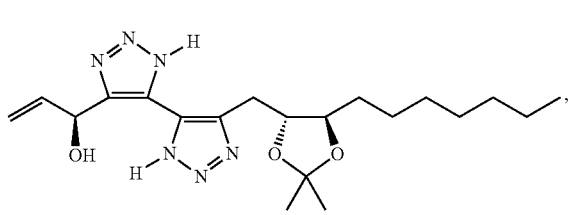

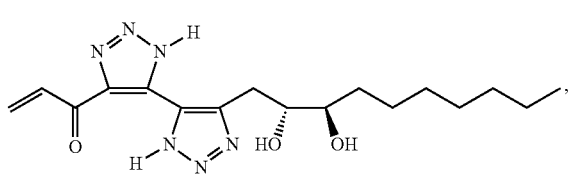

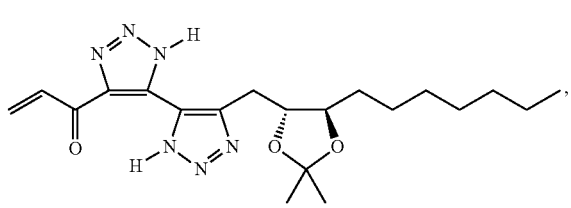

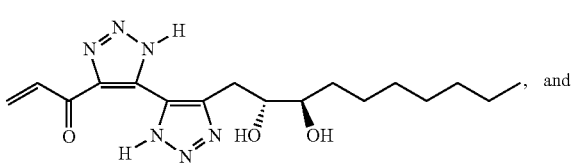, and

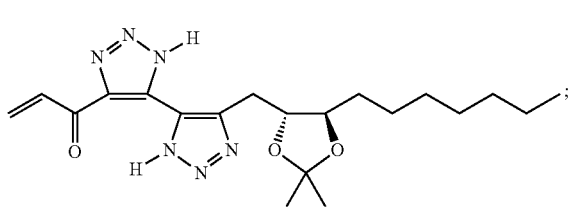;

and pharmaceutically acceptable salts, solvates, and hydrates thereof.

Compounds of Formula (I-i)

The present invention provides Compounds according to Formula (I-i):

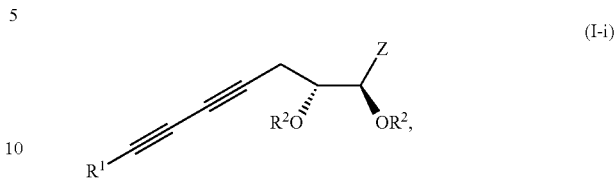

(I-i)

wherein:
$R^1$ is —$C_1$-$C_6$ alkyl or —$C_2$-$C_6$ alkenyl substituted with one or more of a halogen, —CN, —N($R^3$)$_2$, or —(CH$_2$)$_n$OR$^3$;
each $R^2$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl;
$R^3$ is —H, —$C_1$-$C_6$ alkyl, —$C_2$-$C_6$ alkenyl, —$C_2$-$C_6$ alkynyl, or aryl;
Z is —$C_1$-$C_{10}$ alkyl; and
n is 0-6;
and pharmaceutically acceptable salts, solvates, and hydrates thereof.

In one embodiment, $R^1$ is —(CH$_2$)$_n$OR$^3$.
In one embodiment, n is 0.
In another embodiment, n is 1.
In one embodiment, $R^3$ is —H.
In another embodiment, $R^2$ is —$C_1$-$C_6$ alkyl.
In still another embodiment, $R^2$ is —C(O)$R^5$.
In another embodiment, both $R^2$ groups combine to form —C(O)—.
In a further embodiment, both $R^2$ groups combine to form —C(CH$_3$)$_2$—.
In another embodiment, Z is —$C_7$ alkyl.

Illustrative examples of compounds of Formula (I-i) are:

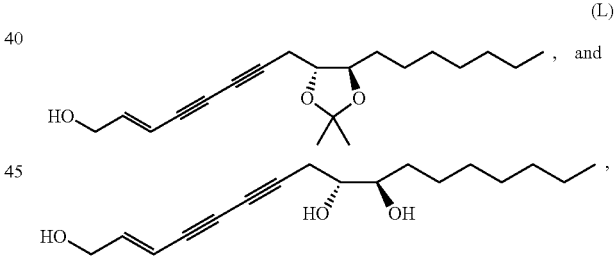

(L)

and pharmaceutically acceptable salts, solvates, and hydrates thereof.

Compounds of Formula (I-j)

The present invention provides Compounds according to Formula (I-j):

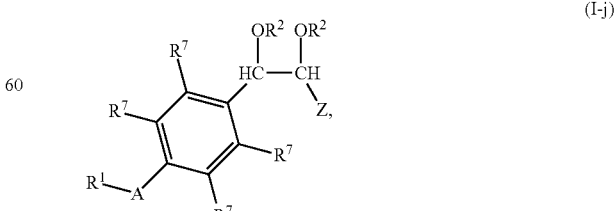

(I-j)

wherein:

$R^1$ is —H, —$C_1$-$C_6$ alkyl or —$C$—$C_6$ alkenyl;

each $R^2$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl;

each $R^7$ is independently —H, -aryl, or —$YR^3$;

each Y is independently —$NR^3$—, —O—, or —$SO_2$—;

each $R^3$ is independently —H, —$C_1$-$C_6$ alkyl, —$C$—$C_6$ alkenyl, —$C$—$C_6$ alkynyl, or —C(O)—$C_1$-$C_6$ alkyl;

A is —C(O)—, —$CHOR^b$—, —C(O)-(paraphenylene)-, or —$CHOR^b$-(paraphenylene)- wherein $R^b$ is —H, —$C_1$-$C_6$ alkyl, —C(O)—$C_1$-$C_6$ alkyl —C(O)—$C_1$-$C_6$ aryl, and the paraphenylene may be substituted with one to four $R^7$; and Z is —$C_1$-$C_{10}$ alkyl, and pharmaceutically acceptable salts, solvates, and hydrates thereof.

In one embodiment, $R^1$ is —$C_1$-$C_6$ alkyl.
In a specific embodiment, $R^1$ is ethyl.
In one embodiment, $R^1$ is —$C_2$-$C_6$ alkenyl.
In a specific embodiment, $R^1$ is —CH=$CH_2$.
In another specific embodiment, $R^1$ is —H.
In one embodiment, each $R^2$ is —C(O)—$C_1$-$C_6$ alkyl.
In a specific embodiment, each $R^2$ is acetyl.
In another embodiment, both $R^2$ groups combine to form combine to form —C(O)— or —C($R^a$)($R^a$)—, wherein each $R^a$ is independently —H, —$C_1$-$C_6$ alkyl or phenyl.
In another embodiment, both $R^2$ groups combine to form combine to form —C($R^a$)($R^a$)—, wherein each $R^a$ is independently —H or —$C_1$-$C_6$ alkyl.
In a specific embodiment, both $R^2$ groups combine to form combine to form —C($R^a$)($R^a$)—, wherein each $R^a$ is independently —H.
In another embodiment, both $R^2$ groups combine to form combine to form —C($R^a$)($R^a$)—, wherein each $R^a$ is independently —$C_1$-$C_6$ alkyl.
In a specific embodiment, both $R^2$ groups combine to form combine to form —C($R^a$)($R^a$)—, wherein each $R^a$ is independently —$CH_3$.
In a specific embodiment, both $R^2$ groups are —H.
In one embodiment, at least one $R^7$ is —H.
In another embodiment, all $R^7$ are —H.
In one embodiment, A is —C(O)—.
In another embodiment, A is —$CHOR^b$—.
In yet another embodiment, A is —$CHOR^b$— and $R^b$ is H.
In one embodiment, A is —$CHOR^b$—, and the carbon of A is of (S) chirality.
In another embodiment, A is —$CHOR^b$—, and the carbon of A is of (R) chirality.
In one embodiment, A is —$CHOR^b$—, the carbon of A is of (S) chirality, and $R^b$ is H.
In another embodiment, A is —$CHOR^b$—, the carbon of A is of (R) chirality, and $R^b$ is H.
In one embodiment, A is —C(O)-(paraphenylene)- or —$CHOR^b$—(paraphenylene)-.
In one embodiment, A is —C(O)-(paraphenylene)- or —$CHOR^b$—(paraphenylene)- and $R^7$ is —H.
In one embodiment, A is —C(O)-(paraphenylene)-.
In one embodiment, A is —$CHOR^b$—(paraphenylene)-.
In one embodiment, A is —$CHOR^b$—(paraphenylene)- wherein $R^b$ is —H.

In a specific embodiment, Z is hexyl.
In another specific embodiment, Z is heptyl.
In another specific embodiment, Z is octyl.
In one embodiment, each $R^7$ is —H.
In another embodiment, at least one $R^7$ is —H.
In one embodiment, at least one $R^7$ is $YR^3$.
In one embodiment, at least one $R^7$ is $YR^3$, wherein Y is $NR^3$.
In one embodiment, at least one $R^7$ is $YR^3$, wherein Y is O.
In one embodiment, at least one $R^7$ is $YR^3$, wherein Y is $NR^3$ and each $R^3$ is independently —H, —$C_1$-$C_6$ alkyl, or —C(O)—$C_1$-$C_6$ alkyl.
In one embodiment, at least one $R^7$ is $YR^3$, wherein Y is O and $R^3$ is —H, —$C_1$-$C_6$ alkyl, or —C(O)—$C_1$-$C_6$ alkyl.
In one embodiment, $R^3$ is —H.
In another embodiment, $R^3$ is methyl.
In yet another embodiment, $R^3$ is acetyl.

Illustrative examples of the Compounds of Formula (I-j) include the compounds of Formula (I-j') as set forth below:

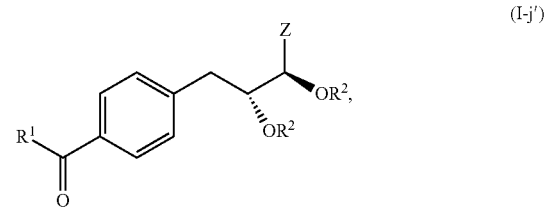

(I-j')

wherein $R^1$, $R^2$, and Z are as defined above for Formula (I-j).

Illustrative examples of Compounds of Formula (I-j') include:

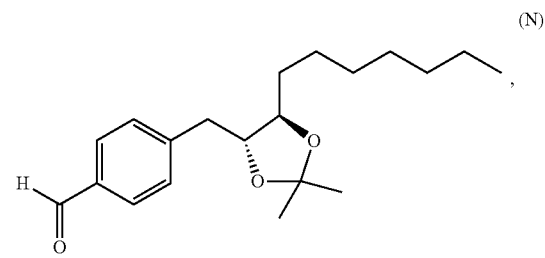

(N)

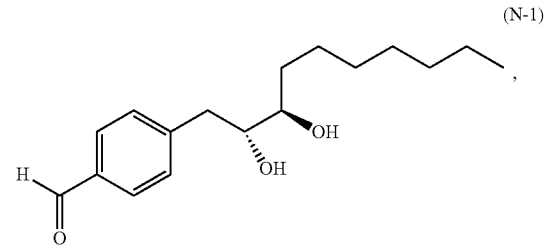

(N-1)

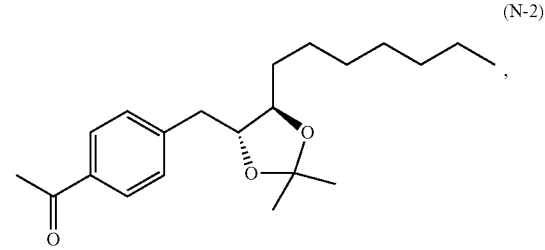

(N-2)

-continued
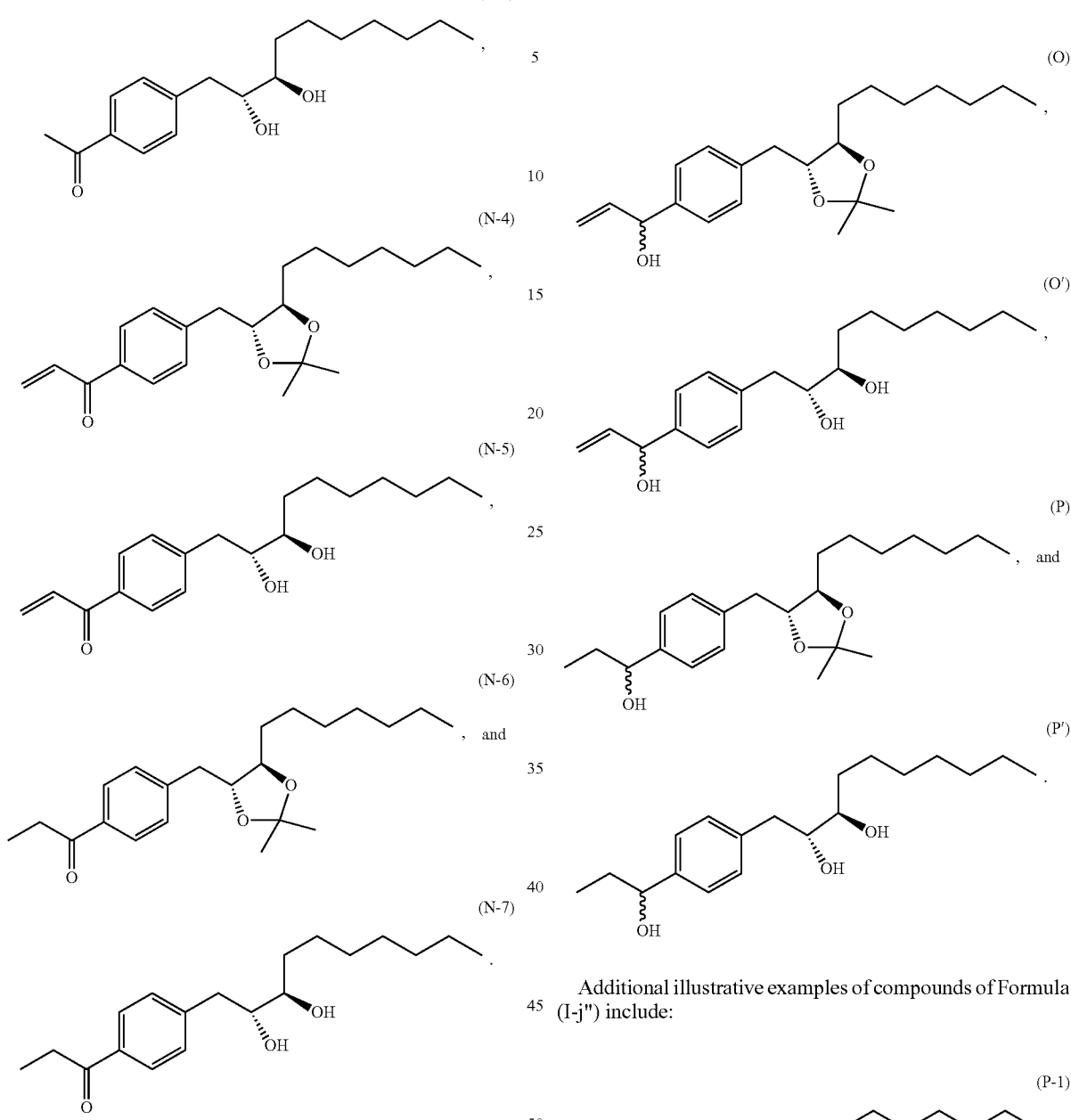
Additional illustrative examples of the Compounds of Formula (I-j) include the compounds of Formula (I-j″) as set forth below:
wherein $R^1$, $R^2$, and Z are as defined for Formula (I-j).
Illustrative examples of compounds of Formula (I-j″) include:
Additional illustrative examples of compounds of Formula (I-j″) include:
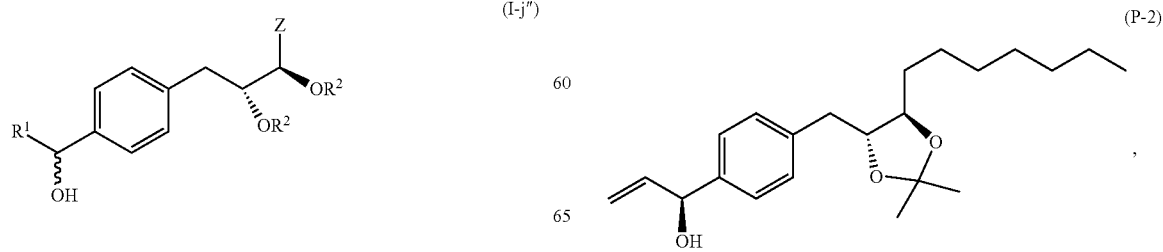

-continued

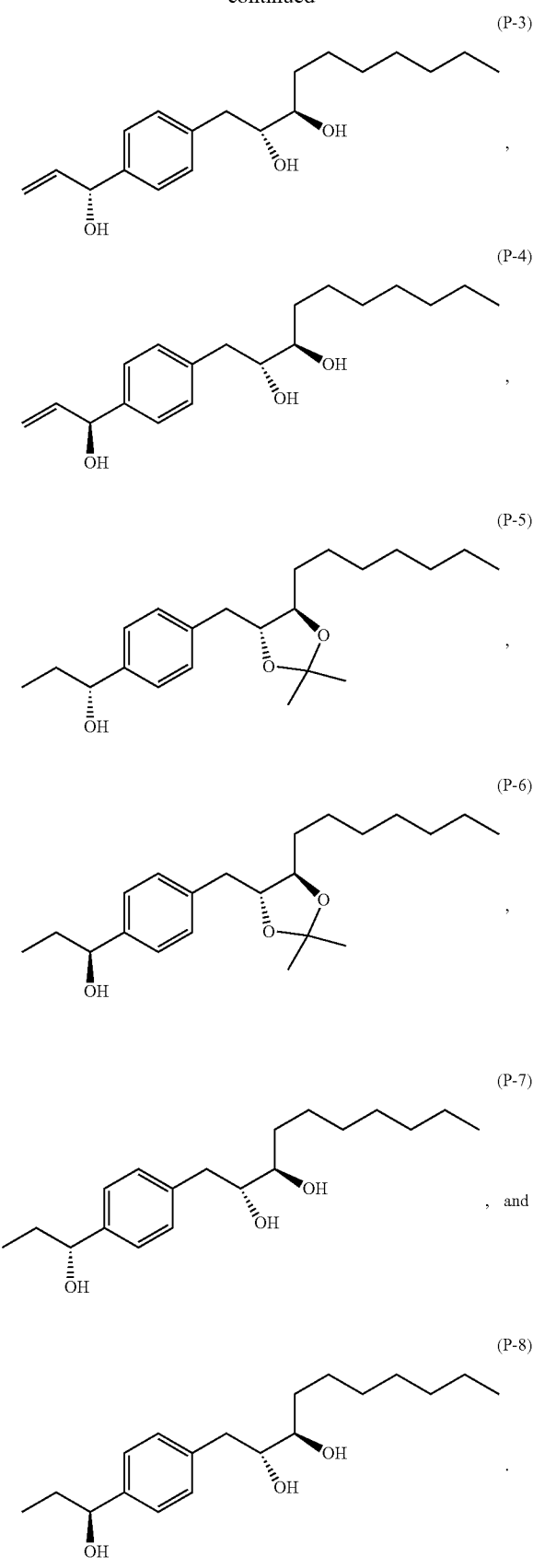

Compounds of Formula (I-k)

The present invention provides Compounds according to Formula (I-k):

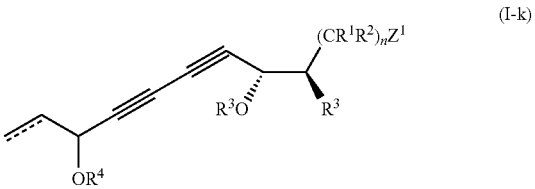

wherein n is 0-7;

$Z^1$ is $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl;

$R^1$ and $R^2$ are each independently —H, $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, aryl, —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl;

each $R^3$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl; and $R^4$ is —H, —$C_1$-$C_6$ alkyl, —$C_2$-$C_6$ alkenyl, —C(O)—$C_1$-$C_6$ alkyl, or —C(O)-aryl, and pharmaceutically acceptable salts, solvates, or hydrates thereof.

In one embodiment, n is 0.
In one embodiment, n is 1.
In one embodiment, n is 2.
In one embodiment, n is 6.
In one embodiment, $R^1$ and $R^2$ are both H.
In one embodiment, one or more $R^1$ is —$C_1$-$C_6$ alkyl.
In another embodiment, one $R^1$ is —$C_1$-$C_6$ alkyl.
In one embodiment, the carbon to which $R^1$ is attached has S stereochemistry.
In one embodiment, the carbon to which $R^1$ is attached has R stereochemistry.
In one embodiment, the carbon to which $R^2$ is attached has S stereochemistry.
In one embodiment, the carbon to which $R^2$ is attached has R stereochemistry.
In another embodiment, $R^1$ is H and one or more $R^2$ is —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl.

In another embodiment, $R^1$ is H and one $R^2$ is —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl.

In one embodiment, both $R^3$ are H.
In one embodiment, both $R^3$ are —$C_1$-$C_6$ alkyl, such as methyl.
In another embodiment, both $R^3$ are —C(O)$R^5$.

In another embodiment, both $R^3$ groups combine to form —C(O)—.

In a further embodiment, both $R^3$ groups combine to form —C(CH$_3$)$_2$—.

In one embodiment, $R^4$ is —H.

In one embodiment, $Z^1$ is $C_3$-$C_8$ monocyclic cycloalkyl.

In one embodiment, $Z^1$ is 5- or -6-membered monocyclic heteroaryl.

In one embodiment, $Z^1$ is 7- to 10-membered bicyclic heteroaryl.

In one embodiment, $Z^1$ is oxygen-containing 3- to 7-membered monocyclic heterocycle.

In one embodiment, $Z^1$ is aryl.

In one embodiment, $Z^1$ is cyclopropyl.

In another embodiment, $Z^1$ is cyclopentyl.

In another embodiment, $Z^1$ is cyclohexyl.

In another embodiment, $Z^1$ is phenyl.

Illustrative examples of the Compounds of Formula (I-k) include the compounds of Formula (I-k') as set forth below:

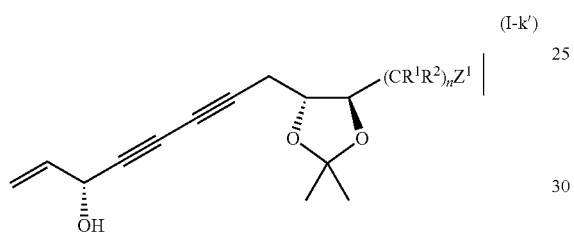

wherein n, $R^1$-$R^2$ and $Z^1$ are as defined for formula (I-k).

Illustrative examples of the Compounds of Formula (I-k) include the compounds of Formula (I-k") as set forth below:

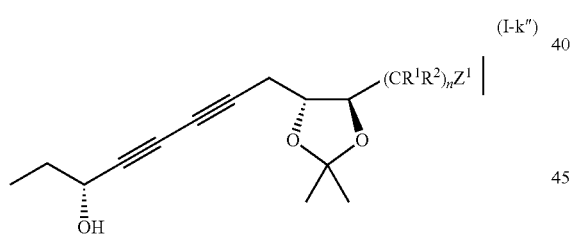

wherein n, $R^1$-$R^2$ and $Z^1$ are as defined for formula (I-k).

Illustrative examples of the Compounds of Formula (I-k) include the compounds of Formula (I-k'") as set forth below:

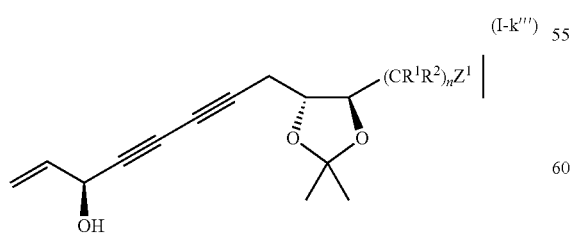

wherein n, $R^1$-$R^2$ and $Z^1$ are as defined for formula (I-k).

Illustrative examples of the Compounds of Formula (I-k) include the compounds of Formula (I-"") as set forth below:

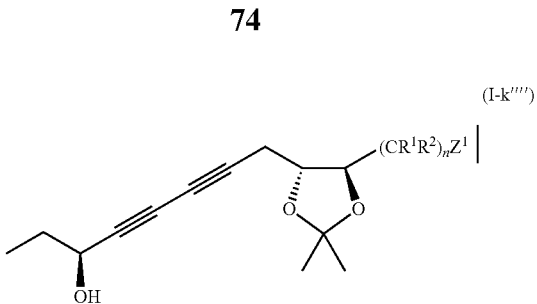

wherein n, $R^1$-$R^2$ and $Z^1$ are as defined for formula (I-k).

Illustrative compounds of Formula Ik are:

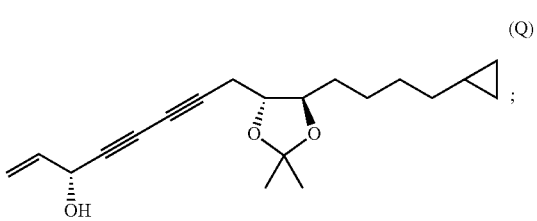
(Q)

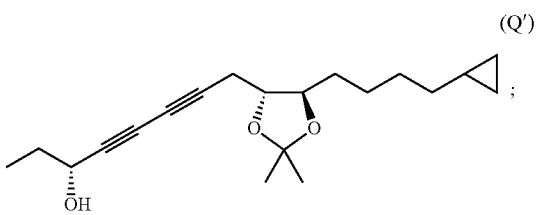
(Q')

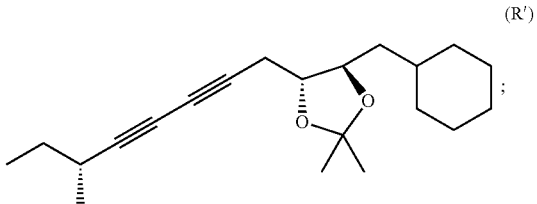
(R')

47

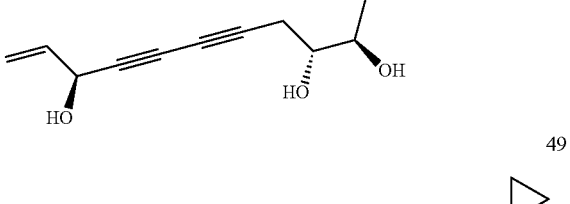
49

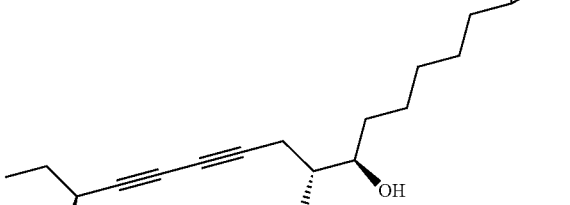

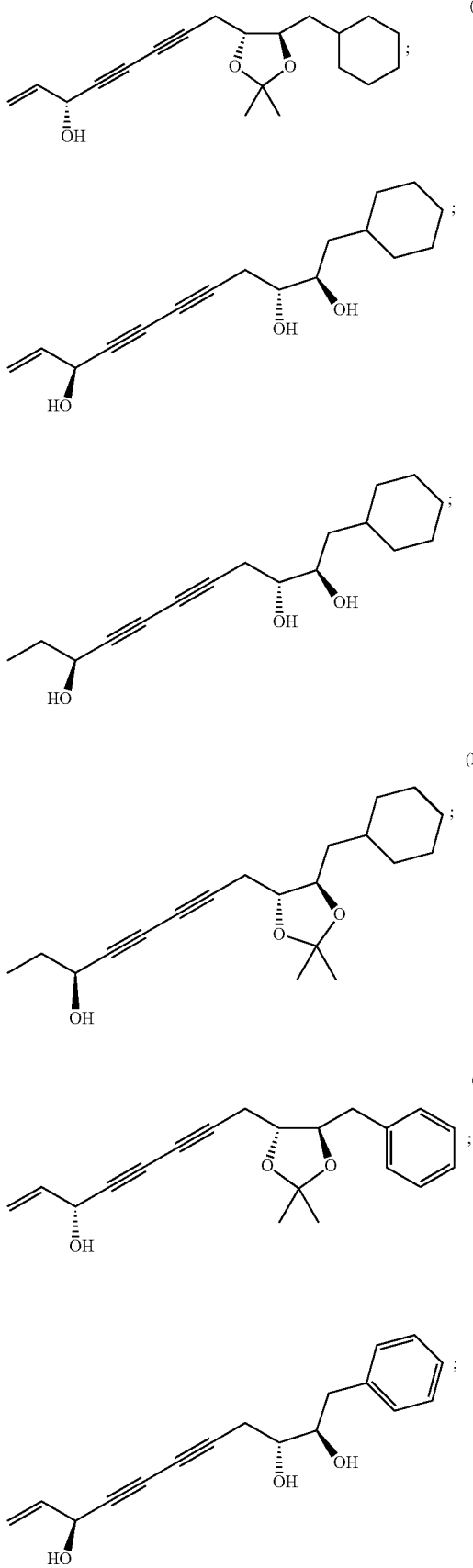

The present invention provides Compounds according to Formula (I-1):

$$\text{(I-1)}$$

wherein
n is 0-6;
$Z^1$ is $C_1$-$C_6$ alkyl;
$R^1$ and $R^2$ are each independently —H, $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, aryl, —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl;
or two $R^1$ groups on adjacent carbons combine to form $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl;
each $R^3$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl; and
$R^4$ is —H, —$C_1$-$C_6$ alkyl, —$C_2$-$C_6$ alkenyl, —C(O)—$C_1$-$C_6$ alkyl, or —C(O)-aryl,
and pharmaceutically acceptable salts, solvates, or hydrates thereof.
In one embodiment, n is 0.
In one embodiment, n is 1.
In one embodiment, n is 2.
In one embodiment, n is 6.
In one embodiment, $R^1$ and $R^2$ are both H.

In one embodiment, one or more $R^1$ is —$C_1$-$C_6$ alkyl.

In another embodiment, one $R^1$ is —$C_1$-$C_6$ alkyl.

In one embodiment, the carbon to which $R^1$ is attached has S stereochemistry.

In one embodiment, the carbon to which $R^1$ is attached has R stereochemistry.

In one embodiment, the carbon to which $R^2$ is attached has S stereochemistry.

In one embodiment, the carbon to which $R^2$ is attached has R stereochemistry.

In another embodiment, $R^1$ is H and one or more $R^2$ is —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl.

In another embodiment, $R^1$ is H and one $R^2$ is —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl.

In another embodiment, $R^1$ and $R^2$ combine to form a $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl group.

In one embodiment, $R^1$ and $R^2$ combine to form a $C_3$-$C_8$ monocyclic cycloalkyl group, such as a cyclopropyl, cyclobutyl, cyclopentyl, or cyclohexyl group.

In another embodiment, $R^1$ and $R^2$ combine to form a cyclopropyl group.

In one embodiment, both $R^3$ are H.

In one embodiment, both $R^3$ are —$C_1$-$C_6$ alkyl, such as methyl.

In another embodiment, both $R^3$ are —C(O)$R^5$.

In another embodiment, both $R^3$ groups combine to form —C(O)—.

In a further embodiment, both $R^3$ groups combine to form —C(CH$_3$)$_2$—.

In one embodiment, $R^4$ is —H.

In one embodiment, $Z^1$ is methyl.

In one embodiment, $Z^1$ is ethyl.

In one embodiment, $Z^1$ is propyl.

In one embodiment, $Z^1$ is butyl.

In one embodiment, $Z^1$ is sec-butyl.

In one embodiment, $Z^1$ is pentyl.

Illustrative compounds of Formula I-l are:

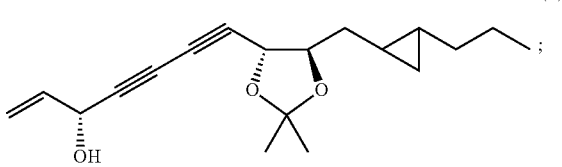

(T)

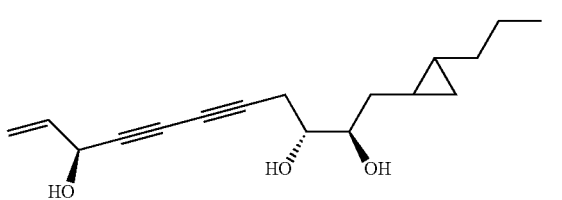

72

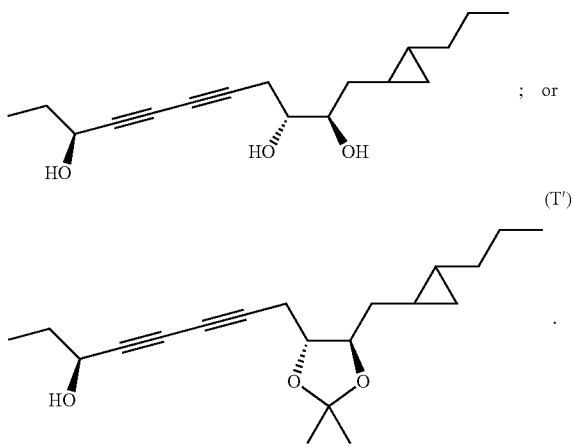

73

; or (T')

Compounds of Formula (I-m)

The present invention provides Compounds according to Formula (I-m):

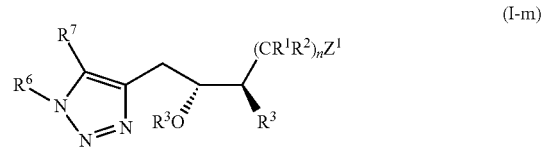

(I-m)

wherein n is 0-7;

$Z^1$ is $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl;

$R^1$ and $R^2$ are each independently —H, $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, aryl, —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl;

each $R^3$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl;

$R^6$ and $R^7$ are each independently —H, -aryl, —$C_1$-$C_6$ alkyl, ZC(O)—, ZOC(O)—, —X—Z, or —SO$_2$Z;

each X is independently —$C_1$-$C_6$ alkylene-, —$C_2$-$C_6$ alkenylene- or —$C_2$-$C_6$ alkynylene-, wherein the $C_1$-$C_6$ alkylene, —$C_2$-$C_6$ alkenylene- or —$C_2$-$C_6$ alkynylene- may be substituted with one or more $C_3$-$C_8$ monocyclic cycloalkyl, $C_3$-$C_8$ monocyclic cycloalkenyl, 5- or -6-membered monocyclic heteroaryl, 7- to 10-membered bicyclic heteroaryl, oxygen-containing 3- to 7-membered monocyclic heterocycle, aryl, —$C_1$-$C_6$ alkyl, -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl; and Z is —H, -aryl, —C$_1$-C$_6$ alkyl, —C$_2$-C$_6$ alkenyl, —C$_2$-C$_6$ alkynyl, —C$_3$-C$_8$ monocyclic cycloalkyl, —C$_3$-C$_8$ monocyclic cycloalkenyl, -(5 or -6-membered monocyclic heteroaryl) or -(7 to -10-membered bicyclic heteroaryl), and pharmaceutically acceptable salts, solvates, or hydrates thereof.

In one embodiment, n is 1.

In one embodiment, n is 2.

In one embodiment, n is 6.

In one embodiment, n is 7.

In one embodiment, R$^1$ and R$^2$ are both H.

In one embodiment, one or more R$^1$ is —C$_1$-C$_6$ alkyl.

In another embodiment, one R$^1$ is —C$_1$-C$_6$ alkyl.

In one embodiment, the carbon to which R$^1$ is attached has S stereochemistry.

In one embodiment, the carbon to which R$^1$ is attached has R stereochemistry.

In one embodiment, the carbon to which R$^2$ is attached has S stereochemistry.

In one embodiment, the carbon to which R$^2$ is attached has R stereochemistry.

In another embodiment, R$^1$ is H and one or more R$^2$ is —C$_1$-C$_6$ alkyl, -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl.

In another embodiment, R$^1$ is H and one R$^2$ is —C$_1$-C$_6$ alkyl, -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl.

In one embodiment, both R$^3$ are H.

In one embodiment, both R$^3$ are —C$_1$-C$_6$ alkyl, such as methyl.

In another embodiment, both R$^3$ are —C(O)R$^5$.

In another embodiment, both R$^3$ groups combine to form —C(O)—.

In a further embodiment, both R$^3$ groups combine to form —C(CH$_3$)$_2$—.

In one embodiment, R$^6$ and R$^7$ are —H.

In one embodiment, R$^6$ is benzyl.

In another embodiment, R$^7$ is —H.

In yet another embodiment, R$^7$ is propyl.

In still another embodiment, R$^7$ is propyl substituted by OH.

In one embodiment, X is optionally substituted propylene and Z is H.

In another embodiment, X is propylene substituted by OH and Z is H.

In one embodiment, Z$^1$ is methyl.

In one embodiment, Z$^1$ is ethyl.

In one embodiment, Z$^1$ is propyl.

In one embodiment, Z$^1$ is butyl.

In one embodiment, Z$^1$ is sec-butyl.

In one embodiment, Z$^1$ is pentyl.

Illustrative compounds of Formula (I-m) include:

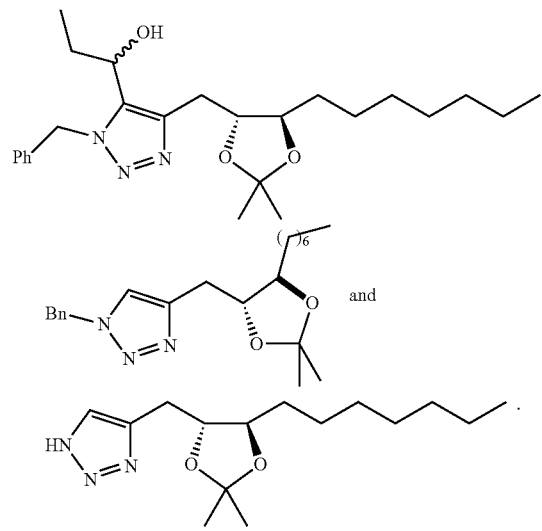

Compounds of Formula (I-n)

The present invention provides Compounds according to Formula (I-n):

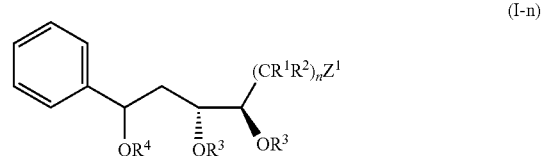

(I-n)

wherein n is 0-7;

Z$^1$ is C$_3$-C$_8$ monocyclic cycloalkyl, C$_3$-C$_8$ monocyclic cycloalkenyl, 5- or -6-membered monocyclic heteroaryl, 7- to 10-membered bicyclic heteroaryl, oxygen-containing 3- to 7-membered monocyclic heterocycle, or aryl;

R$^1$ and R$^2$ are each independently —H, C$_3$-C$_8$ monocyclic cycloalkyl, C$_3$-C$_8$ monocyclic cycloalkenyl, 5- or -6-membered monocyclic heteroaryl, 7- to 10-membered bicyclic heteroaryl, oxygen-containing 3- to 7-membered monocyclic heterocycle, aryl, —C$_1$-C$_6$ alkyl, -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl;

each R$^3$ is independently —H, —C$_1$-C$_6$ alkyl, or —C(O)—C$_1$-C$_6$ alkyl, or both R$^2$ groups combine to form —C(O)— or —C(R$^a$)(R$^a$)—, wherein each R$^a$ is independently —H, —C$_1$-C$_6$ alkyl or phenyl;

R$^4$ is —H, —C$_1$-C$_6$ alkyl, —C$_2$-C$_6$ alkenyl, —C(O)—C$_1$-C$_6$ alkyl, or —C(O)-aryl, and pharmaceutically acceptable salts, solvates, or hydrates thereof.

In one embodiment, n is 1.

In one embodiment, n is 2.

In one embodiment, n is 6.

In one embodiment, n is 7.

In one embodiment, R$^1$ and R$^2$ are both H.

In one embodiment, both R$^3$ are H.

In one embodiment, both R$^3$ are —C$_1$-C$_6$ alkyl, such as methyl.

In another embodiment, both R³ are —C(O)CH₃.

In another embodiment, both R³ groups combine to form —C(O)—.

In a further embodiment, both R³ groups combine to form —C(CH₃)₂—.

In one embodiment, R⁴ is —H.

Illustrative compounds of Formula (I-n) are

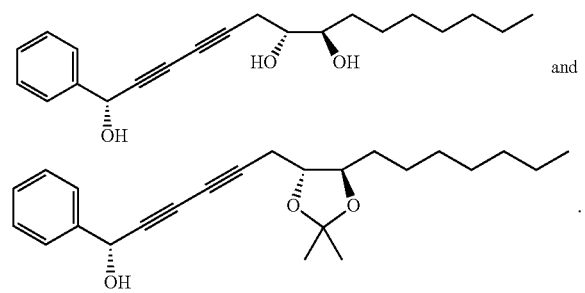

and

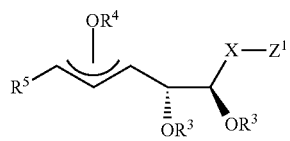

In one embodiment, compounds of the invention include compounds of Formula (I-o):

$$\text{(I-o)}$$

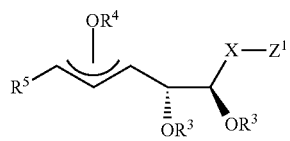

wherein

X is —$C_1$-$C_6$ alkylene-, —$C_2$-$C_6$ alkenylene- or —$C_2$-$C_6$ alkynylene-;

$Z^1$ is $C_1$-$C_6$ alkyl;

each $R^3$ is independently —H, —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl, $R^4$ is —H, —$C_1$-$C_6$ alkyl, —$C_2$-$C_6$ alkenyl, —C(O)—$C_1$-$C_6$ alkyl, or —C(O)-aryl;

$R^5$ is optionally substituted aryl, and pharmaceutically acceptable salts, solvates, or hydrates thereof.

In one embodiment, X is —$C_1$-$C_6$ alkylene-.

In one embodiment, X is hexylene.

In one embodiment, X is pentylene.

In one embodiment, Z is methyl.

In one embodiment, both R³ are H.

In one embodiment, both R³ are —$C_1$-$C_6$ alkyl, such as methyl.

In another embodiment, both R³ are —C(O)CH₃.

In another embodiment, both R³ groups combine to form —C(O)—.

In a further embodiment, both R³ groups combine to form —C(CH₃)₂—.

In one embodiment, R⁴ is —H.

In another embodiment, R⁴ is methyl.

In one embodiment, R⁵ is phenyl.

Illustrative compounds of Formula (I-o) include

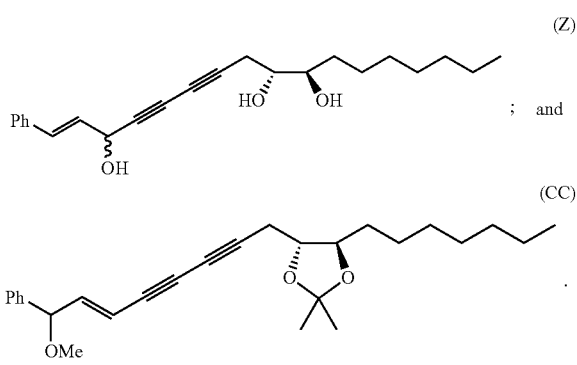

In one embodiment, Compounds of the invention, for example, any one of Formula (I), or (I-a)-(I-o), do not include panaxytriol,

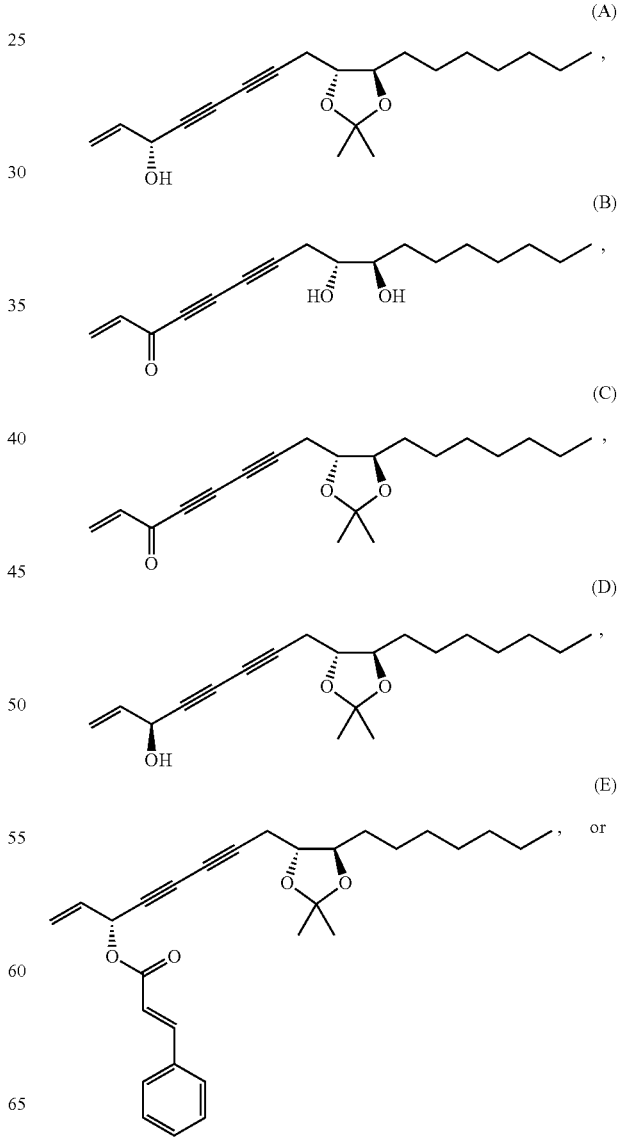

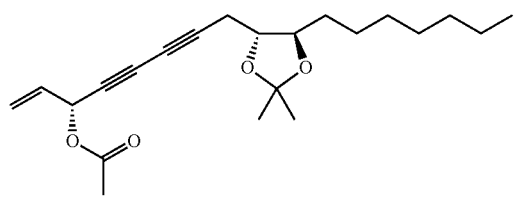
(F)
or any combination thereof.
In another embodiment, Compounds of the invention, for example, any one of Formula (I) or (I-a)-(I-o), do not include panaxytriol,
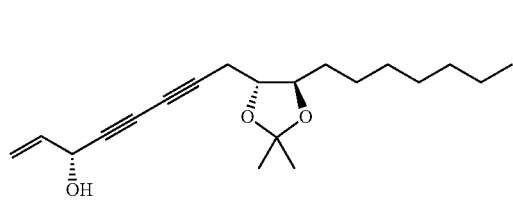
(A)
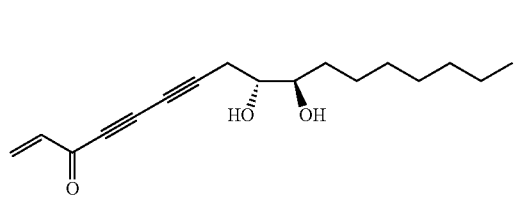
(B)
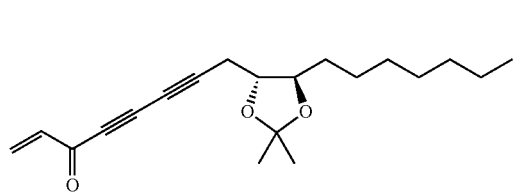
(C)
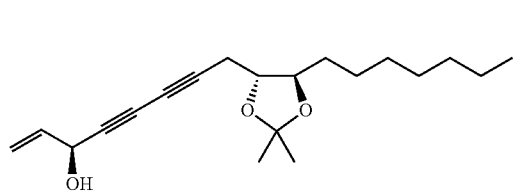
(D)
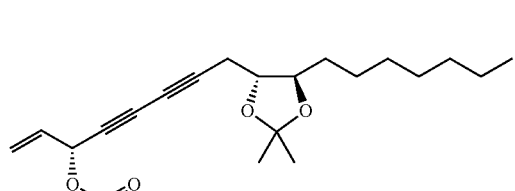
(E)
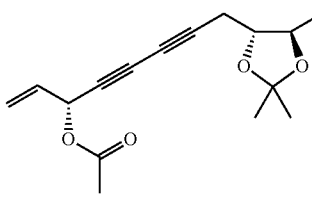
(F)
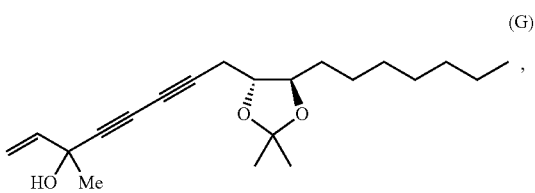
(G)
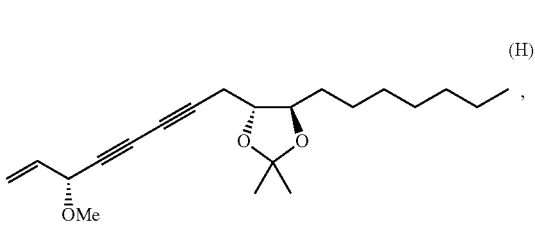
(H)
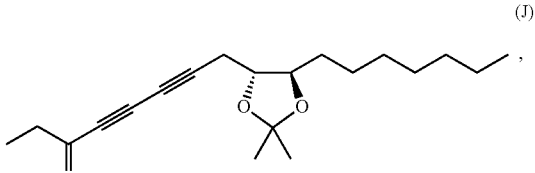
(J)
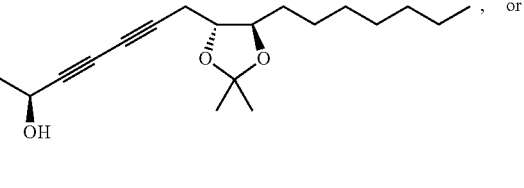
(K), or
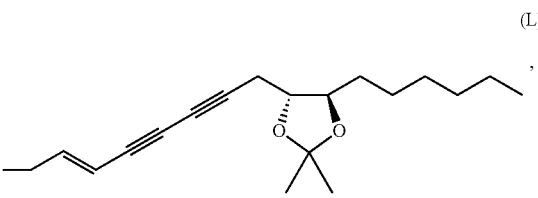
(L)
or any combination thereof.
In another embodiment, Compounds of the invention, for example, any one of Formula (I) or (I-a)-(I-o), do not include panaxacol, dihydropanaxacol, or 10-acetylpanaxytriol.

4.4 Methods for Making Compounds

Compounds of Formula (I)

Scheme 1 sets forth methodology that is useful for making the Compounds of formula (I), wherein A is —C≡C—C≡C— and m is 1.

of formula 6 can be derivatized using methodology known to one skilled in organic chemistry to provide the Compounds of formula (I), wherein A is —C≡C—C≡C—, m is 1, and $R^2$ is —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl. Alternatively, I in compound 3 can be Br.

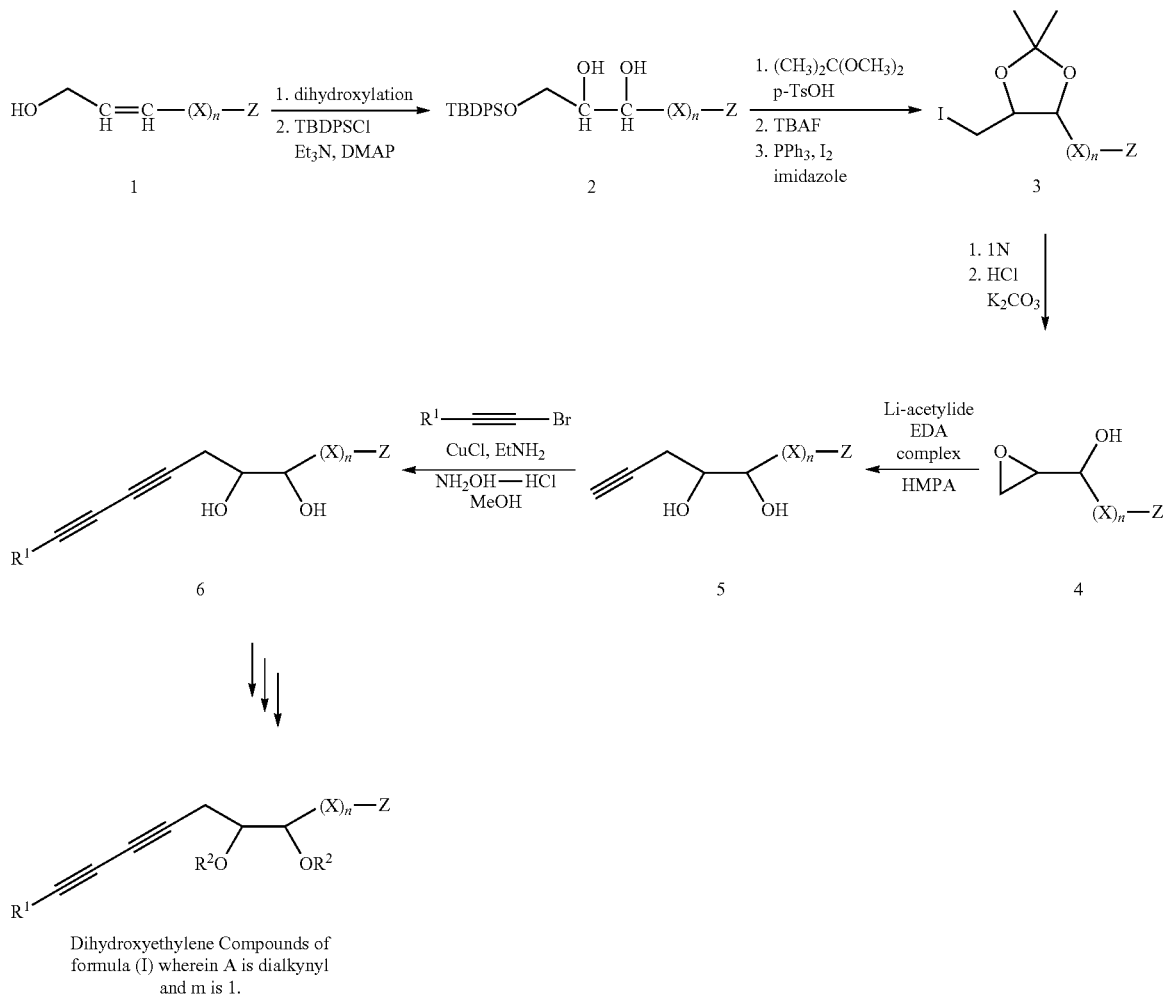

Scheme 1

Dihydroxyethylene Compounds of formula (I) wherein A is dialkynyl and m is 1.

wherein $R^1$, $R^2$, X, Z and n are as defined above for the Compounds of formula (I), A is —C≡C—C≡C— and m is 1.

The double bond of a compound of formula 1 can be dihydroxylated, followed by protection of the primary alcohol as its TBDPS ether to provide a diol of formula 2. Following acetonide protection of the diol, the TBDPS group can be removed and the resultant primary hydroxy group converted to an iodide to provide a compound of formula 3. Removal of the acetonide group of 3 and epoxide formation from the resultant iodo diol provides epoxide 4, which can then be converted to an alkynyl compound of formula 5 upon reaction with a lithium acetylide EDA complex. Coupling of the terminal alkynyl group of 5 with an alkynyl bromide of formula $R^1$—C≡C—Br provides a dialkynyl compound of formula 6, where $R^2$ of the Compounds is —H. Compounds The compounds of formula 1 can be made by reacting a compound of formula Z—(X)$_n$—CHO with (carbethoxymethylene)triphenylphosphorane using a Wittig reaction (See March, *Advanced Organic Chemistry: Reactions, Mechanisms, and Structure*, fourth edition, John Wiley and Sons, 1992, p. 956-963), followed by reduction of the ethyl ester group of the resultant product using, for example, DIBAL, to provide the compounds of formula 1.

The compounds of formula $R^1$—C≡C—Br can be made by reacting a terminal acetylene of formula $R^1$—C≡CH with NBS in the presence of silver nitrate.

Scheme 2 sets forth methodology useful for making the Compounds of formula (I), wherein A is —C≡C—C≡C— and m is an integer ranging from 2 to 6.

Scheme 2

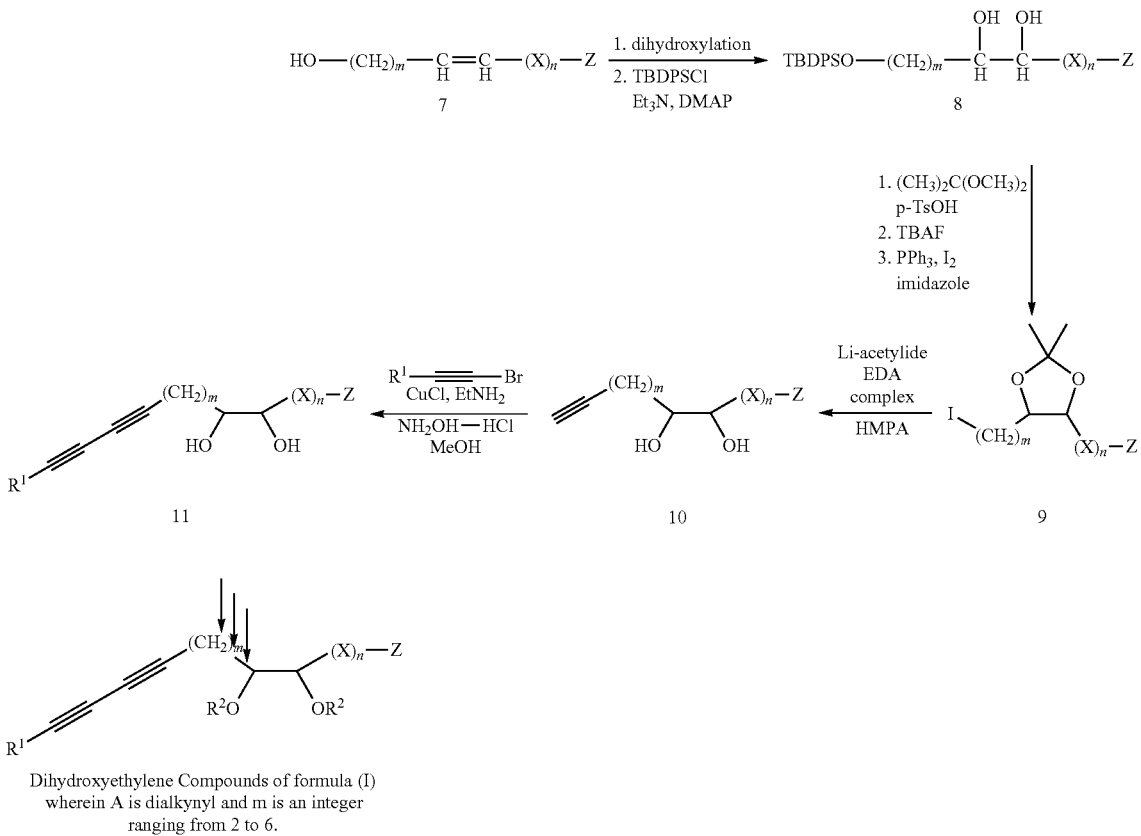

wherein $R^1$, $R^2$, X, Z and n are as defined above for the Compounds of formula (I); A is —C≡C—C≡C— and m is an integer ranging from 2 to 6.

The double bond of a compound of formula 7 can be dihydroxylated, followed by protection of the primary alcohol as its TBDPS ether to provide a diol of formula 8. Following acetonide protection of the diol, the TBDPS group can be removed and the resultant hydroxy group converted to an iodide to provide a compound of formula 9. The compound of formula 9 can then be reacted with a lithium acetylide EDA complex to provide an alkynyl compound of formula 10. Coupling of 10 with an alkynyl bromide of formula $R^1$—C≡C—Br provides a dialkynyl compound of formula 11, where $R^2$ of the Compounds of formula (I) is —H. Compounds of formula 11 can be derivatized using methodology known to one skilled in organic chemistry to provide the Compounds of formula (I), wherein A is —C≡C—C≡C—, m is an integer ranging from 2 to 6, and $R^2$ is —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl.

The compounds of formula 7 can be made by reacting a compound of formula Z—(X)$_n$—CHO with a compound of formula EtOC(O)—(CH$_2$)$_m$—CH$_2$PPh$_3$ using a Wittig reaction (See March, pages 956-963), followed by reduction of the ethyl ester group of the resultant product using, for example, DIBAL, to provide the compounds of formula 7.

Scheme 3 sets forth methodology useful for making the Compounds of Formula (I), wherein A is -(para)-phenylene- and $R^1$ is ($R^3$)($R^4$)C(H)—, or an oxygen-containing -3 to -7-membered monocyclic heterocycle, and for making Compounds of Formula (I-j).

Scheme 3

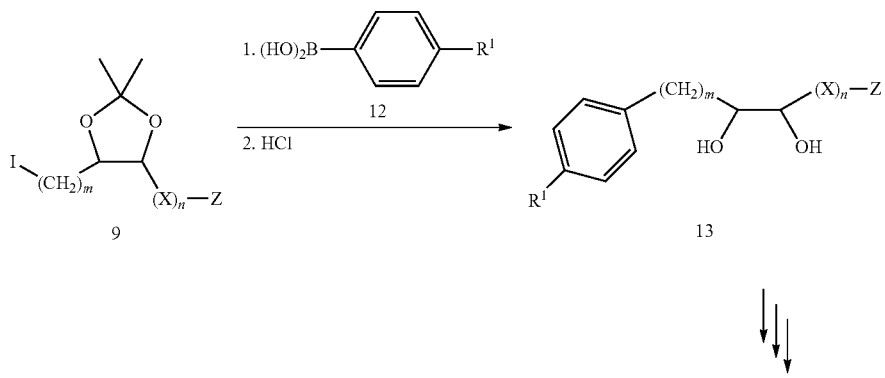

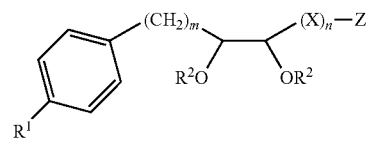

Dihydroxyethylene Compounds of formula (I), wherein A is -(para)-phenylene and $R^1$ is $(R^3)(R^4)C(H)-$ or an oxygen-containing -3 to -7-membered monocyclic heterocycle wherein $R^2$, X, Z, m and n are as defined above for the Compounds of formula (I), $R^1$ is $(R^3)(R^4)C(H)—$ or an oxygen-containing -3 to -7-membered monocyclic heterocycle.

An iodo compound of formula 9 can be coupled with a phenyl boronic acid compound of formula 12 using Suzuki coupling methodology, for example, as set forth in Zapf et al., *Transition Metals for Organic Synthesis* 211-229 (2d ed. 2004). Subsequent acetonide removal provides a diol compound of formula 13, where $R^2$ of the Compounds of formula (I) is —H. Compounds of formula 13 can be derivatized using methodology known to one skilled in organic chemistry to provide the Compounds of formula (I), wherein A is -(para)-phenylene-, $R^1$ is $(R^3)(R^4)C(H)—$ or an oxygen-containing -3 to -7-membered monocyclic heterocycle, and $R^2$ is —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl.

The phenyl boronic acid compounds of formula 12 may be commercially available, or alternatively, can be made by first reacting the corresponding phenyl halide with lithium or magnesium to make a lithium or Grignard reagent. The lithium or Grignard reagent can then be reacted with trimethylborate to form a boronic acid ester which is then hydrolyzed using, for example, HCl to provide a boronic acid compound of formula 12.

Alternatively, the phenyl-alkyl coupling depicted in Scheme 3 can be accomplished using a B-alkyl Suzuki-Miyaura coupling reaction. Thus, the boronate group can be appended instead to the alkyl chain bearing the 1,2-diol, which is then coupled to a chloro-, bromo-, or iodo-substituted aryl group using a palladium catalyst, e.g. tetrakistriphenylphospine palladium.

Scheme 3A sets forth methodology useful for making compounds of Formula (I-j).

Scheme 3A

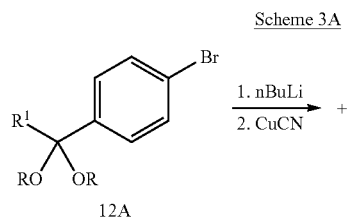

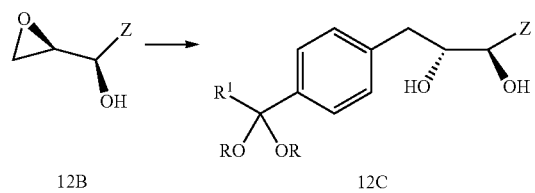

A bromo compound of formula 12A can be lithiated and used to open an epoxide using a copper catalyst, e.g. as described in Zapf et al., *Transition Metals for Organic Synthesis* (2d ed. 2004). For example, a 4-bromobenzene acetal, e.g. 4-bromobenzaldehyde dimethylacetal, is lithiated with a lithium base, e.g. an alkyl lithium, for example, n-butyl lithium (nBuLi). Next, a copper salt is added, e.g. copper cyanide, then an epoxide is added, for example, (R)-1-((R)-oxiran-2-yl)-octan-1-ol. The reaction may be monitored using standard techniques, e.g. TLC or HPLC, then quenched, and the product purified. The diol may be protected, e.g. as an acetonide. The aldehyde may be deprotected, then alkylated, for example using a Gringard reagent, yielding a secondary alcohol at the aldehyde position. The reactions can be performed at reduced temperature, e.g. about −78° C. to about −30° C., and/or may be warmed to about room temperature. Specific stereoisomers can be made using appropriate stereoisomers of the epoxide. Pure enantiomers can be isolated by chiral chromatography or derivatization of the product with a chiral auxiliary and purification. Alternatively, enantiomericly pure products may be made by stereoselectively reducing the product aldehyde, or oxidizing the product secondary alcohol, optionally with protection of the diol, to a ketone then stereoselectively reducing the ketone to an enantiospecific product secondary alcohol. The oxidation and stereoselective reduction can be performed using methods disclosed herein or such as those disclosed in March, Ed., *Advanced Organic Chemistry*, 4th ed. Wiley, (1992) p. 1158-1238. Protection of the diol can be accomplished using methods disclosed herein and in Green, et al., Eds. *Greene's Protective Groups in Organic Synthesis*, 4th ed. Wiley, (2007) p. 299-366. Compounds (M), (N), (O), and (P) can be produced using the method of Scheme 3A.

Compounds of Formula (I-b) and (I-k)

Scheme 4 sets forth methodology useful for making the Compounds of formula (I-b) or (I-k), wherein m is 1.

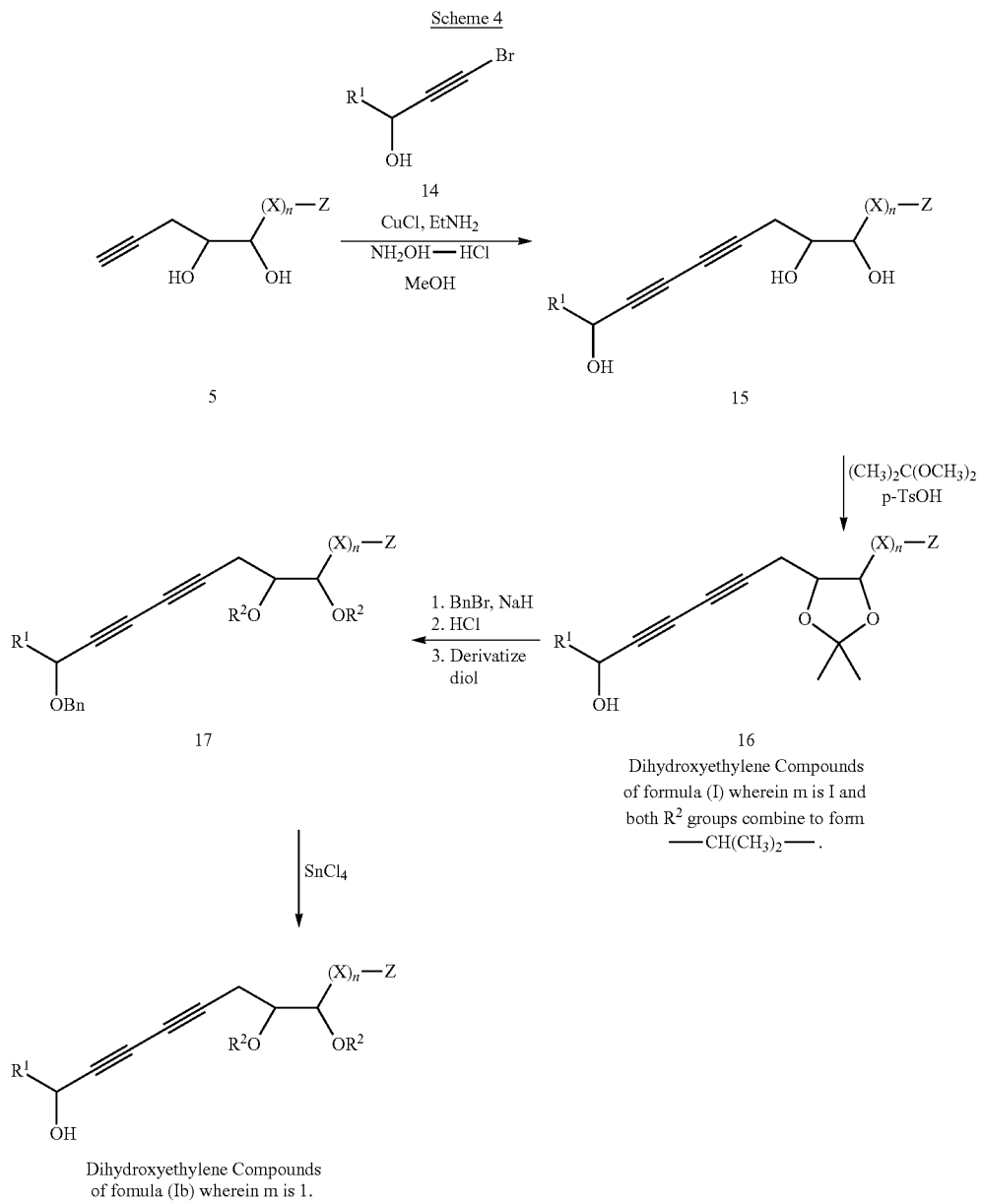

wherein $R^1$, $R^2$, X, Z and n are as defined above for the Compounds of formula (I-b), and m is 1.

A terminal alkyne of formula 5 can be coupled with an alkynyl bromide of formula 14 to provide a dialkynyl compound of formula 15. The diol group of a compound of formula 15 can be protected as its acetonide derivative to provide a compound of formula 16, which corresponds to the Compounds of formula (I-b) or (I-k), wherein m is 1 and both $R^2$ groups combine to form —$CH_2$—. Alternatively, the propargylic hydroxyl group of the compounds of formula 16 may be protected as its benzyl ether followed by removal of the acetonide group using HCl and derivatization of the resultant diol to provide the benzyl protected intermediate compounds of formula 17. The compounds of formula 17 can then be reacted with $SnCl_4$ to remove the benzyl protecting group and provide the compounds of formula (I-b) or (I-k), wherein m is 1 and $R^2$ is other than that wherein both $R^2$ groups combine to form —$CH_2$—.

A compound of formula 14 can be made by reacting an aldehyde of formula $R^1$—CHO with HC≡C—MgBr, followed by bromination of the resultant Grignard adduct using NBS in the presence of silver nitrate.

Scheme 5 sets forth methodology useful for making the Compounds of formula (I-b) or (I-k), wherein m is an integer ranging from 2 to 6.

Scheme 5

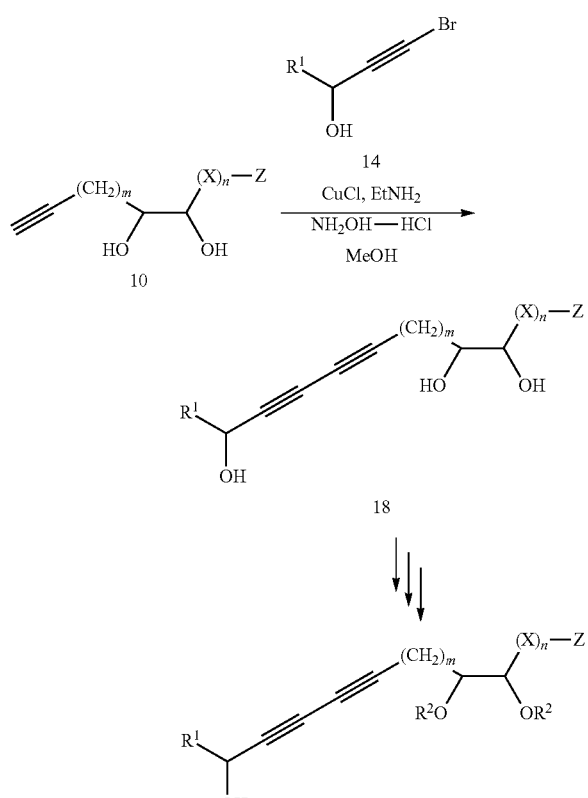

Dihydroxyethylene Compounds of formula (Ib) wherein m is an integer ranging from 2 to 6 wherein $R^1$, $R^2$, X, Z and n are as defined above for the Compounds of formula (I-b) or (I-k), and m is an integer ranging from 2 to 6.

A terminal alkyne of formula 10 can be coupled with an alkynyl bromide of formula 14 to provide a dialkynyl compound of formula 18. The diol group of a compound of formula 18 can be derivatized using methodology known to one skilled in organic chemistry to provide the Compounds of formula (I-b) or (I-k), wherein m is an integer ranging from 2 to 6.

Compounds of Formula (I-c) and (I-g)

Scheme 6 sets forth methodology useful for making the Compounds of formula (I-c).

Scheme 6 wherein $R^1$, $R^2$, X, Z, m and n are as defined above for the Compounds of formula (I-c) or (I-g).

An iodo compound of formula 9 can be coupled with a biphenyl boronic acid compound of formula 19 using Suzuki coupling methodology, followed by acetonide removal to provide a diol compound of formula 20, where $R^2$ of the Compounds is —H. Compounds of formula 20 can be derivatized using methodology known to one skilled in organic chemistry to provide the Compounds of formula (I-c), wherein $R^1$ is $(R^3)(R^4)C(H)$— or an oxygen-containing -3 to -7-membered monocyclic heterocycle, and $R^2$ is —$C_1$-$C_6$ alkyl, or —C(O)—$C_1$-$C_6$ alkyl, or both $R^2$ groups combine to form —C(O)— or —$C(R^a)(R^a)$—, wherein each $R^a$ is independently —H, —$C_1$-$C_6$ alkyl or phenyl.

The compounds of formula 19 may be commercially available or, if not commercially available, can be made by coupling two appropriately substituted phenyl compounds using Suzuki coupling methodology as described, for example, in Miyaura et al., *Synth. Commun.*, 11:513 (1981).

Compounds of Formula (I-d) and (I-e)

Scheme 7 sets forth methodology useful for making the Compounds of formula (I-d), wherein A is —C≡C—C≡C— and m is 1.

Scheme 7

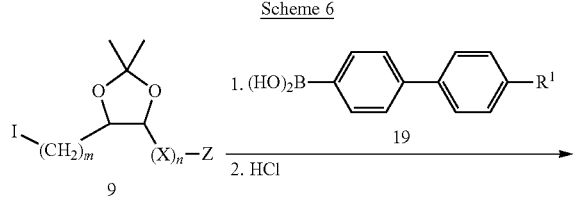

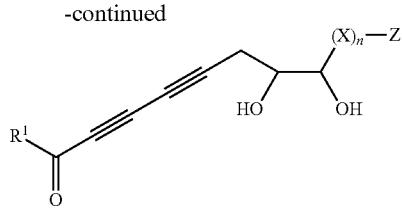

21

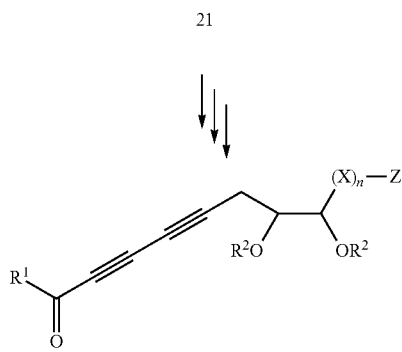

wherein $R^1$, $R^2$, X, Z and n are as defined above for the Compounds of formula (I-d), and m is 1. The methodology is useful for forming 3-keto Compounds of the invention, including Formula (I-e).

A compound of formula 15 (which can be made using the method described in Scheme 1), can be oxidized using manganese dioxide to provide a diol of formula 21, where $R^2$ of the Compounds is —H. Compounds of formula 21 can be derivatized using methodology known to one skilled in organic chemistry to provide the Compounds of formula (I-d), wherein A is —C≡C—C≡C—, m is 1, and $R^2$ is —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl.

Scheme 8 sets forth methodology useful for making the Compounds of formula (I-d), wherein A is —C≡C—C≡C— and m is an integer ranging from 2 to 6.

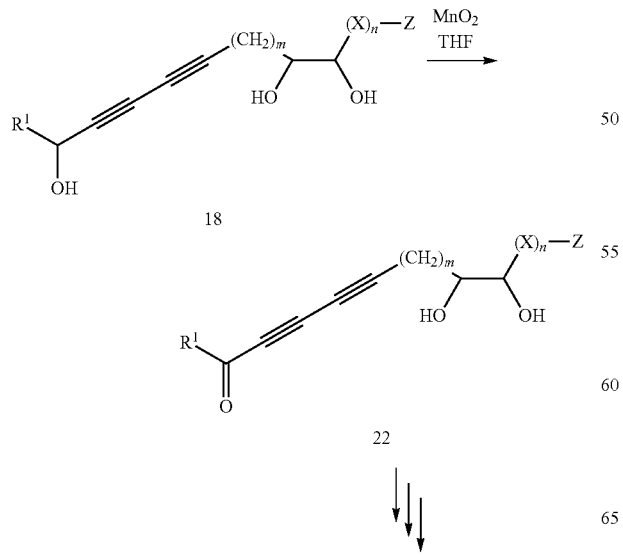

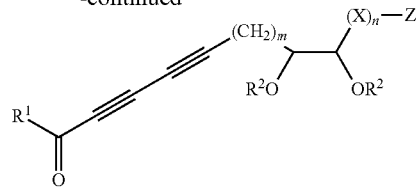

Dihydroxyethylene Compounds of formula (Id)
wherein A is dialkynyl
and m is an integer ranging from 2 to 6 wherein $R^1$, $R^2$, X, Z and n are as defined above for the Compounds of formula (I-d), and m is an integer ranging from 2 to 6.

A compound of formula 18 can be oxidized using manganese dioxide to provide the diol of formula 22, where $R^2$ of the Compounds is —H. Compounds of formula 22 can be derivatized using methodology known to one skilled in organic chemistry to provide the Compounds of formula (I-d), wherein A is —C≡C—C≡C—, m is an integer ranging from 2 to 6, and $R^2$ is —$C_1$-$C_6$ alkyl, or —C(O)—$C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl.

Scheme 9 sets forth methodology useful for making the Compounds of formula (I-d), wherein A is -(para)-phenylene-.

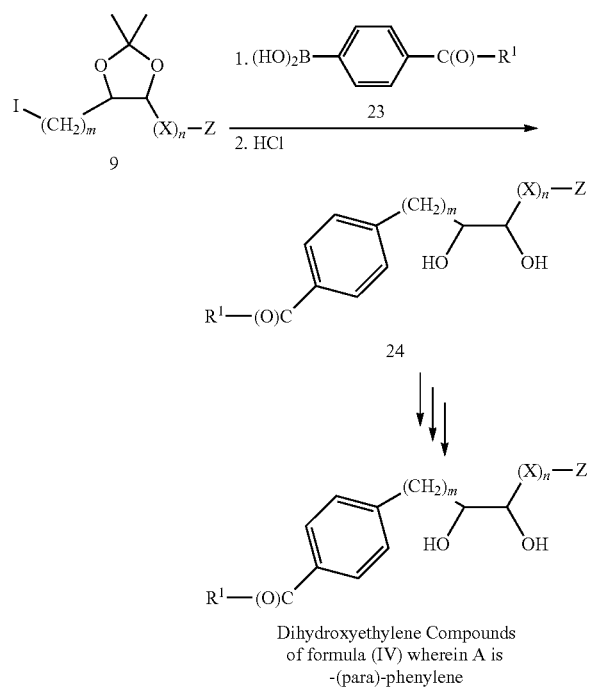

Dihydroxyethylene Compounds
of formula (IV) wherein A is
-(para)-phenylene wherein $R^1$, $R^2$, X, Z, m and n are as defined above for the Compounds of formula (I-d).

An iodo compound of formula 9 can be coupled with a biphenyl boronic acid compound of formula 23 using Suzuki coupling methodology, followed by acid mediated removal of the acetonide group to provide the diol of formula 24. Diol 24 can be left as is, or which can be derivatized using methodology known to one skilled in organic chemistry to provide the remainder of the Compounds of formula (I-d), wherein A is -(para)-phenylene-.

Alternatively, the phenyl-alkyl coupling depicted in Scheme 3 can be accomplished using a B-alkyl Suzuki-Miyaura coupling reaction. Thus, the boronate group can be appended instead to the alkyl chain bearing the 1,2-diol, which is then coupled to a chloro-, bromo-, or iodo-substituted aryl group using a palladium catalyst, e.g. tetrakistriphenylphospine palladium.

Scheme 10 sets forth methodology useful for making both the (R) and (S) configurations of the chiral propargylic carbon atom present in the Compounds of formula (I-b) or (I-k), or alternatively, in the Compounds of formulas (I) and (I-c) when $R^1$ is $(R^3)(R^4)C(H)$— and A is —C≡C—C≡C—.

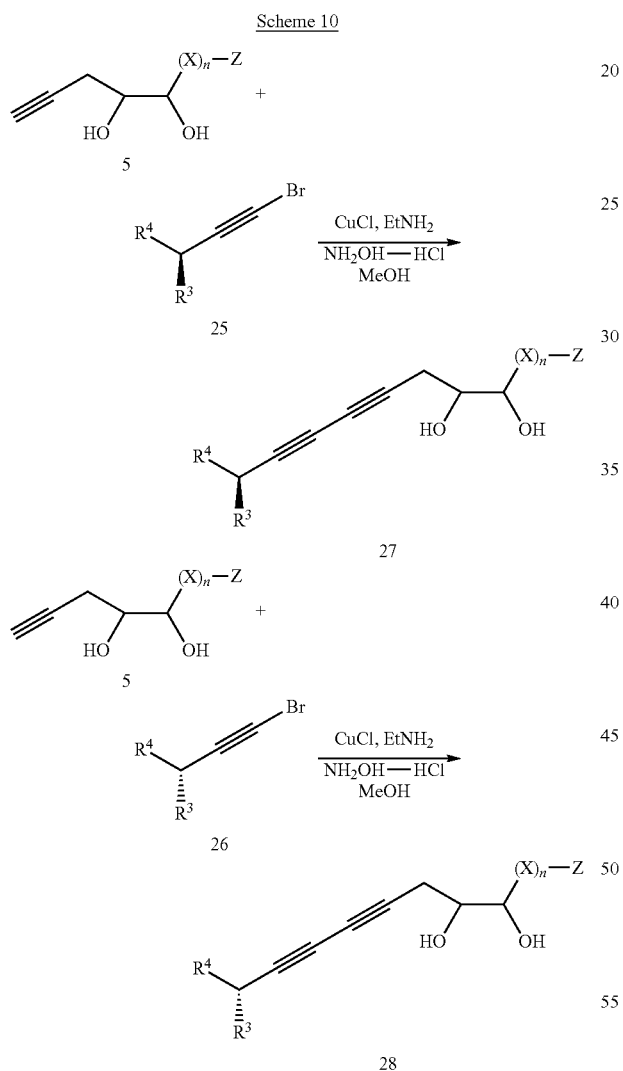

A terminal alkynyl intermediate of, for example, formula 5, can be reacted with a chiral alkynyl bromide of formula 25 or formula 26 to provide the Compounds of formulas 27 and 28, respectively. It is to be noted that the Compounds of formula 5 are depicted as the starting material in Scheme 10 for sake of example only. The general methodology outlined in Scheme 10 can also be applied to terminal alkynyl intermediate 10, to provide both the R and S propargylic stereoisomers in the Compounds of formula (I-b) or (I-k), or alternatively, in the Compounds of formulas (I) and (I-c) when $R^1$ is $(R^3)(R^4)C(H)$— and A is —C≡C—C≡C—.

Scheme 11 sets forth methodology useful for making the chiral alkynyl bromide intermediates of formulas 25 and 26.

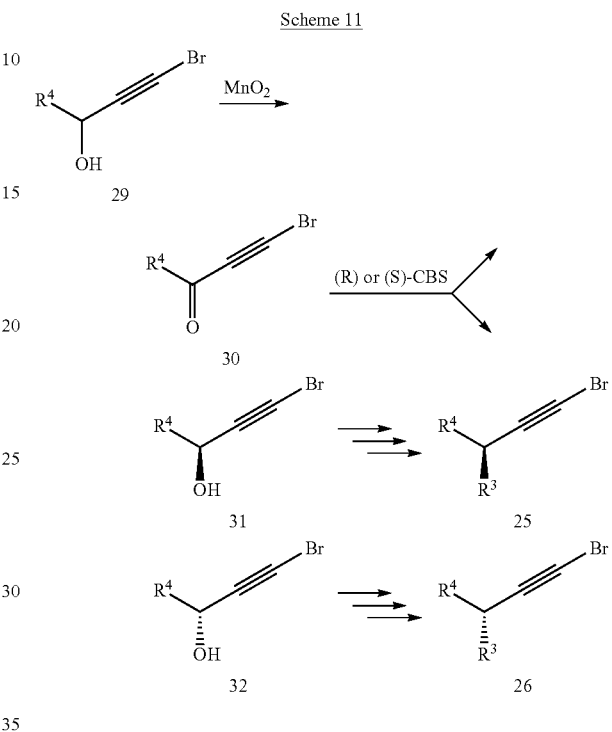

A propargylic alcohol of formula 29 (which can be made using the method described above for the synthesis of compound 14) can be oxidized using manganese dioxide to provide a compound of formula 30. The carbonyl group of 30 can then be selectively reduced using either (R) or (S)-CBS to provide a chiral propargylic alcohol of formula 31 or 32. The hydroxyl group of 31 or 32 can then be derivatized using methods known to one skilled in the art of organic synthesis to provide the intermediates of formulas 25 and 26 wherein $R^3$ is —SH, —NH₂, —Cl, —F, —CN, —NO₂, —CF₃ or —CCl₃. For example, Compounds of the invention, including compounds 31 and 32 may be converted to other Compounds of the invention, including compounds 26 and 25, via a Mitsunobu reaction, for example as set forth in "Simplification of the Mitsunobu Reaction. Di-p-chlorobenzyl Azodicarboxylate: A New Azodicarboxylate." B. H. Lipshutz, D. W. Chung, B. Rich, R. Corral. *Org. Lett.*, 2006, 8, 5069-5072, which is herein incorporated by reference in its entirety.

Where the Schemes do not illustrate diol stereochemistry, the four possible stereoisomers of the diol, (R,S), (R,R), (S,R) and (S,S), of the Compounds of can be made using dihydroxylation methodology set forth, for example, in Sharpless, et al., *J. Org. Chem.*, 57:2768 (1992), and March, p. 822-825. The two possible stereoisomers of the tertiary or secondary hydroxyl (R, S) remote from the diol can also be made by asymmetric methodology, for example, as set forth in March, p. 920-929. The disclosures of each of these citations are incorporated herein by reference in their entireties. It will be appreciated that enantiomerically pure starting materials can be used to generate specific enantiomers of the products.

Panaxytriol

Panaxytriol can be extracted from red ginseng, for example, using ethyl acetate, and purified using chromatography on a silica gel column as described by Matsunaga et al., *Chem. Pharm. Bull.* 37:1279-1291 (1989). Examples of synthetic pathways useful for making Compounds are generalized in the Schemes herein.

A synthetic route to panaxytriol is as follows. Compound 1 can be made by reacting n-octanal with (carbethoxymethylene)triphenylphosphorane using a Wittig reaction (see, e.g., March, *Advanced Organic Chemistry: Reactions, Mechanisms, and Structure* 956-963 (4th ed. 1992), followed by reduction of the ethyl ester group of the resultant product using, for example, DIBAL. Schemes 12 and 13 set forth methodology useful for making panaxytriol.

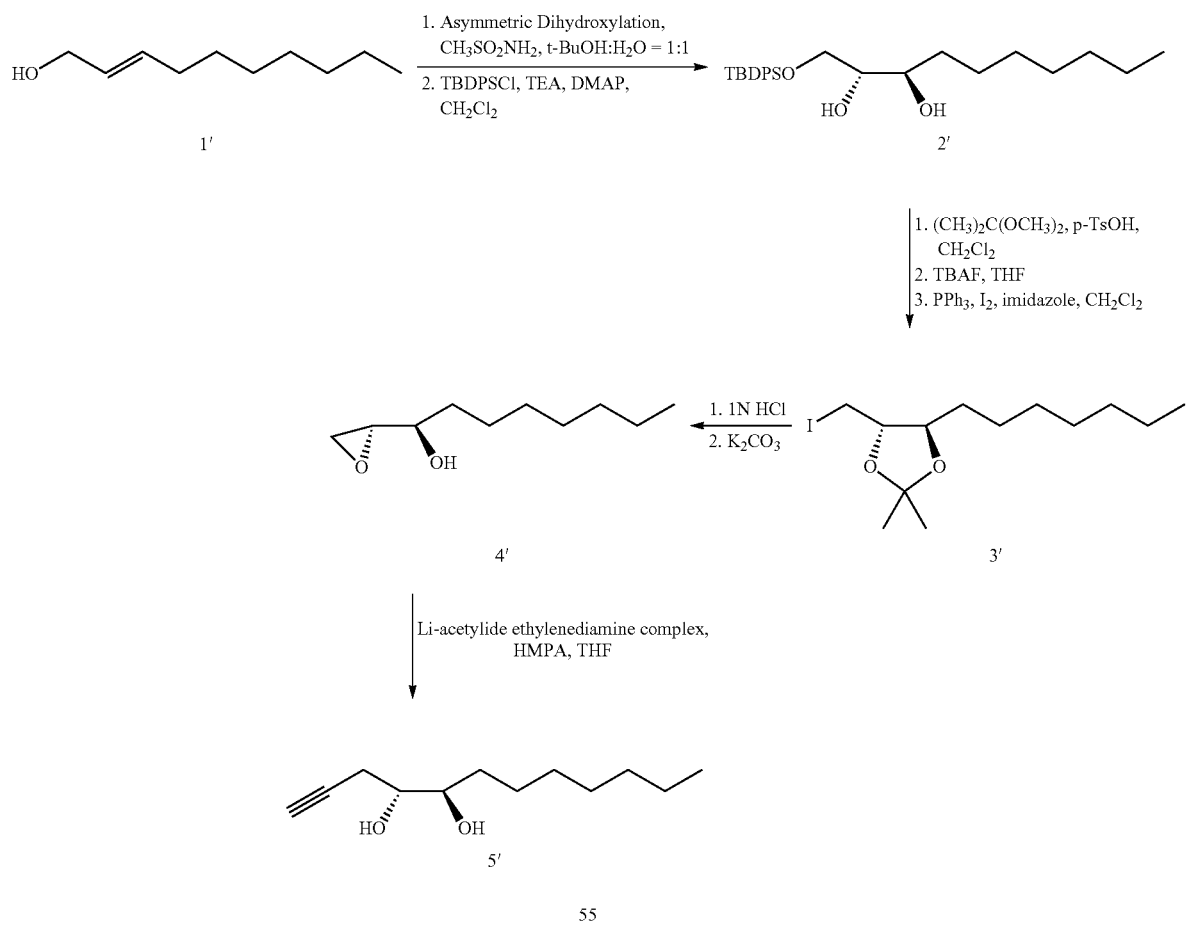

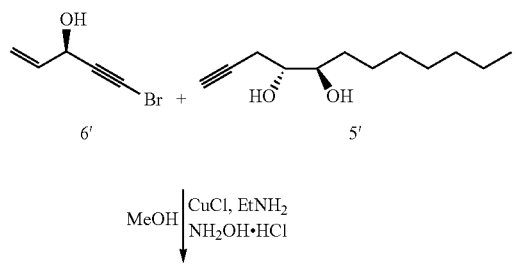

A Sharpless asymmetric dihydroxylation (Kolb et al., *Chem. Rev.* 94: 2483 (1994)) of compound 1' is followed by TBDPS protection of the primary alcohol to provide the diol 2'. Following acetonide protection of the diol 2', the TBDPS group is removed and the resultant primary alcohol is converted to an iodide to provide the iodide 3'. The iodide 3' is deprotected and treated with $K_2CO_3$ to provide the epoxide 4'. The epoxide 4' is alkylated, for example using Li-acetylide, to provide the terminal alkyne 5'.

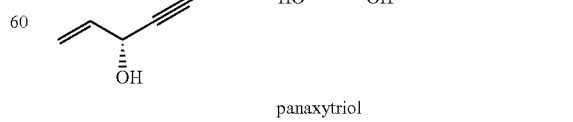

panaxytriol

Coupling of the alkynyl bromide 6' (prepared as described in the Examples) and the terminal alkyne 5' in the presence of cuprous chloride provides panaxytriol. Other Cu(I) sources can also be used in these alkyne couplings disclosed herein. The procedure is also described in Chodkiewicz, W. *Ann. Chian. Paris,* 2: 819 (1957); Randsma, L. *Preparative Acetylenic Chemistry* 2$^{nd}$ Ed., Elsevier (1988); see also Siemsen et al., *Angew. Chem. Int. Ed.,* 39: 2632 (2000), each of which are incorporated by reference in their entireties.

Scheme 14 sets forth methodology useful attaching an acetonide, as in making compounds such as (A).

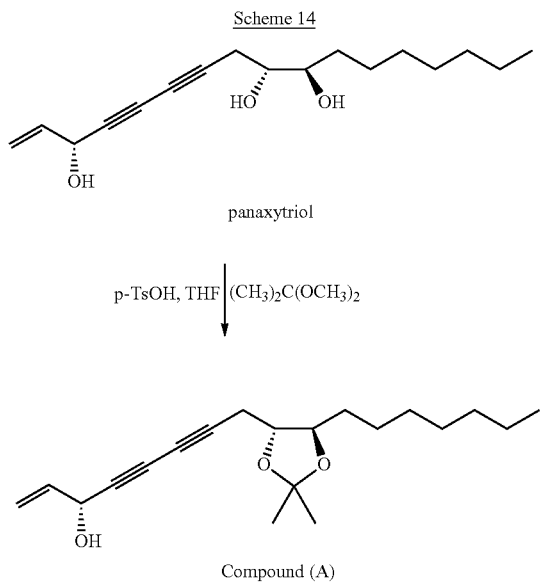

Panaxytriol can be reacted with 2,2-dimethoxypropane and a protic acid in a solvent such as THF to provide the Compound (A). Examples of a protic acid include, but are not limited to, p-Toluenesulfonic acid (p-TsOH or tosic acid), PPTS (pyridinium p-toluenesulfonate), HCl and HBr. In one embodiment, the protic acid is anhydrous. When HCl or HBr is used, it can be bubbled through the reaction mixture. In one embodiment, the amount of the protic acid is a catalytic amount. In one embodiment, the amount of the protic acid is from about 0.01 mol equivalents to about 5 mol equivalents per 1 mol of panaxytriol.

Scheme 15 sets forth methodology useful for making compounds such as (B).

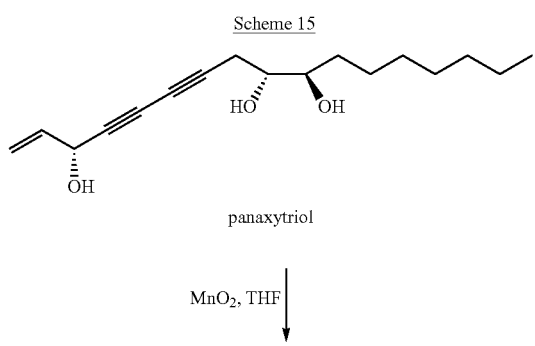

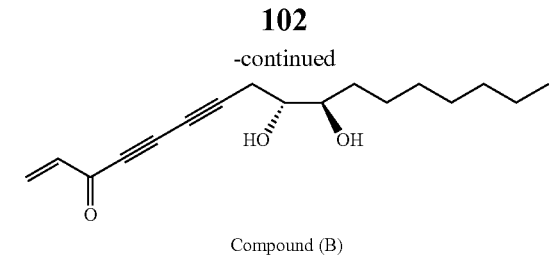

Oxidation of the allylic hydroxyl group of panaxytriol provides Compound (B). Examples of suitable oxidizing agents include, but are not limited to, MnO$_2$ and Dess-Martin Periodinane Reagent (see Dess and Martin (1983), *J. Org. Soc.,* 48: 4155). In one embodiment, about 0.5 mol equivalents to about 10 mol equivalents of the oxidizing agent per 1 mol of panaxytriol is used to carry out the reaction.

Scheme 16 sets forth methodology useful for making compounds such as (C).

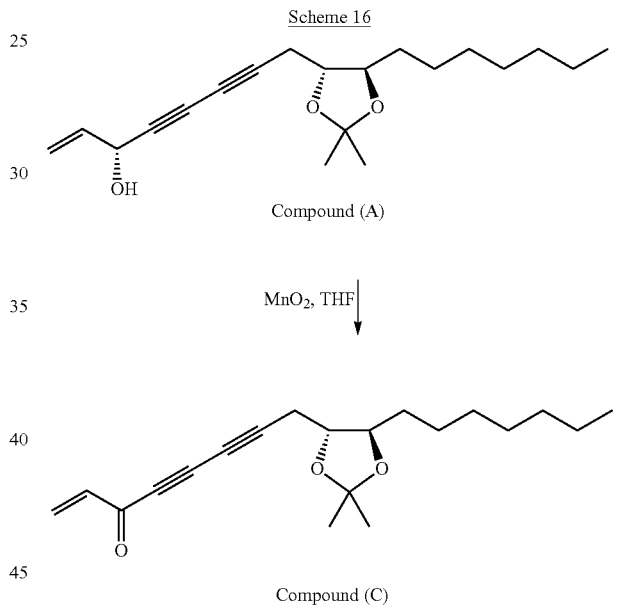

Oxidation of the allylic hydroxyl group of Compound (A) or its enantiomer at the hydroxide provides Compound (C). Suitable oxidizing agents include those described above for the oxidation of panaxytriol to Compound (B).

Scheme 17 sets forth methodology useful for making compounds such as (D).

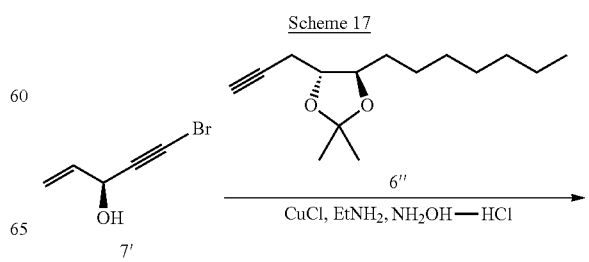

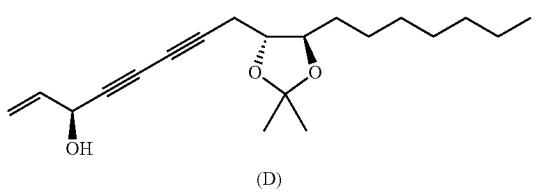

(D)

Coupling (Chodkiewicz, W. *Ann. Chian. Paris*, 2: 819 (1957); Randsma, L. *Preparative Acetylenic Chemistry* 2$^{nd}$ Ed., Elsevier (1988); see also Siemsen et al., *Angew. Chem. Int. Ed.*, 39: 2632 (2000)) of the alkynyl bromide 7' (prepared as described in the Examples, below) and the terminal alkyne 6", in the presence of cuprous chloride provides Compound D. The terminal alkyne 6" may be made by reacting Compound 5 with 2,2-dimethoxypropane and a protic acid neat or in a solvent such as THF to provide the Compound 6, under conditions as disclosed for making Compound (A).

Scheme 18 sets forth methodology useful for making compounds such as (E).

Scheme 19

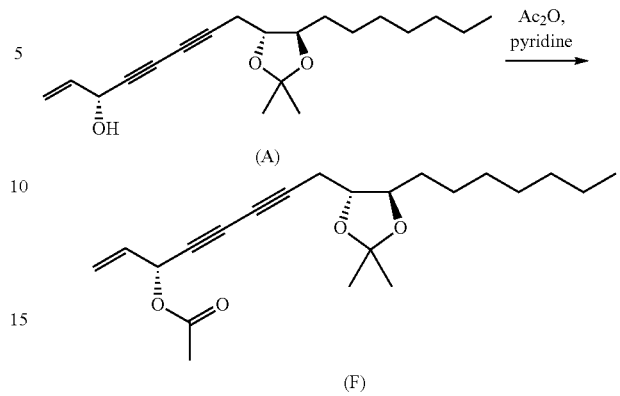

Acetylation of Compound (A) with an acyl source such as acetic anhydride or acetyl chloride in the presence of a base such as pyridine, or a tertiary amine base, optionally also in the presence of a catalyst, such as DMAP, provides Compound (F).

Scheme 18

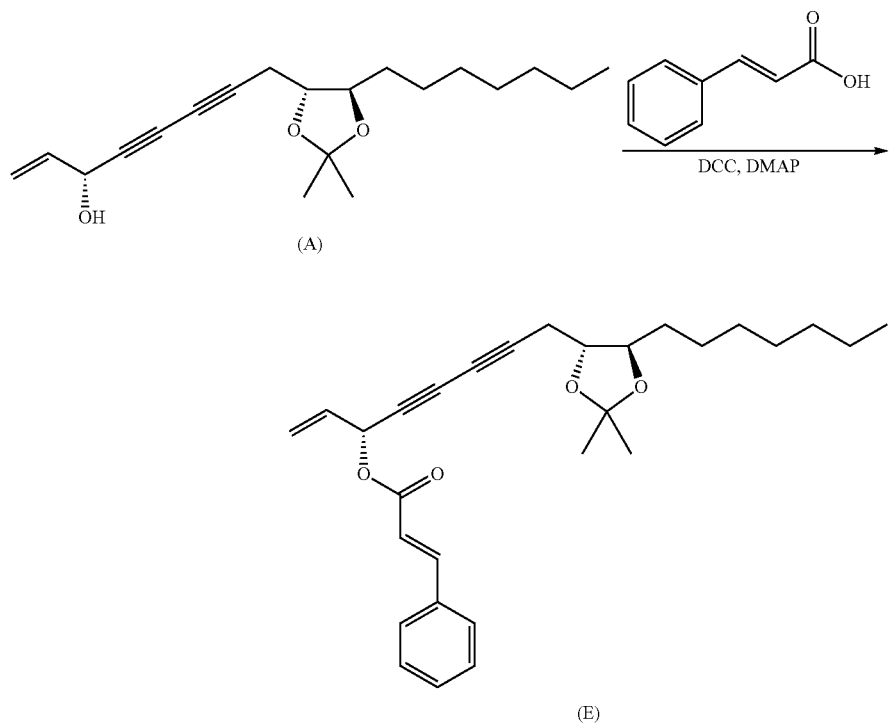

Coupling of Compound (A) with trans-cinnamic acid in the presence of a coupling agent such as DCC, EDC, or CDI, optionally also in the presence of a catalyst, such as DMAP, and/or a base, such as a tertiary amine base, for example triethylamine or Hunig's base, provides Compound (E).

Scheme 19 sets forth methodology useful for making compounds such as (F).

Useful synthetic procedures can also be found in Yun, et al. "Straightforward Synthesis of Panaxytriol: An Active Component of Red Ginseng." *J. Org. Chem.* 2003, 68: 4519-4522; and in Yun, et al. "Total Synthesis as a Resource in Drug Discovery: The First In Vivo Evaluation of Panaxytriol and Its Derivatives." *J. Org. Chem.* 2005, 70: 10375-10380; each of which are herein incorporated by reference in its entirety.

Scheme 20 sets forth methodology useful for making compounds such as (G).

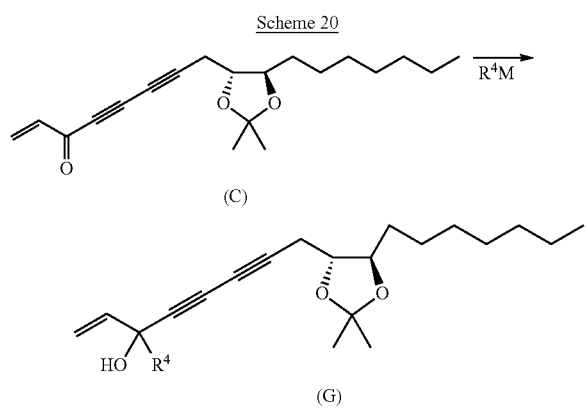

Compound (C) can be alkylated with an alkyl nucleophile to provide compounds of the invention where one $R^4$ is —$C_1$-$C_6$ alkyl, —$C_2$-$C_6$ alkenyl or —$C_2$-$C_6$ alkynyl. "M" in Scheme 9-1 can be a cation, for example comprising a metal. Non-limiting examples of suitable nucleophiles include Grignard reagents, boronates, cuprates, lithiates, or zincates of a —$C_1$-$C_6$ alkyl, —$C_2$-$C_6$ alkenyl or —$C_2$-$C_6$ alkynyl. Stereospecific addition can be achieved through the use of a chiral ligand, such as chiral amino alcohols known to a person skilled in the art, and as taught in March, 4$^{th}$ ed., p. 920-929. Compound (G) is made by the above method when $R^4$ is methyl. In one embodiment, $R^4M$ is methyllithium.

Scheme 21 sets forth methodology useful for making Compounds such as (H) and esters of Compounds of the invention.

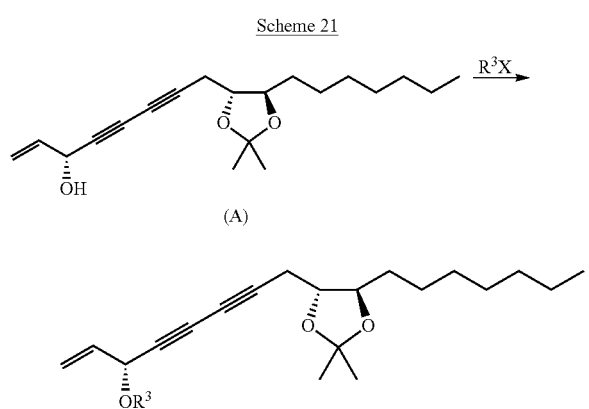

Compound (A) can be reacted with an electrophile where $R^3$ is —$C_1$-$C_6$ alkyl, —$C_2$-$C_6$ alkenyl, —$C_2$-$C_6$ alkynyl, -aryl, or —$C(O)R^5$ and X is a leaving group, for example a halogen (e.g. Cl, Br, or I) or sulfonate (e.g. OTf, OTs, OMs). Other examples of alkylating reagents include $(R^3)_3OBF_4$, such as $Me_3OBF_4$. A base is often present in the reaction. Examples of suitable bases include proton sponge, tertiary amine bases, NaH, KH, etc., depending on the electrophile and conditions employed, as will be apparent to one skilled in the art. Compound H is made when $R^3$ is methyl.

Scheme 22 sets forth methodology useful for making compounds such as (J).

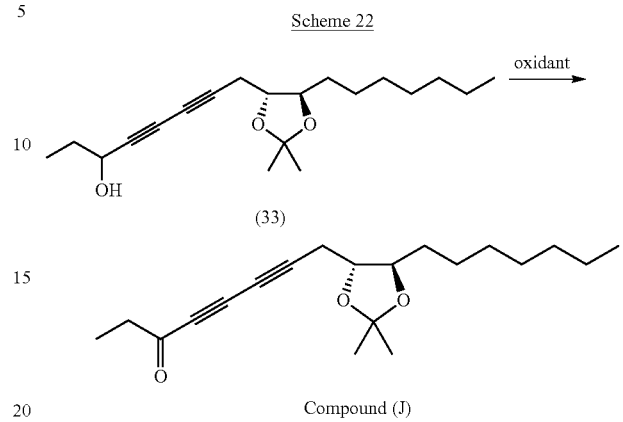

Compound 33 can be oxidized, for example with tetrapropylammoniumperruthenate (TPAP) and N-methyl-morpholine N-oxide (NMO), $MnO_2$, PCC, or in a Swern oxidation, in an organic solvent, to provide Compound (J). Compound 33 can have a defined stereochemistry, such as Compound (K). A catalytic, stoichiometric or excess amount of oxidant can be employed, such as from about 0.02-20 eq., (e.g. about 0.02 to 0.5 eq., 0.1 eq., or 5-10 eq.). Salts may be removed from the reaction mixture by filtration, for example, through a short column of Celite, and the reaction mixture purified to provide Compound (J). In one embodiment, the oxidant is TPAP/NMO at about 0.1 eq. of TPAP and 2 eq. of NMO to substrate. In one embodiment, the solvent is dry. In one embodiment, the solvent is THF.

Scheme 23 sets forth methodology useful for making compounds such as (K).

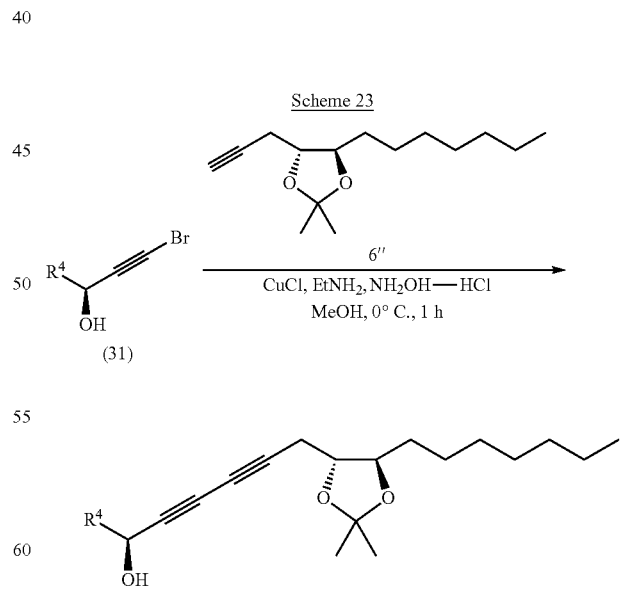

The teachings of Scheme 13 can be used to synthesize compounds where $R^4$ is alkyl, such as Compound (K), using compound 31 from Scheme 11. Compound (K) is produced when $R^4$ is ethyl.

Scheme 24 sets forth methodology useful for making compounds of Formula (I-h) using Click chemistry.

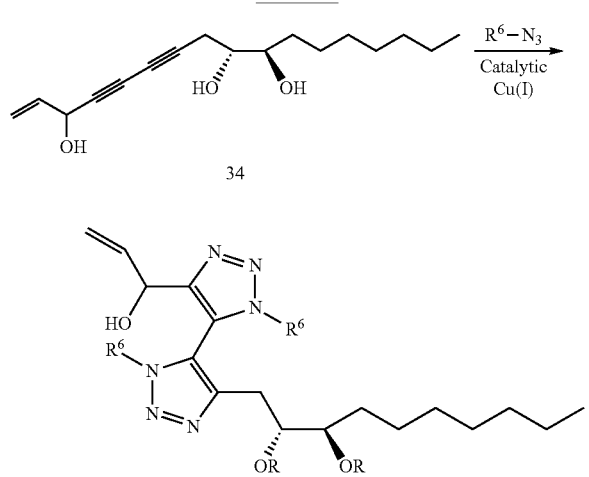

Compound 34 or a stereoisomer thereof, such as panaxytriol, can be reacted with a functionalized azide in the presence of catalytic copper(I) to yield compounds of Formula (I-h). Copper(I) can be added directly, for example as CuCl, or generated in situ, for example from $CuSO_4$ and ascorbic acid or an ascorbate salt. To minimize solubility concerns, a mixture of water and solvents such as DMSO or NMP may be used.

Scheme 25 sets forth methodology useful for making compounds of Formula (I-i), such as compound (L).

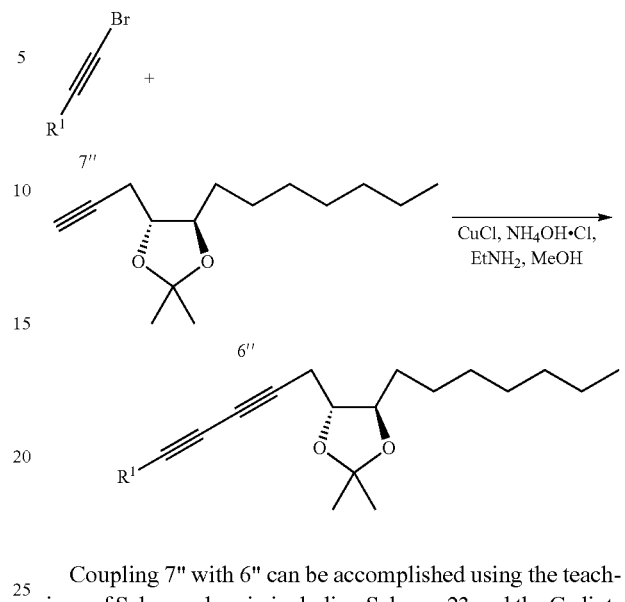

Coupling 7" with 6" can be accomplished using the teachings of Schemes herein including Scheme 23 and the Cadiot-Chodkewicz reaction. Compound (L) is produced when $R^1$ is

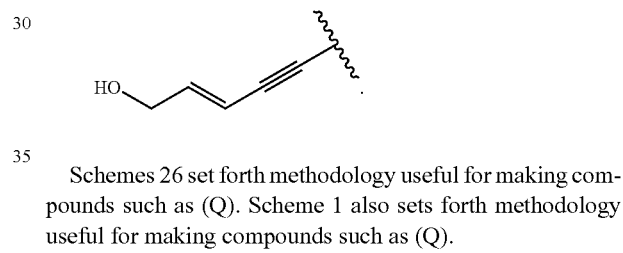

Schemes 26 set forth methodology useful for making compounds such as (Q). Scheme 1 also sets forth methodology useful for making compounds such as (Q).

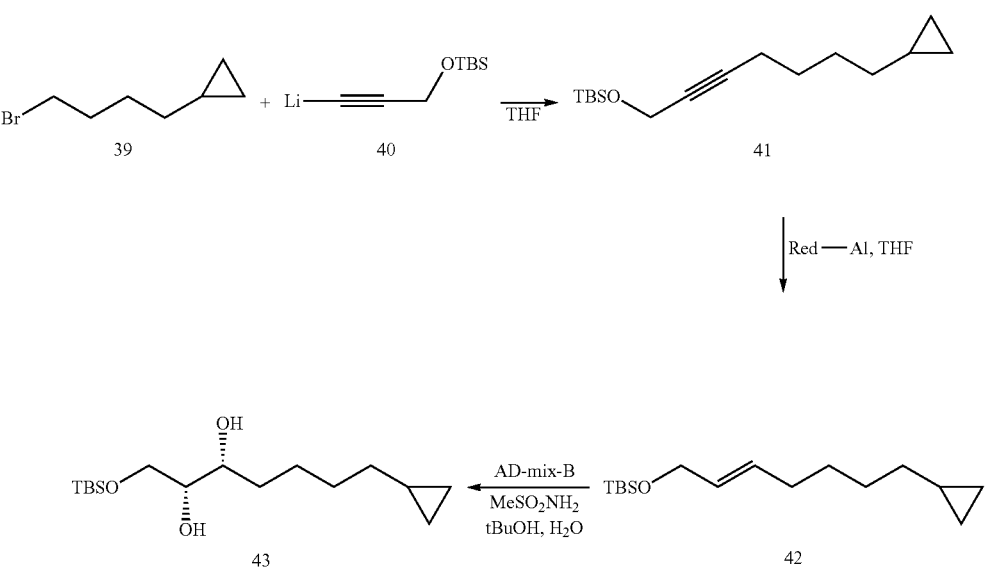

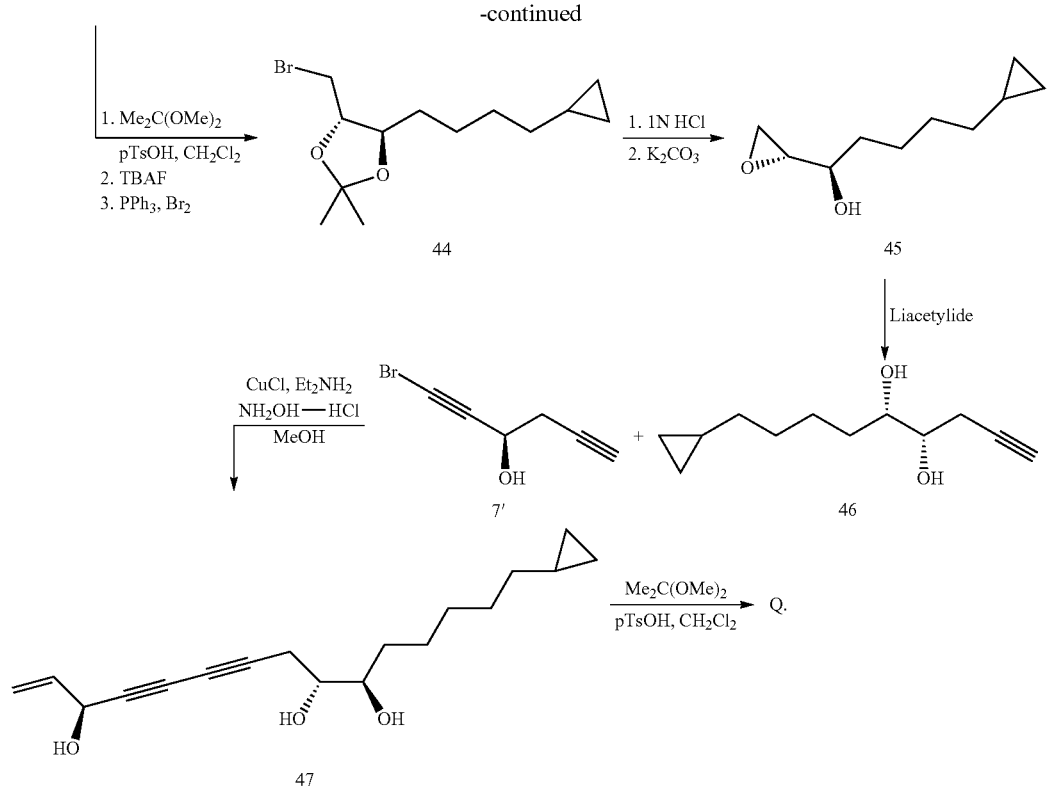

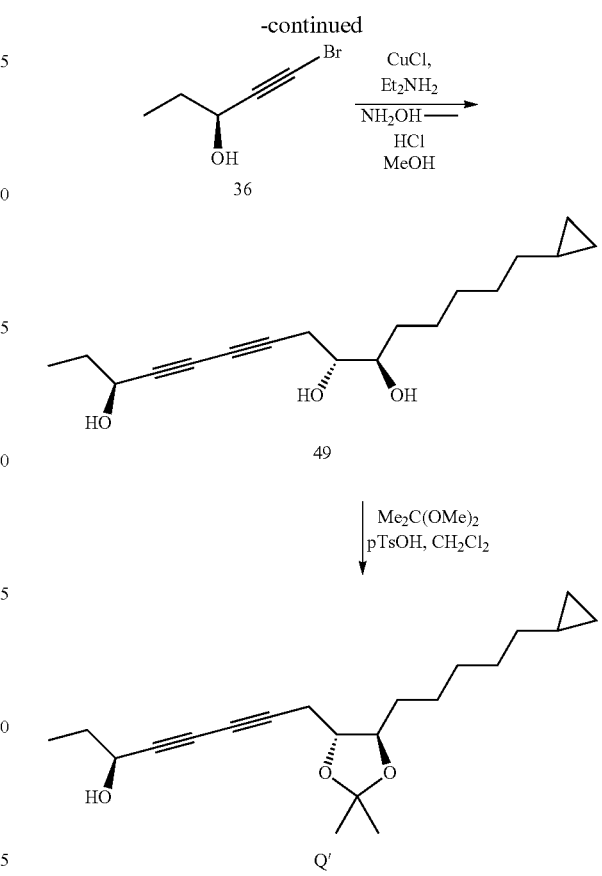

The starting bromide, 39 can be prepared as in O'Connor, E. J.; Brandt, S.; Helquist, P. *Journal of American Chemical Society* 1987, 109, pp 3739-3747, herein incorporated by reference. Bromide 39 can be coupled with an alkynyl nucleophile, for example compound 40, to produce compound 41, which can be partially reduced to compound 42 using Red-Al, for example. Compound 42 can be dihydroxylated, for example via a Sharpless Asymmetric Dihydroxylation with AD-mix-β, as in Sharpless, et al., *J. Org. Chem.*, Vol. 57, No. 10, 1992, incorporated by reference herein, yielding compound 43. Compound 43 can be protected as the acetonide, the TBS group removed, and the alcohol converted to a leaving group, for example bromide as in compound 44. Acidic deprotection of the acetonide and subsequent substitution leads to the epoxide 45, which can be converted to the alkyne 46 via attack by a nucleophilic alkyne, for example lithium acetylide. Alkyne 46 can be coupled to 7' as in Scheme 23 or via a Cadiot-Chodkewitz reaction, yielding compound 47, which can be protected as the acetonide, yielding compound (Q).

More saturated derivatives of compound (Q) such as (Q') can be made as shown in Scheme 27, by coupling compound 36 with 48, as in Schemes 1 or 23.

Scheme 27

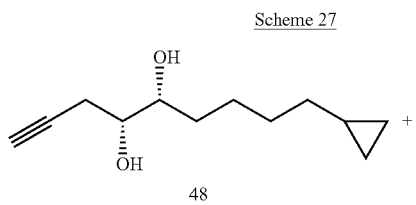

Scheme 28 sets forth methodology useful for making compounds such as (R).

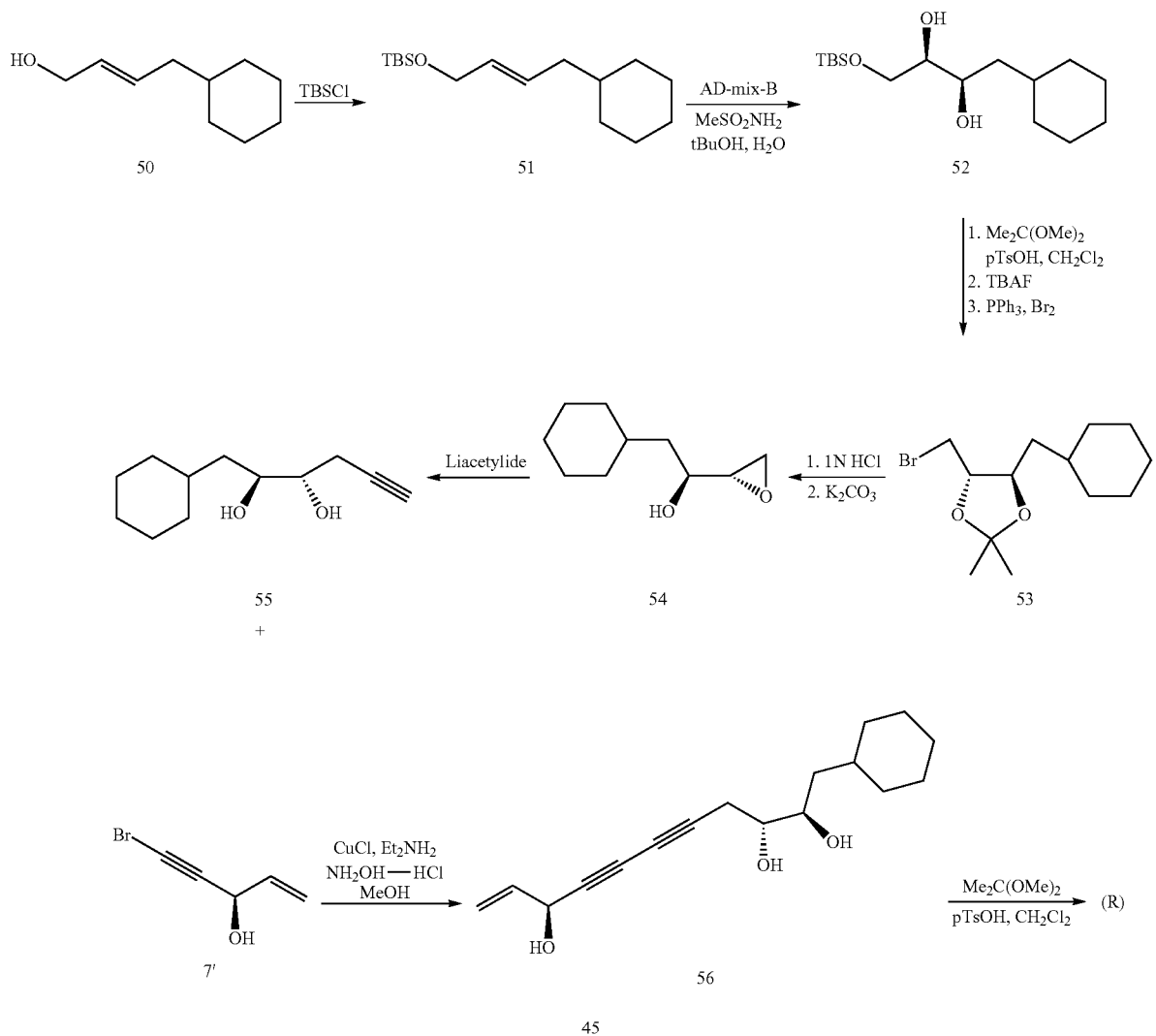

Compound R can be prepared in a similar manner as described in Scheme 26, using the materials depicted in Scheme 28 and starting from compound 50, which can be prepared as described in Pasto, M.; Castejon, P.; Moyano, A.; Pericas, M. A.; Riera, A. *Journal of Organic Chemistry,* 1996, 61, pp 6033-6037, incorporated herein by reference.

More saturated derivatives of compound (R) such as (R') can be made as shown in Scheme 29, by coupling compound 36 with 55, as in Schemes 1 or 23.

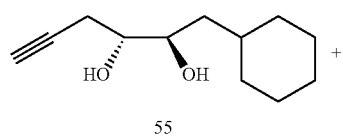

Scheme 29

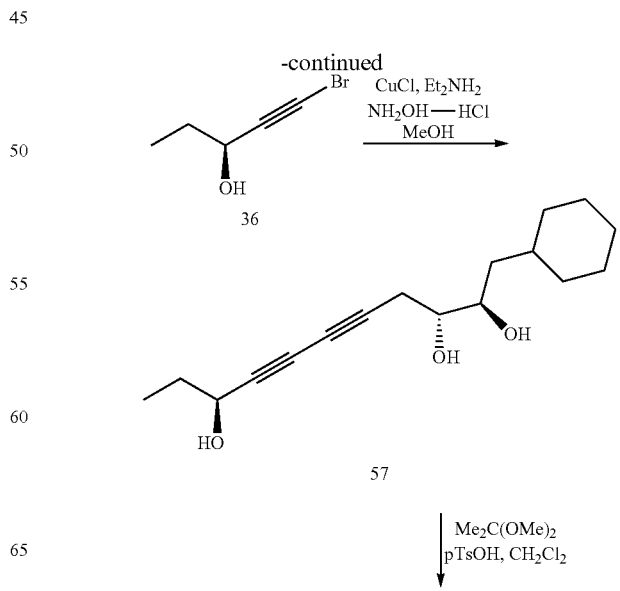

-continued

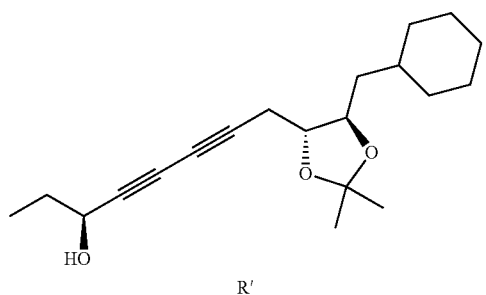

R'

Scheme 28 sets forth methodology useful for making compounds such as (S).

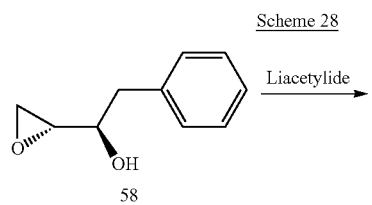

The starting epoxide, 58 can be prepared as described in Fernandes, R. A. *Tetrahedron: Asymmetry,* 2008, 19, pp 15-18, herein incorporated by reference in its entirety. Epoxide 58 can be opened with an acetyllde yielding compound 59. Compound 59 can be coupled with bromide 7' as in Scheme 23 or via a Cadiot-Chodkewitz reaction, yielding compound 61, which can be protected as the acetonide under acidic conditions, yielding compound (Q).

More saturated derivatives of compound (S) such as (S') can be made as shown in Scheme 29, by coupling compound 36 with 59 as in Schemes 1 or 23.

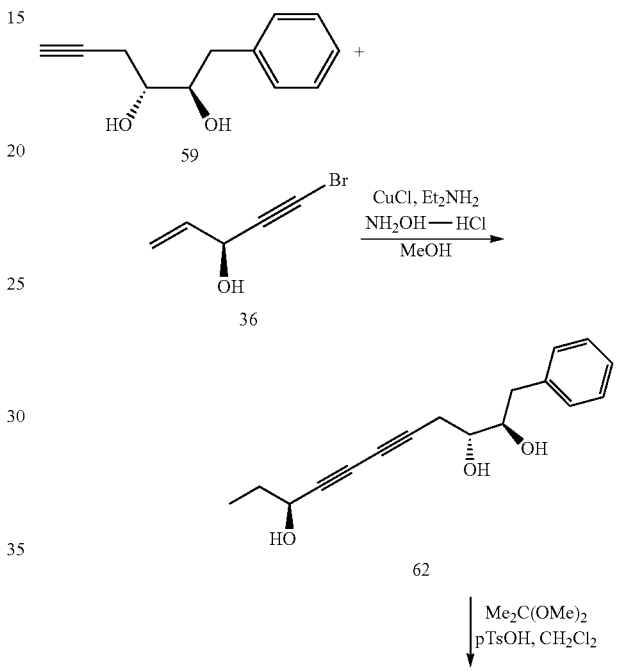

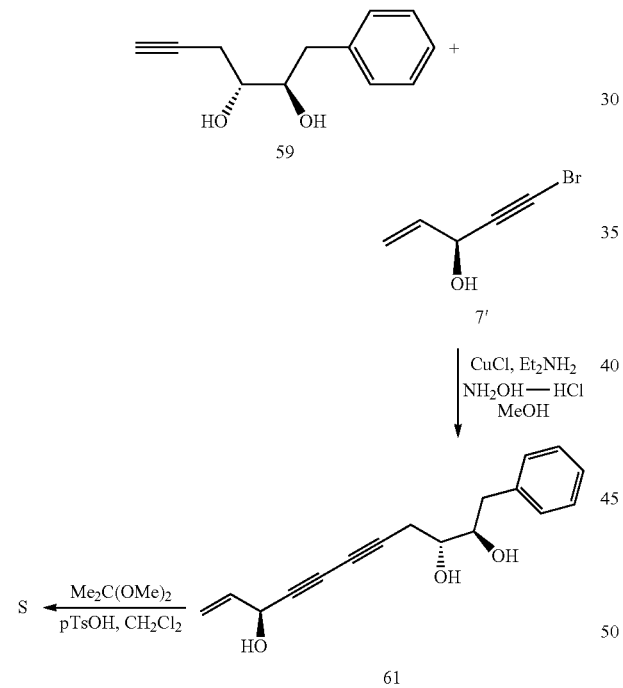

Scheme 30 sets forth methodology useful for making Compound (T).

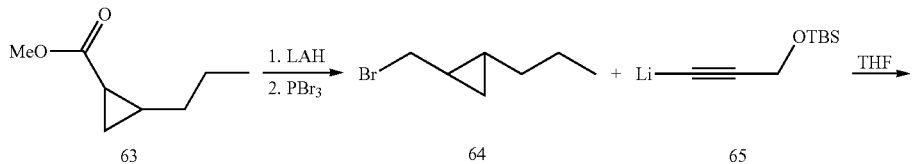

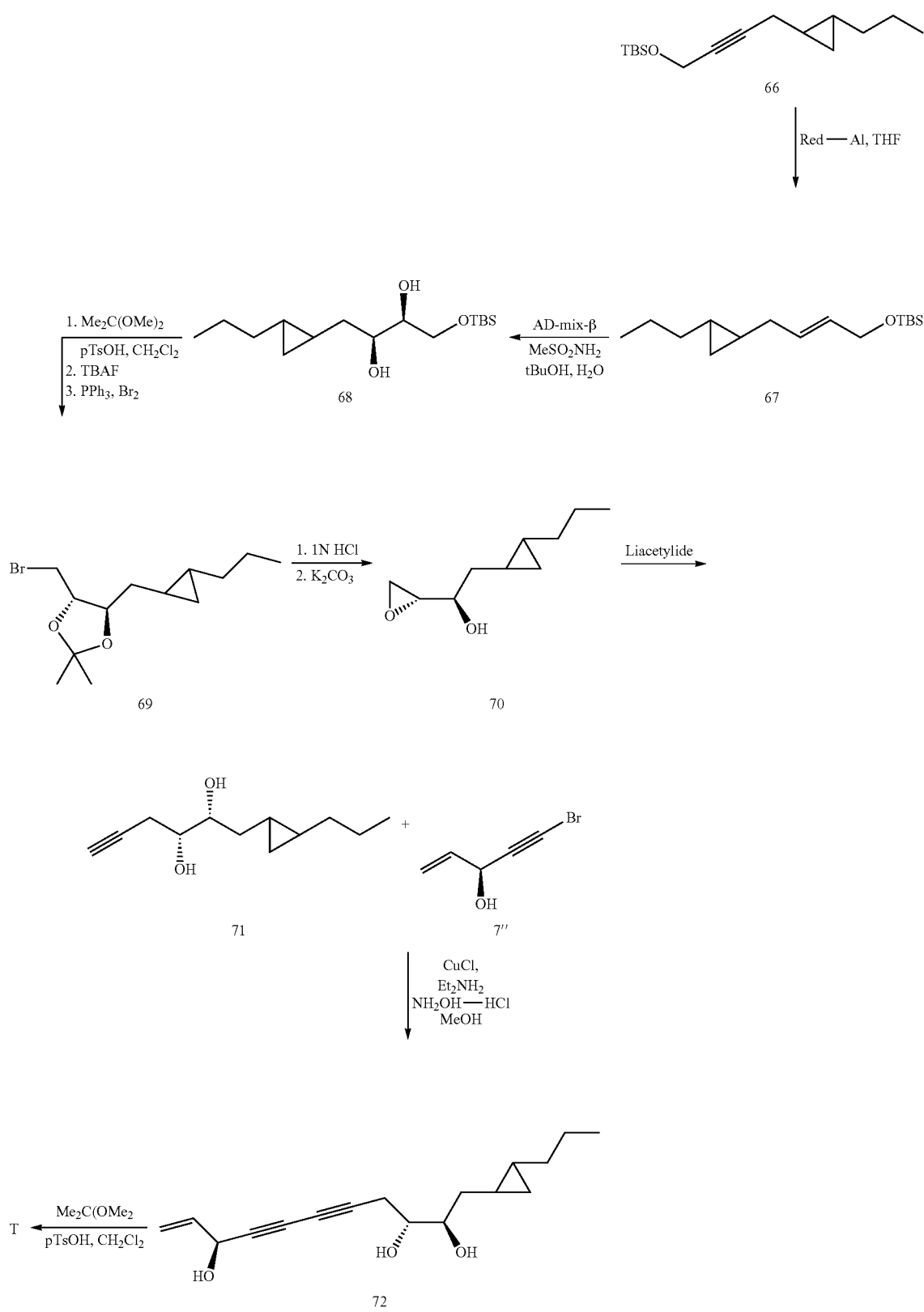

More saturated derivatives of compound (T) such as (T') can be made as shown in Scheme 31, by coupling compound 36 with 71 as in Schemes 1 or 23.

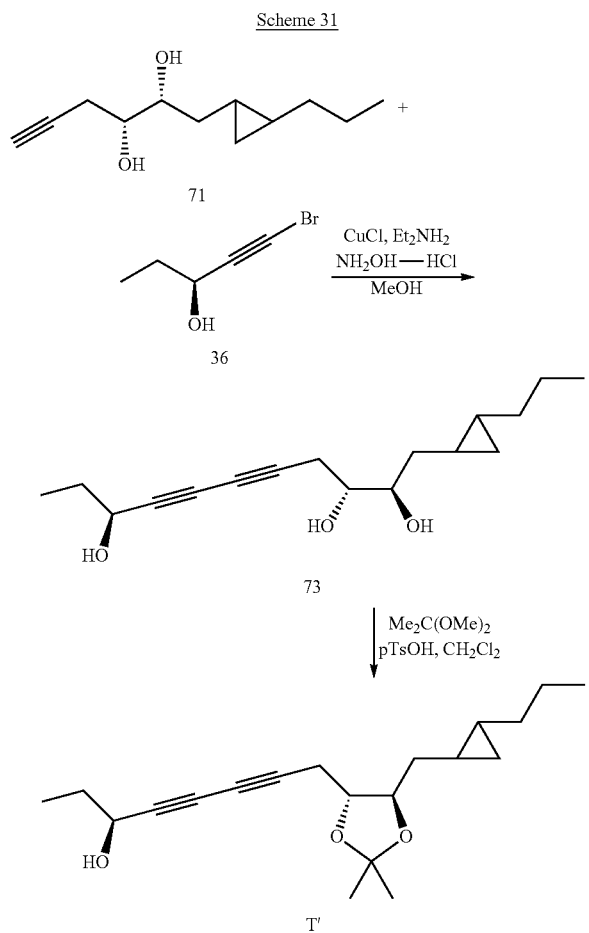

4.5 Methods for Using the Compounds of the Invention

In accordance with the invention, a Compound and a tubulin-biding drug are administered to a subject in need of treatment or prevention of a Condition. In one embodiment, methods of the invention do not include administering panaxytriol.

Methods for Treating or Preventing Cancer Using Compounds of the Invention

Compounds of the invention are useful for the treatment or prevention of cancer.

The invention provides methods for treating or preventing cancer, comprising administering to a subject in need of such treatment or prevention an effective amount of a Compound.

A Compound and a tubulin-binding drug are useful for the treatment or prevention of cancer.

The invention provides methods for treating or preventing cancer, comprising administering to a subject in need of such treatment or prevention an effective amount of a Compound.

The invention provides methods for treating or preventing cancer, comprising administering to a subject in need of such treatment or prevention an effective amount of a Compound and a tubulin-binding drug.

Compounds of the invention show activity in the treatment and prevention of cancer, for example antitumor activity. Particularly, panaxytriol and compounds (A), (D), and (K) have shown anticancer activity for prevention and treatment, as discussed in the Examples. Compounds of the invention also show a synergistic effect with tubulin-binding drugs, including the anticancer drug, fludelone, iso-oxazole-fludelone, and paclitaxel. Compounds of the invention also aid the therapeutic action of anticancer drugs including paclitaxel, fludelone, iso-oxazole-fludelone, cyclophosphamide and 5-fluororuracil, isodehydelone. In one aspect, the compounds of invention act synergistically with anticancer drugs to improve treatment outcomes and reduce side effects. In one aspect, the compounds of invention act synergistically with tubulin-binding drugs to treat cancer. In another aspect, compounds of the invention show synergy with the tubulin-binding drug, epothilone, in the treatment of cancer. In yet another aspect, the synergy allows lower dosages of an anticancer agent, for example, a tubulin-binding drug, to be efficacious in treating cancer. Thus, compounds of the invention can reduce the side effects associated with toxic anti-cancer drugs by allowing lower dosages of the drugs to be administered.

Synergism between a Compound of the invention and a tubulin-binding drug, for example fludelone, can result in reduction of the required dose of the drug, and lead to reduced toxicity while retaining a given degree of therapeutic effect. In one aspect, the compounds have synergistic effects with other chemotherapeutic agents, increasing the therapeutic effect of the agent, and reducing the toxicity of toxic therapeutic agents, including anticancer agents.

In one embodiment, the subject in need of treatment or prevention of cancer is considered to have a genetic risk for cancer. Examples of cancers that are associated with a genetic risk include, but are not limited to, breast cancer, colorectal cancer, uterine cancer, ovarian cancer, skin cancer and stomach cancer.

Examples of cancers that are treatable or preventable comprising administering a Compound optionally in combination with a tubulin-binding drug include, but are not limited to, the cancers disclosed below in Table 1 and metastases thereof.

TABLE 1

| Solid tumors, including but not limited to: |
|---|
| fibrosarcoma |
| myxosarcoma |
| liposarcoma |
| chondrosarcoma |
| osteogenic sarcoma |
| chordoma |
| angiosarcoma |
| endotheliosarcoma |
| lymphangiosarcoma |
| lymphangioendotheliosarcoma |
| synovioma |
| mesothelioma |
| Ewing's tumor |
| leiomyosarcoma |
| rhabdomyosarcoma |
| colon cancer |
| colorectal cancer |
| kidney cancer |
| pancreatic cancer |
| bone cancer |
| breast cancer |
| ovarian cancer |
| prostate cancer |
| esophageal cancer |
| stomach cancer |
| oral cancer |
| nasal cancer |

TABLE 1-continued throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
head and neck cancer
skin cancer
melanoma
neuroblastoma
retinoblastoma
Leukemias:

acute lymphoblastic leukemia ("ALL")
acute lymphoblastic B-cell leukemia
acute lymphoblastic T-cell leukemia
acute myeloblastic leukemia ("AML")
acute promyelocytic leukemia ("APL")
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia ("CML")
chronic lymphocytic leukemia ("CLL")
hairy cell leukemia
multiple myeloma
Lymphomas:

Hodgkin's Disease
Multiple myeloma
Waldenström's macroglobulinemia
Heavy chain disease
Polycythemia vera
CNS and brain cancers:

glioma
pilocytic astrocytoma
astrocytoma
anaplastic astrocytoma
glioblastoma multiforme
medulloblastoma
craniopharyngioma
ependymoma
pinealoma
hemangioblastoma
acoustic neuroma
oligodendroglioma
meningioma
vestibular schwannoma
adenoma
metastatic brain tumor
meningioma
spinal tumor
medulloblastoma In one embodiment the cancer comprises lung cancer, breast cancer, colorectal cancer, prostate cancer, a leukemia, a lymphoma, a skin cancer, a brain cancer, a cancer of the central nervous system, ovarian cancer, uterine cancer, stomach cancer, pancreatic cancer, esophageal cancer, kidney cancer, liver cancer, or a head and neck cancer.

In another embodiment the cancer comprises metastatic cancer. In another embodiment, the cancer is an indolent cancer, such as prostate cancer, breast cancer, lung cancer or a lymphoma.

In still another embodiment, the subject has previously undergone or is presently undergoing treatment for cancer. Such previous treatments include, but are not limited to, prior chemotherapy, radiation therapy, surgery or immunotherapy, such as cancer vaccines.

A Compound or composition of the invention is also useful for the treatment or prevention of a cancer caused by a virus. Such viruses include human papilloma virus, which can lead to cervical cancer (see, e.g., Hernandez-Avila et al., Archives of Medical Research (1997) 28:265-271); Epstein-Barr virus (EBV), which can lead to lymphoma (see, e.g., Herrmann et al., J Pathol (2003) 199(2):140-5); hepatitis B or C virus, which can lead to liver carcinoma (see, e.g., El-Serag, J Clin Gastroenterol (2002) 35(5 Suppl 2):572-8); human T cell leukemia virus (HTLV)-I, which can lead to T-cell leukemia (see e.g., Mortreux et al., Leukemia (2003) 17(1):26-38); human herpesvirus-8 infection, which can lead to Kaposi's sarcoma (see, e.g., Kadow et al., Curr Opin Investig Drugs (2002) 3(11):1574-9); and Human Immune deficiency Virus (HIV) infection, which can lead to cancer as a consequence of immunodeficiency (see, e.g., Dal Maso et al., Lancet Oncol (2003) 4(2):110-9).

A Compound or composition of the invention can be administered to a subject to treat or to prevent the progression of a cancer, including but not limited to the cancers listed in Table 1. Such prophylactic use includes that in which non-neoplastic cell growth consisting of hyperplasia, metaplasia, or most particularly, dysplasia has occurred.

The presence of one or more characteristics of a transformed or malignant phenotype, displayed in vivo or in vitro in a cell sample from a subject, can indicate the desirability of prophylactic or therapeutic administration of a Compound or composition of the invention. Such characteristics can be displayed in addition to the presence of abnormal cell growth characterized as hyperplasia, metaplasia, or dysplasia. The abnormal cell growth can indicate the desirability of prophylactic or therapeutic administration of a Compound or composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also Id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, can be treated or prevented according to the present methods, by administering the compounds or compositions of the invention to a subject.

In another embodiment, fibrocystic disease (cystic hyperplasia, mammary dysplasia, particularly adenosis (benign epithelial hyperplasia)) can be treated or prevented according to the present methods, by administering the compounds or compositions of the invention to a subject.

In other embodiments, a subject that exhibits one or more of the following predisposing factors for malignancy can be administered with an effective amount of a Compound or composition of the invention: a chromosomal translocation associated with a malignancy (e.g., the Philadelphia chromosome for chronic myelogenous leukemia, t(14; 18) for follicular lymphoma); familial polyposis or Gardner's syndrome; benign monoclonal gammopathy; a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome); and exposure to carcinogens (e.g., smoking, second-hand smoke exposure, and inhalation of or contacting with certain chemicals).

Administration of an effective amount of a Compound or composition of the invention is useful for maintenance therapy of cancer. Maintenance therapy can help keep cancer under control and help keep a subject disease free for an extended period of time.

In one embodiment, maintenance therapy is administered to a subject that is in remission.

Administration of an effective amount of a Compound or composition of the invention is useful for treating a micrometastasis. In one embodiment, the subject is treated for a micrometastasis after the subject achieves remission after being treated with chemotherapy, radiation therapy, surgery, or a combination thereof.

In addition, administration of an effective amount of a Compound of the invention and a tubulin-binding drug is useful for preventing a micrometastasis. Without being bound by theory, it is believed that a micrometastasis is therapeutically suppressible by a variety of mechanisms including direct tumor cell kill, cytotoxic disruption of paracrine growth signals from normal tissues, and targeted inhibition of prometastatic pathways.

In one embodiment, a Compound or composition of the invention is administered at doses commonly employed when such agents are used as monotherapy for the treatment of cancer.

In another embodiment, a Compound of the invention and a tubulin-binding drug, for example, in a composition of the invention, act synergistically. In another embodiment, a Compound and a tubulin-binding drug, for example, in a composition of the invention, are administered at doses that are less than the doses commonly employed when such agents are used as monotherapy for the treatment of cancer.

The dosage and dosing schedule of a Compound or composition of the invention, can depend on various parameters, including, but not limited to, the cancer being treated, the patient's general health, and the administering physician's discretion.

A Compound of the invention, or a composition of the invention comprising a Compound but not a tubulin-binding drug, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a tubulin-binding drug to a subject in need thereof. In various embodiments, a Compound of the invention or a composition of the invention comprising a Compound but not a tubulin-binding drug, and a tubulin-binding drug are administered 5 seconds apart, 15 seconds apart, 30 seconds apart, 1 minute apart, 5 minutes apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart. In one embodiment, a Compound of the invention or a composition of the invention comprising a Compound but not a tubulin-binding drug, and a tubulin-binding drug are administered within 3 hours of each other. In another embodiment, a Compound of the invention and a tubulin-binding drug are administered 1 minute to 24 hours apart.

In one embodiment, a Compound of the invention and a tubulin-binding drug are present in the same composition. In one embodiment, a composition of the invention is useful for oral administration. In another embodiment, a composition of the invention is useful for intravenous administration.

Cancers that can be treated or prevented by administering a Compound or a composition of the invention include, but are not limited to, the list of cancers set forth in Table 1.

The Compound and the tubulin-binding drug can act additively or synergistically. A synergistic combination of a Compound of the invention and a tubulin-binding drug might allow the use of lower dosages of one or both of these agents, and/or less frequent dosages of one or both of the Compound of the invention and a tubulin-binding drug, and/or less frequent administration of the agents could reduce any toxicity associated with the administration of the agents to a subject; without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

In one embodiment, a Compound of the invention and a tubulin-binding drug act synergistically when administered in doses typically employed when such agents are used as monotherapy for the treatment of cancer. In another embodiment, a Compound of the invention and a tubulin-binding drug act synergistically when administered in doses that are less than doses typically employed when such agents are used as monotherapy for the treatment of cancer.

In some embodiments, administration of a Compound of the invention reduces the effective amount of a tubulin-binding drug by 2-fold, 5-fold, 10-fold, 20-fold, 50-fold, 100-fold, or 1000-fold. Reduction of the effective amount of tubulin-binding drug can result in reduction of adverse side-effects associated with administration of the tubulin-binding drug. A Compound of the invention can increase a subject's tolerance of a tubulin-binding or other anti-cancer drug and reduce the side effects of the drug. This can allow increased dosing of a drug. The increased tolerance can be caused by induction of chemoprotective phase II enzymes by a Compound of the invention.

In one embodiment, the tubulin-binding drug is administered orally.

In another embodiment, the tubulin-binding drug is administered intravenously.

In yet another embodiment, compounds of the invention have an anticancer effect, with no or little toxicity.

Combination Chemotherapy

In one embodiment, the methods for treating or preventing cancer further comprise administering an effective amount of another anticancer agent.

In one embodiment, the other anticancer agent useful in the methods and compositions of the present invention includes, but is not limited to, a drug listed in Table 2 or a pharmaceutically acceptable salt thereof.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| | Procarbazine |
| | Temozolomide |
| Platinum complexes: | Cisplatin |
| | Carboplatin |
| | Aroplatin |
| | Oxaliplatin |
| DNA Topoisomerase Inhibitors | |
| Epipodophyllins: | Topotecan |
| | Irinotecan |
| | 9-aminocamptothecin |
| | Camptothecin |
| | Crisnatol |
| Mitomycins: | Mitomycin C |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | Deferoxamine |
| Pyrimidine analogs: | |
| Uracil analogs: | 5-Fluorouracil |
| | Fluoxuridine |
| | Doxifluridine |
| | Ralitrexed |
| Cytosine analogs: | Cytarabine |
| | Cytosine arabinoside |
| | Fludarabine |
| | Gemcitabine |
| | Capecitabine |
| Purine analogs: | Mercaptopurine |
| | Thioguanine |
| | O-6-benzylguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | Pyrazoloimidazole |
| Hormonal therapies: | |
| Receptor antagonists: | |
| Anti-estrogen: | Tamoxifen |
| | Raloxifene |
| | Megestrol |
| LHRH agonists: | Goserelin |
| | Leuprolide acetate |
| Anti-androgens: | Flutamide |
| | Bicalutamide |

TABLE 2-continued

| Retinoids/Deltoids | |
|---|---|
| | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A (2BA-2-DMHA) |
| Cytokines: | Interferon-α |
| | Interferon-β |
| | Interferon-γ |
| | Tumor necrosis factor |
| | Interleukin-2 |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic gonadotropin (hCG) |
| | IM-862 |
| | Interleukins |
| | Kringle 5 (plasminogen fragment) |
| | Marimastat |
| | Metalloproteinase inhibitors |
| | 2-Methoxyestra diol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |
| | Tetrathiomolybdate |
| | Thalidomide |
| | Thrombospondin-1 (TSP-1) |
| | TNP-470 |
| | Transforming growth factor-beta (TGF-β) |
| | Vasculostatin |
| | Vasostatin (calreticulin fragment) |

TABLE 2-continued

|  |  |
|---|---|
|  | ZD6126 |
|  | ZD 6474 |
|  | farnesyl transferase inhibitors (FTI) |
|  | Bisphosphonates |
| Antimitotic agents: | trityl cysteine |
| Others: |  |
| Isoprenylation inhibitors: |  |
| Dopaminergic neurotoxins: | 1-methyl-4-phenylpyridinium ion |
| Cell cycle inhibitors: | Staurosporine |
| Actinomycins: | Actinomycin D |
|  | Dactinomycin |
| Bleomycins: | Bleomycin A2 |
|  | Bleomycin B2 |
|  | Peplomycin |
| Anthracyclines: | Daunorubicin |
|  | Doxorubicin |
|  | Idarubicin |
|  | Epirubicin |
|  | Pirarubicin |
|  | Zorubicin |
|  | Mitoxantrone |
| MDR inhibitors: | Verapamil |
|  | Ardeemin |
|  | Ningalin |
| $Ca^{2+}$ ATPase inhibitors: | Thapsigargin |
| Anti-Metastatis agents | Metastatin |
|  | GLiY-SD-ME-1 |
| Kinase inhibitors | Sorafenib |
|  | Imatinib |
|  | Gefinitib |
|  | Lapatinib |
|  | Dasatinib |
|  | Nilotinib |
|  | Temsirolimus |
|  | Erlotinib |

In another embodiment, additional other anticancer agents useful in the methods and compositions of the present invention include, but are not limited to, the following compounds or a pharmaceutically acceptable salt thereof: abiraterone, acivicin, aclarubicin, acodazole, acronine, acylfulvene, adecypenol, adozelesin, aldesleukin, an ALL-TK antagonist, altretamine, ambamustine, ambomycin, ametantrone, amidox, amifostine, aminoglutethimide, aminolevulinic acid, amrubicin, amsacrine, anagrelide, anastrozole, andrographolide, an angiogenesis inhibitor, antarelix, anthramycin, an apoptosis gene modulator, apurinic acid, ara-CDP-DL-PTBA, arginine deaminase, L-asparaginase, asperlin, asulacrine, atamestane, atrimustine, axinastatin 1, axinastatin 2, axinastatin 3, azacitidine, azasetron, azatoxin, azetepa, azatyrosine, azotomycin, batimastat, benzodepa, bisantrene, bisnafide, bizelesin, brequinar, bropirimine, balanol, a BCR/ABL antagonist, beta-alethine, betaclamycin B, betulinic acid, bisaziridinylspermine, bisnafide, bistratene A, bizelesin, calcipotriol, calphostin C, calusterone, canarypox IL-2, carubicin, carboxyamidotriazole, CaRest M3, CARN 700, carzelesin, castanospermine, cecropin B, cetrorelix, chloroquinoxaline, cicaprost, cirolemycin, cladribine, clotrimazole, collismycin A, collismycin B, conagenin, crambescidin 816, crisnatol, cryptophycin 8, cryptophycin A derivatives, cyclopentanthraquinones, cycloplatam, cypemycin, cytostatin, dacliximab, decitabine, dehydrodidemnin B, deslorelin, dexifosfamide, dexormaplatin, dexrazoxane, dexdiaziquone, didemnin B, didox, diethylnorspermine, dihydro-5-acytidine, dihydrotaxol, dioxamycin, diphenyl spiromustine, docosanol, dolasetron, droloxifene, dronabinol, duazomycin, duocarmycin SA, ecomustine, edatrexate, eflornithine, elsamitrucin, enloplatin, enpromate, epipropidine, erbulozole, esorubicin, estramustine, estramustine, an estrogen antagonist, etanidazole, etoprine, exemestane, fadrozole, fazarabine, fenretinide, finasteride, flavopiridol, flezelastine, fluasterone, fluorodaunorunicin, floxuridine, fluorocitabine, forfenimex, formestane, fostriecin, fotemustine, gadolinium texaphyrin, galocitabine, ganirelix, a gelatinase inhibitor, a glutathione inhibitor, hepsulfam, herbimycin A, heregulin, hexamethylene bisacetamide, hypericin, ibandronic acid, idoxifene, idramantone, ilmofosine, ilomastat, imatinib mesylate, imidazoacridones, imiquimod, an IGF-1 inhibitor, iobenguane, iodoipomeanol, iproplatin, irsogladine, isobengazole, isohomohalicondrin B, itasetron, jasplakinolide, leucovorin, levamisole, leuprorelin, liarozole, lissoclinamide 7, lobaplatin, lombricine, lometrexol, lonidamine, losoxantrone, lovastatin, loxoribine, lurtotecan, lutetium texaphyrin, lysofylline, mannostatin A, masoprocol, maspin, a matrix metalloproteinase inhibitor, mechlorethamine, megestrol acetate melphalan, metoclopramide, mifepristone, miltefosine, mirimostim, mitoguazone, mitolactol, mitonafide, mofarotene, molgramostim, mopidamol, a multiple drug resistance gene inhibitor, myriaporone, N-acetyldinaline, nafarelin, nagrestip, napavin, naphterpin, nartograstim, nedaplatin, nemorubicin, neridronic acid, nilutamide, nisamycin, a nitrogen mustard, a nitric oxide modulator, a nitrosourea, nitrullyn, octreotide, okicenone, onapristone, oracin, ormaplatin, osaterone, oxaunomycin, palauamine, palmitoylpamidronic acid, panaxytriol, panomifene, parabactin, pazelliptine, pegaspargase, peldesine, peliomycin, pentamustine, pentosan, pentostatin, pentrozole, peplomycin, perfosfamide, perflubron, perfosfamide, phenazinomycin, a phosphatase inhibitor, picibanil, pilocarpine, pipobroman, piposulfan, piritrexim, placetin A, placetin B, plicamycin, porfiromycin, plomestane, porfimer sodium, porfiromycin, prednimustine, prednisone, prostaglandin J2, microalgal, puromycin, pyrazoloacridine, pyrazofurin, a raf antagonist, raltitrexed, ramosetron, a ras farnesyl protein transferase inhibitor, a ras-GAP inhibitor, retelliptine demethylated, RII retinamide, riboprine, rogletimide, rohitukine, romurtide, roquinimex, rubiginone B1, ruboxyl, safingol, saintopin, SarCNU, sarcophytol A, sargramostim, semustine, a signal transduction modulator, simtrazene, sizofuran, sobuzoxane, solverol, sonermin, sparfosic acid, sparfosate, sparsomycin, spicamycin D, spiromustine, spiroplatin, splenopentin, a stem-cell division inhibitor, stipiamide, streptonigrin, a stromelysin inhibitor, sulfinosine, suradista, suramin, swainsonine, talisomycin, tallimustine, tauromustine, tazarotene, tecogalan, tegafur, tellurapyrylium, a telomerase inhibitor, teloxantrone, temoporfin, teroxirone, testolactone, tetrachlorodecaoxide, tetrazomine, thaliblastine, thiamiprine, thiocoraline, thrombopoietin, thymalfasin, thymotrinan, tirapazamine, titanocene, topsentin, toremifene, trestolone, tretinoin, triacetyluridine, triciribine, trimetrexate, triptorelin, tropisetron, tubulozole, turosteride, a tyrosine kinase inhibitor, ubenimex, uracil mustard, uredepa, vapreotide, variolin B, velaresol, veramine, verteporfin, vinxaltine, vinepidine, vinglycinate, vinleurosine, vinrosidine, vinzolidine, vitaxin, vorozole, zanoterone, zeniplatin, zilascorb, zinostatin, and zorubicin.

In another embodiment, additional other anticancer agents useful in the methods and compositions of the present invention include kinase inhibitors and monoclonal antibodies.

Multi-Therapy for Cancer

A Compound of the invention, optionally in combination with a tubulin-binding drug or other anticancer drug can be administered to a subject that has undergone or is currently undergoing one or more additional anticancer therapies including, but not limited to, surgery, radiation therapy, or immunotherapy, such as a cancer vaccine.

In one embodiment, the invention provides methods for treating or preventing cancer comprising administering to a subject in need thereof (a) an amount of a Compound of the invention and a tubulin-binding drug or other anticancer drug effective to treat or prevent cancer; and (b) another anticancer therapy including, but not limited to, surgery, radiation therapy, or immunotherapy, such as a cancer vaccine.

In another embodiment, the invention provides methods for treating or preventing cancer comprising administering to a subject in need thereof (a) an amount of a Compound of the invention effective to treat or prevent cancer; and (b) another anticancer therapy including, but not limited to, surgery, radiation therapy, or immunotherapy, such as a cancer vaccine.

A Compound of the invention or a tubulin-binding drug can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer therapy to a subject in need thereof. In various embodiments, (a) a Compound of the invention and a tubulin-binding drug, and (b) another anticancer therapy are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, no more than 48 hours apart, no more than one week apart, no more than two weeks apart, no more than three weeks apart, no more than one month apart, no more than two months apart, no more than three months apart or no more than six months apart. In one embodiment, (a) a Compound of the invention and a tubulin-binding drug, and (b) another anticancer therapy are administered within 3 hours of each other. In another embodiment, (a) a Compound of the invention and a tubulin-binding drug, and (b) another anticancer therapy are administered 1 minute to 24 hours apart.

In one embodiment, the other anticancer therapy is radiation therapy.

In another embodiment, the other anticancer therapy is surgery.

In still another embodiment, the other anticancer therapy is immunotherapy.

In another embodiment, the other anticancer therapy is hormonal therapy.

In a specific embodiment, the present methods for treating or preventing cancer comprise administering a Compound of the invention, a tubulin-binding drug and radiation therapy. The radiation therapy can be administered concurrently with, prior to, or subsequent to the Compound of the invention or tubulin-binding drug; in one embodiment, at least an hour, five hours, 12 hours, a day, a week, a month; in another embodiment, several months (e.g., up to three months), prior or subsequent to administration of the Compound of the invention or a tubulin-binding drug.

Where the other anticancer therapy is radiation therapy, any radiation therapy protocol can be used depending upon the type of cancer to be treated. For example, but not by way of limitation, X-ray radiation can be administered; in particular, high-energy megavoltage (radiation of greater that 1 MeV energy) can be used for a deep tumor, and electron beam and orthovoltage X-ray radiation can be used for skin cancer. A gamma-ray emitting radioisotope, such as a radioactive isotope of radium, cobalt and other element, can also be administered.

Additionally, in one embodiment the invention provides methods for treating cancer comprising administering a Compound of the invention and a tubulin-binding drug as an alternative to chemotherapy or radiation therapy where the chemotherapy or the radiation therapy results in negative side effects, in the subject being treated. The subject being treated can, optionally, be treated with another anticancer therapy such as surgery, radiation therapy, or immunotherapy.

The Compound of the invention and a tubulin-binding drug can also be used in vitro or ex vivo, such as for the treatment of certain cancers, including, but not limited to leukemias and lymphomas, wherein such treatment involves an autologous stem cell transplant. This can involve a process in which the subject's autologous hematopoietic stem cells are harvested and purged of all cancer cells by administration of a Compound of the invention and a tubulin-binding drug and/or radiation, and the resultant stem cells are infused back into the subject. Supportive care can be subsequently provided while bone marrow function is restored and the subject recovers.

Methods for Treating or Preventing a Neurotrophic Disorder

Administration of an effective amount of a Compound of the invention can be used to treat or prevent a neurotrophic disorder. In one embodiment, the Compound is panaxytriol.

In one embodiment, administration of an effective amount of a Compound of the invention and a tubulin-binding drug can be used to treat or prevent a neurotrophic disorder. In one embodiment, the Compound is panaxytriol.

Accordingly, the invention provides methods for treating or preventing a neurotrophic disorder, comprising administering to a subject in need of such treatment or prevention an effective amount of a Compound of the invention, optionally with a tubulin-binding drug.

Examples of neurotrophic disorders that are treatable or preventable using a Compound of the invention, optionally with a tubulin-binding drug include, but are not limited to, neutrotrophic atrophy; neurotrophic keratitis; a disease associated with cognitive dysfunction, such as dementia or Alzheimer's disease; a neurodegenerative disease, such as amyotrophic lateral sclerosis or stroke; a pain disorder, such as neuropathic pain or cancer pain; a psychotic disorder such as schizophrenia; a movement disorder, such as Parkinson's disease; or a seizure disorder, such as temporal lobe epilepsy.

In one embodiment, Compounds of the invention can be used for treatment of neurotrophic disorders, for example neurotrophic disorders involving growth factor proteins (e.g. nerve growth factor.) Compounds of the invention have shown activity in a neurite outgrowth assay using PC12 cells. Particularly, enhanced neurite outgrowth has been observed in PC12 cells when subjected to panaxytriol and nerve growth factor (NGF) when compared to a control of only NGF.

In one embodiment, the neurotrophic disorder is a disease associated with cognitive dysfunction.

In another embodiment, the neurotrophic disorder is a neurodegenerative disease.

In yet another embodiment, the neurotrophic disorder is a pain disorder.

In another embodiment, the neurotrophic disorder is a psychotic disorder.

In a further embodiment, the neurotrophic disorder is a movement disorder.

In another embodiment, the neurotrophic disorder is a seizure disorder.

5.4.5 Therapeutic/Prophylactic Administration

In one embodiment, the invention provides compositions useful for treating or preventing a Condition. The compositions are suitable for internal or external use and comprise a physiologically acceptable carrier or vehicle and an effective amount of a Compound of the invention optionally with a tubulin-binding drug, or other anticancer agent.

A Compound of the invention can be administered in amounts that are effective to treat or prevent a Condition in a subject. A Compound of the invention and a tubulin-binding drug can be administered in amounts that are effective to treat or prevent a Condition in a subject.

Administration of a Compound of the invention optionally with a tubulin-binding drug can be accomplished via any mode of administration for therapeutic agents. These modes include systemic or local administration such as oral, nasal, parenteral, transdermal, subcutaneous, vaginal, buccal, rectal or topical administration modes.

In one embodiment, a Compound of the invention optionally with a tubulin-binding drug is administered orally.

In embodiment, when the Compound of the invention is panaxytriol, it is administered by oral administration of a root of a *Panax* genus, or an extract thereof, and the tubulin-binding drug is administered separately. Oral administration of a root of a *Panax* genus can comprise ingesting the root of a *Panax* genus, or an extract thereof. In this embodiment, the tubulin-binding drug is administered separately, either before, after, or concurrently with ingestion of the root of a *Panax* genus or an extract thereof. In this embodiment, the mode of administration of the tubulin-binding drug can be any mode suitable for administration of the tubulin-binding drug.

Depending on the intended mode of administration, compositions comprising an effective amount of a Compound of the invention optionally with a tubulin-binding drug can be in solid, semi-solid or liquid dosage form, such as, for example, injectables, tablets, suppositories, pills, time-release capsules, elixirs, tinctures, emulsions, syrups, powders, liquids, suspensions, or the like, in one embodiment in unit dosages and consistent with conventional pharmaceutical practices. Likewise, the compositions can also be administered in intravenous (both bolus and infusion), intraperitoneal, subcutaneous or intramuscular form, all using other forms known to those skilled in the art.

Illustrative pharmaceutical compositions include tablets and gelatin capsules. Illustrative carriers or vehicles include a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution or dispersion. For example, a Compound of the invention optionally with a tubulin-binding drug are admixed with a pharmaceutically acceptable solvent such as, for example, water, saline, aqueous dextrose, glycerol, ethanol, and the like, to thereby form an injectable isotonic solution or suspension.

A Compound of the invention optionally with a tubulin-binding drug can be also formulated as a suppository that can be prepared from fatty emulsions or suspensions, using polyalkylene glycols such as propylene glycol, as the carrier.

A Compound of the invention optionally with a tubulin-binding drug can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

A Compound of the invention optionally with a tubulin-binding drug can also be delivered by the use of monoclonal antibodies as individual carriers to which the Compound of the invention molecules and tubulin-binding drugs are coupled. The Compounds and tubulin-binding drugs can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the Compounds and tubulin-binding drugs can be coupled to a class of biodegradable polymers useful in achieving controlled release of a drug, for example, polylactic acid, poly-epsilon caprolactone, polyhydroxy butyric acid, polyorthoesters, polyacetals, polydihydropyrans, polycyanoacrylates and cross-linked or amphipathic block copolymers of hydrogels.

Parental injectable administration can be used for subcutaneous, intramuscular or intravenous injections and infusions. Injectables can be prepared in conventional forms, either as liquid solutions or suspensions or solid forms suitable for dissolving in liquid prior to injection.

In one embodiment, the Compound of the invention and a tubulin-binding drug are administered intravenously.

One embodiment, for parenteral administration employs the implantation of a slow-release or sustained-released system, according to U.S. Pat. No. 3,710,795, incorporated herein by reference.

The compositions can be sterilized or can contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, the compositions can also contain other therapeutically useful substances.

Compositions can be prepared according to conventional mixing, granulating or coating methods, respectively, and the present pharmaceutical compositions can contain from about 0.1% to about 99%, preferably from about 1% to about 70% of the Compound of the invention and a tubulin-binding drug by weight or volume.

The dosage regimen utilizing the Compound can be selected in accordance with a variety of factors including type, species, age, weight, sex and medical condition of the subject; the severity of the Condition; the route of administration; the renal or hepatic function of the subject; and the particular Compound employed. A person skilled in the art can readily determine or prescribe the effective amount of the Compound of the invention or tubulin-binding drug useful for treating or preventing a Condition. Dosage strategies are also provided in L. S. Goodman, et al., *The Pharmacological Basis of Therapeutics*, 201-26 (5th ed. 1975), which is herein incorporated by reference in its entirety.

The dosage regimen utilizing the Compound and a tubulin-binding drug can be selected in accordance with a variety of factors including type, species, age, weight, sex and medical condition of the subject; the severity of the Condition; the route of administration; the renal or hepatic function of the subject; and the particular Compound of the invention or tubulin-binding drug employed. A person skilled in the art can readily determine or prescribe the effective amount of the Compound of the invention or tubulin-binding drug useful for treating or preventing a Condition. Dosage strategies are also provided in L. S. Goodman, et al., *The Pharmacological Basis of Therapeutics*, 201-26 (5th ed. 1975), which is herein incorporated by reference in its entirety.

Effective dosage amounts of a Compound of the invention, when administered to a subject, range from about 0.05 to about 1000 mg of the Compound per day. Compositions for in vivo or in vitro use can contain about 0.5, 1.0, 2.5, 5.0, 10.0, 15.0, 25.0, 50.0, 100.0, 250.0, 500.0 or 1000.0 mg of a Compound of the invention. In one embodiment, the compositions are in the form of a tablet that can be scored. Effective plasma levels of the Compounds can range from about 0.002 mg to about 50 mg per kg of body weight per day. The amount of a Compound of the invention that, in combination with a tubulin-binding drug, is effective for the treatment or prevention of a Condition can be determined using clinical techniques that are known to those of skill in the art. In addition, in vitro and in vivo assays can optionally be employed to help identify optimal dosage ranges. The precise dose to be employed can also depend on the route of administration, and the seriousness of the Condition and can be decided according to the judgment of the practitioner and each subject's circumstances in view of, e.g., published clinical studies. Suitable effective dosage amounts, however, can range from about 10 micrograms to about 5 grams about every 4 hours, in one embodiment about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one Compound of the invention is administered, the effective dosage amounts correspond to the total amount administered.

Effective dosage amounts of a tubulin-binding drug, when administered to a subject, range from about 0.05 to about 1000 mg of the tubulin-binding drug per day. Compositions for in vivo or in vitro use can contain about 0.5, 1.0, 2.5, 5.0, 10.0, 15.0, 25.0, 50.0, 100.0, 250.0, 500.0 or 1000.0 mg of the tubulin-binding drug. In one embodiment, the compositions are in the form of a tablet that can be scored. Effective plasma levels of the tubulin-binding drug can range from about 0.002 mg to about 50 mg per kg of body weight per day. The amount of a tubulin-binding drug that, in combination with a Compound of the invention, is effective for the treatment or prevention of a Condition can be determined using clinical techniques that are known to those of skill in the art. In addition, in vitro and in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. Suitable effective dosage amounts, however, can range from about 10 micrograms to about 5 grams about every 4 hours, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one tubulin-binding drug is administered, the effective dosage amounts correspond to the total amount administered.

A Compound of the invention can be administered in a single daily dose, or the total daily dosage can be administered in divided doses of two, three or four times daily. Furthermore, a Compound of the invention can be administered in intranasal form via topical use of suitable intranasal vehicles, or via transdermal routes, using those forms of transdermal skin patches known to those of skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of a Compound of the invention ranges from about 0.1% to about 15%, weight/weight or weight/volume.

A Compound of the invention and a tubulin-binding drug can be administered in a single daily dose, or the total daily dosage can be administered in divided doses of two, three or four times daily. Furthermore, a Compound of the invention and a tubulin-binding drug can be administered in intranasal form via topical use of suitable intranasal vehicles, or via transdermal routes, using those forms of transdermal skin patches known to those of skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of a Compound of the invention and a tubulin-binding drug ranges from about 0.1% to about 15%, weight/weight or weight/volume.

In one embodiment, the compositions comprise a total amount of a Compound of the invention and a tubulin-binding drug that is effective to treat or prevent a Condition. In another embodiment, the amount of Compound of the invention and the tubulin-binding drug is at least about 0.01% of the combined combination chemotherapy agents by weight of the composition. When intended for oral administration, this amount can be varied from about 0.1% to about 80% by weight of the composition. Some oral compositions can comprise from about 4% to about 50% of a Compound of the invention and a tubulin-binding drug. Other compositions of the present invention are prepared so that a parenteral dosage unit contains from about 0.01% to about 2% by weight of the composition.

The Compounds and tubulin-binding drugs can be assayed in vitro or in vivo for the desired therapeutic or prophylactic activity prior to use in humans. Animal model systems can be used to demonstrate safety and efficacy.

The present methods for treating or preventing a Condition in a subject in need thereof can further comprise administering another prophylactic or therapeutic agent to the subject being administered a Compound of the invention, optionally with a tubulin-binding drug. In one embodiment the other prophylactic or therapeutic agent is administered in an effective amount. The other prophylactic or therapeutic agent includes, but is not limited to, an antiemetic agent, a hematopoietic colony stimulating factor, an anxiolytic agent, and an analgesic agent.

In a further embodiment, the Compound of the invention, optionally with a tubulin-binding drug can be administered prior to, concurrently with, or after the other prophylactic or therapeutic agent, or on the same day, or within 1 hour, 2 hours, 12 hours, 24 hours, 48 hours or 72 hours of each other.

Effective amounts of the prophylactic or therapeutic agents are known to those skilled in the art. However, it is well within the skilled artisan's purview to determine the other prophylactic or therapeutic agent's optimal effective amount range. In one embodiment of the invention, the effective amount of the Compound of the invention is less than its effective amount would be where the tubulin-binding drug is not administered. In this case, without being bound by theory, it is believed that the Compound of the invention and the tubulin-binding drug act synergistically to treat or prevent a Condition.

In one embodiment, the other prophylactic or therapeutic agent is an antiemetic agent. Antiemetic agents useful in the methods of the present invention include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine and tropisetron.

In one embodiment, the other prophylactic or therapeutic agent is a hematopoietic colony stimulating factor. Hematopoietic colony stimulating factors useful in the methods of the present invention include, but are not limited to, filgrastim, sargramostim, molgramostim and epoietin alfa.

In one embodiment, the other prophylactic or therapeutic agent is an opioid analgesic agent. Opioid analgesic agents useful in the methods of the present invention include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene.

In one embodiment, the other prophylactic or therapeutic agent is a non-opioid analgesic agent. Non-opioid analgesic agents useful in the methods of the present invention include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In one embodiment, the other prophylactic or therapeutic agent is an anxiolytic agent. Anxiolytic agents useful in the methods of the present invention include, but are not limited to, buspirone, and benzodiazepines such as diazepam, lorazepam, oxazapam, chlorazepate, clonazepam, chlordiazepoxide and alprazolam.

The compositions of the invention can be sold or used as prescription products, or alternatively as over-the-counter products. In one embodiment, the compositions of the invention can be sold or used as nutraceutical products.

Induction of Chemoprotective Phase II Enzymes

Compounds of the invention have potent phase II enzyme induction activity. In one embodiment, panaxytriol has potent phase II enzyme induction activity. In another embodiment, Compounds besides panaxytriol have potent chemoprotective phase II enzyme induction activity.

There is accumulating evidence that phase II enzymes often do not operate at their full capacity, can be activated in many tissues, and that induction of these enzymes is an effective and sufficient strategy for protecting against cancer and many other types of toxicities, including oxidative stress. Chemoprotective phase II enzymes protect against carcinogenesis and oxidative stress, and elevate the expression of genes involved in the detoxification of electrophiles and free radicals that contribute to carcinogenesis. Such elevation can be seen by increased DNA, RNA, or protein synthesis. Thus, induction of chemoprotective phase II enzymes may be a novel mechanism for cancer prevention and/or treatment. In one embodiment, compounds of the invention can prevent cancer or lower its risk of onset though the induction of chemoprotective phase II enzymes in a subject in need thereof when administered thereto. In another embodiment, administration of compounds of the invention reduce the risk of developing cancer, including cancers of the lung, gastrointestinal tract, liver, pancreas and ovary.

In some embodiments, chemoprotective phase II enzymes induced by Compounds of the invention are antioxidant enzymes, for example free-radical scavenging enzymes or superoxide elimination enzymes. In other embodiments, the chemoprotective phase II enzyme induced by compounds of the invention is AKR1C, AKR1C2, AKR1C3, heme oxygenase-1 (HO-1), quinone reductase (i.e. NAD(P)H:quinone reductase, NQO1), superoxide dismutase, glutathione peroxidase, nuclear erythroid-2 related factor 2 (Nrf2), or UDP-glucuronosyl transferase 2B7, or a combination or selection thereof. In yet another embodiment, the compounds induce the expression one or more chemoprotective phase II enzymes through binding to an Antioxidant Response Element or ARE. The compounds may induce chemoprotective phase II enzymes by activating the ARE, including the Nrf2/ARE signaling pathway. In one embodiment, the compounds my also induce the expression of chemoprotective phase II enzymes by increasing the translocation of Nrf2 into the nucleus, which can then heterodimerize with Maf proteins and trigger the transcription of ARE-related genes, such as those for the proteins listed above, and ultimately to translation and post-translational modification of the corresponding gene products. Chemoprotective phase II enzymes are further described in Paul Talalay, *BioFactors* 2000, 12:5-11, which is hereby incorporated by reference in its entirety.

In one embodiment, Compounds of the invention cause a reduction in oxidative stress markers in healthy volunteers consistent with induction of antioxidant phase 2 enzymes.

In another embodiment, Compounds of the invention increase the expression of chemoprotective phase II enzymes in a subject, when administered thereto.

In another embodiment, Compounds of the invention increase the synthesis of nucleic acids in a cell, for example genes corresponding to chemoprotective phase II enzymes, when administered thereto.

In one embodiment, Compounds of the invention cause cell growth when administered to a subject. In another embodiment, Compounds of the invention cause an enhancement of the immune system of a subject when administered thereto.

In another embodiment, compounds of the invention increase the synthesis of nucleic acids, for example DNA or RNA, in a cell when administered thereto. Compounds of the invention cause an increase in [$^3$H] thymidine uptake in spleen cells in vitro. This effect is believed to correlate with increased nucleic acid, such as DNA, synthesis. Increased DNA synthesis is also believed to correlate with cell growth, cell division, and protein synthesis. In one embodiment, compounds of the invention increase the expression of proteins in a cell when administered thereto. The observed increased [$^3$H] thymidine uptake in spleen cells is believed to correlate with these effects in cells of the immune system, thus leading to enhancement of the immune system and its ability to fight disease, including cancer and tumors.

Methods of Enhancing Cell Survival

In another embodiment, compounds of the invention may increase the health of a subject to which it is administered by methods taught herein. As shown herein, compounds of the invention cause the proliferation, enhance survival, and increase the life-span of healthy cells, in concentrations or dosages taught herein. This is shown for healthy cells in vitro, in Tables 7 and 8, Examples 24 and 25, and in FIG. 9 showing the experimental results as actual cell counts. The compounds cause the proliferation of normal cells of the immune system, including splenocytes and lymphocytes, as reflected by increasing their synthesis of DNA. DNA synthesis is known to correlate with cell proliferation. In another embodiment, compounds of the invention increase cell survival. This can occur through increasing DNA synthesis of a cell or increasing proliferation of normal cells. In one embodiment, compounds of the invention increase the proliferation of cells of the immune system. In another embodiment, compounds of the invention increase a subject's immune response, for example by the increasing the proliferation of cells of the immune system. Consequences of increased proliferation of immune cells include increased capability to fight diseases or infections.

Uses of Compounds of Formula (I) to Improve Cancer Treatment Outcomes

In one embodiment, compounds of the invention increase body weight when administered in combination with a chemotherapeutic agent. In another embodiment, compounds of the invention prevent or reduce the loss of body weight that occurs with cancer treatments including chemotherapy. In yet another embodiment, Compounds of the invention reduce the toxicity of cytotoxic agents.

In one embodiment, the invention provides a method for increasing or maintaining body weight during chemotherapy comprising administering a compound of Formula (I) to a subject in need thereof. A compound of Formula (I) can be administered concurrently with a cytotoxic agent, before, or after administration of the cytotoxic agent, as described herein. In an embodiment the invention provides a method for reducing the cytotoxicity of cytotoxic agents comprising administering a compound of Formula (I) to a subject in need thereof. In one embodiment, the invention provides the use of a compound of Formula (I), of any one of Formula (I-a)-(I-o) or any one of Compounds (A)-(HH) for increasing or maintaining body weight during chemotherapy. In another embodiment, the invention provides the use of compounds of the invention for reducing the cytotoxicity of cytotoxic agents. In one embodiment, the cytotoxic agent is a chemotherapeutic, for example as taught in Tables 1 and 2. In one embodiment, the cytotoxic agent is fludelone, iso-oxazole-fludelone, isodehydelone, 5-fluorouracil, cyclophosphamide, paclitaxel (TAXOL), or vinblastine.

In another embodiment, the invention provides a method for reducing the toxicity of a cytotoxic agent, such as a chemotherapeutic agent, comprising administering a compound of Formula (I) or any of Formulae (I-a)-(I-o) to a cell or subject in need thereof. In one embodiment, the chemotherapeutic agent is a tubulin-binding agent. In another embodiment, the chemotherapeutic agent is paclitaxel. In yet another embodiment, the chemotherapeutic agent is Fludelone. In still another embodiment, the chemotherapeutic agent is Iso-Flu. In one embodiment, the toxicity reduced is neurotoxicity. In one embodiment, the neurotoxic effect is peripheral neuropathy. In another embodiment, the neurotoxic effect is partial paralysis. In one embodiment, the subject as been administered a cytotoxic agent previously. In another embodiment, the compound of Formula (I) or any of Formulae (I-a)-(I-o) is administered concurrently with a cytotoxic agent. In another embodiment, the compound of Formula (I) or any of Formulae (I-a)-(I-o) is administered prior to administration of a cytotoxic agent.

In another embodiment, the invention provides a method for reducing peripheral neuropathy, comprising administering a compound of Formula (I), or any of Formulae (I-a)-(I-o), to a cell or subject in need thereof. The peripheral neuropathy can be induced by a cytotoxic agent, e.g. a cancer chemotherapeutic agent. Such chemotherapeutic agents include fludelone, iso-oxazole-fludelone, isodehydelone, and paclitaxel, or those otherwise disclosed herein. In one embodiment, the compound of Formula (I), or any of Formulae (I-a)-(I-o), is orally active, and thus can be administered orally to a subject.

In one embodiment, the invention provides a method for reducing the body weight loss that accompanies the administration of chemotherapeutic agents, comprising administering a compound of Formula (I), or any of Formulae (I-a)-(I-o), to a cell or subject in need thereof, such as a subject undergoing cancer treatment. Such chemotherapeutic agents may include fludelone, iso-oxazole-fludelone, isodehydelone, cyclophosphamide, 5-fluorouracil, and paclitaxel, or those otherwise disclosed herein. In one embodiment, the compound of Formula (I), or any of Formulae (I-a)-(I-o), is orally active, and thus can be administered orally to a subject.

In one embodiment, Compounds of the invention reduce the toxicity of anticancer agents. The compounds also reduce the physiological symptoms caused by the use of anticancer agents in a subject, when administered to a subject in need thereof. In one embodiment, the compound of Formula (I), or any of Formulae (I-a)-(I-o), is orally active, and thus can be administered orally to a subject.

In another embodiment, the invention provides a method for enhancing cell survival comprising administering a compound of Formula (I), or any of Formulae (I-a)-(I-o), to a cell or subject in need thereof, for example cells or a subject exposed to toxic agents, e.g. cancer chemotherapy agents.

In another embodiment, compounds of the invention are cytotoxic to cancer cells at higher dosages than that at which they are useful for increasing cell proliferation. In one embodiment, the compounds at higher dosages can inhibit DNA, RNA, and/or protein synthesis in a cell, as shown herein. At high doses, some compounds of Formula (I) lead to cell growth suppression, and may be useful to treat or prevent the growth of cancer cells in vitro and in vivo. Thus, in one embodiment, the invention provides a method for suppressing cell growth, inhibiting DNA synthesis, inhibiting RNA synthesis, or inhibiting protein synthesis, comprising administering a compound of Formula (I), or any of Formulae (I-a)-(I-o), to a subject in need thereof. Compounds of the invention, therefore, also are useful in treating cancer.

In one embodiment, Compounds of the invention reduce inflammation. Compounds of the invention can be administered to a subject in need thereof in order to treat inflammation. Indications capable of treatment by the Compounds of the invention include rheumatoid arthritis, inflammatory bowel syndrome, ulcerative colitis, Crohn's disease, joint pain, headaches, or other pain.

In one embodiment, compounds of Formula (I), or any of Formulae (I-a)-(I-o), are useful as nutraceuticals. Compounds of the invention can sustain or enhance the general health or well-being of a subject to which they are administered. In one embodiment, compounds of the invention sustain or enhance the general health or well-being of a subject to which they are administered orally to a subject, for example a subject in need of sustaining or improving their general well-being. Thus, compounds of the invention can improve the health of a subject when administered thereto. As noted herein, compounds of the invention can have this effect when administered orally.

In another embodiment, the invention provides a composition comprising a compound of Formula (I), or any of Formulae (I-a)-(I-o), for stimulating the immune system or enhancing the general well-being of a subject when administered to a subject. For example, Compounds of Formula (I), or any of Formulae (I-a)-(I-o), e.g. Compounds A, D or K, can be used as general tonics or a well-being pill (i.e., a nutraceutical). In one embodiment, compounds of the invention promote health and well-being of a subject when administered at low doses. Without wishing to be bound by theory, compounds of the invention may have a regulatory effect on processes described herein, and may not have an acute effect. Compounds of the invention may reduce physical or chemical stress on cells or in a subject. Compounds can have this effect over a prolonged duration, for example from 24 to 120 hours after administration. Compounds can also have a delayed onset of action.

In one embodiment, Compounds of Formula (I), or any of Formulae (I-a)-(I-o), prolong white blood cell survival when administered to a subject in need thereof. This effect can also be seen in vitro. In another embodiment, Compounds of Formula (I), or any of Formulae (I-a)-(I-o), enhance the immune system of a subject in need thereof when administered thereto. In yet another embodiment, Compounds of the invention stimulate human lymphocytes activity or production, and mouse splenocyte activity or production. In still another embodiment, compounds of Formula (I), or any of Formulae (I-a)-(I-o), stimulate DNA and/or RNA synthesis. Compounds of the invention show an unusually high dynamic/kinetic parameter ($m \gg 1$), and unusually prolonged pharmacological effect at low concentrations. In yet another embodiment, Compounds of the invention prevent cancer by inducing Phase 2 enzymes and by enhancing the immune system. In still another embodiment, Compounds of the invention extend the life span of a subject when administered thereto.

In one embodiment, the invention provides compositions comprising a compound of Formula (I) for improving or enhancing the general well-being of a subject. The subject can be in need of an improvement in their general well-being. In another embodiment, the invention provides compositions comprising a compound of Formula (I) for reducing physico-chemical stress. Physico-chemical stress can be, for example, acute or chronic toxicity caused by cytotoxic agents, for example cancer chemotherapeutic agents, or environmental toxins, for example dioxins or benzene. In another embodiment, the invention provides compositions comprising a compound of Formula (I) for promoting the healing of injuries in a subject in need thereof. The injuries can be physical injuries, or caused by chemical or radiation damage, for example by cancer chemo- or radiation therapy.

In yet another embodiment, the invention provides compositions comprising a compound of Formula (I) for enhancing the immune system of a subject. The subject can be in need of such immune system enhancement, for example due to a naturally or genetically suppressed immune system, as occurs during cancer chemotherapy, or due to exposure to environmental toxins for example dioxins. In one embodiment, the immune system is enhanced by induction of a chemoprotective phase II enzyme.

In one embodiment, the invention provides tools to study the effects of ginseng extracts, such as by the screening methods disclosed herein. Compounds A and D are single chemical entities (i.e., not a mixture) and are more potent than ginseng extracts, which include the natural compound panaxytriol as seen in Table 2X. A single entity is easier to study, to standardize, to characterize and to manage as a new drug. Ginseng or ginseng extracts or preparations vary by their sources and factors including geographical locations, weather conditions, altitudes and conditions of cultivation. Previous studies using ginseng extracts in vitro, in animals and in humans are marred by uncertainties and contradictions among numerous reports mainly due to using unstandardized extracts or fractions, non-optimal conditions for experimentation or a lack of understanding of extraordinary pharmacological properties of ginseng or ginseng products. The present invention illuminates the pharmacological properties of ginseng and ginseng extracts, and helps explain the lack of understanding and uncertain experimental results using ginseng and ginseng products. The inventors have discovered that active agents in ginseng and compounds of the invention can have a bi-phasic effect (as seen in FIGS. 8, 10, and 11), delayed onset of therapeutic action, and a prolonged duration of activity, as shown by the figures.

Kits

The invention encompasses kits that can simplify the administration of a Compound of the invention optionally with a unit dosage form of a tubulin-binding drug to a subject.

The invention also encompasses kits that can simplify the administration to a subject of a Compound of the invention optionally with a unit dosage form of a chemotherapeutic or cytotoxic drug.

The invention also encompasses kits that can simplify the administration of a Compound of the invention to a subject. The invention also encompasses kits that can simplify the administration to a subject of a Compound of the invention optionally with a unit dosage form of a drug. In some embodiments, the drug can be a cancer chemotherapeutic drug, a cytotoxic drug, or a neurotoxic drug.

A kit of the invention comprises a unit dosage form of a Compound of the invention optionally with a unit dosage form of a tubulin-binding drug or other chemotherapeutic drug. In one embodiment the unit dosage form is a container, which can be sterile, containing an effective amount of a Compound of the invention and a tubulin-binding drug and a physiologically acceptable carrier or vehicle. In another embodiment, the unit dosage form is a container, which can be sterile, containing an effective amount of a Compound of the invention and a physiologically acceptable carrier or vehicle. The kit can further comprise a label or printed instructions instructing the use of the Compound of the invention or use of the Compound of the invention and a tubulin-binding drug to treat or prevent a cancer or a Condition. The kit can also further comprise a unit dosage form of another prophylactic or therapeutic agent, for example, a container containing an effective amount of the other prophylactic or therapeutic agent. In one embodiment the kit comprises a container containing an effective amount of a Compound of the invention and a tubulin-binding drug and an effective amount of another prophylactic or therapeutic agent. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The invention is further described in the following examples, which do not limit the scope of the invention described in the claims. The following examples illustrate methods of syntheses of Compounds and demonstrate their usefulness for treating or preventing a Condition, optionally in combination with a tubulin-binding, chemotherapeutic, or other cytotoxic drug.

5. EXAMPLES

General Synthetic Methods

All commercial materials were used without further purification unless otherwise noted. Commercial materials were often obtained from Sigma-Aldrich or TCI America. THF, diethyl ether and methylene chloride used as reaction solvents were obtained from a dry system (alumina) and used without further drying. Alternatively, solvents were reagent grade and purified by standard techniques: THF was distilled from Na-benzophenone or filtered through a dry-solvent system; $CH_2Cl_2$ was distilled from $CaH_2$ or filtered through a dry-solvent system. Other solvents were Aldrich "anhydrous" grade solvents. Hexamethylphosphoramide was freshly distilled over calcium hydride under vacuum. All reactions were performed under a positive pressure of argon atmosphere in flame-dried vessels. Reactions were magnetically stirred and monitored by thin layer chromatography on Merck silica gel 60-$F_{254}$ coated 0.25 mm plates, unless indicated otherwise. Yields reported are for isolated, spectroscopically pure compounds. Melting points are uncorrected. $^1H$ spectra were obtained on a Bruker DRX-300, DRX-400, or a DMX 500 MHz instrument and are reported in parts per million ($\delta$) from residual non deuterated solvent as an internal reference. $^{13}C$ NMR spectra were recorded on AMX-75 MHz Bruker instruments and are reported in parts per million ($\delta$) from residual non deuterated solvent as an internal reference. Abbreviations for $^1H$ NMR: s=singlet, d=doublet, t=triplet, q=quartlet, m=multiplet, or br=broad. $CDCl_3$ was allowed to stand over $K_2CO_3$ and 4 A MS to neutralize and dry prior to NMR sample preparation. Infrared (IR) spectra were taken as a thin film on a Perkin Elmer FT-IR Spectrometer Paragon 1000. Optical rotations were recorded on a Jasco DIP-1000 polarimeter using a 1 dm cell at the standard or reported temperature and concentrations. High resolution mass spectra were recorded on a JEOL-DX-303 HF or a a JEOL HX110 mass spectrometer. Analytical thin layer chromatography was performed on E. Merck silica gel 60 F254 plates (0.25 mm) Liquid column chromatography was performed using forced flow of a mixture of solvents on E. Merck silica gel 60 (40-63 mm), or flash chromatography was performed with Sorbent Technology silica gel 60 (particle size 32-63 µm), unless otherwise indicated. Purification by preparative Thin Layer Chromatography (TLC) was performed using silica gel GF plates (1000 microns) or Merck silica gel 60-$F_{254}$ coated 0.50 mm plates. When required, the stereochemistry was established by suitable one-dimensional or multi-dimensional NMR studies.

General Biological Methods

The cytotoxicity $IC_{50}$ of each compound was measured with the XTT assay using the 2,3-bis(2-methoxy-4-nitro-5-sulfophenyl)-5-[(phenylamino)carbonyl]-2H-tetrazolium hydroxide (XTT) microculture method as described in Scudiero et al., *Cancer Res.*, 48:4827 (1988), the contents of which are hereby incorporated by reference in their entirety. The CCK-8 assay is a cell counting kit-8 (CCK-8) tetrazolium assay using a 96-well microplate (Dojindo Molecular Technologies, Inc., Rockville, Md.) (M. Ishiyama et al., Biol. Pharm. Bull. 19: 1518, 1996). Absorbance was measured by Powerwave a XS microplate spectrophotometer. This method described is considered a general method in vitro cytotoxicity studies.

The data in Tables 2X, 3A-E, 4, 5, and 6 were obtained using the cell counting kit-8 (CCK-8) tetrazolium assay in a 96-well microplate. Five to seven concentrations of each compound in triplicate were used, and the $IC_{50}$ values were determined by CompuSyn software automation (Chou T C. and Martin N. ComboSyn, Inc., 2006) based on the median-effect equation and plot (Chou T C. J. Theor. Biol. 59:235-276, 1976; Chou T C. Pharmacol. Rev. 58: 621-681, 2006). The mass-action law parameters reported are defined as follows: Dm (the median-effect dose) signifies potency (e.g., $IC_{50}$); the m value defines the shape of the dose-effect curve (the kinetic order), where m=1, >1, and <1 indicates hyperbolic, sigmoidal, and flat sigmoidal, respectively. The r value defines the correlation coefficient of the median-effect plot which signifies the conformity to the mass-action law principle (Chou T C. J. Theor. Biol. 59:235-276, 1976; Chou T C. Pharmacol. Rev. 58:621-681, 2006). These parameters were determined by CompuSyn simulation (available at http://www.combosyn.com).

General Discussion

Figure 2:
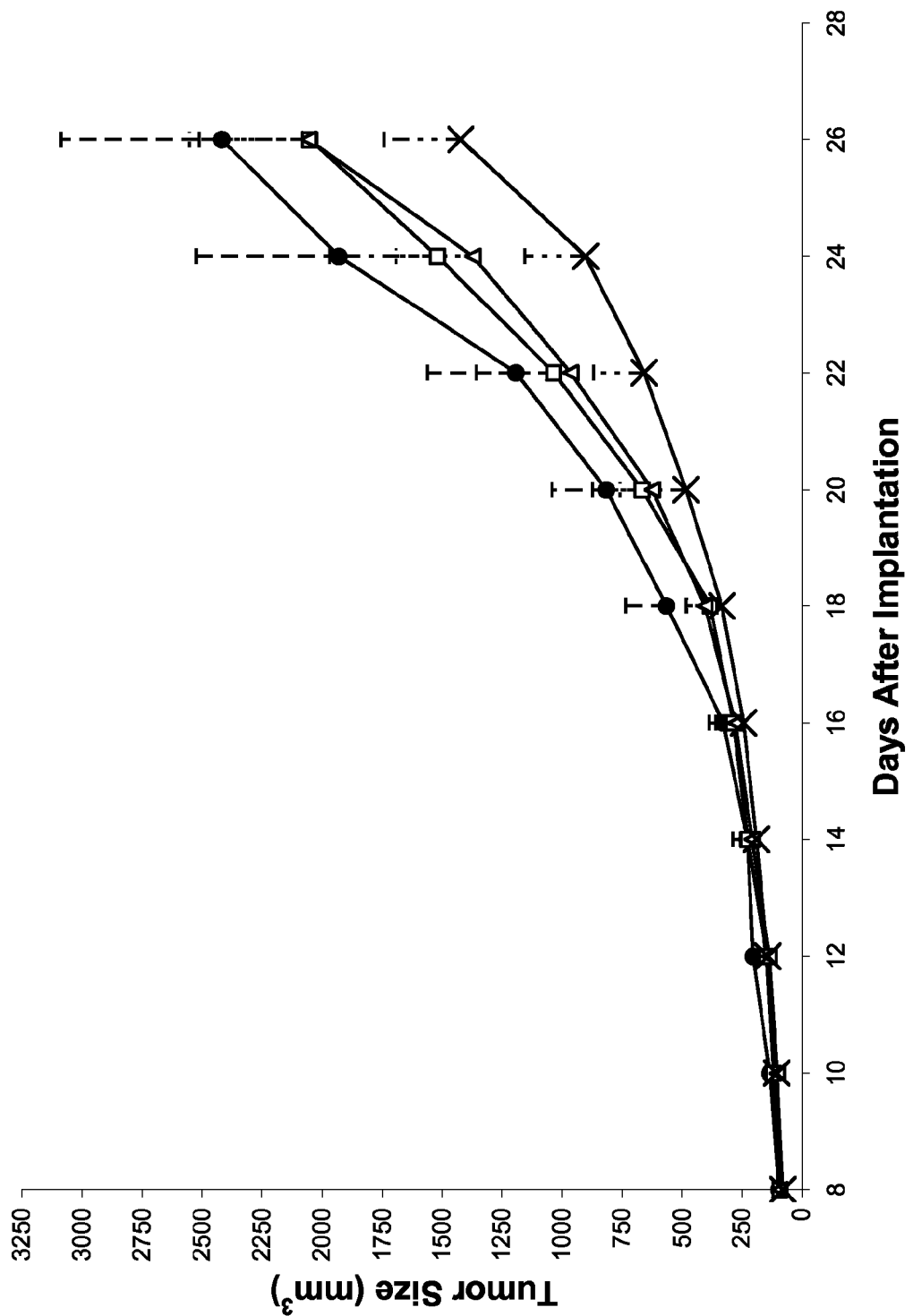
Figure 3:
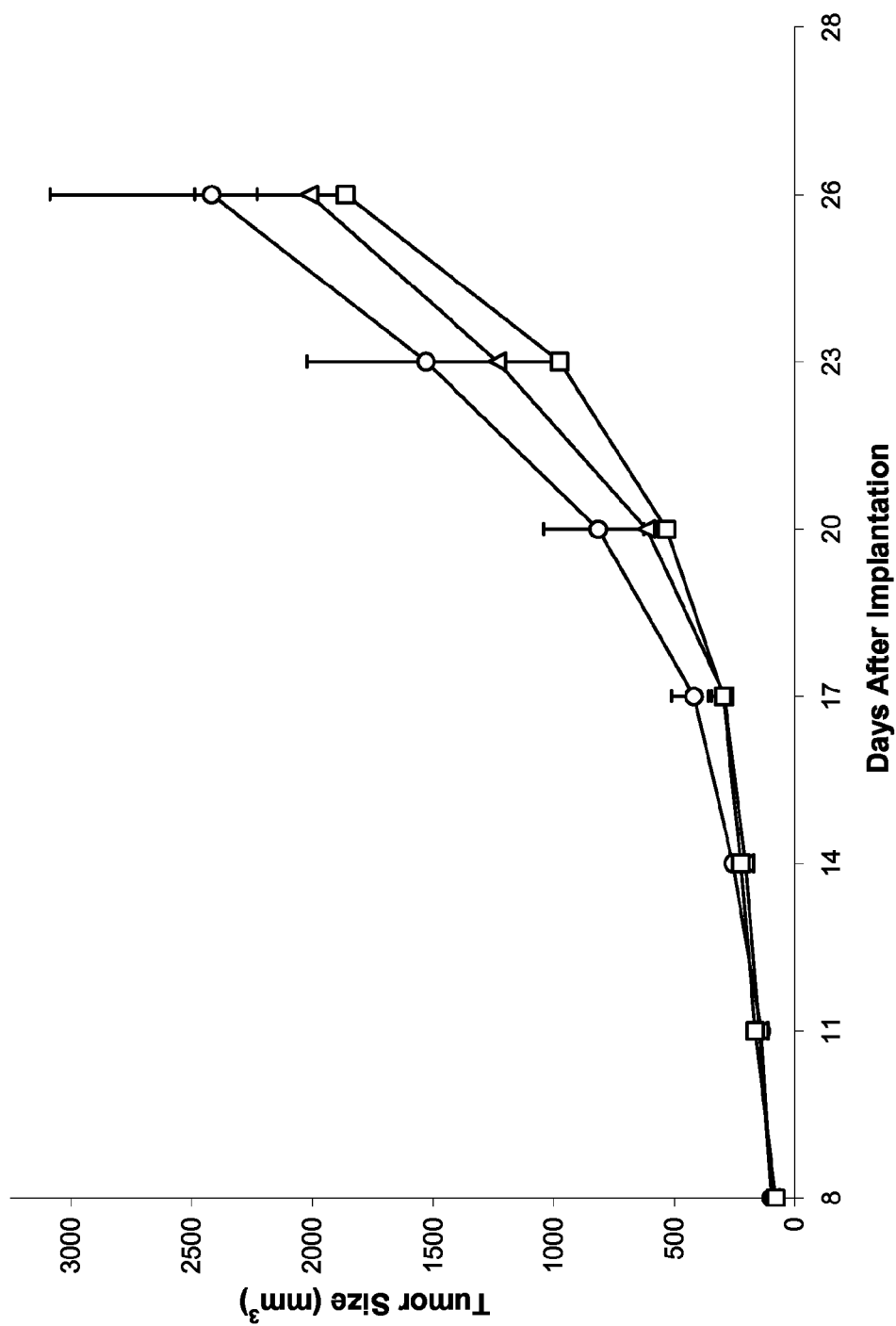

Illustrative Compounds of Formula (I) (e.g. Compounds (A) and (D)) show significant anticancer activity and do not appear to be cross-resistant to TAXOL or vinblastine and thus not substrates for multiple drug resistance. They have broad tumor cell antiproliferative activities (Tables 2X-4) and sigmoidal dose-effect curves in vitro (m>1) (Table 5) indicating higher order dynamics or modes of action. Panaxytriol, Compound A and Compound D showed antitumor effects against MX-1 xenografts (FIGS. 2, 3 and 4), but Compound D was more effective at lower doses than panaxytriol.

Figure 8A:
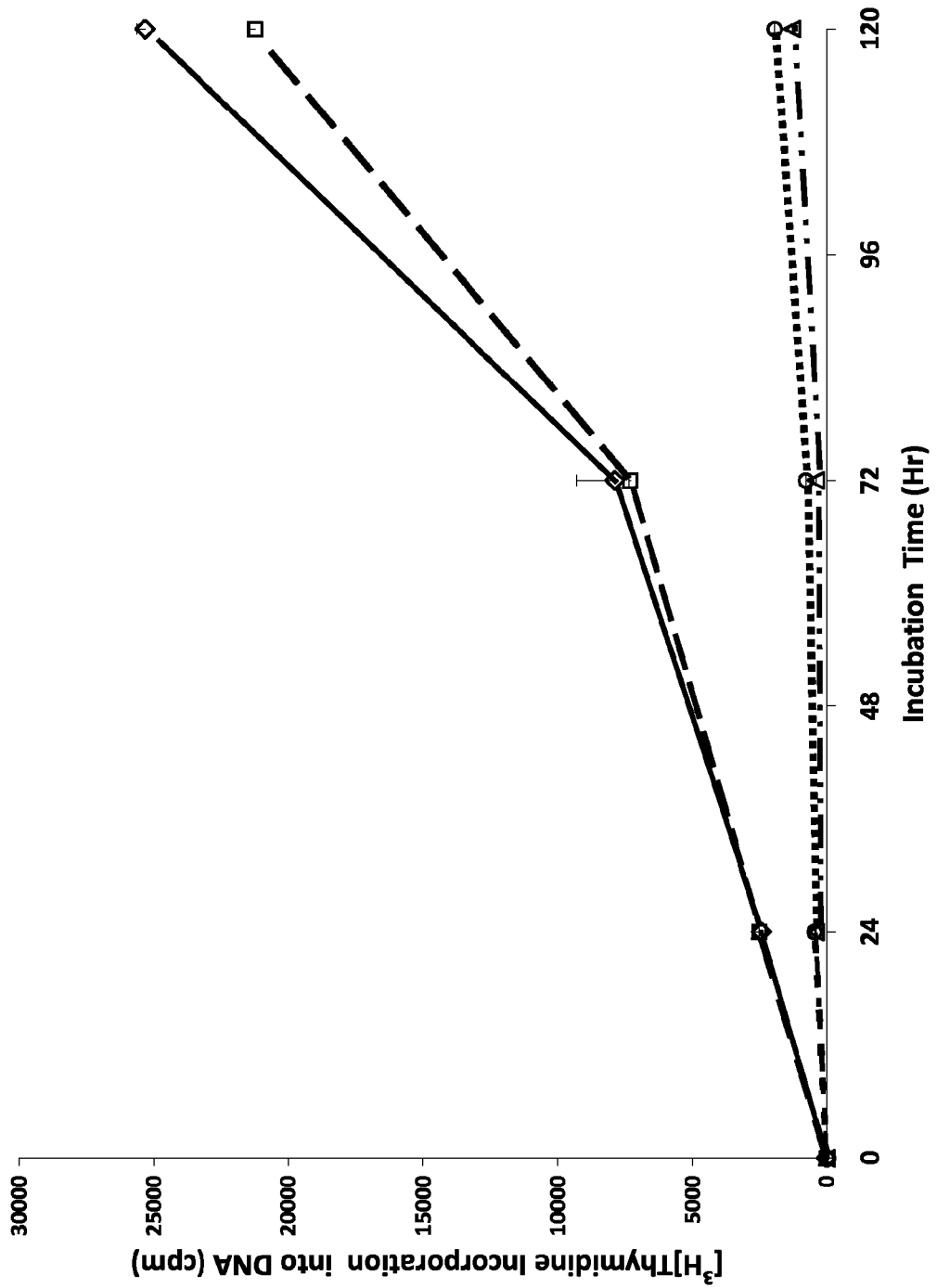
FIG. 8B shows a dose-response curve for panaxytriol on stimulation of DNA synthesis (i.e. cell proliferation) in cultured, human PBMC lymphocytes as measured by radiolabeled thymidine incorporation into DNA. ○ represents the dose effect of panaxytriol at 24 hrs; □ represents the dose effect of panaxytriol at 72 hrs; Δ represents the dose effect of panaxytriol at 120 hrs.
FIG. 8C shows a dose-response curve for Compound D on stimulation of DNA synthesis (i.e. cell proliferation) in cultured, human PBMC lymphocytes as measured by radiolabeled thymidine incorporation into DNA. ○ represents the dose effect of Compound D at 24 hrs; □ represents the dose effect of Compound D at 72 hrs; and Δ represents the dose effect of Compound D at 120 hrs.
FIG. 8D is an overlay of FIGS. 8B and 8C, ○ represents the dose effect of panaxytriol at 24 hrs; □ represents the dose effect of panaxytriol at 72 hrs; Δ represents the dose effect of panaxytriol at 120 hrs; ◊ represents the dose effect of Compound D at 24 hrs; ■ represents the dose effect of Compound D at 72 hrs; and X represents the dose effect of Compound D at 120 hrs.
FIG. 8E is a reverse plot of FIG. 8B showing the effects of different concentrations of panaxytriol at various time points on the proliferation of cultured, human PBMC lymphocytes as measured by radiolabeled thymidine incorporation into DNA. ○ represents Panaxytriol at 0.3 uM; □ represents Panaxytriol at 1 uM; Δ represents Panaxytriol at 3 uM; and ◊ represents Panaxytriol at 10 uM.
FIG. 8F is a reverse plot of FIG. 8C showing the effects of different concentrations of panaxytriol at various time points on the proliferation of cultured, human PBMC lymphocytes as measured by radiolabeled thymidine incorporation into DNA. ○ represents Compound D at 0.3 uM; □ represents Compound D at 1 uM; Δ represents Compound D at 3 uM; and ◊ represents Compound D at 10 uM.
FIG. 8G is an overlay of FIGS. 8E and 8F. ○ represents Panaxytriol at 0.3 uM; □ represents Panaxytriol at 1 uM; Δ represents Panaxytriol at 3 uM; ◊ represents Panaxytriol at 10 uM; ● represents Compound D at 0.3 uM; ■ represents Compound D at 1 uM; ▲ represents Compound D at 3 uM; and ♦ represents Compound D at 10 uM.
Figure 8B:
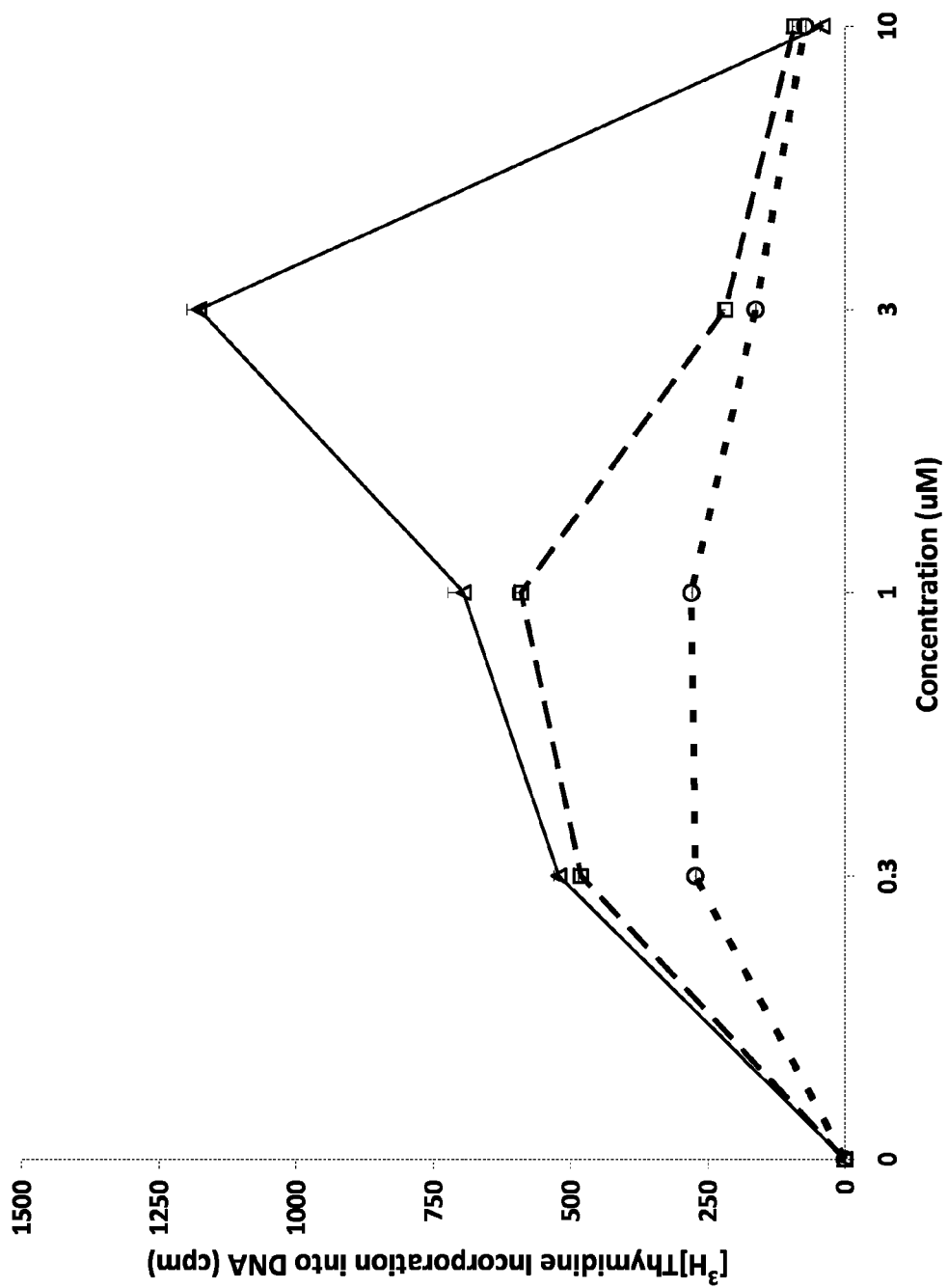
Figure 8C:
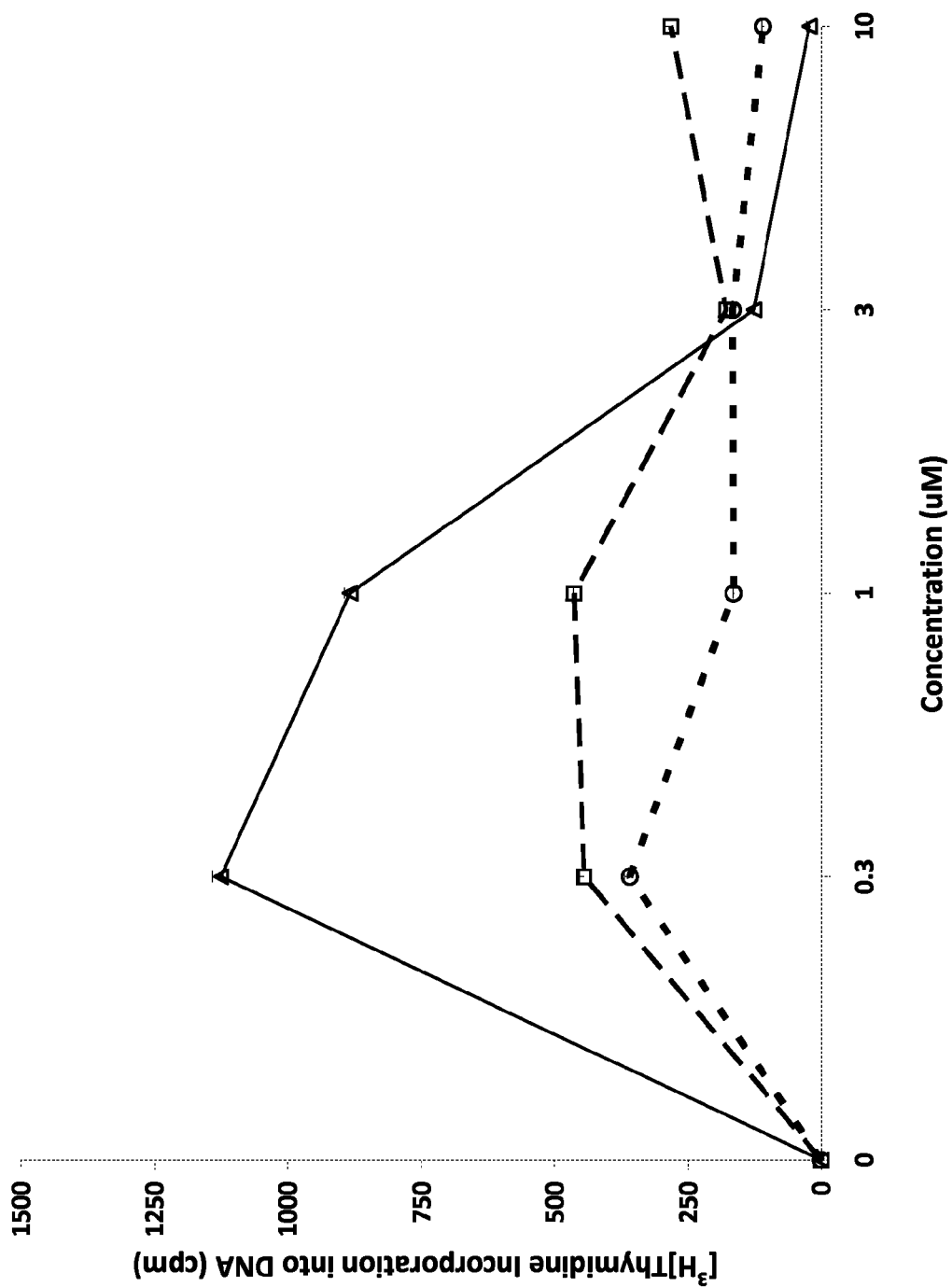
Figure 8D:
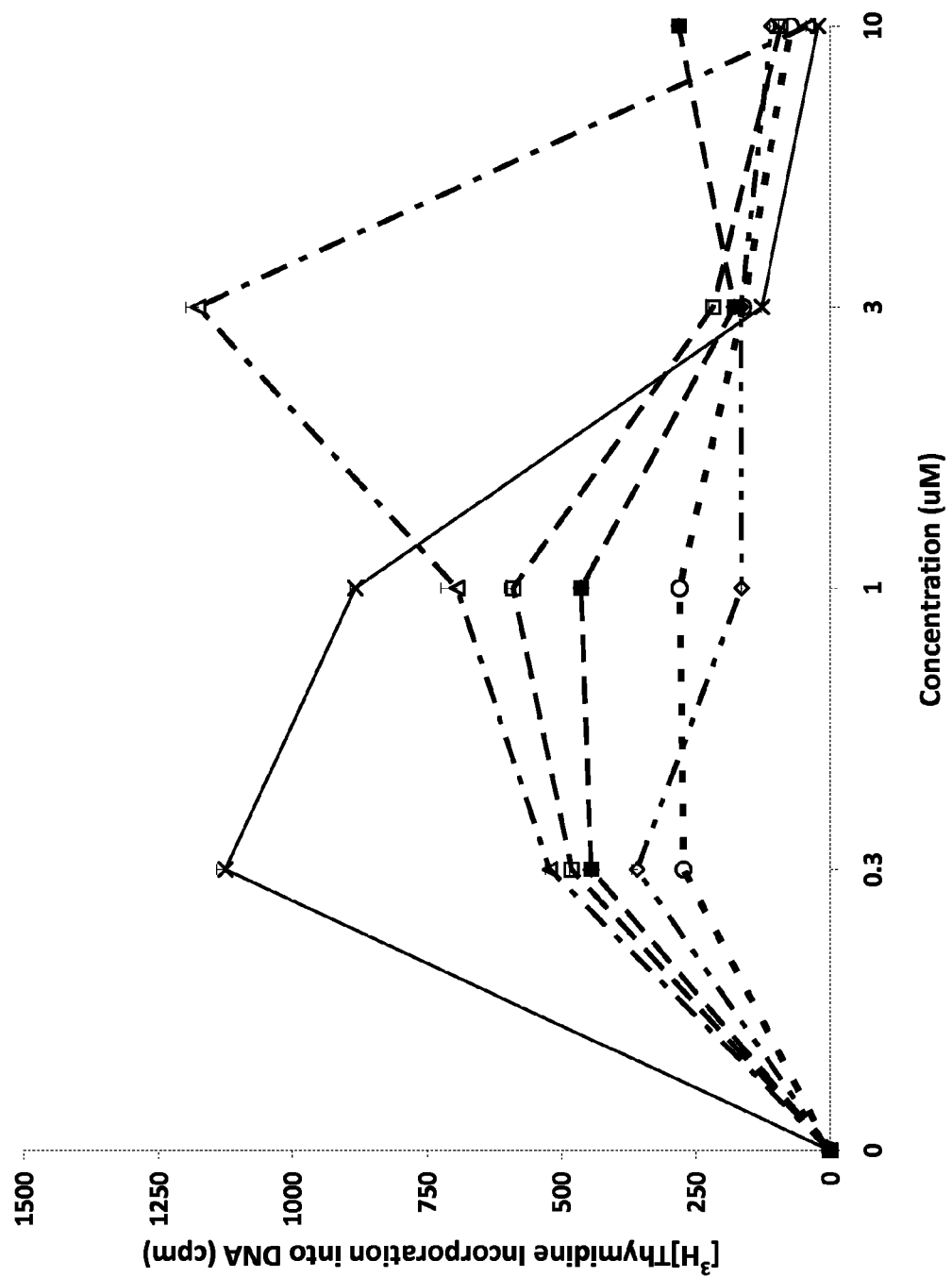
Figure 8E:
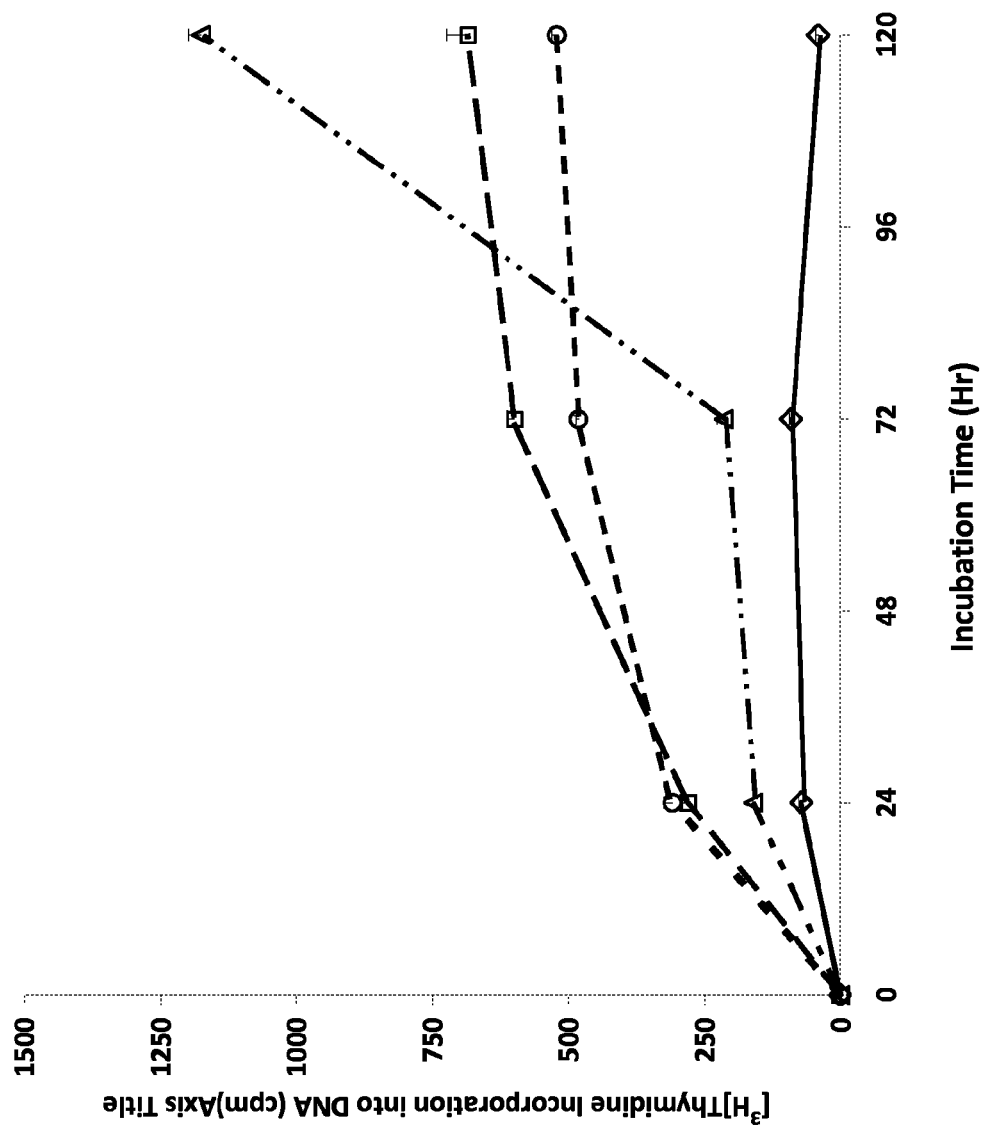
Figure 8F:
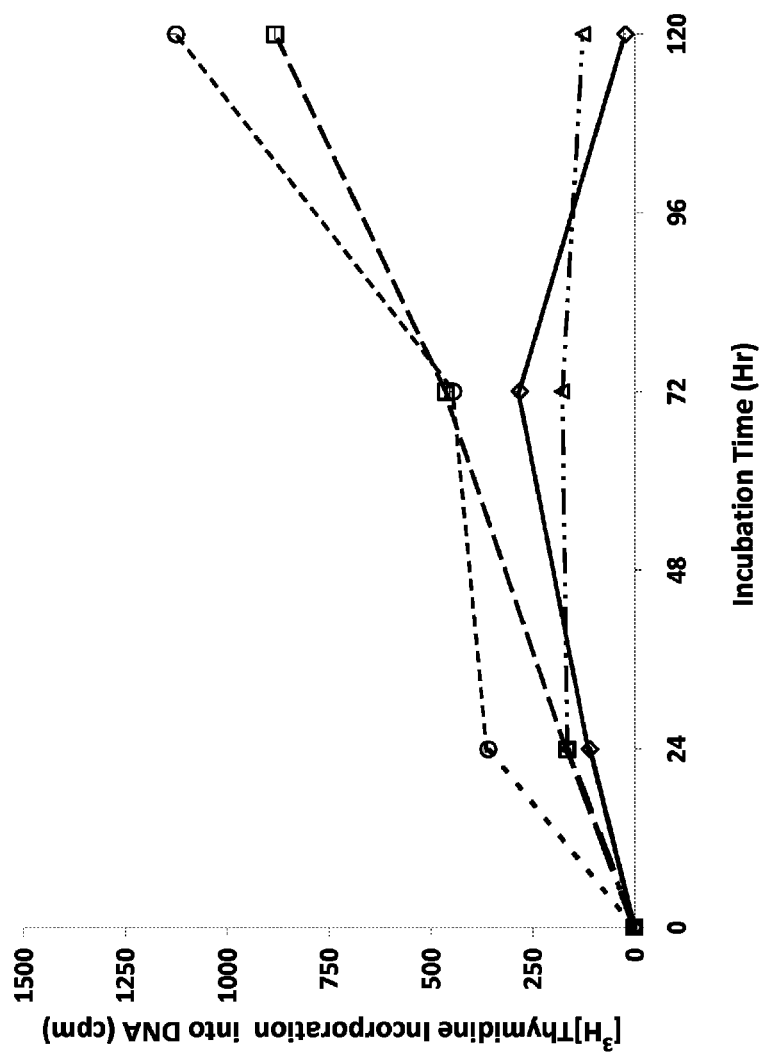
Figure 8G:
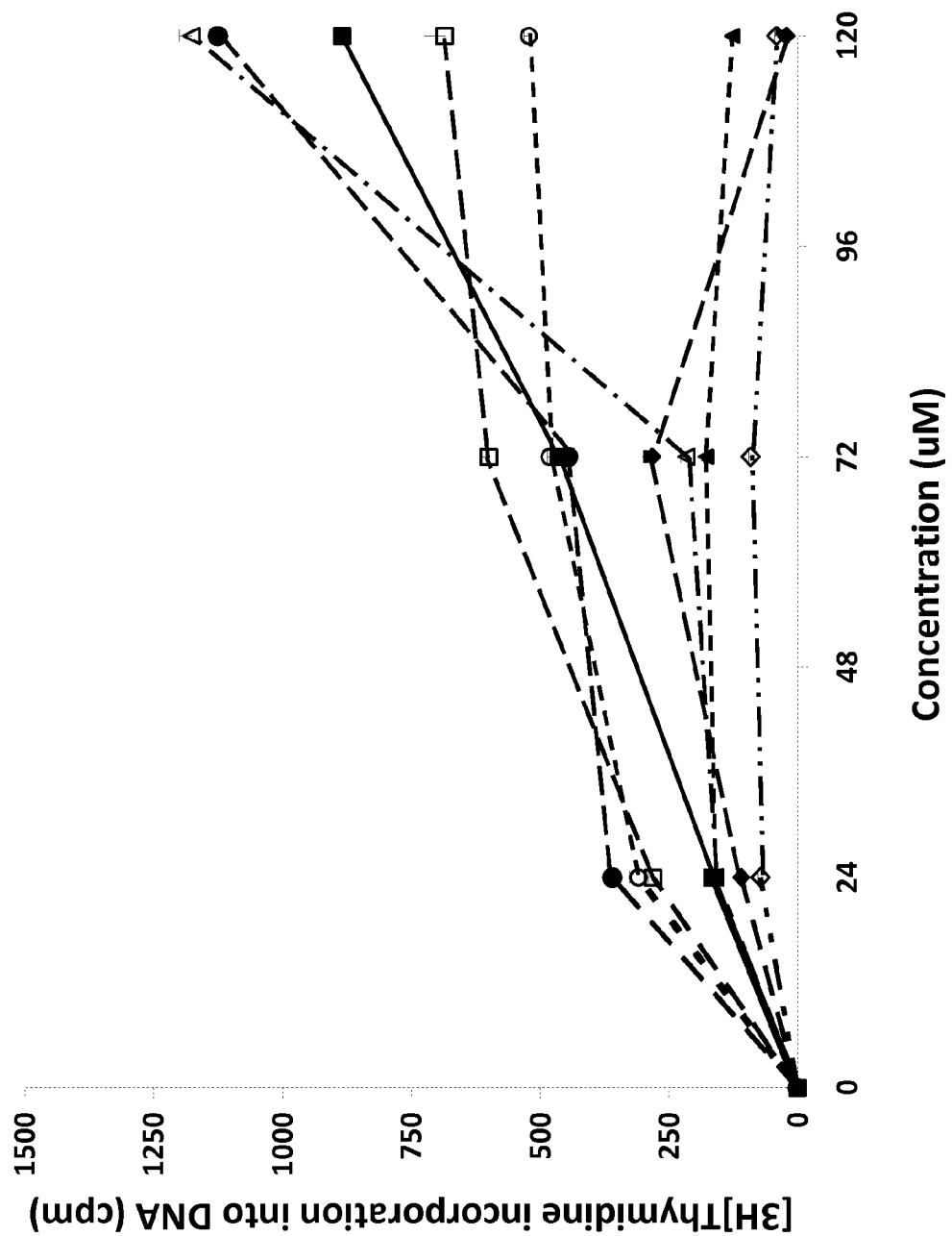

Illustrative Compounds of Formula (I) stimulated normal human lymphocyte DNA synthesis (Table 6) and normal CD-1 mouse splenocytes DNA synthesis (Table 7). They show a biphasic dose-effect relationship (e.g. inverted V- or U-Shape) as seen in FIGS. 8B, C, D; 9A, B; 10B, C, E, F; and 11C). Compounds of Formula (I) also activated lymphocytes and splenocytes (both immunologic cells) at low doses (0.01-0.3 µM) but showed a marked reduction in effect at moderate doses (1-10 µM) (FIGS. 10 and 11).

The proliferative activity life-span of normal mouse splenocytes in vitro was prolonged by panaxytriol and Compound (D) (FIGS. 10 and 11). Panaxytriol and Compound (D) also increased the survival of normal PBMC lymphocytes at low concentrations (Tables 8). Panaxytriol and Compound (D) also reduced or delayed spontaneous cell death of normal human lymphocytes at low concentrations (0.1-0.3 µM), but increased cell death at high concentrations (3-10 µM) (FIGS. 9A, B).

Figure 4A:
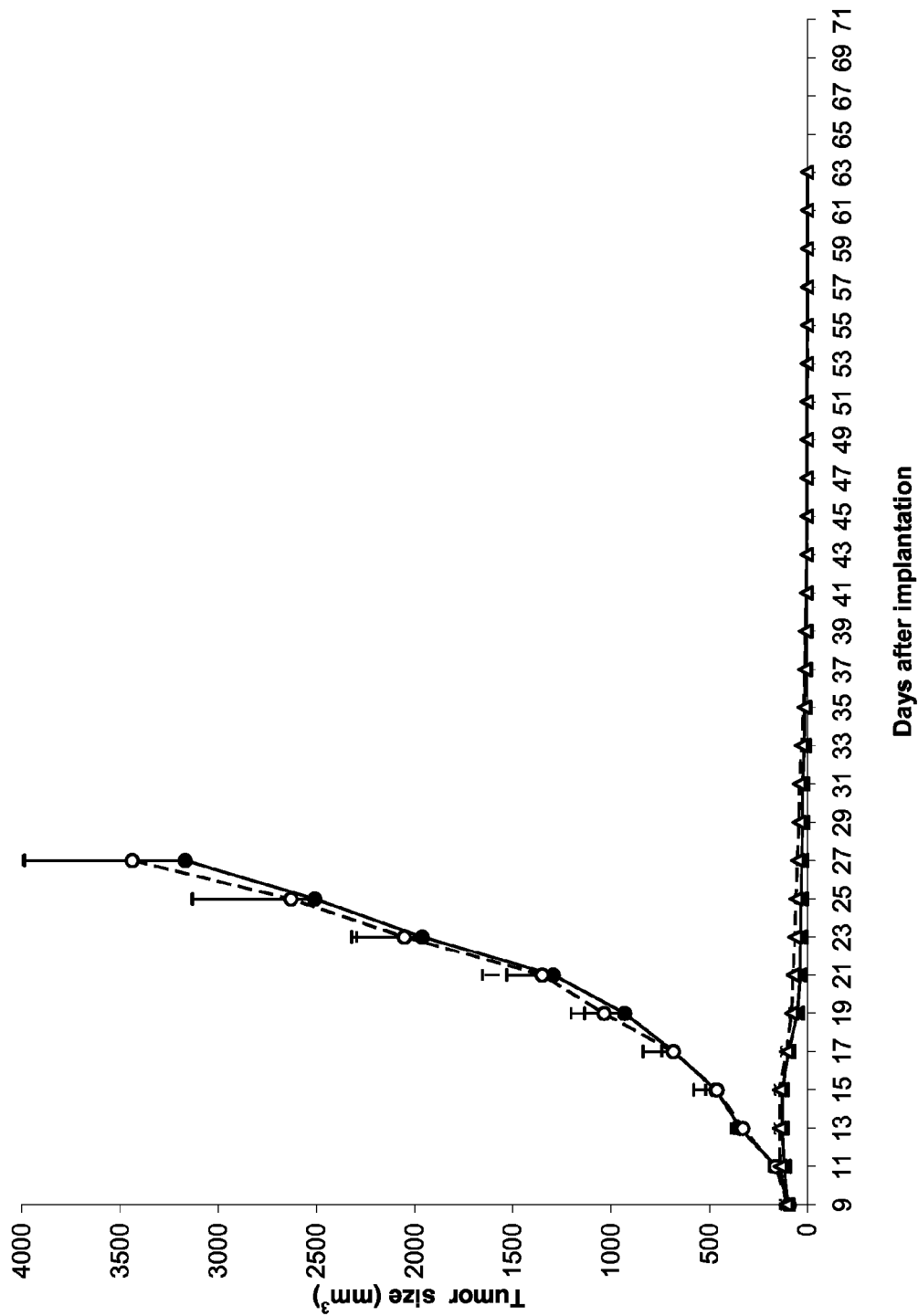
Figure 4B:
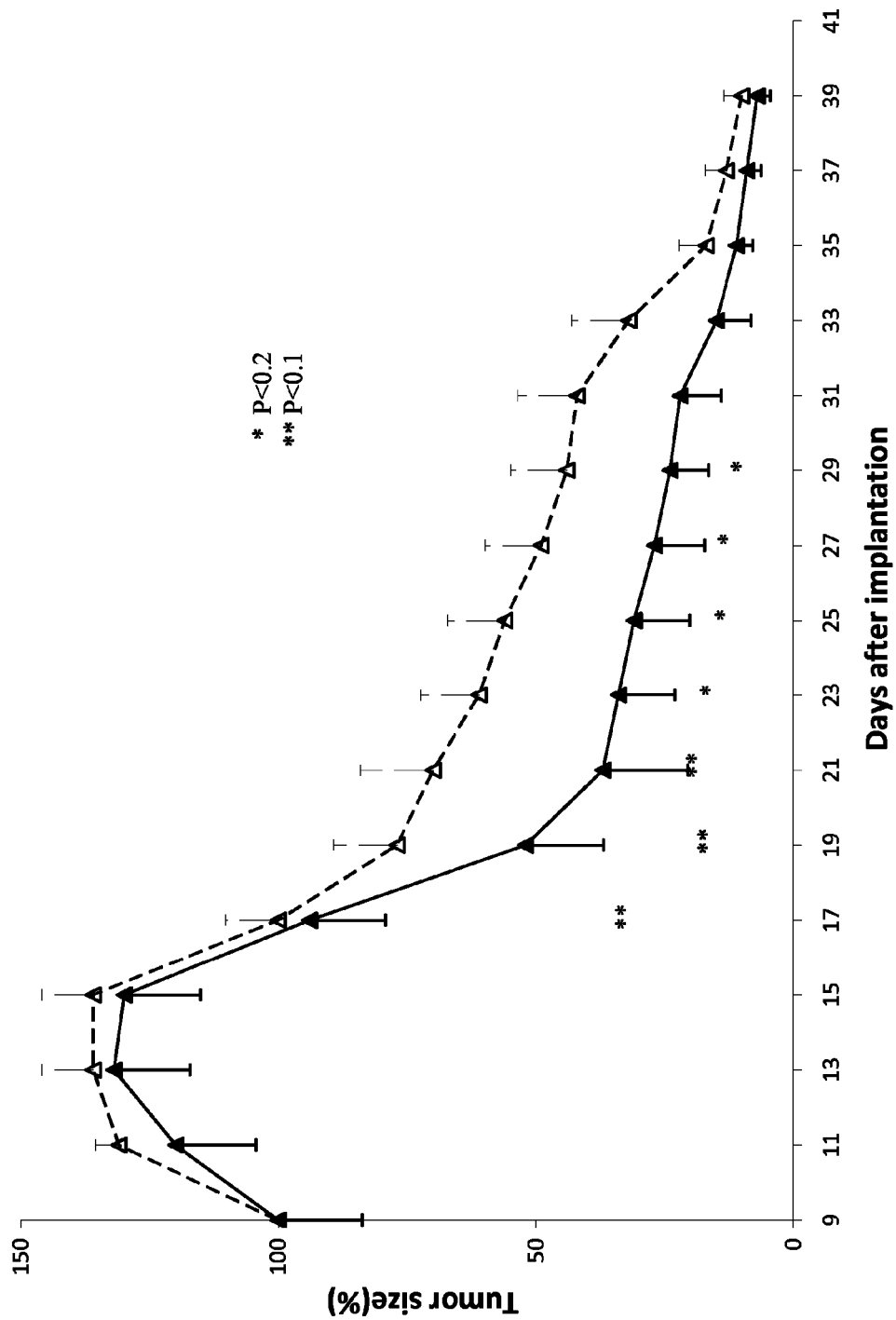
Figure 4C:
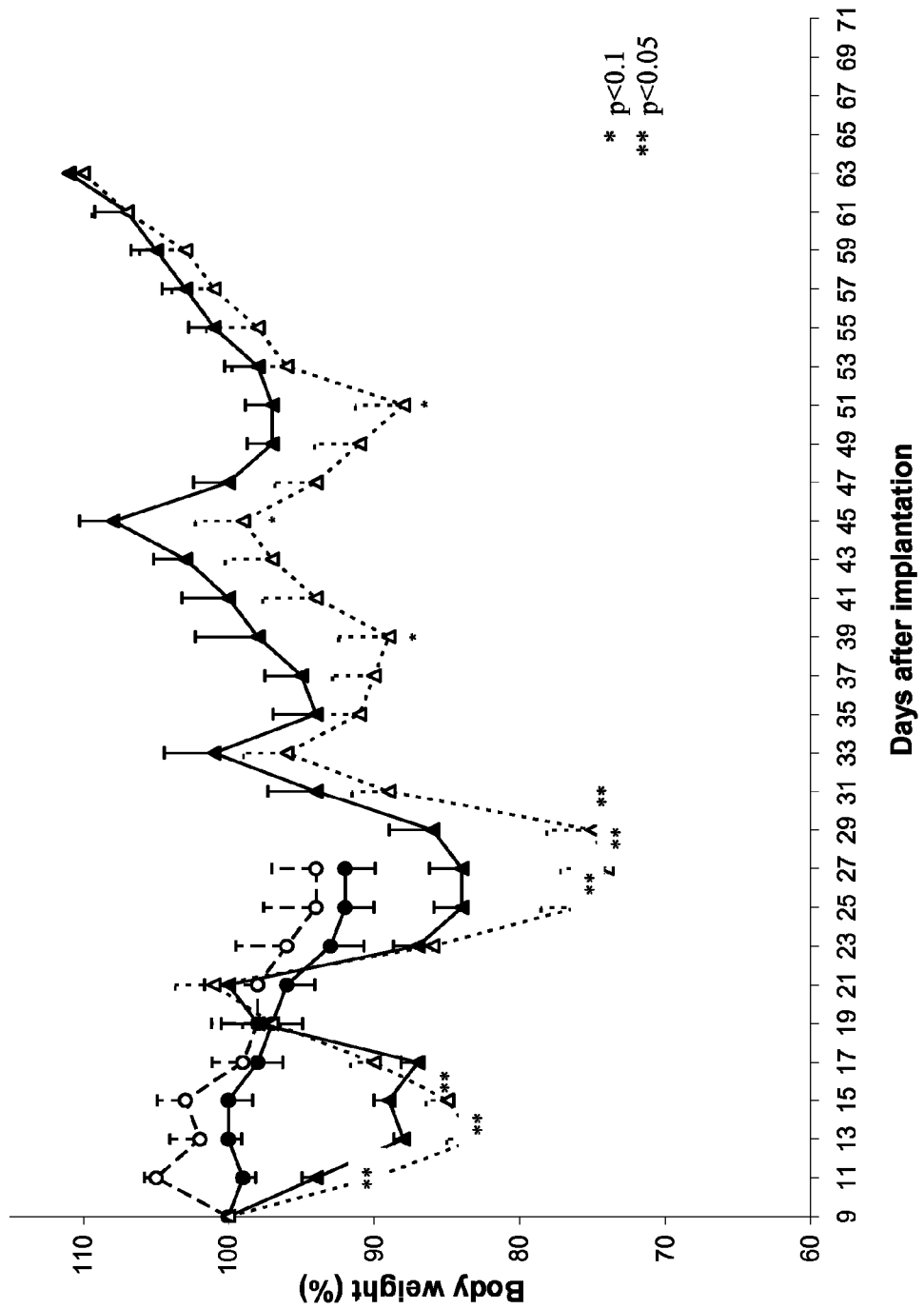
Figure 5A:
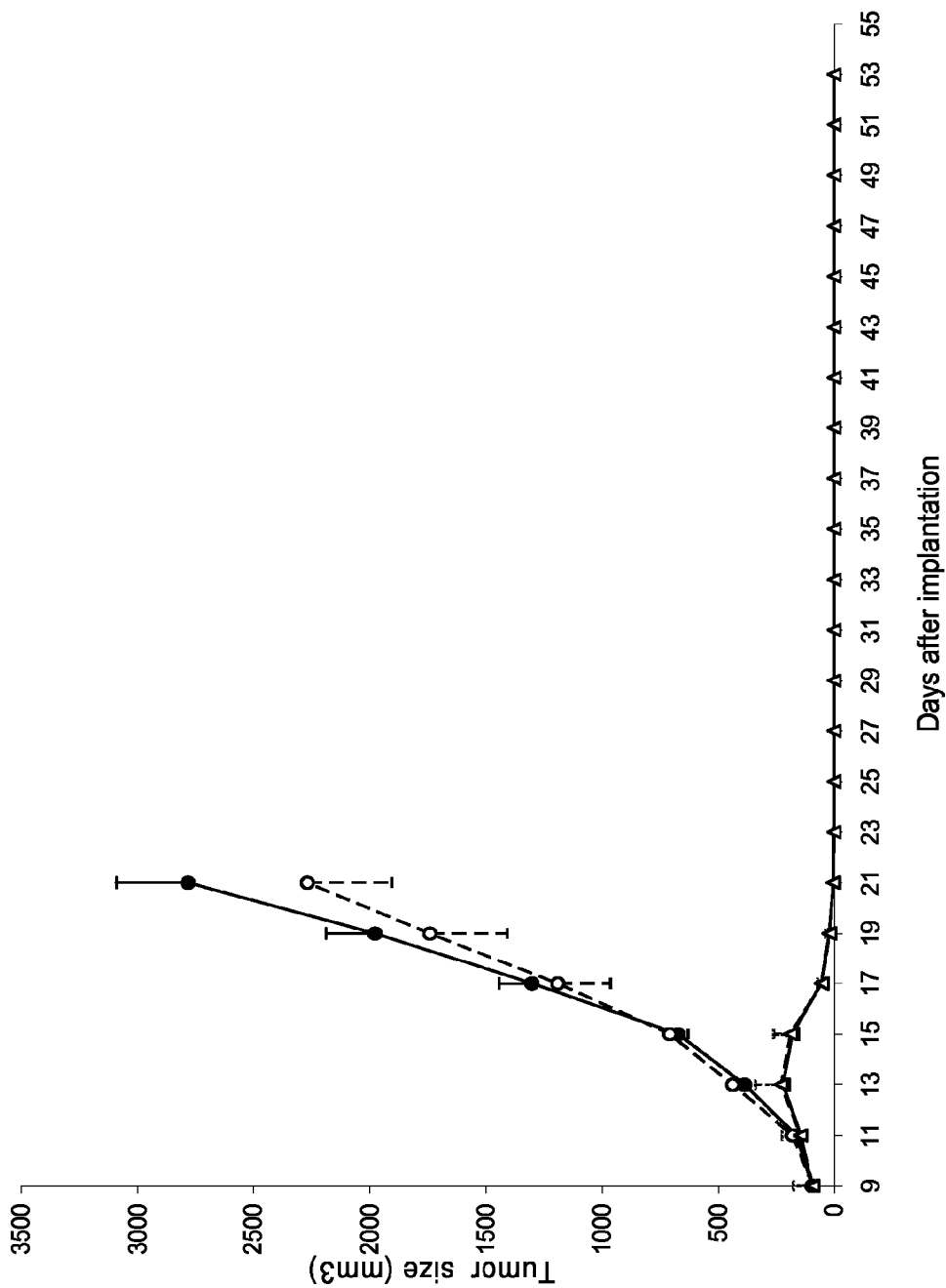
Figure 5B:
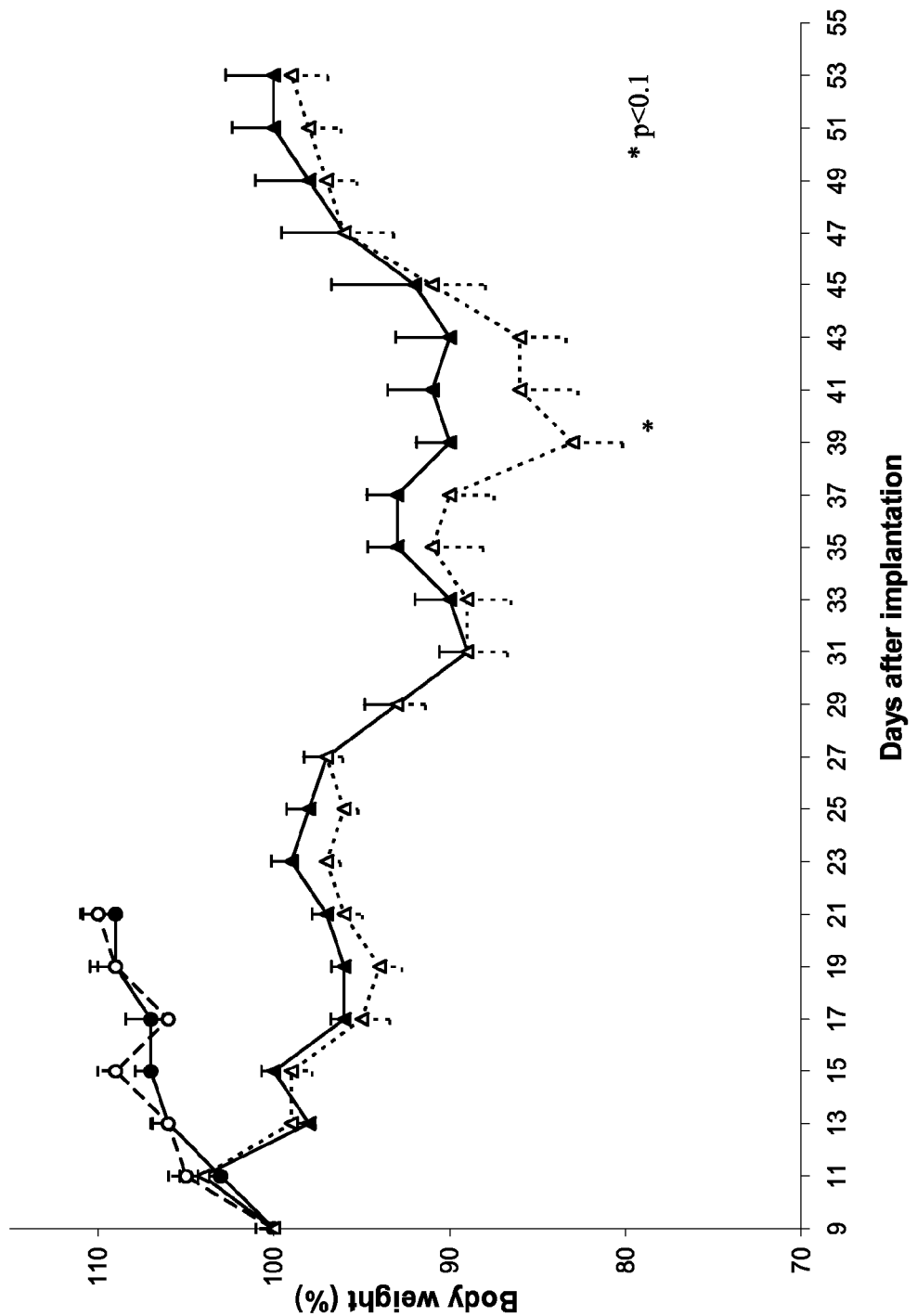

Surprisingly, compounds of Formula (I), including Formulae (I-a)-(I-o), markedly decreased body-weight loss caused by illustrative cytotoxic agents. Compound (D) showed this protective effect when used in conjunction with a tubulin-binding anticancer drug (iso-oxazole-fludelone, FIGS. 4C, 7B), a DNA-alkylating agent (cyclophosphamide, FIG. 5B), and an antimetabolite (5-fluoro-uracil, FIG. 6B). Compounds of Formula (I), including Formulae (I-a)-(I-o), also increased the anti-cancer therapeutic effect against xenograft tumors by the tubulin-binding anticancer drug (iso-oxazole-fludelone, FIGS. 4A and B, 7A), a DNA-alkylating agent (cyclophosphamide, FIG. 5A), and an antimetabolite (5-fluoro-uracil, FIG. 6A) For MX-1 xenograft bearing nude mice, Compound D (at 10 mg/kg, Q3D×3, Q6D×3, i.v.) reduced the tumor size and increased the subject body-weight (FIGS. 4A-C). Compound D increased the effect of other anticancer chemotherapeutic agents (e.g., 5-Fluorouracil, 5-FU) and reduced the 5-FU-induced nude mice toxicity-death-rate (from 5/8 deaths reduced to 2/8 deaths) (FIGS. 5A, B).

Panaxytriol (PXT) and Fludelone (a $2^{nd}$ generation microtubule binding anti-tumor epothilone) are synergistic against the growth of mammary carcinoma MX-1 cells (with CI values of 0.61-0.816, where CI<1, indicates synergism) and have a favorable dose-reduction index (DRI>1) (PXT DRI=1.46-2.7; Fludelone DRI=2.27-46.73) while maintaining the same antiproliferative effect (Table 5).

Furthermore, panaxytriol and Compound D at a low concentration (30 µM and 6 µM respectively) during a short incubation (e.g., 15 min) activate DNA and RNA synthesis but are both inhibitory at a higher concentration (e.g., 100 µM) for a longer (60 min) incubation. For protein synthesis, both compounds showed inhibitory effects. These results again showed bi-phasic effects. See Table 9.

Compounds of Formula I, Compounds A and D, show sigmoidal dose-effect curves (m>1), bi-phasic characteristics of effects (inverted U- or V-shape curves), delayed onset of effects and duration of effects (e.g., maximal stimulation of lymphocyte at 120 hrs, and maximal splenocyte stimulation at 48 or 72 hrs), and marked stimulatory effect at low concentrations (e.g., 0.01-0.1 µM, but little stimulatory or inhibitory effect at 10 µM).

Figure 6A:
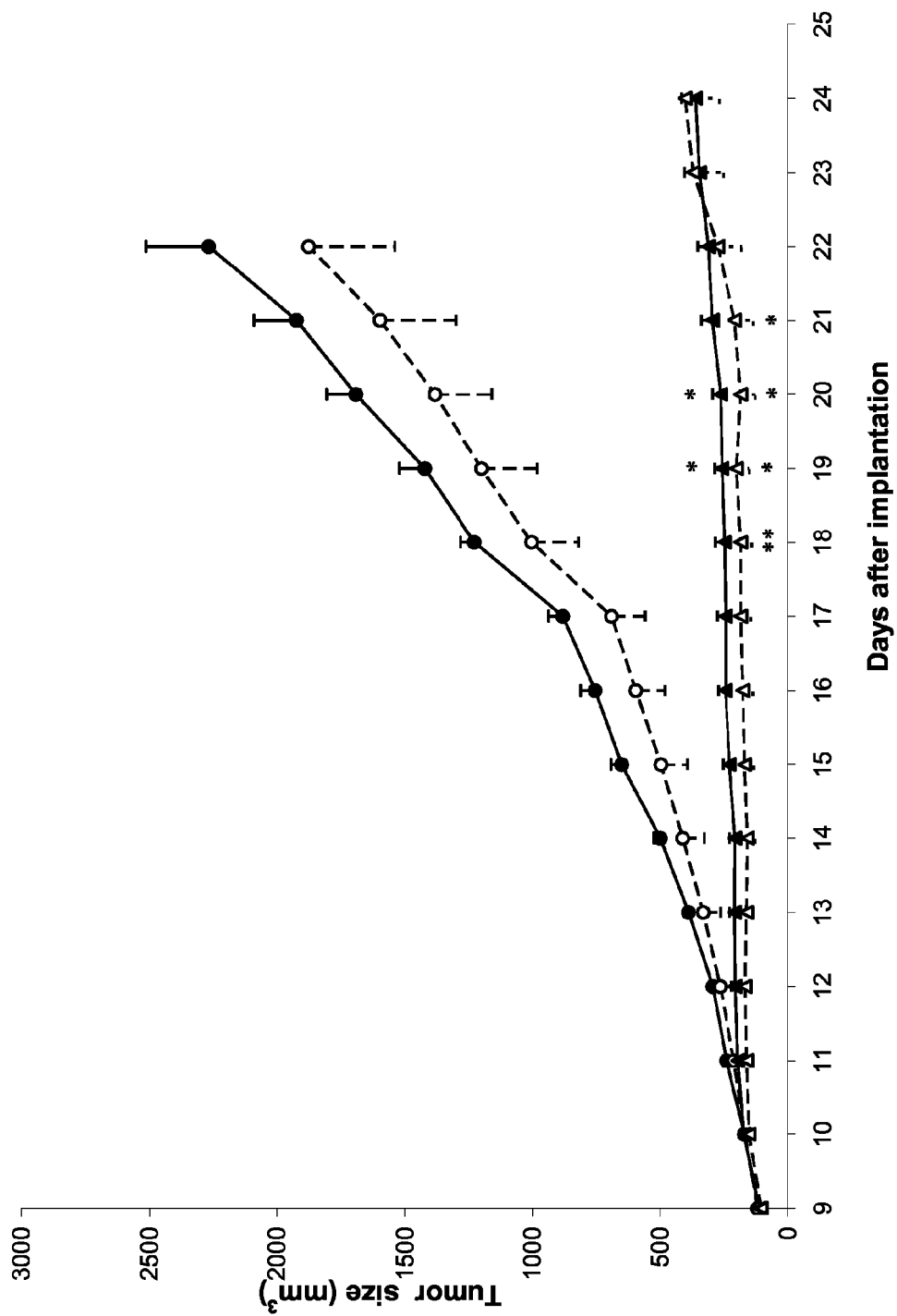
Figure 6B:
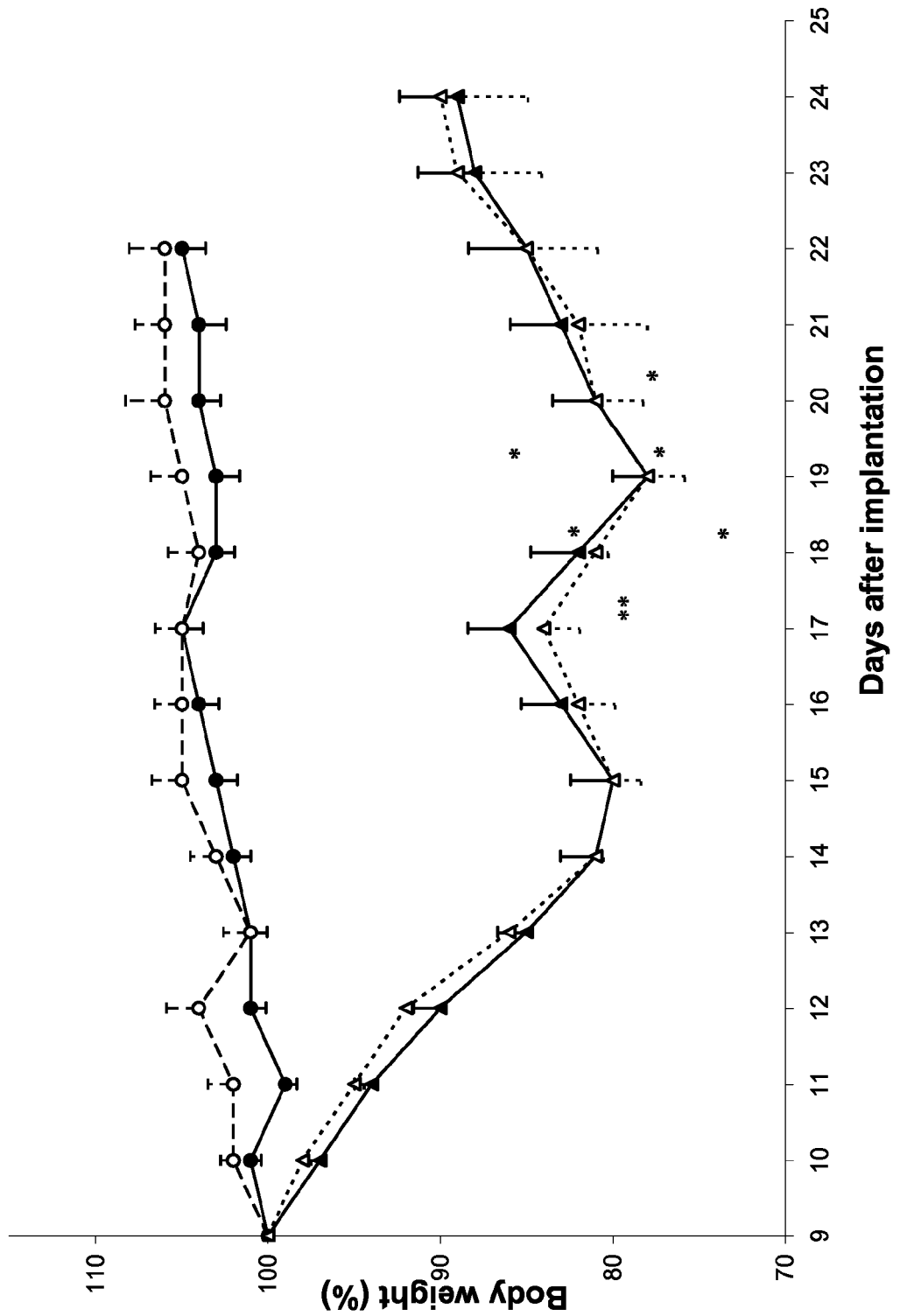
Figure 7A:
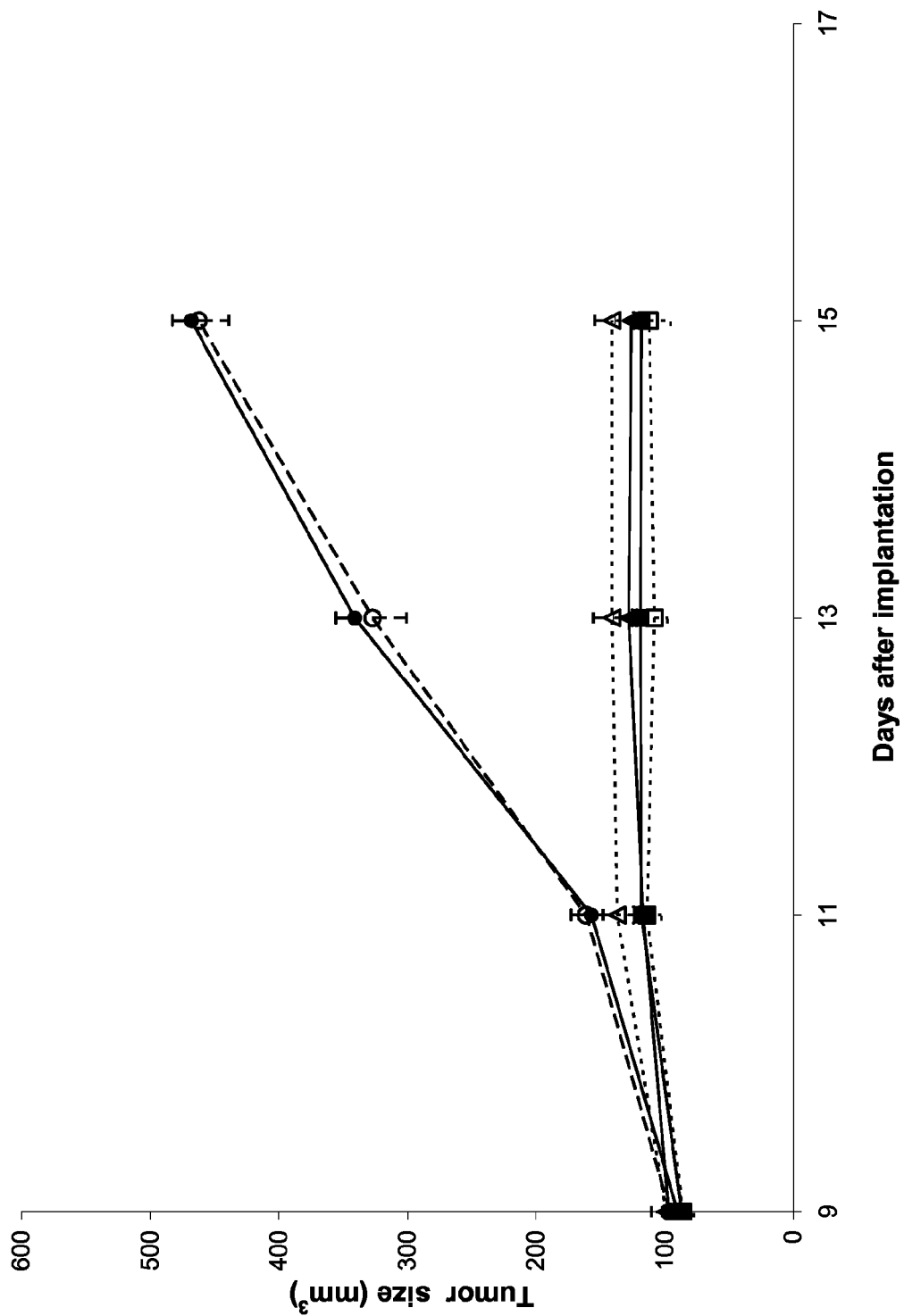
Figure 7B:
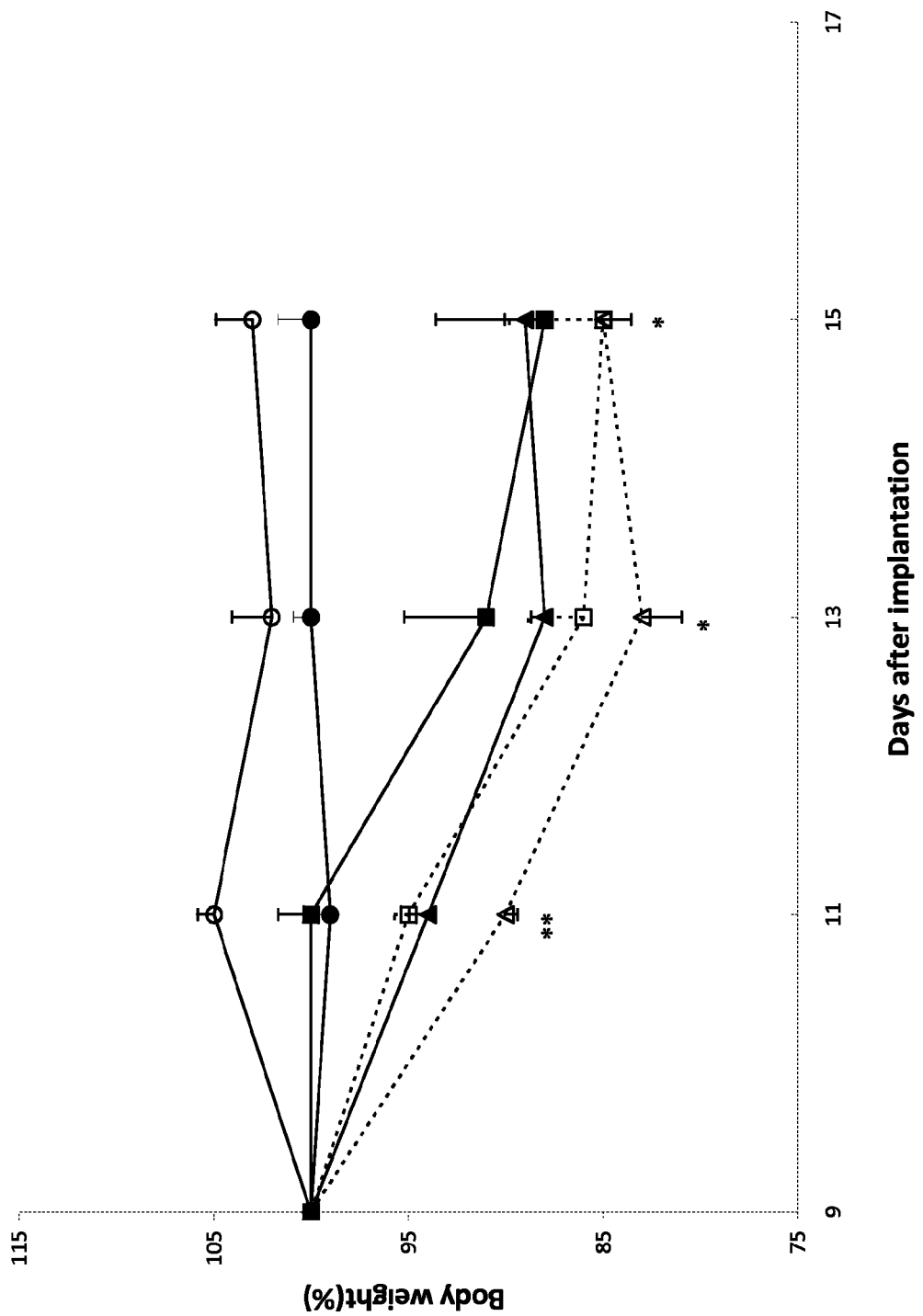

Compound D reduced the toxicities induced by various chemotherapeutic agents such as microtubule targeting compounds (e.g., iso-oxazole-fludelone, FIGS. 4A, B, C; 7A, B), alkylating agents (e.g., cyclophosphamide, FIGS. 5A, B) and antimetabolite agents such as 5-fluoro-uracil (5FU) (FIGS. 6A, B). Compound D by itself suppressed MX-1 mammary carcinoma xenograft 10% at a dose of 10 mg/kg i.v. Q4D×4. While co-treatment with Compound D did not significantly reduce the acute body-weight decrease due to 5-fluorouracil (5FU) (an antimetabolite anticancer agent) at 50 mg/kg i.v. QD×5, and the therapeutic effect of 5FU was not significantly increased; however, the 5FU-treated group had 5/8 animals die at this high dose of 5FU toxicity but the 5FU+Compound D treated group had only 2/8 animals die (FIGS. 6A, B).

Figure 1A:
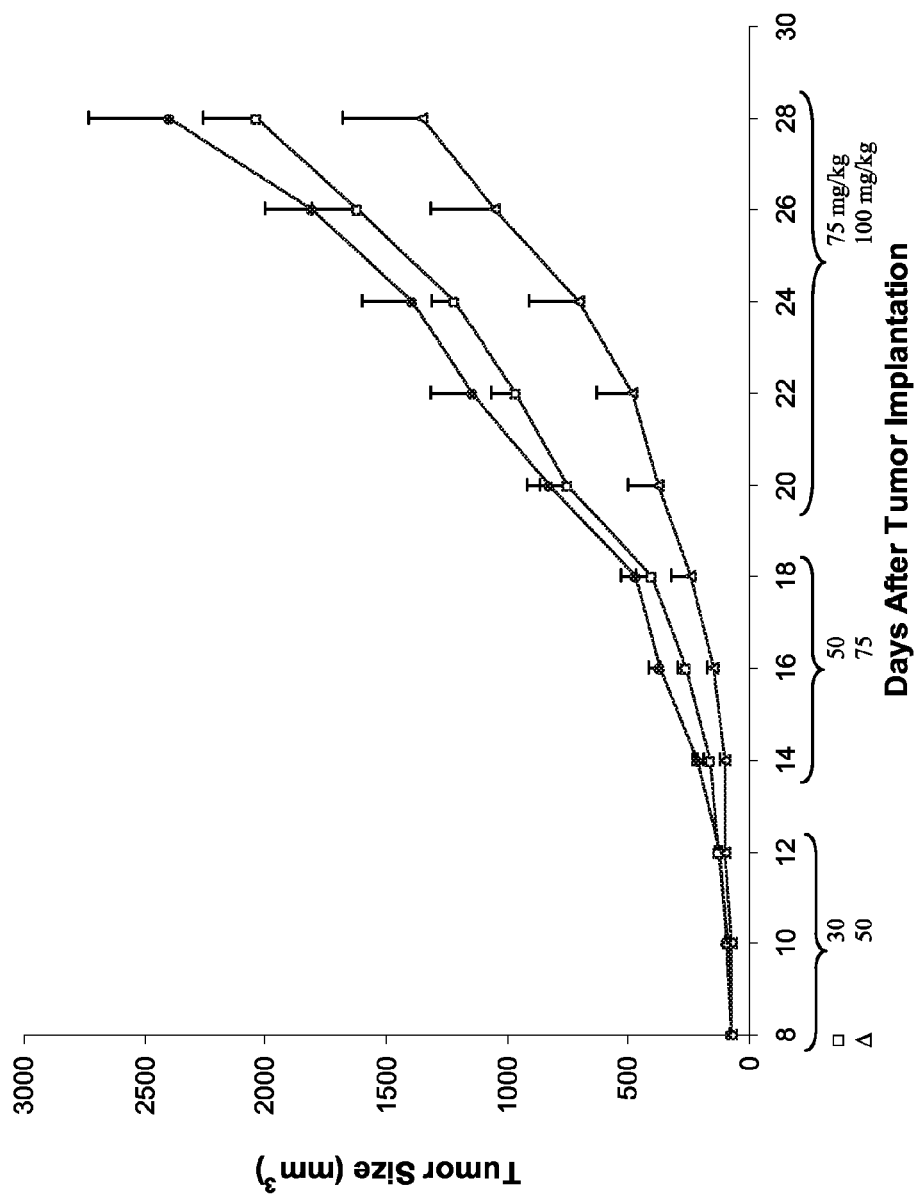
Figure 1B:
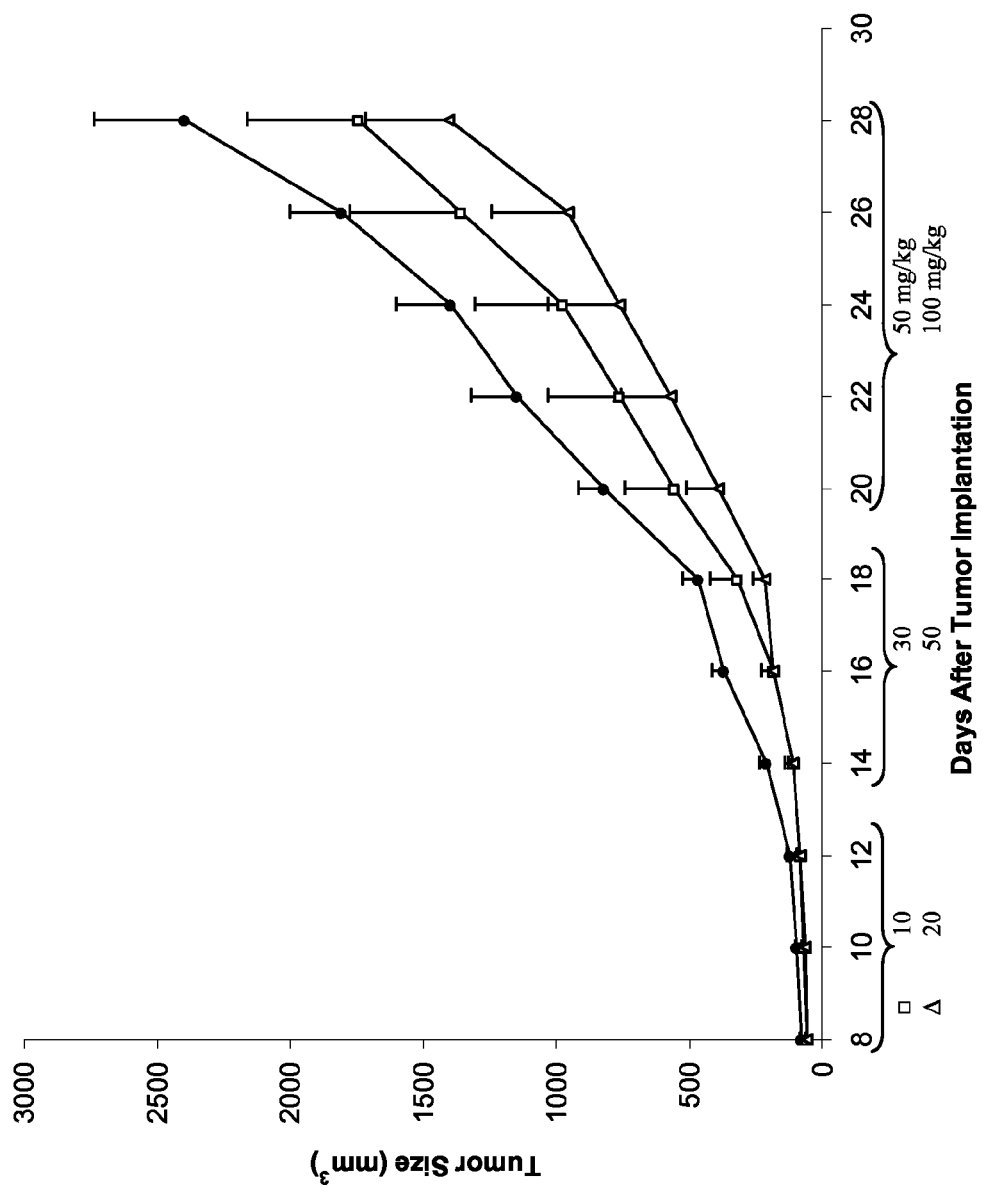
Figure 1C:
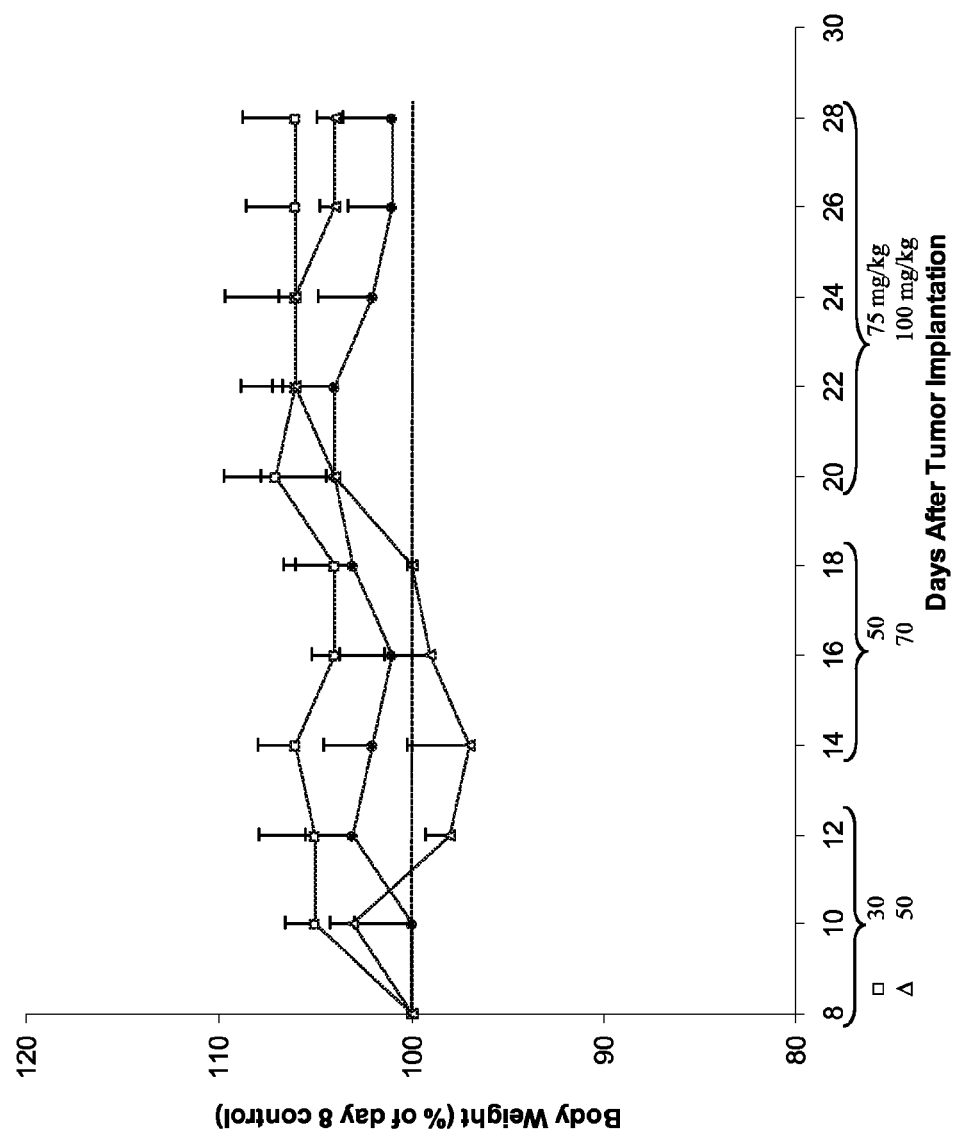
Figure 1D:
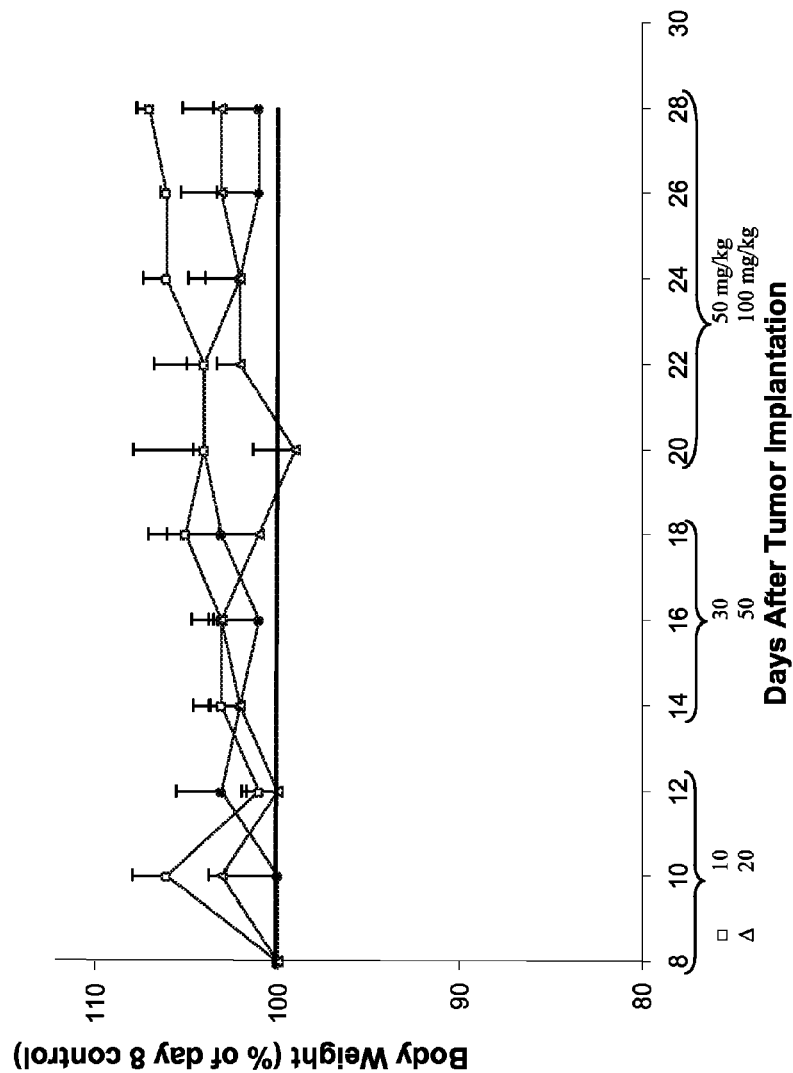

Panaxytriol (PXT) Q2D i.v. injection 50-100 mg/kg of multiple doses suppressed MX-1 mammary carcinoma xenograft tumor growth by 53% without a drop in body-weight, indicating that panaxytriol also has antitumor effects by itself (FIG. 1A). Compound D 15 mg/kg Q2D×1, 40 mg/kg Q2D×4 inhibited MX-1 xenograft 38.3%. Compound D had a slightly lesser effect against MX-1 tumor than panaxytriol in some experiments, but it was about 10-fold or more potent in other properties such as the concentrations for lymphocyte or splenocyte maximal activation (FIGS. 8, 9, 10, and 11). For example, the maximal human lymphocyte stimulation concentration for Compound D is 0.3 µM at 120 hrs compared to 3 µM at 120 hrs for PXT (FIG. 8B, C, D).

5.1 Example 1

Synthesis of Panaxytriol

A. Synthesis of Alkynyl Bromide 6'

(R)-Me-CBS reagent (1.0 M Toluene, 2.14 mL, 2.14 mmol) was transferred into a freshly flame-dried flask, and the toluene was removed in vacuo over 1 day. The CBS reagent was diluted with a THF solution of 5-trimethylsilyl-1-penten-4-yn-3-one (163 mg, 1.07 mmol), and the resultant solution was cooled to −30° C. At −30° C., BH$_3$-Me$_2$S (0.589 mL, 1.18 mmol) was slowly added over 10 min. After addition of BH$_3$-Me$_2$S, TLC analyses indicated that the reaction was complete. Methanol was slowly added, and reaction mixture was slowly warmed to room temperature. The reaction mixture was diluted with diethyl ether, and the resultant organic phase was washed with 2:1 (v:v) NaOH/saturated NaHCO$_3$ solution until the aqueous phase was clear, and then washed with brine. After being dried over MgSO$_4$, the organic phase was removed, diluted with diethyl ether, and to this was added a solution of 0.5 M HCl in methanol (4.5 mL, 2.14 mmol). Precipitates were removed by filtration. The crude product in the solvent mixture was purified by flash column chromatography (hexane/ether 5:1) to provide (3R)-5-trimethylsilyl-1-penten-4-yn-3-ol (0.163 g, 100% yield) as a colorless oil: R$_f$: 0.4 (hexane/dichloromethane 2:1); $[\alpha]_D^{20.0°}$: −24.1 (c=1, CHCl$_3$); $^1$H NMR (400 MHz, CDCl$_3$): δ 5.95 (ddd, 1H, J=17.0, 10.1, 5.29 Hz), 5.46 (d, 1H, J=7.0 Hz), 5.21 (d, 1H, J=10.1 Hz), 4.86 (d, 1H, J=3.87 Hz), 2.17 (br s, 1H), 0.16 (s, 9H); $^{13}$C NMR (75 MHz, CDCl$_3$) δ 137.0, 116.8, 104.9, 91.3, 63.9, 0.2; IR (neat) v: 3368.7, 2961.3, 2927.0, 2855.3, 2174.4, 1250.9, 843.7 cm$^{-1}$; HRMS: calculated 154.28, found 154.0817 for [M]$^+$.

Following protocols in Sullivan et al. (1973), *J. Org. Chem.* 38:2143; and Ohtani et al. (1991), *J. Am. Chem. Soc.* 113: 4092 a Mosher ester derived from (3R)-5-trimethylsilyl-1-penten-4-yn-3-ol was prepared using (R)-MTPA-Cl. The $^1$H NMR signals (δ 6.091, 5.868) of the Mosher ester of (3R)-5-trimethylsilyl-1-penten-4-yn-3-ol appeared at higher fields than those (δ 6.119 and 5.958) of the S-isomer ((3S)-5-trimethylsilyl-1-penten-4-yn-3-ol). The resultant (3R)-5-trimethylsilyl-1-penten-4-yn-3-ol (204 mg, 1.32 mmol) was dissolved in acetone. NBS (353 mg, 1.98 mmol) and silver nitrate (45 mg, 0.26 mmol) were added to this solution. The reaction mixture was stirred at room temperature for 1 hr. The mixture was cooled to 0° C., mixed with cold water, and extracted with diethyl ether. The extract was washed with water and brine, dried over MgSO$_4$, and concentrated under reduced pressure. The residue was purified by flash column chromatography (hexane/ether 4:1) to) provide compound 6' (212 mg, 100%) as a colorless oil: R$_f$: 0.49 (hexane/ether 2:1); $[\alpha]_D^{20.4°}$: −31.61 (c=1, CHCl$_3$); $^1$H NMR (400 MHz, CDCl$_3$): δ 5.94 (m, 1H), 5.47 (d, 1H, J=17.0 Hz), 5.24 (d, 1H, J=10.1 Hz), 4.88 (d, 1H, J=5.34 Hz), 2.44 (br s, 1H); $^{13}$C NMR (75 MHz, CDCl$_3$): δ 136.7, 117.4, 79.3, 64.3, 47.2; IR (neat): v 3361.2, 2918.7, 2852.9, 2356.6 cm$^{-1}$; HRMS: calculated 161.00, found 161.0334 for [M]$^+$.

B. Synthesis of Terminal Alkyne 5'

To a solution of lithium acetylide-EDA complex (0.330 g, 3.58 mmol) in THF and HMPA (0.2 mL) was added the epoxide 4' (0.206 g, 1.19 mmol) at 0° C. The reaction mixture was stirred at that temperature overnight, quenched with saturated ammonium chloride, extracted with ethyl acetate, washed with brine, dried over MgSO$_4$, and concentrated under reduced pressure. The residue was purified using flash column chromatography (hexane/ethyl acetate 4:1) to provide the terminal alkyne 5' (0.189 g, 80%) as a yellow oil: R$_f$ 0.24 (hexane/ethyl acetate 3:1); $[\alpha]_D^{19.7°}$ +0.1131 (c=1, CHCl$_3$); $^1$H NMR (400 MHz, CDCl$_3$): δ 3.61 (m, 2H), 2.47 (m, 2H), 2.31 (br s, 2H), 2.06 (s, 1H), 1.50-1.24 (m, 12H), 0.87 (t, 3H, J=6.75 Hz); $^{13}$C NMR (75 MHz, CDCl$_3$): δ 81.0, 73.6, 72.5, 71.4, 34.1, 32.4, 30.1, 29.8, 26.2, 24.7, 23.3, 14.7; IR (neat) IR (neat): v 3392.1, 2924.1, 2855.1, 2362.0, 1653.2, 1457.1 cm$^{-1}$; HRMS: calculated 198.30, found 181.2777 for [M−H$_2$O+H]$^+$.

C. Synthesis of Panaxytriol

CuCl (1.5 mg), NH$_2$OH.HCl (10 mg) and ethylamine (0.23 mL) were added to a methanol solution of the terminal alkyne 5' (41 mg, 0.207 mmol) at room temperature. A dichloromethane solution of the alkynyl bromide 6' (24.4 mg, 0.151 mmol) was added dropwise to the reaction mixture at 0° C. over 1 hour using a syringe pump. For an additional 1 hour, the reaction mixture was stirred at 0° C. The reaction mixture was quenched with water, extracted with dichloromethane, washed with brine, dried over MgSO$_4$, and concentrated under reduced pressure. The residue was purified using flash column chromatography (hexane/ethyl acetate 2:1) to provide panaxytriol (38.7 mg, 92% isolated): R$_f$: 0.13 (hexane/ethyl acetate 2:1); $[\alpha]_D^{25°}$: −21.8 (c=0.8, CHCl$_3$); $^1$H NMR (400 MHz, CDCl$_3$): δ 5.94 (ddd, 1H, J=17.0, 10.1, 5.35 Hz), 5.47 (ddd, 1H, J=17.0, 1.31, 1.21 Hz), 5.25 (ddd, 1H, J=10.4, 1.25, 1.15 Hz), 4.92 (d, 1H, J=5.35 Hz), 3.62 (m, 2H), 2.58 (d, 2H, J=5.78 Hz), 2.11 (br s, 3H), 1.51-1.25 (m, 12H), 0.88 (t, 3H, J=6.73 Hz); $^{13}$C NMR (75 MHz, CDCl$_3$): δ 36.4, 117.6, 78.5, 75.1, 73.5, 72.5, 71.3, 66.9, 63.9, 34.0, 32.2, 29.9, 29.6, 26.0, 25.4, 23.0, 14.5; IR (neat): v 3524.8, 2930.7, 2854.8, 2360.0, 1457.1 cm$^{-1}$; HRMS: calculated 278.39, found 261.1047 for [M−H$_2$O+H]$^+$.

5.2 Example 2

Synthesis of Compound (A)

To a THF solution of panaxytriol (0.61 g, 2.191 mmol) were added Me$_2$C(OCH$_3$)$_2$ (3 mL, 21.91 mmol) and p-TsOH (42 mg, 0.2191 mmol) at room temperature. After stirring overnight, the reaction mixture was quenched with saturated NaHCO$_3$. After an aqueous workup, the resultant mixture was purified using flash column chromatography (hexane/ethyl acetate 15:1 to 7:1) to provide Compound (A) (0.6567 g, 94%) as a colorless oil: R$_f$: 0.19 (hexane:ethyl acetate=8:1); $[\alpha]_D^{25.7°}$: +5.0 (c=0.47, acetone); $^1$H NMR (400 MHz, CDCl$_3$): δ 5.95 (ddd, 1H, J=17.0, 10.1, 5.3 Hz), 5.46 (d, 1H, J=17.0 Hz), 5.25 (d, 1H, J=10.1 Hz), 4.91 (d, 1H, J=5.3 Hz), 3.80 (dt, 1H, J=7.7, 4.2 Hz), 3.72 (dt, 1H, J=7.9, 5.3 Hz), 2.60 (m, 2H), 1.2-1.7 (m, 12H), 1.37 (s, 6H), 0.89 (t, 3H, J=6.8 Hz); $^{13}$C NMR (75 MHz, CDCl$_3$): δ 136.3, 117.6, 109.1, 80.9, 78.6, 77.2, 75.0, 71.5, 66.9, 64.0, 33.5, 32.4, 30.3, 29.8, 28.0, 27.7, 26.6, 24.2, 23.3, 14.8; IR (neat): v 3434.8, 2927.4, 2856.3, 2256.2, 1716.7, 1458.2, 1377.4, 1242.1, 1220.6, 1066.2, 985.9, 930.6 cm$^{-1}$; HRMS: calculated for [M-CH$_3$—H] 303.1960, found 303.1946.

5.3 Example 3

Synthesis of Compound (B)

To a THF solution of panaxytriol (6 mg, 0.02155 mmol) was added MnO$_2$ (22 mg, 0.251 mmol) at room temperature. After stirring overnight, the reaction mixture was filtered through a short column of Celite and the solvent was removed. The concentrated reaction mixture was purified using flash column chromatography (hexane/ethyl acetate 4:1 to 2:1) to provide the Compound (B) (4.5 mg, 76%) as a colorless oil: R$_f$: 0.19 (hexane:ethyl acetate=3:1); $[\alpha]_D^{20.7°}$: +14.4 (c=0.44, CHCl$_3$); $^1$H NMR (400 MHz, CDCl$_3$): δ 6.55 (d, 1H, J=17.3 Hz), 6.41 (dd, 1H, J=17.3, 10.0 Hz), 6.22 (d, 1H, J=10.0 Hz), 3.72 (m, 1H), 3.61 (m, 1H), 2.68 (d, 2H, J=6.2 Hz), 1.2-1.6 (m, 12H), 0.88 (t, 3H, J=6.6 Hz); $^{13}$C NMR (75 MHz, CDCl$_3$): δ 178.1, 138.1, 134.8, 86.5, 77.6, 73.4, 72.3, 71.2, 66.1, 34.0, 32.3, 29.9, 29.6, 25.9, 25.7, 23.0, 14.9; IR (neat): v 3300.3, 2945.4, 2850.4, 2231.9, 2150.6, 1650.8, 1607.1, 1463.4, 1400.9, 1257.2, 1163.5, 1132.3, 1094.8, 1026.0, 976.1, 938.6, 788.6 cm$^{-1}$; HRMS: calculated for [M+H] 277.1804, found 277.1808.

5.4 Example 4

Synthesis of Compound (C)

To a THF solution of Compound (A) (29.9 mg, 0.09389 mmol) was added MnO$_2$ (81.6 mg, 0.9389 mmol) at room temperature. After stirring overnight, the reaction mixture was filtered through a short column of Celite and solvent was removed. The concentrated reaction mixture was purified using flash column chromatography (hexane/ethyl acetate 4:1 to 2:1) to provide the Compound (C) (18.4 mg, 62%) as a colorless oil: R$_f$ 0.48 (hexane:ethyl acetate=8:1); $[\alpha]_D^{22.6°}$: +8.6 (c=0.5, CHCl$_3$); $^1$H NMR (400 MHz, CDCl$_3$): δ 6.57 (d, 1H, J=17.3 Hz), 6.41 (dd, 1H, J=17.4, 10.0 Hz), 6.22 (d, 1H, J=10.0 Hz), 3.77 (m, 2H), 2.69 (m, 2H), 1.59 (m, 2H), 1.41 (s, 6H), 1.26-1.40 (m, 10H), 0.88 (t, 3H, J=6.6 Hz); $^{13}$C NMR (75 MHz, CDCl$_3$): δ 178.1, 138.2, 134.7, 109.3, 85.6, 80.7, 78.2, 71.2, 66.2, 33.2, 32.2, 30.0, 29.5, 27.8, 27.4, 26.3, 24.2, 23.0, 14.5; IR (neat): v 2985.9, 2929.1, 2857.5, 2236.0, 2153.0, 1734.0, 1717.0, 1645.5, 1616.4, 1456.5, 1379.2, 1290.0, 1243.0, 1163.6, 1070.0, 980.0, 789.3 cm$^{-1}$; HRMS: calculated for [M+H] 317.2117, found 317.2123.

5.5 Example 5

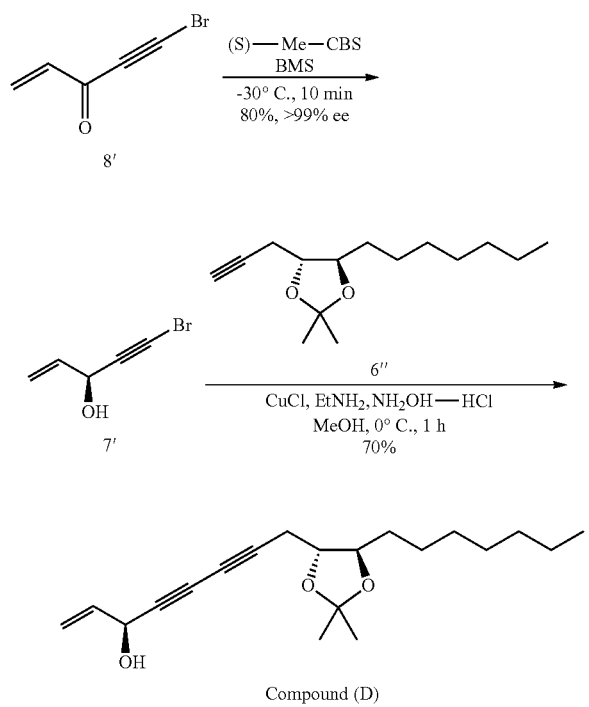

Synthesis of Compound (D)

(S)-Me-CBS reagent (2.14 mL, 2.14 mmol, 1.0 M in toluene solution) was transferred into a freshly flame-dried flask, and the toluene was completely removed in vacuo over 1 day. The (S)-Me-CBS reagent was diluted with THF, the resulting solution was transferred to a flask containing compound 8' (160 mg, 1.05 mmol) at room temperature, and the reaction was cooled to −30° C. At −30° C., BH$_3$-Me$_2$S (BMS) (0.60 mL, 1.2 mmol) was added slowly over 15 minutes. After addition of BMS, thin-layer chromatography (TLC) analysis indicated the reaction was complete. Methanol was slowly added and the reaction mixture was slowly warmed to room temperature. The reaction mixture was diluted with diethyl ether, washed with 2:1 (v:v) NaOH/sat. NaHCO$_3$ solution until the aqueous phase was clear, and then washed with brine. After being dried over MgSO$_4$, the solvent was removed. The crude material was purified by silica-gel column chromatography to afford the desired product 7' (130 mg, 80%, >99% ee) as a colorless oil. CuCl (2.0 mg), NH$_2$OH—HCl (10.0 mg) and ethylamine (0.23 mL) were added to a methanol solution of acetonide compound 6'' (see Scheme above) (45 mg, 0.205 mmol) at room temperature. The acetonide 6'' can be made by converting Compound 5 to an acetonide under conditions disclosed for making Compound (A) in Example 2. A methylene chloride solution of compound 7' (25 mg, 0.152 mmol) was added dropwise to the reaction mixture at 0° C. over 1 hour. The reaction mixture was stirred at 0° C. for an additional hour. The reaction mixture was quenched with water and extracted with methylene chloride. The methylene chloride extract was washed with brine, dried over MgSO$_4$, and concentrated in vacuo. The residue was purified by silica-gel column chromatography to afford Compound (D) (36 mg, 80%) as a colorless oil. $^1$H NMR (400 MHz, CDCl$_3$): δ 5.90 (ddd, 1H, J=17.0, 10.0, 5.6 Hz), 5.41 (d, 1H, J=17.0 Hz), 5.20 (d, 1H, J=10.0 Hz), 4.86 (d, 1H, J=5.6 Hz), 3.82 (dt, 1H, J=7.8, 4.0 Hz), 3.65 (dt, 1H, J=8.0, 5.2 Hz), 2.59 (m, 2H), 1.2-1.7 (m, 12H), 1.36 (s, 6H), 0.90 (m, 3H). $^{13}$C NMR (100 MHz, CDCl$_3$): δ 136.0, 117.2, 108.5, 80.4, 78.1, 76.7, 75.1, 72.0, 66.4, 64.0, 33.2, 21.8, 30.2, 29.4, 28.0, 27.5, 26.3, 24.1, 23.0, 14.6. MS (EI+) calcd for [M+H] C$_{20}$H$_{31}$O$_3$: 319.2274; found 319.2268. A repetition of the above procedure yielded the product with the following analytical data: $^1$H NMR (400 MHz, CDCl$_3$): δ 5.92 (ddd, 1H, J=17.0, 10.0, 5.6 Hz), 5.46 (d, 1H, J=17.0 Hz), 5.24 (d, 1H, J=10.0 Hz), 4.89 (s, 1H), 3.78 (dt, 1H, J=7.8, 4.0 Hz), 3.68 (dt, 1H, J=8.0, 5.2 Hz), 2.59 (m, 2H), 1.2-1.7 (m, 12H), 1.36 (s, 6H), 0.90 (m, 3H). $^{13}$C NMR (100 MHz, CDCl$_3$): δ 136.0, 117.1, 108.7, 80.4, 78.1, 74.6, 71.0, 66.4, 63.5, 32.9, 31.8, 30.7, 29.6, 29.1, 27.4, 27.0, 26.0, 23.6, 22.6, 14.1. MS (EI+) calcd for [M+H] C$_{20}$H$_{31}$O$_3$: 319.2274; found 319.2259. [α]$_D^{23}$=+13.4° (c=0.3, CHCl$_3$).

5.6 Example 6

Synthesis of Compound (E)

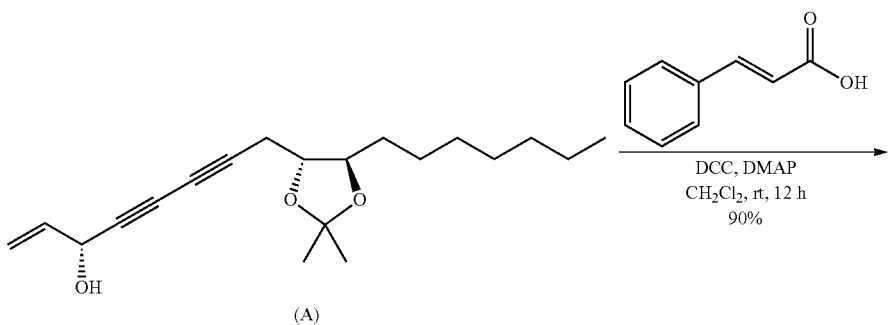

(A)

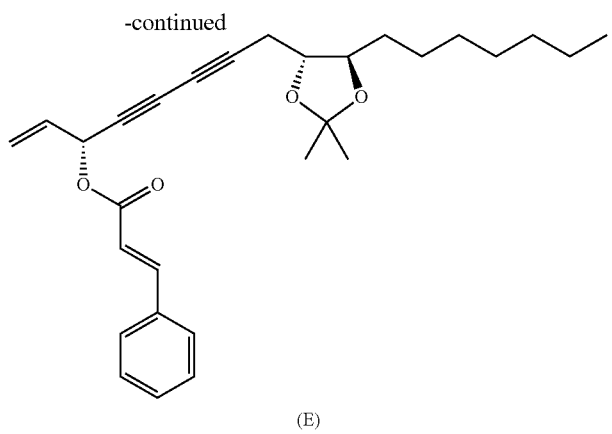

(E)

Compound (A) (23 mg, 0.072 mmol) was dissolved in 1.0 mL of anhydrous methylene chloride. To this solution was added trans-cinnamic acid (21 mg, 0.144 mmol), DCC (28 mg, 0.159 mmol) and DMAP (28 mg, 0.281 mmol). The reaction mixture was stirred at room temperature for 12 hours. The mixture was filtered and washed with methylene chloride. The solution was concentrated in vacuo, and the residue was purified by silica-gel column chromatography using hexane:ethyl acetate (10:1) to afford the ester (E) (29 mg, 90%) as a colorless oil. $^{1}$H NMR (400 MHz, CDCl$_{3}$): δ 7.72 (d, 1H, J=16.0 Hz), 7.52 (m, 2H), 7.37 (m, 3H), 6.42 (d, 1H, J=16.0 Hz), 6.04 (d, 1H, J=5.6 Hz), 5.92 (ddd, 1H, J=17.0, 10.0, 5.6 Hz), 5.58 (d, 1H, J=17.0 Hz), 5.34 (d, 1H, J=10.0 Hz), 3.77 (dt, 1H, J=7.8, 4.0 Hz), 3.70 (dt, 1H, J=8.0, 5.2 Hz), 2.589 (m, 2H), 1.2-1.7 (m, 12H), 1.38 (s, 6H), 0.86 (m, 3H). $^{13}$C NMR (100 MHz, CDCl$_{3}$): δ 165.4, 146.0, 134.2, 132.3, 130.6, 128.9, 128.2, 119.5, 117.2, 108.7, 80.5, 78.1, 71.7, 71.3, 66.4, 64.6, 32.9, 31.8, 29.6, 29.1, 27.4, 27.0, 25.9, 23.6, 22.6, 14.1. MS (EI+) calcd for [M] C$_{29}$H$_{36}$O$_{4}$: 448.2614; found 448.2569. $[α]_D^{23}$=−59.1° (c=1.0, CHCl$_{3}$).

5.7 Example 7

Synthesis of Compound (F)

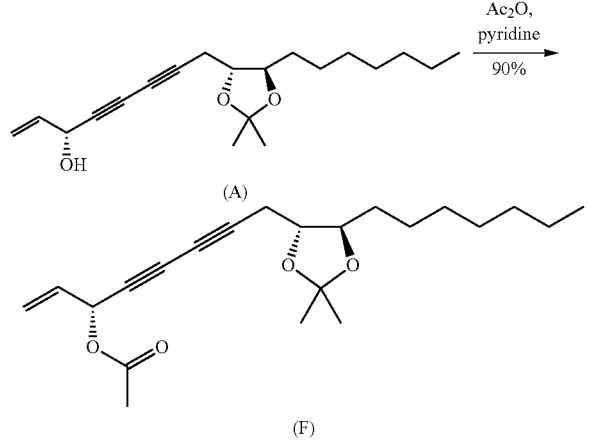

Compound (A) (10 mg, 0.031 mmol) was dissolved in 0.2 mL of anhydrous pyridine. To this solution was added 0.1 mL of acetic anhydride. The reaction mixture was stirred at room temperature for 2 hours. The mixture was quenched with sat. NaHCO$_{3}$, extracted with ethyl acetate, washed with brine and dried over MgSO$_{4}$. The solution was filtered, concentrated in vacuo, and the residue was purified by silica-gel column chromatography using hexane:ethyl acetate (10:1) to afford the acetate (F) (9 mg, 90%) as a colorless oil. Analytical data: $^{1}$H NMR (400 MHz, CDCl$_{3}$): δ 5.89 (s, 1H), 5.85 (m, 1H), 5.50 (d, 1H, J=16.0 Hz), 5.30 (d, 1H, J=10.0 Hz), 3.78 (dt, 1H, J=7.8, 4.0 Hz), 3.71 (dt, 1H, J=8.0, 5.2 Hz), 2.59 (m, 2H), 2.10 (s, 3H), 1.2-1.7 (m, 12H), 1.39 (s, 6H), 0.86 (m, 3H). $^{13}$C NMR (100 MHz, CDCl$_{3}$): δ 169.5, 132.8, 119.4, 108.4, 80.4, 78.1, 71.1, 66.2, 64.5, 32.9, 31.8, 29.6, 29.1, 27.4, 27.0, 25.9, 23.6, 22.6, 20.9, 14.1. MS (EI+) calcd for [M] C$_{22}$H$_{32}$O$_{4}$: 260.2301; found 360.2299. $[α]_D^{23}$=+26.5° (c=0.5, CHCl$_{3}$).

5.8 Example 8

Synthesis of Compound (G)

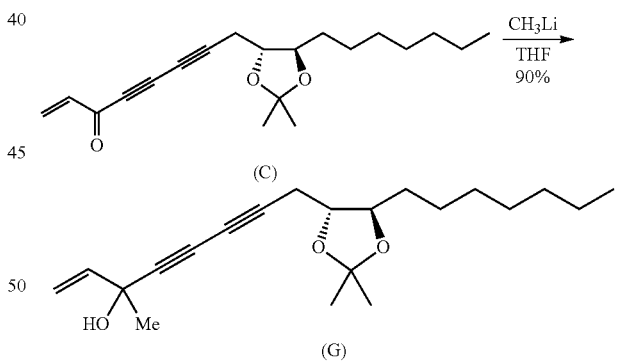

To a solution of Compound (C) in cold, dry THF was added an excess of MeLi. The reaction was stirred until complete by TLC, then quenched with wet solvent and extracted with organic solvent. The extract was washed with brine, dried over MgSO$_{4}$, and concentrated in vacuo. The residue was purified by silica-gel column chromatography to afford compound (G). $^{1}$H NMR (400 MHz, CDCl$_{3}$): δ 5.85 (ddd, 1H, J=17.0, 10.0, 5.6 Hz), 5.44 (d, 1H, J=17.0 Hz), 5.26 (d, 1H, J=10.0 Hz), 4.54 (d, 1H, J=5.6 Hz), 3.78 (dt, 1H, J=7.8, 4.0 Hz), 3.70 (dt, 1H, J=8.0, 5.2 Hz), 3.37 (s, 3H), 2.59 (m, 2H), 1.2-1.7 (m, 12H), 1.38 (s, 6H), 0.86 (m, 3H). $^{13}$C NMR (100 MHz, CDCl$_{3}$): δ 134.1, 118.5, 108.7, 80.5, 78.1, 73.0, 71.9, 66.6, 55.7, 32.9, 31.8, 29.6, 29.1, 28.6, 27.4, 25.9, 23.6, 22.6, 14.1. MS (EI+) calcd for [M] $C_{21}H_{32}O_3$: 332.2351; found 332.2307. $[\alpha]_D^{23}=-2.7°$ (c=0.6, $CHCl_3$).

Alternatively, to a THF solution of Compound (A) (29.9 mg, 0.09389 mmol) is added $MnO_2$ (81.6 mg, 0.9389 mmol) at room temperature. After stirring overnight, the reaction mixture is filtered through a short column of Celite and solvent is removed. The concentrated reaction mixture is purified using flash column chromatography (hexane/ethyl acetate 4:1 to 2:1) to provide the 3-keto product (9'). b.) To a solution of Compound (9') in dry THF at −78° C. is slowly added 1.2 eq. of MeMgCl in dry diethyl ether. The reaction is allowed to warm to room temperature overnight, then cooled to 0° C. and quenched with saturated ammonium chloride (aq.). The aqueous layer is extracted with methylene chloride. The methylene chloride extract is washed with brine, dried over $MgSO_4$, and concentrated in vacuo. The residue then is purified by silica-gel column chromatography or chiral HPLC to afford compound (G).

Alternatively, compound (G) may be prepared as follows. To a solution of 5-trimethylsilyl-1-penten-4-yn-3-one (which can be prepared as in Malacria, M., Roumestant, M. L. *Tetrahedron* 1977, 2813, incorporated herein by reference) dissolved in dry THF, at −78° C. is slowly added 1.2 eq. of MeMgCl in dry diethyl ether. The reaction is allowed to warm to room temperature overnight, then cooled to 0° C. and quenched with saturated ammonium chloride (aq.). The aqueous layer is extracted with methylene chloride. The methylene chloride extract is washed with brine, dried over $MgSO_4$, and concentrated in vacuo. The residue then is purified by silica-gel column chromatography or chiral HPLC to afford the racemic or chiral tertiary alcohol, respectively. To a solution of the purified tertiary alcohol dissolved in acetone is added N-bromosuccinimide (1.5 eq.) and $AgNO_3$ (0.2 eq), and the reaction is stirred for 1 h. The mixture is cooled to 0° C., mixed with cold water, and extracted with ether. The extract is washed with water and brine, dried over $MgSO_4$, and concentrated under reduced pressure. The residue is purified by silica gel column chromatography yielding the bromo-acetonide, compound 38. Compound 38 can be coupled with compound 6" using CuCl and the procedure for coupling compound 6" and purifying the product in Example 5, yielding compound (G).

Alternatively, dimethylzinc can be substituted for the methyl Grignard, and a chiral amino alcohol catalyst, such as (−)-3-exo-(dimethylamino)isoborneol (DAIB) may be added to add the methyl enantioselectively, as disclosed in March, *Advanced Organic Chemistry*, 4th Ed. Wiley & Sons, Inc. New York, p. 920-930, which is herein incorporated by reference 5.9 Example 9

Synthesis of Compound (H)

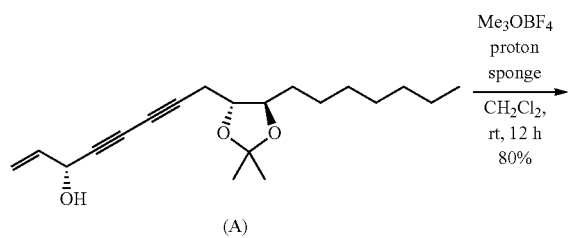

(A)

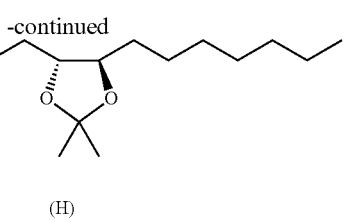

(H)

Compound (A) (32 mg, 0.1 mmol) was dissolved in 1.0 mL of anhydrous methylene chloride. To this solution was added $Me_3OBF_4$ (18 mg, 0.12 mmol), and proton sponge (28 mg, 0.13 mmol). The reaction mixture was stirred at rt for 12 h. The mixture was filtered and washed with methylene chloride. The solution was concentrated in vacuo, and the residue was purified by silica-gel column chromatography to afford the desired methyl ether (H) (26 mg, 80%) as a colorless oil. $^1$H NMR (400 MHz, $CDCl_3$): δ 5.85 (ddd, 1H, J=17.0, 10.0, 5.6 Hz), 5.44 (d, 1H, J=17.0 Hz), 5.26 (d, 1H, J=10.0 Hz), 4.54 (d, 1H, J=5.6 Hz), 3.78 (dt, 1H, J=7.8, 4.0 Hz), 3.70 (dt, 1H, J=8.0, 5.2 Hz), 3.37 (s, 3H), 2.59 (m, 2H), 1.2-1.7 (m, 12H), 1.38 (s, 6H), 0.86 (m, 3H). $^{13}$C NMR (100 MHz, $CDCl_3$): δ 134.1, 118.5, 108.7, 80.5, 78.1, 73.0, 71.9, 66.6, 55.7, 32.9, 31.8, 29.6, 29.1, 28.6, 27.4, 25.9, 23.6, 22.6, 14.1. MS (EI+) calcd for [M] $C_{21}H_{32}O_3$: 332.2351; found 332.2307. $[\alpha]_D^{23}=-2.7°$ (c=0.6, $CHCl_3$).

5.10 Example 10

Synthesis of Compound (J)

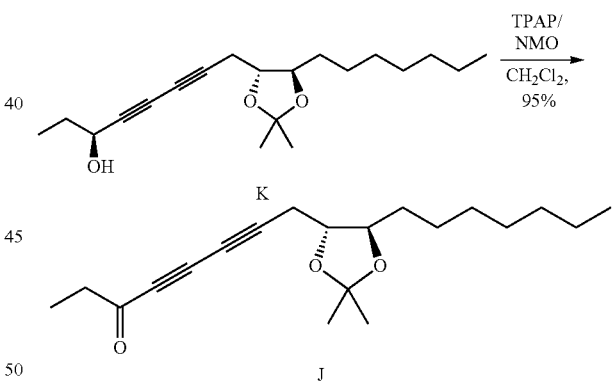

Compound (K) (32.0 mg, 0.1 mmol) and NMO (13 mg, 0.11 mmol) were dissolved in 0.5 mL of anhydrous methylene chloride at room temperature. TPAP (3 mg, 0.01 mmol) was added to the reaction mixture at 0° C. The reaction mixture was stirred at room temperature for an hour. The reaction mixture was filtered through a short silica-gel column, diluted with 2.0 mL of methylene chloride and concentrated in vacuo. The residue was purified by silica-gel column chromatography to afford the desired ketone (J) (30 mg, 95%) as a colorless oil. $^1$H NMR (400 MHz, $CDCl_3$): δ 3.78 (dt, 1H, J=7.8, 4.0 Hz), 3.68 (dt, 1H, J=8.0, 5.2 Hz), 2.66 (m, 1H), 2.57 (m, 2H), 1.66 (m, 2H), 1.2-1.7 (m, 12H), 1.36 (s, 6H), 1.14 (t, 3H, J=8.0 Hz), 0.88 (m, 3H). $^{13}$C NMR (100 MHz, $CDCl_3$): δ 187.5, 108.9, 85.3, 80.4, 78.1, 76.7, 75.4, 72.4, 65.7, 64.0, 38.8, 32.9, 31.8, 30.7, 29.6, 29.1, 27.4, 27.0, 26.0, 23.5, 22.6, 14.1, 9.3, 7.9. MS (EI+) calcd for [M] $C_{20}H_{30}O_3$: 318.2195; found 318.2186. $[\alpha]_D^{23}$=+8.8° (c=0.3, $CHCl_3$).

5.11 Example 11

Synthesis of Compound (K)

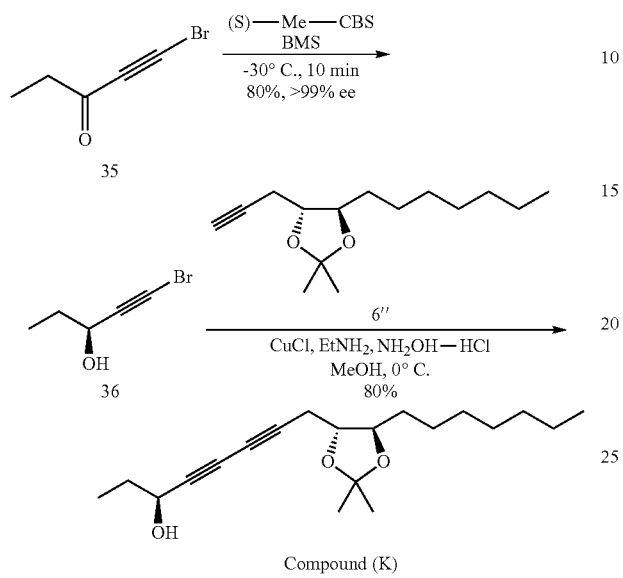

(S)-Me-CBS reagent (2.14 mL, 2.14 mmol, 1.0 M in toluene solution) was transferred into a freshly flame-dried flask, and the toluene was completely removed in vacuo over 1 day. The (S)-Me-CBS reagent was diluted with THF, the resulting solution was transferred to a flask containing compound 35 (160 mg, 1.05 mmol) at room temperature, and the reaction was cooled to −30° C. At −30° C., $BH_3$-$Me_2S$ (BMS) (0.60 mL, 1.2 mmol) was added slowly over 15 minutes. After addition of BMS, thin-layer chromatography (TLC) analysis indicated the reaction was complete. Methanol was slowly added and the reaction mixture was slowly warmed to room temperature. The reaction mixture was diluted with diethyl ether, washed with 2:1 (v:v) NaOH/sat. $NaHCO_3$ solution until the aqueous phase was clear, and then washed with brine. After being dried over $MgSO_4$, the solvent was removed. The crude material was purified by silica-gel column chromatography to afford the desired product 36 (see Scheme above) (130 mg, 80%, >99% ee) as a colorless oil. CuCl (2.0 mg), $NH_2OH.HCl$ (10.0 mg) and ethylamine (0.23 mL) were added to a methanol solution of acetonide compound 6″ (45 mg, 0.205 mmol) at room temperature. The acetonide 6″ can be made by converting Compound 5 to an acetonide under conditions disclosed for making Compound (A) in the Examples. A methylene chloride solution of compound 36 (25 mg, 0.152 mmol) was added dropwise to the reaction mixture at 0° C. over 1 hour. The reaction mixture was stirred at 0° C. for an additional hour. The reaction mixture was quenched with water and extracted with methylene chloride. The methylene chloride extract was washed with brine, dried over $MgSO_4$, and concentrated in vacuo. The residue was purified by silica-gel column chromatography to afford Compound (K) (36 mg, 80%) as a colorless oil. $^1H$ NMR (400 MHz, $CDCl_3$): δ 4.32 (m, 1H), 3.77 (dt, 1H, J=7.8, 4.0 Hz), 3.68 (dt, 1H, J=8.0, 5.2 Hz), 2.57 (m, 2H), 1.94 (d, 1H, J=5.2 Hz), 1.66 (m, 2H), 1.2-1.7 (m, 12H), 1.36 (s, 6H), 0.98 (t, 3H, J=8.0 Hz), 0.90 (m, 3H). $^{13}C$ NMR (100 MHz, $CDCl_3$): δ 108.7, 80.4, 78.1, 76.5, 69.6, 66.6, 64.0, 32.9, 31.8, 30.7, 29.6, 29.1, 27.4, 27.0, 26.0, 23.5, 22.6, 14.1, 9.3. MS (EI+) calcd for [M+H] $C_{20}H_{33}O_3$: 321.2430; found 321.2442. $[\alpha]_D^{23}$=+3.6° (c=0.5, $CHCl_3$).

5.12 Example 12

Synthesis of Di-Triazole Compounds

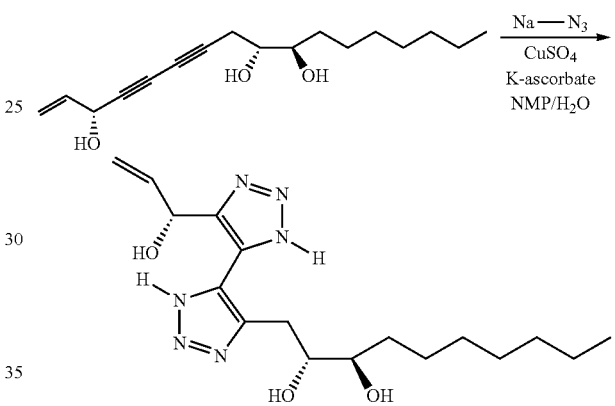

Panaxytriol can be dissolved in an organic solvent, then hydrazoic acid (4 eq.) added and the reaction mixture sealed in a bomb and heated overnight. The reaction is cooled, washed with saturated sodium bicarbonate, and extracted with methylene chloride. The organic layer is washed with brine, dried over $Na_2SO_4$ and concentrated. The residue is purified by flash chromatography to yield the depicted di-triazole. Alternatively, a protected azide, for example tosyl-azide, can be substituted for the toxic hydrazoic acid, yielding the dI-m-tosylated ditriazole product. The tosyl groups can be hydrolyzed to the free diazole product using methods set forth in Greene, et al. *Protective Groups in Organic Synthesis*. 4th ed. Wiley & Sons. Hoboken, N.J., (2007), which is incorporated herein by reference in its entirety. See particularly pages 851-867.

5.13 Example 13

Synthesis of Compound (L)

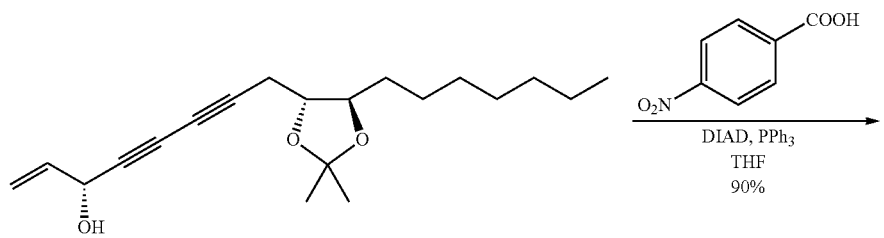

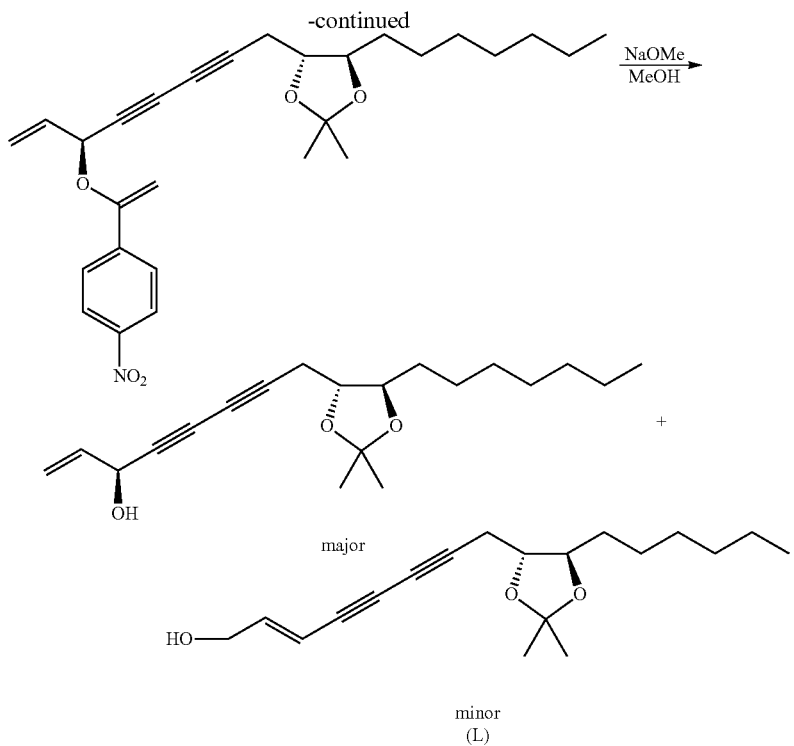

To Compound (A) dissolved in dry THF was added an excess of p-nitrobenzoic acid, triphenylphosphine, and DIAD. The mixture was heated until complete by TLC, then quenched with aqueous solvent and extracted with organic solvent. The extract was purified and the product nitrophenyl ester hydrolyzed with NaOMe/MeOH. After work-up and purification with silica-gel column chromatography, Compound (L) was isolated. Alternatively, Compound (L) may be formed as follows. CuCl (2.0 mg), NH$_2$OH.HCl (10.0 mg) and ethylamine (0.23 mL) are added to a methanol solution of acetonide compound 6"(see Scheme above) (0.205 mmol) at room temperature. The acetonide 6" can be made by converting Compound 5 to an acetonide under conditions disclosed for making Compound (A) in the Examples. A methylene chloride solution of compound 34 (0.152 mmol) is added dropwise to the reaction mixture at 0° C. over 1 hour. The reaction mixture is stirred at 0° C. for an additional hour, then quenched with water and extracted with methylene chloride. The methylene chloride extract is washed with brine, dried over MgSO$_4$, and concentrated in vacuo. The residue is purified by silica-gel column chromatography to afford compound (L).

5.14 Example 14

Synthesis of Compound (M)

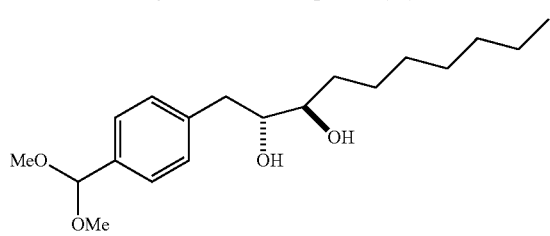 [SMILES: CCCCCCC[C@@H](O)[C@H](O)Cc1ccc(C(OC)OC)cc1]

(2R,3R)-1-(4-(dimethoxymethyl)phenyl)decane-2,3-diol (M)

To a solution of 4-bromobenzaldehyde (80 μL 0.48 mmol) in tetrahydrofuran (THF) (0.8 mL) at −78° C. in a dry ice/acetone bath) was added n-butyl lithium (nBuLi) (0.38 mL, 1.6 M in hexanes) dropwise. The solution was stirred for ten minutes at −78° C. Next, copper cyanide (22 mg, 0.24 mmol) was added and the reaction mixture was warmed to −30° C. briefly until the solids dissolved. After cooling to −78° C., (R)-1-((R)-oxiran-2-yl)-octan-1-ol (27.6 mg, 0.16 mmol) was added dropwise. The reaction mixture was stirred at −20° C. overnight at which time TLC indicated completion of the reaction. Aqueous 10% NH$_3$ in saturated NH$_4$Cl was added to the reaction, which was subsequently allowed to warm to room temperature and extracted with ether. The collected organic layers were washed with brine, dried with MgSO$_4$, filtered, and concentrated. Flash chromatography using a gradient from 0 to 25% EtOAc/Hexanes gave the title compound (39.5 mg, 0.12 mmol, 75%). $^1$H NMR (CDCl$_3$, 400 MHz) δ: 7.40 (2H, d, J=8 Hz), 7.25 (2H, d, J=8.8 Hz), 5.37 (1H, s), 3.70-3.66 (1H, m), 3.51-3.47 (1H, m), 3.34 (6H, s), 2.90 (1H, dd, J=0.01, 13.4 Hz), 2.76 (1H, dd, J=0.02, 13.6 Hz), 2.02 (1H, d, J=5.6 Hz), 1.90 (1H, d, J=4.4 Hz), 1.51-1.29 (12H, m), 0.88 (3H, t, J=6.4 Hz); LRMS (APCI+) calcd for C$_{18}$H$_{29}$O$_3$ [M-MeOH]: 293.2; found 293.5.

5.15 Example 15

Synthesis of Compound (N)

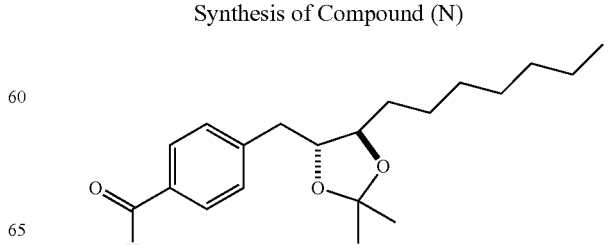

4-(((4R,5R)-5-heptyl-2,2-dimethyl-1,3-dioxolan-4-yl)methyl)benzaldehyde (N)

To a solution of (2R,3R)-1-(4-(dimethoxymethyl)phenyl)decane-2,3-diol (M) (0.38 g, 1.17 mmol) in THF (12 mL) at room temperature was added aqueous acetic acid (6.2 mL, 2.5 M). The reaction mixture was stirred for two hours until TLC indicated completion of the reaction at which time saturated aqueous NaHCO$_3$ was added, and the mixture extracted with ether. The collected organic layers were washed with brine, dried with MgSO$_4$, filtered, and concentrated to yield the free aldehyde (0.309 g, 1.11 mmol, 95%). The crude free aldehyde was dissolved in acetone (5 mL) and to this mixture was added p-toluenesulfonic acid (33 mg, 0.17 mmol). The reaction mixture was stirred overnight, at which time TLC indicated completion of the reaction. Upon completion, triethylamine (24 µL, 0.17 mmol) was added and solvent was evaporated. Flash chromatography of the residue gave the title compound (0.26 g, 0.82 mmol, 74%). $^1$H NMR (CDCl$_3$, 300 MHz) δ 9.90 (1H, s), 7.82 (2H, d, J=8.1 Hz), 7.42 (2H, d, J=7.8 Hz), 3.88-3.83 (1H, m), 3.70-3.65 (1H, m), 2.94 (2H, d, J=5.7 Hz), 1.51-1.29 (12H, m), 1.37 (3H, s), 1.35 (3H, s), 0.88 (3H, t, J=4.8 Hz); LRMS (APCI+) calcd for C$_{20}$H$_{30}$O$_3$ [M+H]: 319.2; found 319.5

5.16 Example 16

Synthesis of Compound (O)

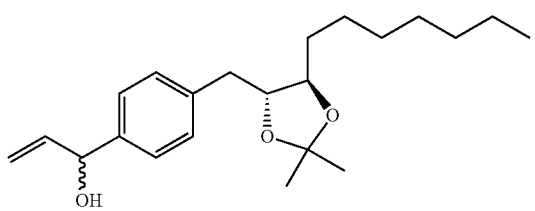 [SMILES: C=CC(O)c1ccc(C[C@H]2OC(C)(C)O[C@@H]2CCCCCCC)cc1]

1-(4-(((4R,5R)-5-heptyl-2,2-dimethyl-1,3-dioxolan-4-yl)methyl)phenyl)prop-2-en-1-ol (O)

To a solution of 4-(((4R,5R)-5-heptyl-2,2-dimethyl-1,3-dioxolan-4-yl)methyl)benzaldehyde (N) (15.5 mg, 0.048 mmol) in THF (1.2 mL) at 0° C. was added vinylmagnesium bromide (55 µL, 1M in THF) dropwise. After 30 minutes, saturated aqueous NH$_4$Cl was added at 0° C., and the mixture was extracted with ether. The collected organic layers were washed with brine, dried with MgSO$_4$, filtered and concentrated to yield the title compound (12.1 mg, 0.035 mmol, 72%). $^1$H NMR (CDCl$_3$, 300 MHz) δ 7.36-7.22 (4H, m), 6.10-5.99 (1H, m), 5.34 (1H, d, J=17.1 Hz), 5.20-5.17 (2H, m), 3.88-3.81 (1H, m), 3.71-3.65 (1H, m), 2.95-2.84 (2H, m), 1.51-1.29 (12H, m), 1.37 (3H, s), 1.35 (3H, s), 0.88 (3H, t, J=4.8 Hz); LRMS (APCI+) calcd for C$_{22}$H$_{35}$O$_3$ [M-H]: 345.2; found 345.4.

5.17 Example 17

Synthesis of Compound (P)

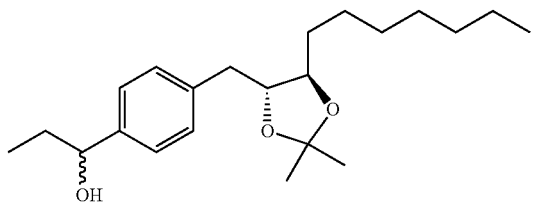 [SMILES: CCCCCCC[C@H]1OC(C)(C)O[C@@H]1Cc1ccc(C(O)CC)cc1]

1-(4-(((4R,5R)-5-heptyl-2,2-dimethyl-1,3-dioxolan-4-yl)methyl)phenyl)propan-1-ol (P)

To a solution of 4-(((4R,5R)-5-heptyl-2,2-dimethyl-1,3-dioxolan-4-yl)methyl)benzaldehyde (N) (16 mg, 0.05 mmol) in THF (0.2 mL) at 0° C. was added ethylmagnesium bromide (20 µL, 3M in THF) dropwise. After one hour, the reaction mixture was heated to refluxing temperature for an additional hour until TLC indicated completion of the reaction. Upon completion, saturated aqueous NH$_4$Cl was added, and the mixture extracted with ether. The collected organic layers were washed with brine, dried with MgSO$_4$, filtered and concentrated. Preparative thin layer chromatography (25% EtOAc/Hex, 250 µm, silica) yielded the title compound (6 mg, 0.017 mmol, 35%). $^1$H NMR (CDCl$_3$, 300 MHz) δ 7.27 (2H, d, J=7.2 Hz), 7.21 (2H, d, J=8.1 Hz), 4.58 (1H, t, J=6.6 Hz), 3.88-3.81 (1H, m), 3.71-3.65 (1H, m), 2.92 (1H, dd, J=0.02, 18.6 Hz), 2.82 (1H, dd, J=0.02, 18.6 Hz), 1.86-1.68 (2H, m), 1.51-1.29 (12H, m), 1.37 (3H, s), 1.35 (3H, s), 0.92-0.85 (6H, m); HRMS (FAB+) calcd for C$_{22}$H$_{35}$O$_3$ [M−H]: 347.2586; found 347.2575, C$_{22}$H$_{35}$O$_3$.

5.18 Example 18

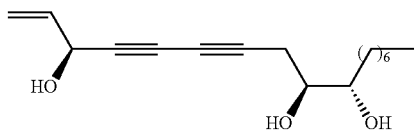

(3S,9S,10S)-heptadeca-1-en-4,6-diyne-3,9,10-triol, ent-panaxytriol (4S,5S)-dodec-1-yne-4,5-diol, was prepared as described in Yun, H.; Chou, T. C.; Dong, H.; Tian Y.; Li, Y-M.; Danishefsky, S. J. *J. Org. Chem.* 2005, 70, 10375-10380, incorporated herein by reference in its entirety, and substituting AD-Mix a during the asymmetric dihydroxylation of 1-tert-butyldimethylsiloxy-2-decene, yielding (4S,5S)-dodec-1-yne-4,5-diol: [α]$^{19.4}_D$-22.2 (c=1.64, CHCl$_3$), $^1$H NMR (400 MHz, CDCl$_3$) δ 3.61 (m, 2H), 2.47 (m, 2H), 2.06 (s, 1H), 1.50-1.24 (m, 12H), 0.87 (t, 6.4 Hz, 3H). Next, (4S,5S)-dodec-1-yne-4,5-diol was coupled with compound 36, (S)-5-bromopent-1-en-4-yn-3-ol, using the method described in Yun, H.; Chou, T. C.; Dong, H.; Tian Y.; Li, Y-M.; Danishefsky, S. J. *J. Org. Chem.* 2005, 70, 10375-10380, yielding the product with $[\alpha]^{19.1}_D$-66.6 (c=0.11, CHCl$_3$) $^1$H NMR (400 MHz, CDCl$_3$) δ 5.94 (ddd, 17.1 Hz, 10.1 Hz, 5.35 Hz, 1H), 5.47 (ddd, 17.1 Hz, 1.31 Hz, 1.21 Hz, 1H), 5.25 (ddd, 10.2 Hz, 1.25 Hz, 1.15 Hz, 1H), 4.92 (br, 1H), 3.61 (m, 2H), 2.58 (d, 5.78 Hz, 2H), 2.14 (br, 3H), 1.51-1.25 (m, 12H), 0.88 (t, 6.6 Hz, 3H). LRMS (APCI+) found 261.0, [M-OH]$^+$.

5.19 Example 19

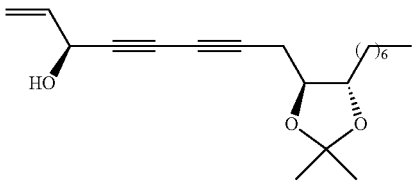

(S)-8-(((4S,5S)-5-heptyl-2,2-dimethyl-1,3-dioxolan-4-yl)octa-1-en-4,6-diyn-3-ol, ent-panaxytriol acetonide (S)-8-(4S,5S)-5-heptyl-2,2-dimethyl-1,3-dioxolan-4-yl) octa-1-en-4,6-diyn-3-ol, ent-panaxytriol acetonide was prepared from (3S,9S,10S)-heptadeca-1-en-4,6-diyne-3,9,10-triol, ent-panaxytriol, by the method described in Yun, H.; Chou, T. C.; Dong, H.; Tian, Y.; Li, Y-M.; Danishefsky, S. J. *J. Org. Chem.* 2005, 70, 10375, yielding the product with: $[\alpha]^{19.3}_D$-70.5 (c=0.13, CHCl$_3$). $^1$H NMR (300 MHz, CDCl$_3$) δ 5.94 (ddd, 17.1 Hz, 10.2 Hz, 5.4 Hz, 1H), 5.47 (d, 17.1 Hz, 1H), 5.26 (d, 10.2 Hz, 1H), 4.92 (d, 5.1 Hz, 1H), 4.36 (t, 6 Hz, 1H), 3.77 (m, 2H), 2.60 (m, 2H), 1.7-1.2 (m, 12H), 1.40 (s, 6H), 0.88 (t, 6.9 Hz, 3H). LRMS (APCI+) found 319.0, [M]$^+$, 333.04, [M+H$_2$O]$^+$.

5.20 Example 20

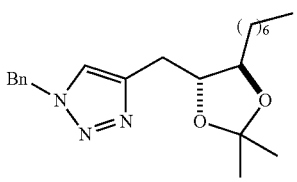

1-benzyl-4-(((4R,5R)-5-heptyl-2,2-dimethyl-1,3-dioxolan-4-yl)methyl)-1H-1,2,3-triazole To a solution of (4R,5R)-4-heptyl-2,2-dimethyl-5-(prop-2-ynyl)-1,3-dioxolane (14 mg, 0.059 mmol) in a water/t-butanol mixture (0.11, 0.11 mL), was added benzyl azide (8.5 µL, 1.1 eq), copper sulfate (56 µL of a 0.1 M sol'n, 0.1 eq), and sodium ascorbate (56 µL of a 1 M sol'n, 1 eq). The mixture was stirred at room temperature overnight to yield the title compound (21.1 mg, 97%). $^1$H NMR (300 MHz, CDCl$_3$) δ 7.35 (m, 3H), 7.25 (m, 2H), 5.54 (d, 14.7 Hz, 1H), 5.45 (d, 14.7 Hz, 1H), 3.86 (m, 1H), 3.64 (m, 1H), 3.03 (dd, 4.2 Hz, 15.3 Hz, 1H), 2.92 (dd, 6.9 Hz, 15.3 Hz, 1H), 1.55-1.23 (m, 12H), 1.26 (s, 3H), 1.23 (s, 3H), 0.87 (t, 6.8 Hz, 3H). LRMS (APCI+) found 372.5, [M+H]$^+$.

5.21 Example 21

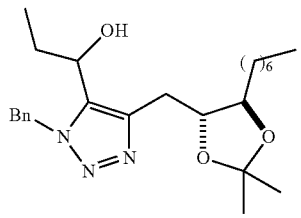

1-(1-benzyl-4-(((4R,5R)-5-heptyl-2,2-dimethyl-1,3-dioxolan-4-yl)methyl)-1H-1,2,3-triazol-5-yl)propan-1-ol To a solution of 1-benzyl-4-(((4R,5R)-5-heptyl-2,2-dimethyl-1,3-dioxolan-4-yl)methyl)-1H-1,2,3-triazole (11 mg, 0.029 mmol) in THF (0.3 mL) at −78° C. was added n-butyllithium (21 µL, 1.6M) to produce a deep red solution. After 5 minutes, propanal (2.3 µL, 1.1 eq) was added and the mixture was warmed to room temperature. After standard workup, the title compound was isolated by silica gel chromatography (7 mg, 54%). $^1$H NMR (400 MHz, CDCl$_3$) δ 7.35 (m, 3H), 7.30 (m, 2H), 5.35 (d, 7.6 Hz, 1H), 5.32 (d, 7.6 Hz, 1H), 4.52 (m, 1H), 3.86 (m, 1H), 3.64 (m, 1H), 3.03 (dd, 3.6 Hz, 16.4 Hz, 1H) 2.96 (dd, 6.8 Hz, 16.4 Hz, 1H), 1.55-1.17 (m, 12H), 1.27 (s, 3H), 1.25 (s, 3H), 1.00 (t, 7.3 Hz, 3H), 0.88 (t, 5.2 Hz, 3H). LRMS (APCI+) found 430.6, [M]$^+$.

5.22 Example 22

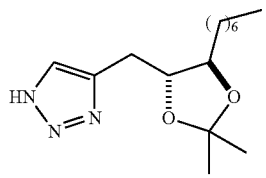

4-(((4R,5R)-5-heptyl-2,2-dimethyl-1,3-dioxolan-4-yl)methyl)-1H-1,2,3-triazole 4-(((4R,5R)-5-heptyl-2,2-dimethyl-1,3-dioxolan-4-yl) methyl)-1H-1,2,3-triazole was isolated from the reaction of (4R,5R)-4-heptyl-2,2-dimethyl-5-(prop-2-ynyl)-1,3-dioxolane with (1-azidopropoxy)trimethylsilane in the presence of copper sulfate and sodium ascorbate in water/t-butanol. $^1$H NMR (400 MHz, CDCl$_3$) δ 7.61 (s, 1H), 3.89 (dt, 4 Hz, 8 Hz, 1H), 3.67 (m, 1H), 3.06 (dd, 3.6 Hz, 15.2 Hz, 1H), 2.93 (dd, 7.2 Hz, 15.2 Hz, 1H), 1.6-1.3 (m, 12H), 1.27 (s, 3H), 1.25 (s, 3H), 0.88 (t, 6.8 Hz, 3H). LRMS (APCI+) found 282.0, [M+H]$^+$.

5.23 Example 23

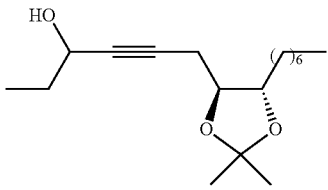

6-(((4S,5S)-5-heptyl-2,2-dimethyl-1,3-dioxolan-4-yl)hex-4-yn-3-ol

To a solution of (4S,5S)-4-heptyl-2,2-dimethyl-5-(prop-2-ynyl)-1,3-dioxolane (19.4 mg, 0.081 mmol) in THF (0.8 mL) at −78° C. was added n-butyllithium (51 μL, 1.6 M). The mixture was stirred for 30 min. at which time propanal (excess) was added. The mixture was stirred at −78° C. for an additional 30 min. The reaction was quenched with sat'd NH$_4$Cl (aq.) at −78° C. The title compound was isolated using a standard workup (22 mg, 92%). $^1$H NMR (400 MHz, CDCl$_3$) δ 4.30 (m, 1H), 3.81 (dt, 4 Hz, 7.6 Hz, 1H), 3.71 (m, 1H), 2.54 (dd, 1.6 Hz, 5.2 Hz, 2H), 1.39 (s, 6H), 1.28 (m, 12H), 0.99 (t, 7.6 Hz, 3H), 0.87 (t, 6.4 Hz, 3H). LRMS (APCI+) found 279.7, [M−H$_2$O]$^+$.

5.24 Example 24

Preparation of (1R,7R,8R)-1-phenyl-2,4-pentadecadiyne-1,7,8-triol

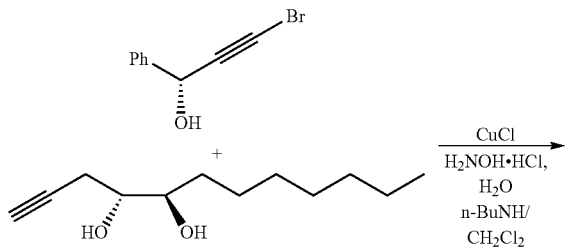

Copper(I) chloride (6.4 mg, 64.6 μmol, 20 mol %) was added to a stirred solution of n-BuNH$_2$ (0.32 mL) and distilled water (0.74 mL) at 0° C., which resulted in a deep blue solution. A few crystals of NH$_2$OH.HCl were added to get a colorless solution which is indicative of the presence of the required Cu(I) salt. At the same temperature was added (4R,5R)-1-dodecyne-4,5-diol (64.1 mg, 0.323 mmol) as a solution in CH$_2$Cl$_2$ (0.6 mL). Then a freshly prepared solution of (R)-3-bromo-1-phenyl-2-propyn-1-ol (75.0 mg, 0.355 mmol, 1.1 equiv) in CH$_2$Cl$_2$ (2.4 mL) was slowly added over 60 min by help of syringe pump under a flow of argon in order to prevent the solution from turning to green or blue (NH$_2$OH.HCl can be added as necessary throughout the reaction). The reaction mixture was allowed to warm up to room temperature. After stiffing for 10~20 minutes, the brownish orange colored solution was extracted three times with CH$_2$Cl$_2$, washed with brine, dried over Na$_2$SO$_4$, filtered and concentrated. The reaction procedure in Cho, E. J.; Kim, M.; Lee, D. Org. Lett. 2006, 8, 5413-54169 and supporting information, both of which are incorporated herein by reference in their entireties, can also be followed. Purification of the crude mixture by gradient flash chromatography on silica gel (hexanes/EtOAc=2.5:1→2:1→1.5:1→1:1) afforded the title compound (83.2 mg, 78%) as a white solid: $^1$H-NMR (CDCl$_3$, 500 MHz) δ 7.51-7.38 (m, 2H), 7.40-7.32 (m, 3H), 5.50 (s, 1H), 3.63-3.60 (m, 2H), 2.62-2.53 (m, 3H), 2.17 (br s, 1H), 1.68 (br s, 1H), 1.50-1.28 (m, 12H), 0.88 (t, J=7.0 Hz, 3H); $^{13}$C-NMR (CDCl$_3$, 75 MHz) δ 139.68, 128.71, 128.62, 126.60, 78.40, 75.64, 73.07, 72.11, 71.23, 66.52, 64.86, 33.49, 31.78, 29.52, 29.20, 25.55, 24.92, 22.62, 14.09.

5.25 Example 25

Preparation of (R)-6-((4R,5R)-5-heptyl-2,2-dimethyl-1,3-dioxolan-4-yl)-1-phenylhexa-2,4-diyn-1-ol

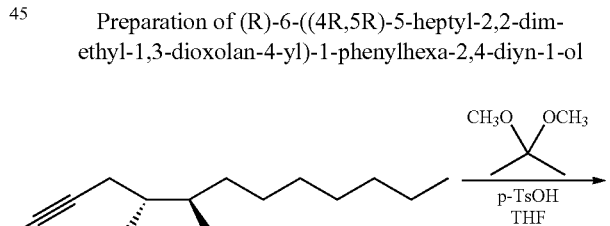

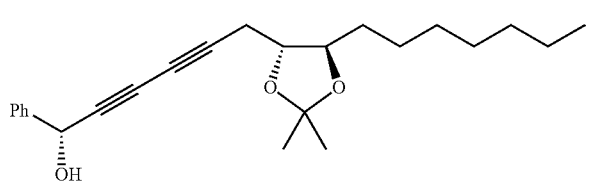

To a stirred mixture of Panaxytriol derivative (1R,7R,8R)-1-phenyl-2,4-pentadecadiyne-1,7,8-triol (12.8 mg, 39.0 μmol, 1.0 equiv) and 2,2-dimethoxypropane (40.6 mg, 390 μmol, 10 equiv) in dry THF (1.0 mL) was added p-TsOH.H₂O (about 1 mg) at 0° C. The cooling bath was removed immediately and the mixture was stirred at room temperature. After 40 min, the reaction was quenched with a saturated solution of NaHCO₃ (1 mL). The mixture was extracted with dichloromethane (4 times). The combined extracts were washed with brine, dried over Na₂SO₄, filtered and concentrated. The crude mixture was purified by gradient flash column chromatography (hexanes/EtOAc=9:18:17:1) to afford the title compound (14.0 mg, 97%) as a pale yellow oil: $^1$H-NMR (CDCl₃, 400 MHz) δ 7.52-7.50 (m, 2H), 7.40-7.32 (m, 3H), 5.50 (s, 1H), 3.83-3.78 (m, 1H), 3.75-3.71 (m, 1H), 2.67-2.56 (m, 2H), 2.30 (br s, 1H), 1.68 (br s, 1H), 1.62-1.26 (m, 12H), 1.40 (s, 6H), 0.88 (t, J=7.0 Hz, 3H); $^{13}$C-NMR (CDCl₃, 100 MHz) δ 139.75, 128.70, 128.62, 126.62, 108.72, 80.46, 78.11, 77.57, 75.53, 71.35, 66.51, 64.97, 32.90, 31.77, 29.62, 29.13, 27.40, 27.03, 25.94, 23.60, 22.62, 14.07.

5.26 Example 26

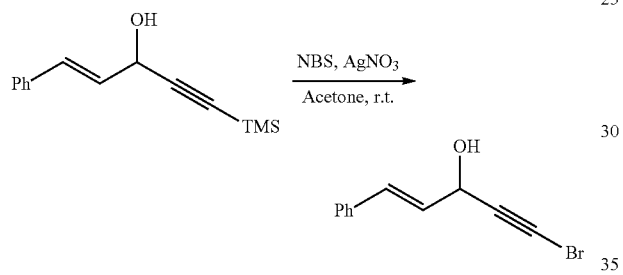

To the TMS acetylene (0.230 g, 1 mmol) (reference: *Tetrahedron Lett*. 2006, 47, 5095, herein incorporated by reference in its entirety) and NBS (0.267 g, 1.5 mmol) in acetone (5 mL) at room temperature was added AgNO₃ (0.034 g, 0.2 mmol). The mixture was stirred at r.t. for 1 hour. The mixture was cooled to 0° C., mixed with cold water and extracted with ether. The extract was washed with water and brine, dried over MgSO₄a, and concentrated under reduced pressure. The residue was purified by silica gel column chromatography (hexane:ethyl acetate=6:1) to give the bromide (0.172 g, yield 73%) as a yellow oil. $^1$H NMR (400 MHz, CDCl₃) δ 7.39-7.41 (m, 2H), 7.31-7.34 (m, 2H), 7.27-7.29 (m, 1H), 6.73-6.77 (d, J=16.0 Hz, 1H), 6.24-6.30 (dd, J=16.0 Hz, 6.0 Hz, 1H), 5.05-5.08 (t, J=6.0 Hz, 1H), 2.11-2.13 (d, J=6.0 Hz, 1H); $^{13}$C NMR (125 MHz, CDCl₃) δ 135.7, 132.3 128.6, 128.2, 127.2, 126.8, 78.9, 63.8, 47.1.

5.27 Example 27

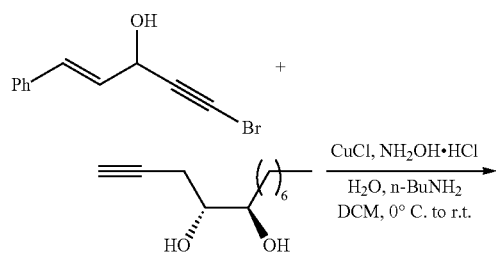

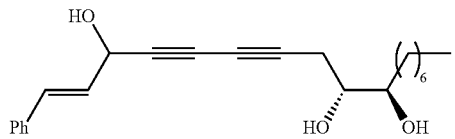

Copper(I) chloride (0.002 g, 0.02 mmol) was added to a stirred solution of n-BuNH₂ (0.3 mL) and distilled water (0.6 mL) at 0° C. to result in a deep blue solution. A few crystals of NH₂OH.HCl were added to get a colorless solution. To this solution, was added alkyne diol (0.024 g, 0.1 mmol) in DCM (0.6 mL) upon which was a yellow suspension formed. Then freshly prepared bromoalkyne (0.036 g, 0.15 mmol) in DCM (0.6 mL) was slowly added under a flow of argon. The reaction mixture was allowed to warm up to room temperature. After stiffing for 5~10 minutes, the brownish orange colored solution was extracted twice with DCM, dried over magnesium sulfate, and concentrated under vacuum. The residue was purified by silica gel column chromatography (hexane:ethyl acetate=2:1) to give the product triol (0.019 g, yield 54%) as a yellow solid. $^1$H NMR (400 MHz, CDCl₃) δ 7.26-7.40 (m, 5H), 6.73-6.77 (d, J=16.0 Hz, 1H), 6.23-6.28 (dd, J=16.0 Hz, 6.0 Hz, 1H), 5.08-5.09 (d, J=6.0 Hz, 1H), 3.65-3.66 (m, 1H), 3.60-3.63 (m, 1H), 2.59-2.60 (d, J=4.0 Hz, 2H), 1.49-1.51 (m, 2H), 1.20-1.40 (m, 10H), 0.86-0.89 (m, 3H); $^{13}$C NMR (125 MHz, CDCl₃) δ 135.8, 132.5, 128.6, 128.2, 127.0, 126.8, 78.3, 74.9, 73.0, 72.1, 71.0, 66.5, 63.2, 33.5, 31.7, 29.5, 29.1, 25.5, 24.9, 22.6, 14.0. LRMS m/z (ESI): [M+H⁺] 355.

5.28 Example 28

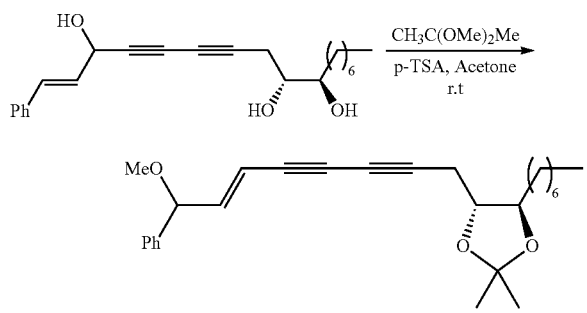

To the triol (0.007 g, 0.02 mmol) in acetone (0.2 mL) was added 2,2-dimethoxypropane (0.1 mL) and a few crystals of para-toluenesulfonic acid (pTsOH or P-TSA). The mixture was stirred overnight. To the mixture was added NaHCO₃ powder. The mixture was concentrated and the residue was separated by silica gel column chromatography (hexane:ethyl acetate=20:1) to give acetonide (0.008 g, yield 99%) as a colorless oil. $^1$H NMR (400 MHz, CDCl₃) δ 7.26-7.40 (m, 5H), 6.28-6.34 (dd, J=16.0 Hz, 6.0 Hz, 1H), 5.74-5.78 (d, J=16.0 Hz, 1H), 4.66-4.67 (d, J=6.0 Hz, 1H), 3.78-3.82 (m, 1H), 3.68-3.74 (m, 1H), 3.30 (s, 3H), 2.62-2.63 (d, J=5.2 Hz, 2H), 1.49-1.51 (m, 2H), 1.39 (s, 6H), 1.25-1.28 (m, 10H), 0.85-0.89 (t, J=6.4 Hz, 3H); LRMS m/z (ESI): [M+H⁺] 409.

5.29 Example 29

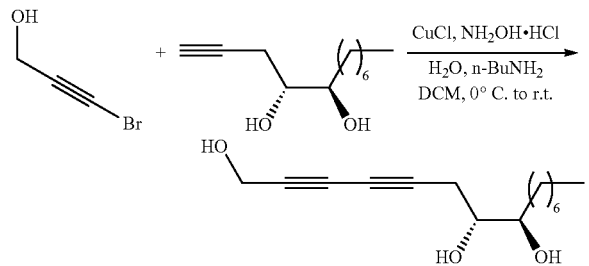

(7R,8R)-tetradeca-2,4-diyne-1,7,8-triol (7R,8R)-tetradeca-2,4-diyne-1,7,8-triol was prepared as in Example 27. The product triol was obtained in 66% yield as white solid. $^1$H NMR (400 MHz, CDCl$_3$) δ 4.34 (s, 1H), 4.32 (s, 2H), 3.64-3.65 (m, 1H), 3.58-3.59 (m, 1H), 2.57-2.58 (m, 2H), 1.48-1.51 (m, 2H), 1.20-1.40 (m, 10H), 0.86-0.90 (t, J=6.4 Hz, 3H); $^{13}$C NMR (125 MHz, CDCl$_3$) δ 74.4, 73.0, 72.1, 70.4, 69.7, 66.6, 51.4, 33.5, 31.7, 29.5, 29.1, 25.5, 24.9, 22.6, 14.0. LRMS m/z (ESI): [M+H$^+$] 285.

5.30 Example 30

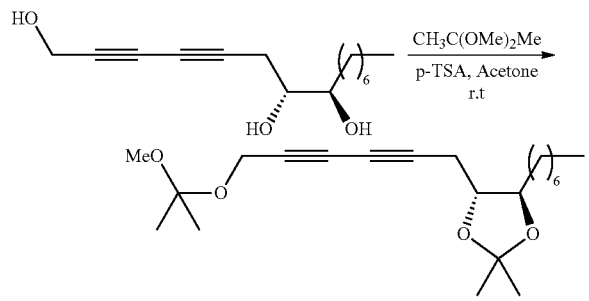

(4R,5R)-4-ethyl-5-(6-(2-methoxypropan-2-yloxy) hexa-2,4-diynyl)-2,2-dimethyl-1,3-dioxolane The title compound was prepared as in Example 27. The product acetonide was obtained in 78% yield as colorless oil. $^1$H NMR (400 MHz, CDCl$_3$) δ 4.15 (s, 2H), 3.78-3.83 (m, 1H), 3.69-3.73 (m, 1H), 3.20 (s, 3H), 2.58-2.60 (d, J=5.6 Hz, 2H), 1.54-1.60 (m, 2H), 1.39 (s, 6H), 1.36 (s, 6H), 1.20-1.36 (m, 10H), 0.86-0.90 (t, J=6.4 Hz, 3H); $^{13}$C NMR (125 MHz, CDCl$_3$) δ 108.6, 101.0, 80.4, 78.1, 75.8, 73.6, 69.6, 66.8, 49.4, 48.8, 32.9, 31.7, 29.6, 29.1, 27.4, 27.0, 25.9, 24.3, 23.5, 22.6, 14.0. LRMS m/z (ESI): [M+H$^+$] 365.

5.31 Example 31

Red Ginseng Extract

The inhibition of cultured human mammary carcinoma MX-1 cell growth by extract of Panax ginseng and fractions thereof was measured using the 2,3-bis(2-methoxy-4-nitro-5-sulfophenyl)-5-[(phenylamino)carbonyl]-2H-tetrazolium hydroxide (XTT) microculture method described in Scudiero et al., Cancer Res., 48:4827 (1988), the contents of which are hereby incorporated by reference in their entirety. Results of the XXT assay following 72-hour incubation with each extract are shown in Table 2X. Fraction 2, containing panoxtriol, showed the most potent inhibition of cell growth.

TABLE 2X

| | Parameters for inhibiting MX-1 cell growth[b] | | |
|---|---|---|---|
| | Dm (IC$_{50}$) | m | r |
| Extract Fraction | | | |
| Water extract | 29.7 μg/ml | 1.523 | 0.972 |
| Crude organic extract | 4.84 μg/ml | 4.34 | 0.996 |
| Organic extract fractions: | | | |
| Fraction 1 (less polar) [Hexane (+Ethyl acetate)] | 2.33 μg/ml | 3.95 | 0.993 |
| Fraction 2 (containing panaxytriol) | 1.58 μg/ml | 2.89 | 0.990 |
| Fraction 3 (more polar) [Ethyl acetate (+Hexane)] | 2.88 μg/ml | 2.56 | 0.999 |

[a]CCK-8 tetrazolium assay using 96-well microplate. Absorbance was measured by Powerwave XS microplate spectrophotometer. Five to seven concentrations of each extract, in triplicate at each concentration, were exposed to the cells for 72-hrs, and the IC$_{50}$ values were determined using CompuSyn software (Chou T C. and Martin N. ComboSyn, Inc., 2006) based on the median-effect equation and plot (Chou T C. J. Theor. Biol. 59: 235-276, 1976; Chou T C. Pharmacol. Rev. 58: 621-681, 2006).
[b]The mass-action law parameters: D$_m$ (the median-effect dose) signifies potency (e.g., IC$_{50}$); the m value defines the shape of the dose-effect curve (the kinetic order), where m = 1, >1, and <1 indicates hyperbolic, sigmoidal, and flat sigmoidal, respectively. The r values define correlation coefficient of the median-effect plot which signifies the conformity to the mass-action law principle (Chou, 1976, 2006). These values were determined using CompuSyn.

5.32 Example 32

Determination of the In vitro Cytotoxicity of Compounds Against Tumor Cell Lines CCRF-CEM human T-cell acute lymphoblastic leukemia cells and the corresponding vinblastine-resistant cells (CCRF-CEM/VBL100) were cultured at an initial density of 5×10$^4$ cells per milliliter. The cultured cells were maintained in a 5% CO$_2$-humidified atmosphere at 37° C. in RPMI medium 1640 (GIBCO/BRL) containing penicillin (100 units/mL), streptomycin (100 μg/mL, GIBCO/BRL), and 10% heat-inactivated fetal bovine serum. The cytotoxicity of each Compound of the invention was measured using the 2,3-bis(2-methoxy-4-nitro-5-sulfophenyl)-5-[(phenylamino)carbonyl]-2H-tetrazolium hydroxide (XTT) microculture method as described in Scudiero et al., Cancer Res., 48:4827 (1988), the contents of which are hereby incorporated by reference in their entirety. Results of the XTT assay following 72-hour inhibition are shown in Tables 3, 3A, and 3B, where VBL means vinblastine resistant cells. All compounds tested exhibited anti-cancer activity in the assay.

TABLE 3

| | IC$_{50}$ (μM) | |
|---|---|---|
| Compound | CCRF-CEM | CCRF ± CEM/VBL[a] |
| panaxytriol | 12.09 ± 1.57 | 14.56 ± 6.92 (1.20x) |
| Compound A | 1.98 ± 0.20 | 2.41 ± 0.05 (1.22x) |
| Compound B | 4.49 ± 0.41 | 6.29 ± 1.41 (1.40x) |
| Compound C | 3.23 ± 0.78 | 3.84 ± 0.08 (1.19x) |

[a]Resistance to Vinblastine was 400-fold as indicated by IC$_{50}$ increases (0.0020 ± 0.0007 μM in CCRF-CEM compared to 0.80 ± 0.10 μM in CCRF-CEM/VBL cell line).

A comparison of the in vitro cytotoxicity of Compounds (D) and (A) in a cancer cell assay was undertaken using the above assay procedure. The results are disclosed in Table 3A, and following.

TABLE 3A

Comparison of cytotoxicity of Compound
(D) with Compound (A) in vitro[a]

| Compound | IC$_{50}$ (µM) | | |
|---|---|---|---|
| | CCRF-CEM | CCRF-CEM/Taxol[b] | CCRF-CEM/VBL[b] |
| (A) | 0.803 | Not Done | 1.122 [1.4-fold resistance][c] |
| (D) | 6.150[d] 0.478 (analog is 1.68-fold more potent) | 17.23[d] 1.035 [2.17-fold resistance][c] | 6.816[d] 0.947 [1.98-fold resistance][c] (analog is 1.19-fold more potent) |

[a]Cell growth inhibition was measured by the above assay using a Powerwave XS spectrophotometer. IC$_{50}$ values were determined in duplicate or triplicate from the dose-effect relationship at six or seven concentrations of each drug using the CompuSyn software by Chou and Martin, discussed below, based on the median-effect principle and plot and serial deletion analysis.
[b]CCRF-CEM/TAXOL and CCRF-CEM/VBL are subcell lines of CCRF-CEM cells that are 283-fold resistant to TAXOL, and 261-fold resistant to Vinblastine, respectively, when comparing with the IC$_{50}$ of the CCRF-CEM cell line.
[c]Numbers in the brackets correspond to the amount of resistance against the tested compound in the drug-resistant cell line, which was determined by comparing the IC$_{50}$s observed in the corresponding assay using the parent, non-drug-resistant cell line to that observed in the drug-resistant cell line. The difference is expressed mathematically by the fold increase in the IC$_{50}$ observed in the assay using the drug-resistant cell line.
[d]These assays were conducted using Compound (A) that had been stored in DMSO at below approximately −20° C. for 4 years and 4 months.

The experimental data in Table 3A show that Compound (D) is about 1.44-fold more potent than Compound (A) in vitro, and that both Compounds (A) and (D) are active against cancer, as shown by activity against illustrative cancer cell lines, and against illustrative TAXOL or vinblastine-resistant (VBL) cell lines.

Table 3A-2 shows the cytotoxicity of panaxytriol (PXT) and Compound D in human CCRF-CEM Leukemic cell lines and sublines resistant to TAXOL or Vinblastine during a 72-hr exposure using the CCK-8 tetrazolium assay in a 96-well microplate. Absorbance was measured by Powerwave XS microplate spectrophotometer. Five to seven concentrations of each compound in triplicate were used for 72-hr exposure, and the IC$_{50}$ values were determined by CompuSyn software automation (Chou and Martin, 2006) based on the median-effect equation and plot (Chou, 1976, 2006).

TABLE 3A-2

| Compound | CCRF-CEM | CCRF-CEM/TAXOL (IC$_{50}$ in µM) | CCRF-CEM/VBL |
|---|---|---|---|
| PXT | 3.681 | 3.093 [0.84 fold][b] | 4.426 [1.20 fold][b] |
| Compound D | 1.138 | 1.021 [0.90 fold] | 2.551 [2.24 fold] |
| TAXOL | 0.0013 | 1.118 [860 fold] | 2.264 [1741 fold] |
| Vinblastine | 0.0011 | 0.282 [256 fold] | 0.669 [608 fold] |

[b]Fold of resistance was determined using the IC$_{50}$ ratio of drug-resistant cells vs. the parent cell line, CCRF-CEM.

The cytotoxicity of Compound (E) was studied using the procedures discussed above for Table 3A. The result is disclosed in Table 3B, which indicates that Compound (E) is also active against cancer as shown by its activity against the illustrative cancer-cell line, CCRF-CEM.

TABLE 3B

Cytotoxic Potency of Compound (E) against
CCRF-CEM cell line growth in vitro[a]

| Compound | IC$_{50}$ (in µM) for human leukemic lymphoblastic leukemia cells CCRF-CEM |
|---|---|
| (E) | 6.512 |

At least Compounds (E)-(H), and (J)-(K) are active against cancer. These compounds were tested for their in vitro cytotoxicity against a cancer cell line, with the following results:

TABLE 3C

Cytotoxic Potency of Compounds against
cancer cell line growth in vitro

| Compound | IC$_{50}$ (in µM) |
|---|---|
| (D) | 0.48 |
| (E) | 642 |
| (F) | 3.88 |
| (G) | 3.77 |
| (H) | 21.57 |
| (J) | 0.83 |
| (K) | 2.03 |
| (L) | 1.92 |

Tables 3D and 3E further show in vitro anticancer activity of compounds of the invention.

TABLE 3D

Comparison of cytotoxicity of Compounds in vitro[a]

| Compound | IC$_{50}$ (µM) for human leukemic lymphoblastic leukemia sublines | | |
|---|---|---|---|
| | CCRF-CEM | CCRF-CEM/TAXOL[b] | CCRF-CEM/Vinblastine[b] |
| Panaxytriol | 5.04 ± 0.86 (n = 3) | 5.22 [1.04x] | 6.39 [1.27x] |
| Compound (A) | 0.803 | Not done | 1.122 [1.4-fold resistance][c] |
| Compound (E) | 641.9 | 156.3 [0.24x]† | 106.5 [0.17x] |
| Compound (D) | 0.478 | 1.035 [2.17-fold resistance][c] | 0.947 [1.98-fold resistance][c] |
| Compound (H) | 21.57 | 15.06 | 26.57 |
| Compound (F) | 3.88 ± 0.85 | 7.58 | 8.56 |
| Compound (L) | 1.92 ± 0.16 | 2.91 | 2.76 |
| Compound (G) | 3.77 ± 0.48 | 6.16 | 7.30 |
| Compound (K) | 2.03 ± 0.13 | 3.57 | 3.30 |
| Compound (J) | 0.83 ± 0.26 | 1.72 | 1.19 |

[a]Cell growth inhibition was measured by CCK-8 assay for leukemic cells after 72-hr incubation using Powerwave XS spectrophotometer. IC$_{50}$ values were determined in duplicate or triplicate from the dose-effect relationship at six or seven concentrations of each drug by using the CompuSyn software by Chou and Martin (2006) based on the median-effect principle and plot and serial deletion analysis. (Chou et al. *Cancer Res.* 65: 9445-9454, 2005).
[b]CCRF-CEM/TAXOL and CCRF-CEM/VBL are subcell lines of CCRF-CEM cells that are 283-fold resistant to TAXOL, and 261-fold resistant to Vinblastine, respectively, when comparing with the IC$_{50}$ of the parent cell line.
[c]Numbers in the brackets are fold of cross-resistance determined by comparison with the corresponding IC$_{50}$ of the parent cell line.

TABLE 3E

| Compound | IC$_{50}$ (µM) for human leukemic lymphoblastic leukemia sublines | | |
|---|---|---|---|
| | CCRF-CEM | CCRF-CEM/ TAXOL[b] | CCRF-CEM/ Vinblastine[b] |
| Compound (N) | 12.64 | 19.35 | 13.59 |
| Compound (O) | 5.25 | 10.27 | 6.52 |
| Compound (P) | 4.18 | 11.86 | 5.14 |

5.33 Example 33

Cytotoxicity of Compounds Against Solid Tumor Cells

As shown in Table 4, the in vitro potency evaluation of Compounds of the invention was expanded to human solid tumor cells, including MX-1 mammary carcinoma, HCT-116 colon carcinoma. Compounds are also evaluated against A-549 lung carcinoma and SK-OV-3 ovarian adenocarcinoma cell lines using the methodology as for Table 3. The potency order for the compounds may vary in different tumor cell lines. The CCK-8 assay was used to determine the IC$_{50}$ values, which are expressed in µM, with exposure of the cells to the drugs for 72 hrs. Absorbance was measured using a Powerwave XS microplate spectrophotometer.

TABLE 4

| | Human Solid Tumor Cells (IC$_{50}$ in µM) | | | |
|---|---|---|---|---|
| Compound | MX-1 (Mammary Carcinoma) | HCT-116 (Colon Carcinoma) | A-549 (Lung Carcinoma) | SK-OV-3 (Ovarian Adenocarcinoma) |
| Compound (A) | 1.915 | 1.275 | 3.947 | 2.997 |
| Compound (D) | 5.321 | 0.617 | 2.845 | 5.078 |
| Compound (K) | 3.445 | 3.173 | 1.024 | 4.026 |
| Compound (J) | 1.472 | 1.091 | 12.550 | 12.985 |

Alternative Therapeutic Effect and Toxicity Studies in Mice

An in vivo assay uses male athymic nude mice bearing the nu/nu gene (6 weeks of age or older, weighing between 20 and 22 g, obtainable from NCI, Frederick, Md.) into which one or more human tumor xenografts are been implanted. The in vivo cytotoxicity of a compound of the invention and a tubulin-binding drug can be determined according to the procedure set forth in Chou et al., *Proc. Natl. Acad. Sci. U.S.A.* 95:15798 (1998), the content of which is herein incorporated by reference in its entirety.

In an example of a breast cancer screening experiment, nude mice are divided into two groups (control and treated) and inoculated with human mammary carcinoma MX-1 xenograft. The treated group is pre-treated with a compound of the invention (e.g. 60 mg/kg, Q2D, i.v. injection) beginning 2 days before tumor implantation. Several parameters were compared for the two groups: (i) The "tumor take" rate; (ii) The course of tumor progression, and (iii) Time course of body-weight changes.

5.34 Example 34

Efficacy of Panaxytriol and Compound (A)

Nude mice having human mammary carcinoma xenograft MX-1 were treated with panaxytriol or Compound (A) at various dosages through the slow i.v. infusion protocol by Chou et al. (Chou, T. C., et al, *Proc. Natl. Acad. Sci. U.S.A.* 95: 15798 (1998), the contents of which are herein incorporated by reference in their entirety). Mice treated with 30 mg/kg of panaxytriol exhibited some suppression of tumor growth, but only moderate reduction in tumor mass was observed. At elevated dosage levels, improved inhibitory effects were observed. Compound (A) demonstrated enhanced in vivo potency, inhibiting tumor growth at levels as low as 10 mg/kg. Elevated dosages led to enhanced tumor-growth suppression. Notably, even at the highest dosage levels (100 mg/kg), no body weight decrease was observed upon treatment with either panaxytriol or Compound (A).

5.35 Example 35

In-Vitro Efficacy of a Combination of a Compound of the Invention and a Tubulin-Binding Drug Efficacy of panaxytriol in combination with Fludelone (an illustrative tubulin-binding anticancer agent) was measured according to procedures described in more detail by Chou et al. (1984) *Adv. Enz. Regul.*, 22:27-55, Chou et al. (1994) *Nat'l Cancer Inst.*, 86:1517-1524, and Chou (2006) *Pharmacological Reviews*, 68:621-681. Software packages used for data analyses were *CalcuSyn for Windows* (Chou and Hayball., Multiple-drug dose effect analyzer and manual, Biosoft, Cambridge Place, Cambridge, U.K (1996)) and *CompuSyn for Drug Combinations* (Chou and Martin, Software for determination of synergism and antagonism and determination of IC$_{50}$, ED$_{50}$ and LD$_{50}$, ComboSyn Inc., Paramus, N.J. (2005)). The entire contents of each of the above references are incorporated by reference in their entireties. The results of the combination of panaxytriol and Fludelone against human mammary carcinoma MX-1 cells growth in vitro[a,e] are shown in Tables 5 and 5A. Table 5 shows the effects of panaxytriol and the microtubule-binding anti-tumor agent Fludelone alone and in combination against human mammary carcinoma MX-1 cell growth in vitro. Table 5 also shows the Dose Reduction Index (DRI) for the combination of panaxytriol and fludelone. DRI quantitates synergy as how many fold less of a dose is required to obtain a given level of effect for a combination of drugs versus the same effect for an individual component of the combination.

TABLE 5

| | Dose-effect parameters[b] | | | Combination Index[c] (CI) at | | | | Dose-Reduction Index[d] (DRI) at | | | |
|---|---|---|---|---|---|---|---|---|---|---|---|
| Compound | m | Dm | r | IC$_{50}$ | IC$_{75}$ | IC$_{90}$ | IC$_{95}$ | IC$_{50}$ | IC$_{75}$ | IC$_{90}$ | IC$_{95}$ |
| Panaxytriol | 2.600 | 3.191 | 0.993 | | | | | | | | |
| Fludelone | 0.619 | 0.0027 | 0.992 | | | | | | | | |
| Panaxytriol | | 1.199 | | | | | | 2.66 | 2.12 | 1.70 | 1.46 |

TABLE 5-continued

| Compound | Dose-effect parameters[b] | | | Combination Index[c] (CI) at | | | | Dose-Reduction Index[d] (DRI) at | | | |
|---|---|---|---|---|---|---|---|---|---|---|---|
| | m | Dm | r | $IC_{50}$ | $IC_{75}$ | $IC_{90}$ | $IC_{95}$ | $IC_{50}$ | $IC_{75}$ | $IC_{90}$ | $IC_{95}$ |
| Panaxytriol + Fludelone | 1.697 | + | 0.984 | 0.816 | 0.613 | 0.635 | 0.708 | | | | |
| Fludelone | | 0.0012 | | (Synergism) | | | | 2.27 | 7.02 | 21.69 | 46.73 |

[a] XTT/CCK-8 assays were carried out using from 6 to 8 concentrations of each drug and their combinations in duplicate. Drug exposure time was 72 hrs. Absorbance was measured by a microplate reader.
[b] The m values signify shapes, m = 1, >1 and <1 represent hyperbolic, sigmoidal, and flat sigmoidal, respectively. The Dm values signifies potency, i.e., the $IC_{50}$ values in µM. The r values are the linear correlation coefficients of the dose-effect plot which signify the conformity to the mass-action law principle. (Chou T C and Talalay P. Adv. Enz. Regul. 22: 27-55, 1984).
[c] CI = 1, <1, and >1 indicates additive effect, synergism, and antagonism, respectively.
[d] DRI represents how many fold dose reduction is allowed at a given effect level as a result of synergistic interaction of two compounds.
[e] The values for m, Dm, r, CI and DRI were calcularad by using a computer software, CompuSyn, by Chou T C and Martin N (ComboSyn, NJ, 2005).

A similar study with the combination of two tubulin binding-drugs (Fludelone and TAXOL) showed no synergy to only moderate synergy. A summary of the results of comparison studies with the combination of Fludelone and Panaxytriol and the combination of Fludelone and TAXOL are shown in Table 5A.

TABLE 5A

| Drug combination | At $IC_{90}$ & $IC_{95}$ | At $IC_{75}$ | At $IC_{50}$ |
|---|---|---|---|
| Fludelone + panaxytriol | Synergism | Synergism | Synergism |
| Fludelone + TAXOL | Moderate Synergism | Slight Synergism | Additive effect |

The results in Tables 5 and 5A indicate that panaxytriol in combination with fludelone—an illustrative tubulin-binding drug, exhibit synergism, while a combination of two tubulin-binding drugs exhibits only an additive effect to merely moderate synergism.

As discussed herein, in vitro studies indicated that the Compounds studied are not (or are only slightly) cross-resistant to TAXOL or to vinblastine (e.g., using the typical multiple drug resistant or MDR cells). Computerized data analysis showed that the effects of panaxytriol and other Compounds of the invention yielded high degrees of sigmoiditis in dose-effect curves (e.g., m values of 1.90 to 3.22) indicating strong cooperative activity with high-order kinetics/dynamics when exerting their effects.

Panaxytriol in combination with the tubulin-binding agent, fludelone, resulted in consistent synergistic effects with a combination index (CI value) of 0.635 to 0.816 for its $IC_{50}$ to $IC_{90}$. (CI<1 indicates synergism), as disclosed in Table 5. As the result of synergy, the doses of both compounds can be markedly reduced and yet maintain a given effect. Based on a computerized simulation, the fludelone doses (concentrations) can be reduced 2.22 to 46.73 fold for its $IC_{50}$ to $IC_{95}$; and the doses of Panaxytriol can be reduced 2.66 to 1.46 fold for its $IC_{50}$ to $IC_{95}$, compared with each drug alone.

5.36 Example 36

Time Course of the Effects on the Compounds on the Proliferation of Human Lymphocytes The effect of compounds of the invention on the proliferation of human lymphocytes at different time points are shown in Table 6 as results of XTT and CCK-8 tetrazolium assays following 24-hour, 72-hour, and 120-hour incubation. All compounds tested exhibited stimulation of human lymphocyte proliferation in the assay. Cultured human PMBC lymphocytes were used in the assay. The procedures employed are taught in the General Biological Methods section.

TABLE 6

| | Incubation Time and Parameters[b] | | | | | | | | |
|---|---|---|---|---|---|---|---|---|---|
| | 24 hr | | | 72 hr | | | 120 hr | | |
| Compound | $D_m$ (µM) | m | r | $D_m$ (µM) | m | r | $D_m$ (µM) | m | r |
| Panaxytriol | 1.636 | 1.212 | 0.999 | 3.481 | 2.175 | 0.988 | 3.165 | 2.163 | 0.966 |
| Compound (D) | 1.074 | 1.029 | 0.989 | 1.524 | 3.332 | 0.977 | 1.756 | 2.619 | 0.999 |

5.37 Example 37

Splenocyte Stimulation

Splenocytes were prepared from CD mice as a single cell suspension, and treated with red blood cell (RBC) lysis buffer (as described at http://www.ebioscience.com/ebioscience/specs/antibody_00/00-4333.htm) to remove RBCs. In a typical experiment, splenocyte stimulations by phytostigmin (PHA), panaxytriol (PXT) or Compound D were measured by using tritium-labeled thymidine, $^3$H-dThd, as a tracer for DNA synthesis. DNA synthesis correlates with cell proliferation. The incubation mixture consisted of splenocyte suspension in RPMI 1640 medium ($1.56 \times 10^6$ cells in 198.5 µl)+3 µg of PHA in 1 µl+ the test compound at various concentrations in 0.5 µl in dimethyl sulfoxide (DMSO), to a final concentration of 200 µl per microplate well. DMSO alone was used in place of the compound in DMSO as a control. The incubation was carried out in 5% $CO_2$-humidified atmosphere at 37° C.

for a designated time [e.g., 24 hr, 48 hr, 72 hr, 96 hr]. At the end of the incubation period, $^3$H-dThd 1 µCi in 1 µl was added for an additional 6 hr incubation. The reaction was stopped by adding one volume of 20% trichloroacetic acid (TCA), homogenized at 3° C. and washed with 20% TCA. The precipitate was heat extracted (90°) with 10% TCA for 15 minutes to obtain the DNA fraction, which has the radiolabel incorporated, in the supernatant. The supernatant was added to a 7-fold volume of Liquicint for scintillation counting, which was accomplished with a Beckman LS 6000 IC spectrometer from Beckman Coulter Co. The incorporation of [$^3$H]dThd into DNA of splenocytes were measured as described above or previously (Chou et al. *Phytotherap. Res.* 3: 237-242, 1989). The results are depicted in FIGS. 11 and 12.

For the cell-counting assays, the cells were washed with RPMI 1640 medium and followed by centrifugation. The cell number was counted with a hemocytometer. Splenocyte suspensions (0.4×10$^6$ cells in 0.2 ml) in flat bottom 96-well plates were incubated with [$^3$H]dThd (1 µCi) for 24-hrs in the absence or presence of phytostigmin (PHA, 0.1 µg/0.2 ml) or panaxytriol (0.03-1 µM). Studies indicate that maximal stimulation occurred at 48 hrs or 72 hrs. Results of a $^3$H thymidine uptake assay are shown in Table 7. The procedure in Table 7 was used to test the splenocytes used in the assays described herein to test the compounds of the invention, shown by PHA stimulation of DNA synthesis. Table 7 shows that PHA and panaxytriol induced stimulation of DNA synthesis by mouse splenocytes. Splenocytes from this culture were used in the assays in FIGS. 11 and 12 and the corresponding Examples.

TABLE 7

| Experiment | Incorporation of [$^3$H]dThd into Mouse Splenocyte DNA (cpm) | t-test P value |
|---|---|---|
| Control | 224 ± 28 | |
| PHA (10 µg/ml) | 1420 ± 17 | <0.00001 |
| Panaxytriol | | |
| 0.03 µM | 227 ± 8.3 | 0.28 |
| 0.1 µM | 251 ± 18 | 0.36 |
| 0.3 µM | 290 ± 20 | <0.06 |
| 1.0 µM | 296 ± 9 | <0.04 |

Panaxytriol was observed to enhance [$^3$H] thymidine uptake into splenic cells in a dose-dependent manner Enhanced $^3$H thymidine uptake into splenic cells indicates an immune enhancement because it correlates with DNA synthesis. Exposure of the splenic cells to Compounds at 0.03, 0.1, 0.3, and 1.0 µM for 24 hours resulted in the immuno-enhancement as seen by increased [$^3$H] thymidine (dThd) uptake. The observed immuno-enhancement is believed to have multiple consequences including the body's improved ability to fight tumors, regardless of whether the tumors occur naturally or are carcinogen induced. Other consequences of immuno-enhancement include the increased capability of fighting other diseases and infections.

5.38 Example 38

Enhancing Effect of Panaxytriol in Human Lymphocytes

The main principle and method of experiments for human PBMC lymphocytes and for mouse splenocytes stimulations were the same, since both measure immunological cell stimulation by PHA, PXT and compounds of the invention. Both the lymphocyte and the splenocyte assays measure the $^3$H-dThd tracer as an indication of DNA synthesis. For PBMC lymphocytes (FIGS. 9A-9G), the experimental methods are those for splenocytes disclosed in Example 24 (FIGS. 11A-11F; FIGS. 12A-12E), except 0.282×10$^6$ PBMC lymphocyte cells in 198.5 µl was used, and the experimental incubation time was extended to 120 hr.

Briefly, to generate the data in Tables 8A and 8B, the compounds were tested in a [$^3$H] thymidine uptake experiment using PBMC human lymphocytes obtained from the New York Blood Center. PBMC human lymphocytes were exposed to compounds at 0.03, 0.1, 0.3, and 1.0 µM for 24 hours, and examined for increased [$^3$H] thymidine uptake. Human lymphocytes were also exposed to compounds for an extended time, e.g., 48 hrs and 72 hrs, instead of 24 hrs, in the [$^3$H] thymidine uptake assay, and examined to determine the extent of increased [$^3$H] thymidine uptake to determine if extended exposure will further increase the immune-enhancing effects of the compounds. Increased [$^3$H] thymidine uptake is interpreted as increased DNA synthesis, which indicates cell growth and division. In the case of immune system cells, this should result in an immune-enhancing effect. The compounds are compared by their IC$_{50}$ values and/or their effect on [$^3$H] thymidine uptake at a given concentration and/or time point.

The effects of panaxytriol and Compound D on the viability of normal human PBMC lymphocytes shown in Tables 8A and 8B were determined using hemacytometer/microscope determinations. PBMC cells were obtained fresh from the New York Blood Center, New York, N.Y. 10021 (Dr. S. B. Jiang). Cell counts were performed in duplicate for 0, 0.1, 0.3, 1.0, 3.0, and 10.0 µM of each compound at the end of 24 hr, 72 hr, and 120 hr incubations. Incubation was carried out in RPMI 1640 medium (GIBCO/BRL) with 10% heat inactivated fetal bovine serum. The cells were maintained in 5% CO$_2$-humidified atmosphere at 37° C. in RPMI medium as described in Chou et al. *Proc. Nat'l. Acad. Sci. USA* 98: 8113-8118, 2001.

Table 8A shows the effect of Panaxytriol on Human PBMC Lymphocyte viability based on actual cell counts. The percentages reported are the number of viable cells relative to the starting point (control). Panaxytriol increases the proliferation and prolongs the life-span of normal lymphocytes at low concentrations and for a long duration, e.g. 24-120 hours), as can Compounds of the invention.

TABLE 8A

| Panaxytriol Concentration | Time (hours) | | | |
|---|---|---|---|---|
| (µM) | 0-hr | 24-hrs | 72-hrs | 120-hrs |
| 0 (No DMSO) | 100% | 93.5% | 83.9% | 72.8% |
| 0 (With DMSO) | 100% | 75.4% | 93.0% | 85.7% |
| 0.1 | | 121.0% | 112.6% | 109.6% |
| 0.3 | | 139.5% | 95.8% | 105.1% |
| 1.0 | | 123.3% | 101.9% | 101.0% |
| 3.0 | | 104.3% | 82.2% | 74.1% |
| 10.0 | | 27.7% | 28.5% | 35.5% |

Table 8B shows the effect of Compound D on Human PBMC Lymphocyte viability based on actual cell counts. The percentages reported are the number of viable cells relative to the starting point (control).

TABLE 8B

| Compound D Concentration | Time (hours) | | | |
|---|---|---|---|---|
| (μM) | 0-hr | 24-hrs | 72-hrs | 120-hrs |
| 0 (No DMSO) | 100% | 93.5% | 83.9% | 72.8% |
| 0 (With DMSO) | 100% | 75.4% | 93.0% | 85.7% |
| 0.1 | | 101.4% | 115.9% | 78.2% |
| 0.3 | | 117.6% | 107.5% | 73.6% |
| 1.0 | | 78.4% | 89.7% | 102.0% |
| 3.0 | | 90.5% | 66.8% | 68.0% |
| 10.0 | | 7.5% | 33.2% | 27.4% |

5.39 Example 39

Table 9 shows the inhibition of precursor incorporation into DNA, RNA and protein of leukemic CCRF CEM cells by Compounds at high concentrations and at varied time of incubation. The radioactive tracer studies were carried out as described by Chou T C, et al. *Cancer Res.* 43: 3074-3079, 1983.

TABLE 9

| Compound | Concentration (μM) | [$^3$H]-dThd → DNA | | [$^3$H]-AdR → RNA | | [$^3$H] Leu → Protein | |
|---|---|---|---|---|---|---|---|
| | | 15 min | 60 min | 15 min | 60 min | 15 min | 60 min |
| | | (% Activation ↑ or Inhibition ↓) | | | | | |
| Panaxytriol | 30 | 21.3 ↑ | | 38.0 ↑ | | 77.8 ↓ | |
| | 100 | | 67.8 ↓ | | 74.4 ↓ | | 67.8 ↓ |
| Compound (D) | 6 | 13.2 ↑ | | 35.3 ↑ | | 45.2 ↓ | |
| | 100 | | 69.5 ↓ | | 72.5 ↓ | | 69.5 ↓ |
| Compound (B) | 15 | 26.1 ↑ | | 30.7 ↑ | | 62.8 ↓ | |
| | 100 | | 78.2 ↓ | | 82.0 ↓ | | 78.2 ↓ |

5.40 Example 40

Oxidation Effects

Table 10 provides evidence that the oxidation products of panaxytriol and Compound (A) are even more potent than their parents. Without wishing to be bound by theory, the oxidized versions may be active metabolites. This theory provides an explanation of the delayed onset of therapeutic effects seen in the figures herein. The oxidized compounds may be active agents that are formed slowly upon metabolic oxidation. Thus, the parent compounds may serve as prodrugs for the oxidized compounds, which may explain the compounds delayed onset of biological effect (as shown in FIGS. 9E, F, G; FIGS. 11B, C; FIGS. 12B, C). The active metabolites may explain the biphasic pharmacological properties of panaxytriol or Compound D that have been observed (FIGS. 9B, C, D; FIGS. 11D, E, F, and FIGS. 12D, E). The delayed onset of action may be also caused by a delay in the metabolic oxidation of compounds of the invention. This could be explained by the fact that panaxytriol has been shown to be an inducer of phase 2 metabolic enzymes (which serve as indirect antioxidants). Induction of the phase 2 enzymes may slow oxidation of the compounds (Ng et al., *Tetrahedron Letters.* 49: 7178-7179 (2008)). A delay in formation of active metabolite could explain the biphasic effect of the compounds, such as seen in a sigmoidal dose-response curves of panaxytriol and Compound D. Furthermore, the biphasic (i.e. "humped") dose-response curve observed for panaxytriol and Compound (D) could be explained by the eventual breakdown of these oxidation products. The oxidized compounds, although more active, may thus be less stable than their parent compounds.

Table 10 shows the cytotoxic activity of compounds against human lymphoblastic leukemic T-cell growth relative to their stabilities during storage at −20° C. in DMSO[a,b]

TABLE 10

| | | IC$_{50}$ in μM | |
|---|---|---|---|
| Compound | Date of Assay | CCRF-CEM | CCRF-CEM/ VBL[c] |
| Panaxytriol | Jul. 25, 2003 | 6.34 ± 0.51[d] | 4.71 ± 0.73[d] |
| Compound A | (Fresh) | 1.21 ± 0.03 | 1.22 ± 0.15 |
| Compound (B) | | 0.72 ± 0.14 | 0.95 |
| Compound (C) | | 0.404 | 0.70 |
| Panaxytriol | Aug. 22, 2003 | 10.98 | 19.45 |
| Compound A | (Stored) | 2.12 | 2.37 |

TABLE 10-continued

| | | IC$_{50}$ in μM | |
|---|---|---|---|
| Compound | Date of Assay | CCRF-CEM | CCRF-CEM/ VBL[c] |
| Compound (B) | | 4.78 | 5.29 |
| Compound (C) | | 2.68 | 3.90 |

[a]Jul. 25, 2003 and Aug. 22, 2003 experiments had used the same corresponding solutions. Activities reduced during storage.
[b]XTT microplate assay was used after 72 hr incubation (For experimental procedures, see Chou et al. Proc. Nat'l. Acad. Sci. USA 95: 9642-9647, 1998).
[c]CCRF-CEM/VBL cells are resistant to Vinblastine (720-fold resistant) comparing to IC$_{50}$ values with those of CCRF-CEM cells.
[d]The numbers with ± sign were assayed in duplicates. Each assay used 6-8 concentrations.

5.41 Example 41

Effect of Compound (D) on Toxicity of Cytotoxic Drugs

A. Effects on Acute Toxicities

Nude mice will be inoculated with MX-1 xenograft. The animals will be divided into four groups: Group 1 receives no treatment; Group 2 will be treated with Iso-Flu (10 mg/kg, Q4D×4, i.v. injection, beginning 10 days after tumor implantation) which is expected to produce acute toxicity; Group 3 will be treated with Compound (D) (30 mg/kg, Q2D, i.v. injection) only two days prior during and after Iso-Flu treatment, according to Group 2, and Group 4 will be treated with both Iso-Flu and Compound (D), respectively, as described for Groups 2 and 3. Several parameters will be compared among these groups: (i) The time course of the acute toxicities (body weight decreases, symptoms, or time of death), (ii) The time course of tumor progression; (iii) Histo-pathological changes, if any.

FIG. 15 shows the body weight change in nude mice bearing human colon carcinoma HCT-116 xenograft (n=7) when administered Isodehydelone, a cytotoxic anticancer drug, using a 6 hr-iv. Infusion; Compound (D) (orally); or a combination of Compound (D) (orally) and Isodehydelone (6 hr-iv. infusion). The experiments were run as described for FIGS. 4 and 7. The results show that Compound (D) administered orally reduces the toxicity and lethality of isodehydelone alone. Two mice died while undergoing treatment with isodehydelone alone (on days 26 and 64), while none died when Compound (D) was administered orally alongside iv Isodehydelone. Also, the mice given Compound (D) retained their body weight significantly better when undergoing Isodehydelone treatment than those not taking oral Compound (D) (P<0.1 or <0.05 as indicated in FIG. 15).

B. Effects on Chronic Toxicities (e.g., Peripheral Neuropathy)

Nude mice can be inoculated with MX-1 xenograft. The animals can be divided into four groups: Group 1 will receive no treatment; Group 2 will be treated with "high therapeutic doses" of a cytotoxic drug (e.g. Iso-Flu (25 mg/kg, Q6D×3, 6 hr-i.v. infusion, beginning 10 days after tumor implantation)) to produce marked antitumor effects (including tumor suppression, shrinkage and/or complete remission) and chronic peripheral neuropathy some time (e.g. several months) after the cytotoxic agent treatments; Group 3 will be treated with a Compound of the invention only (e.g. Compound D or K, 30 mg/kg, Q2D, i.v. injection)) several (e.g. 2) days prior, during and after the cytotoxic agent treatments, corresponding to the treatment plan as described in Group 2 above; and Group 4 will be treated with both the cytotoxic agent and a Compound of the invention, respectively, as described for Groups 2 and 3.

The following parameters can be compared among 4 groups: (i) The course of therapeutic effects. Whether the combination would induce therapeutic benefits will also be examined; (ii) The time course of body weight changes or recovery; (iii) The evidence of chronic peripheral neuropathy and its time of events, its frequency, and its recovery, if any. The neuropathy include difficult of movement, weakness and inactivity, hind-leg paralysis or death; and (iv) Any other symptoms or histo-pathology, if any.

The above in vivo experiments can be pooled so that the control (untreated) group and the single-entity treated group can be shared to trim the experimental size, save time and efforts, reduce the animal usage and costs, and conserve the compounds.

5.42 Example 42

Compound K Reduces the Toxic Effect of Prolonged Doses of Paclitaxel

A. Effect on Paclitaxel-Induced Body Weight Loss

Compound K (30 mg/kg, Q4D, i.v. beginning on days 7 and 4 days after) reduced high-dose paclitaxel-induced toxicity and neurotoxicity in vivo in MX-1 xenograft bearing nude mice. Paclitaxel (25 mg/kg, i.v. injection Q2D×4) was administered in two Rounds, the First Round (Days 9, 11, 13 & 15) and the Second Round (Days 27, 29, 31 & 33).

As shown in FIG. 14, Compound K reduced the paclitaxel-induced body-weight (BW) loss in both Rounds of paclitaxel treatment (p<0.05). The First Round of high dose paclitaxel treatment (Days 9, 11, 13 & 15) led to a BW loss of approximately 25%. Compound K slightly reduced the BW loss due to paclitaxel in Round 1. However, Compound K significantly improved BW recovery after Round 1 as seen by a 7.7% decrease in BW for the combination of Compound K and paclitaxel vs. a 13.2% decrease with paclitaxel alone (see FIG. 14, Days 25-27). For the Second Round of high dose paclitaxel treatment (Days 27, 29, 31 & 33), Compound K substantially reduced BW loss, but the rate of BW recovery was slower. On Day 59, the paclitaxel-treated mice had recovered to 93.5% of the BW of the control mice. The mice treated with Compound K and paclitaxel showed a BW recovery to 101.2% of the control mice. The differences in BW recovery at days 49-63 were statistically very significant (p<0.05). Compound K reduced paclitaxel-induced toxicity and improved recovery.

B. Effect on Paclitaxel-Induced Neurotoxicity

The MX-1 xenograft nude mice in A. were also tracked for paclitaxel-induced neurotoxicity (as determined by peripheral neuropathy) using the above procedure and as detailed in Tables 11A-C, below. The results are also given in Tables 11A-C. The "toxicity score" (or "Total Score" in Tables 11A-C) is determined by adding the neurotoxicity ratings. The ratings used are: Normal (−, a toxicity score of 0); slightly unable to balance (+, a toxicity score of 1); hind-leg paralysis (++, a toxicity score of 2); and 4-leg paralysis and death (+++, none observed). Compound K at 30 mg/kg by itself showed no toxicity nor anticancer effect.

The First Round of paclitaxel treatment (see Table 11A) yielded a total toxicity score of 53, whereas Compound K in combination with paclitaxel yielded a remarkably lower neurotoxicity, with a total toxicity score of only 27. Paclitaxel-induced neurotoxicity recovery was much slower than body weight (BW) recovery. A slower recovery is expected because nerve cell damage is more difficult and time consuming to repair than damage to other tissues.

TABLE 11A

| Group | No. | \multicolumn{10}{c}{Neurotoxicity (paralysis) on day after implantation} | Total score |
|---|---|---|---|---|---|---|---|---|---|---|---|---|
| | | 09 | 11 | 13 | 15 | 17 | 19 | 21 | 23 | 25 | 27 | |
| Paclitaxel | A1 | − | − | − | − | + | ++ | ++ | ++ | ++ | + | 10  53 |
| 25 mg/kg | A2 | − | − | − | − | + | ++ | ++ | + | + | − | 7 |
| iv. inj. | A3 | − | − | − | − | + | ++ | ++ | ++ | + | − | 8 |
| (Q2D×4)x2 | A4 | − | − | − | − | + | ++ | ++ | + | + | + | 8 |
| | A5 | − | − | − | − | + | ++ | ++ | ++ | + | − | 8 |
| | A6 | − | − | − | − | − | + | + | − | − | − | 2 |
| | A7 | − | − | − | − | − | − | − | − | − | − | 0 |

TABLE 11A-continued

| Group | No. | 09 | 11 | 13 | 15 | 17 | 19 | 21 | 23 | 25 | 27 | Total score | |
|---|---|---|---|---|---|---|---|---|---|---|---|---|---|
| | A8 | − | − | − | − | + | ++ | ++ | + | − | − | 5 | |
| | A9 | − | − | − | − | − | − | + | + | + | − | 3 | |
| | A10 | − | − | − | − | + | + | − | − | − | − | 2 | |
| Paclitaxel | B1 | − | − | − | − | − | + | + | − | − | − | 2 | 27 |
| 25 mg/kg | B2 | − | − | − | − | + | ++ | ++ | ++ | + | − | 8 | |
| iv. inj. | B3 | − | − | − | − | − | − | − | − | − | − | 0 | |
| (Q2Dx4)x2 + | B4 | − | − | − | − | − | + | − | − | − | − | 1 | |
| Compound K | B5 | − | − | − | − | − | + | + | − | − | − | 2 | |
| 30 mg/kg | B6 | − | − | − | − | − | − | − | − | − | − | 0 | |
| iv. inj. | B7 | − | − | − | − | + | ++ | ++ | + | + | + | 8 | |
| Q4Dx14 | B8 | − | − | − | − | − | − | − | − | − | − | 0 | |
| | B9 | − | − | − | − | − | + | + | + | + | − | 4 | |
| | B10 | − | − | − | − | − | + | + | − | − | − | 2 | |
| ↑: iv. inj. (TAXOL) | | ↑ | ↑ | ↑ | ↑ | | | | | | | | |

The Second Round of paclitaxel treatment showed a marked increase in total toxicity, with paclitaxel alone yielding a severe total toxicity score of 165 (see Tables 11B and C). The combination of Compound K and paclitaxel showed a lesser total toxicity score of 136 (see Tables 11B and C). It is believed that the more severe toxicity observed in the Second Round reduced the protective effect of Compound K (i.e. for the First Round, the paclitaxel alone total toxicity score was 53 while the Compound K and paclitaxel combination total toxicity score was 27). TAXOL was injected at days 27, 29, 31, and 33.

In the First Round, at the 6th day after paclitaxel treatment (Day 27), paclitaxel yielded a toxicity score of 2, while the combination of Compound K and paclitaxel yielded a toxicity score of 1. In the Second Round, 12 days after the paclitaxel treatment (Day 59), the score was 6 for paclitaxel and 4 for the combination of Compound K and paclitaxel. It is possible that in the clinical use of paclitaxel, slow infusion of paclitaxel over a long period of time will reduce peripheral neuropathy, but this concept is frequently ignored.

TABLE 11B

| Group | No. | 29 | 31 | 33 | 35 | 37 | 39 | 41 | 43 | 45 | 47 | 49 | 51 |
|---|---|---|---|---|---|---|---|---|---|---|---|---|---|
| Paclitaxel | A1 | − | − | − | + | + | ++ | ++ | ++ | ++ | ++ | ++ | ++ |
| 25 mg/kg | A2 | − | − | − | + | ++ | ++ | ++ | ++ | ++ | ++ | + | + |
| iv. inj. | A3 | − | − | + | ++ | ++ | ++ | ++ | ++ | ++ | ++ | ++ | + |
| (Q2Dx4)x2 | A4 | − | − | − | ++ | ++ | ++ | ++ | ++ | ++ | ++ | ++ | ++ |
| | A5 | − | − | − | + | + | ++ | ++ | ++ | ++ | ++ | ++ | ++ |
| | A6 | − | − | − | − | − | + | + | − | − | − | − | − |
| | A7 | − | − | − | ++ | ++ | ++ | ++ | ++ | ++ | + | + | + |
| | A8 | − | − | + | ++ | ++ | ++ | ++ | ++ | ++ | ++ | ++ | ++ |
| | A9 | − | − | − | + | + | + | + | + | + | + | + | + |
| | A10 | − | − | − | − | + | + | − | − | − | − | − | − |
| Paclitaxel | B1 | − | − | − | ++ | ++ | ++ | ++ | ++ | ++ | ++ | ++ | ++ |
| 25 mg/kg | B2 | − | − | − | ++ | ++ | ++ | ++ | ++ | ++ | + | + | + |
| iv. inj. | B3 | − | − | − | + | + | + | ++ | + | + | ++ | ++ | + |
| (Q2Dx4)x2 + | B4 | − | − | − | + | ++ | ++ | ++ | + | + | + | + | + |
| Compound K | B5 | − | − | − | − | ++ | ++ | ++ | ++ | ++ | ++ | ++ | ++ |
| 30 mg/kg | B6 | − | − | − | + | + | + | + | + | + | − | − | − |
| iv. inj. | B7 | − | − | + | ++ | ++ | ++ | ++ | ++ | ++ | ++ | ++ | ++ |
| Q4Dx14 | B8 | − | − | − | + | + | + | + | + | + | + | + | − |
| | B9 | − | − | − | − | + | + | + | − | − | − | − | − |
| | B10 | − | − | − | − | − | − | − | − | − | − | − | − |
| ↑: iv. inj. (TAXOL) | | ↑ | ↑ | ↑ | | | | | | | | | |

TABLE 11C

| Group | No. | 53 | 55 | 57 | 59 | 61 | 63 | 65 | $2^{nd}$ Cycle Total Score | $1^{st}$ & $2^{nd}$ Cycle Total Score |
|---|---|---|---|---|---|---|---|---|---|---|
| Taxol_25 mg/kg | A1 | ++ | + | + | + | + | + | + | 24 | 181 | 34 | 234 |
| iv. inj. | A2 | + | + | + | + | + | − | − | 20 | | 27 | |
| (Q2Dx4)x2 | A3 | + | + | + | + | + | + | + | 25 | | 33 | |
| | A4 | ++ | ++ | + | − | − | − | − | 23 | | 31 | |

TABLE 11C-continued

| Group | No. | \multicolumn{7}{c}{Neurotoxicity (paralysis) on day after implantation} | $2^{nd}$ Cycle Total Score | $1^{st}$ & $2^{nd}$ Cycle Total Score |
|---|---|---|---|---|---|---|---|---|---|---|
| | | 53 | 55 | 57 | 59 | 61 | 63 | 65 | | |
| | A5 | ++ | ++ | + | + | + | + | + | 25 | 33 |
| | A6 | − | − | − | − | − | − | − | 2 | 4 |
| | A7 | − | − | − | − | − | − | − | 15 | 15 |
| | A8 | ++ | ++ | ++ | ++ | ++ | + | + | 30 | 35 |
| | A9 | + | + | + | + | + | + | − | 15 | 18 |
| | A10 | − | − | − | − | − | − | − | 2 | 4 |
| Taxol | B1 | ++ | ++ | ++ | ++ | ++ | + | − | 29 | 145 | 31 | 172 |
| 25 mg/kg | B2 | + | + | − | − | − | − | − | 17 | 25 |
| iv. inj. | B3 | + | + | + | − | − | − | − | 15 | 15 |
| (Q2Dx4)x2 + | B4 | + | + | + | + | + | + | + | 19 | 20 |
| Compound K | B5 | ++ | + | + | − | − | − | − | 20 | 22 |
| 30 mg/kg | B6 | − | − | − | − | − | − | − | 6 | 6 |
| iv. inj. | B7 | ++ | ++ | + | + | + | + | + | 28 | 36 |
| Q4Dx14 | B8 | − | − | − | − | − | − | − | 8 | 8 |
| | B9 | − | − | − | − | − | − | − | 3 | 7 |
| | B10 | − | − | − | − | − | − | − | 0 | 2 |

The above experiments indicate that Compound K appears superior to Compound D in reducing the general toxicity (as seen by reduced body weight loss) and neurotoxicity (as seen by reduced peripheral neuropathy) that is induced by high-dose paclitaxel. Also, Compound K has an improved shelf life from being more stable than Compound D.

C. Oral Administration of Compound K

Compound K was administered orally (50 mg/kg, Q3D) in vivo to nude mice bearing MX-1 Xenografts as described above, both alone and in combination with paclitaxel treatment 25 mg/kg, i.v. Q2D. Body weight and peripheral neuropathy were monitored as in A. and B. above, to determine the toxicity-reducing effectiveness of orally-administered Compounds of the invention. The results are shown in Tables 11D and E. Compound K at 50 mg/kg by itself showed no toxicity or anticancer effect at the doses tested.

TABLE 11D

| Group | No. | \multicolumn{8}{c}{Neurotoxicity (paralysis) on day after implantation} | $1^{st}$ Total score |
|---|---|---|---|---|---|---|---|---|---|---|
| | | 12 | 14 | 16 | 18 | 20 | 22 | 24 | 26 | |
| Paclitaxel | A1 | − | − | − | − | − | − | − | − | 13 |
| 25 mg/kg | A2 | − | − | − | − | − | − | − | − | |
| iv. inj. | A3 | − | − | − | − | + | + | + | + | 4 |
| (Q2Dx4)x2 | A4 | − | − | − | − | − | − | − | − | |
| | A5 | − | − | − | − | − | − | − | − | |
| | A6 | − | − | − | − | + | + | + | − | 3 |
| | A7 | − | − | − | − | − | + | + | − | 2 |
| | A8 | − | − | − | − | − | − | + | + | 2 |
| | A9 | − | − | − | − | − | + | + | − | 2 |
| | A10 | − | − | − | − | − | − | − | − | |
| | A11 | − | − | − | − | − | − | − | − | |
| Paclitaxel | B1 | − | − | − | − | + | + | + | + | 4 | 10 |
| 25 mg/kg | B2 | − | − | − | − | − | − | − | − | |
| iv. inj. | B3 | − | − | − | − | + | + | − | − | 2 |
| (Q2Dx4)x2 + | B4 | − | − | − | − | − | − | − | − | |
| Compound K | B5 | − | − | − | − | − | − | − | − | |
| 50 mg/kg | B6 | − | − | − | − | − | − | − | − | |
| oral | B7 | − | − | − | − | − | + | + | − | 2 |
| Q3Dx9 | B8 | − | − | − | − | − | + | + | − | 2 |
| | B9 | − | − | − | − | − | − | − | − | |
| | B10 | − | − | − | − | − | − | − | − | |
| | B11 | − | − | − | − | − | − | − | − | |
| ↑: iv. inj. (TAXOL) | | ↑ | ↑ | ↑ | ↑ | | | | | |

TABLE 11E

| Group | No. | \multicolumn{8}{c}{Neurotoxicity (paralysis) on day after implantation} | $2^{nd}$ Total Score up to day 42 |
|---|---|---|---|---|---|---|---|---|---|---|
| | | 28 | 30 | 32 | 34 | 36 | 38 | 40 | 42 | |
| Paclitaxel | A1 | − | − | − | − | + | ++ | ++ | + | 6 | 79 |
| 25 mg/kg | A2 | − | − | − | − | + | + | + | + | 4 |
| iv. inj. | A3 | − | − | − | + | ++ | ++ | ++ | ++ | 10 |

TABLE 11E-continued

| | | Neurotoxicity (paralysis) on day after implantation | | | | | | | | |
|---|---|---|---|---|---|---|---|---|---|---|
| Group | No. | 28 | 30 | 32 | 34 | 36 | 38 | 40 | 42 | 2nd Total Score up to day 42 |
| (Q2Dx4)x2 | A4 | − | − | − | + | ++ | ++ | ++ | ++ | 9 |
| | A5 | − | − | − | − | ++ | ++ | ++ | ++ | 8 |
| | A6 | − | − | − | + | + | ++ | + | + | 6 |
| | A7 | − | − | − | + | ++ | ++ | ++ | ++ | 9 |
| | A8 | + | − | − | − | ++ | ++ | ++ | ++ | 9 |
| | A9 | − | − | − | − | + | ++ | ++ | ++ | 7 |
| | A10 | − | − | − | − | − | + | ++ | ++ | 5 |
| | A11 | − | − | − | − | ++ | ++ | + | + | 6 |
| Paclitaxel | B1 | + | − | − | − | ++ | ++ | + | + | 7 | 66 |
| 25 mg/kg | B2 | − | − | − | − | ++ | ++ | ++ | ++ | 8 |
| iv. inj. | B3 | − | − | − | − | + | + | + | + | 4 |
| (Q2Dx4)x2 + | B4 | − | − | − | − | − | − | − | − | 0 |
| Compound K | B5 | − | − | − | − | ++ | ++ | ++ | + | 7 |
| 50 mg/kg | B6 | − | − | − | − | ++ | ++ | ++ | ++ | 8 |
| oral | B7 | − | − | − | − | + | ++ | ++ | ++ | 7 |
| Q3Dx9 | B8 | − | − | − | − | + | ++ | ++ | ++ | 7 |
| | B9 | − | − | − | + | ++ | ++ | ++ | ++ | 9 |
| | B10 | − | − | − | − | + | + | + | + | 4 |
| | B11 | − | − | − | − | − | ++ | ++ | + | 5 |
| ↑: iv. inj. (TAXOL) | ↑ | ↑ | ↑ | ↑ | | | | | | |

5.43 Example 43

In-Vitro Neurotrophic Activity of Panaxytriol

Rat pheochromocytoma cells (PC12 cells) were treated with 50 ng/mL of nerve growth factor (NGF) and with 60 μM panaxytriol for 96 hr. The cells were then compared with a similarly prepared control, lacking panaxytriol. As shown in FIG. 13, although no neurite growth was observed in the absence of panaxytriol, the sample treated with 60 μM panaxytriol demonstrated significant neurite outgrowth. This finding confirms that panaxytriol is useful for treating or preventing a neurotrophic disorder. CCRF-CEM human T-cell acute lymphoblastic leukemia cells and the corresponding vinblastine-resistant cells (CCRF-CEM/VBL100) were cultured at an initial density of $5 \times 10^4$ cells per milliliter. The cultured cells were then maintained in a 5% $CO_2$-humidified atmosphere at 37° C. in RPMI medium 1640 (GIBCO/BRL) containing penicillin (100 units/mL), streptomycin (100 μg/mL, GIBCO/BRL), and 10% heat-inactivated fetal bovine serum. The cytotoxicity of each Compound of the invention was measured using the 2,3-bis(2-methoxy-4-nitro-5-sulfophenyl)-5-[(phenylamino)carbonyl]-2H-tetrazolium hydroxide (XTT) microculture method as described in Scudiero et al., *Cancer Res.*, 48:4827 (1988). Results of the XXT assay following 72-hour inhibition are shown in Tables 3, 3A, and 3B, where VBL means vinblastine resistant cells. All compounds tested exhibited anti-cancer activity in the assay.

5.43 Example 43

A. Chemoprotective Phase II Enzyme Induction and Activity Assays

Pure panaxytriol was dissolved in dimethyl sulfoxide. Phase 2 enzyme inducer activity was measured using a rapid assay of activity of representative phase 2 enzyme in a cell line. This assay was originally developed by Prochaska and colleagues as in Prochaska H J, Santamaria A B, Talalay P. "Rapid detection of inducers of enzymes that protect against carcinogens." *Proc Natl Acad Sci USA* 1992; 89:2394-2398, and has been further refined as in Fahey J W, Dinkova-Kostova A T, Stephenson K K, Talalay P. "The "Prochaska" microtiter plate bioassay for inducers of NQO1." *Methods Enzymol.* 2004; 382:243-258, each of which are incorporated by reference in its entirety. Briefly, Hepa 1c1c7 murine hepatoma cells were grown in 96-well microtiter plates. Serial dilutions of the extracts or compounds which were assayed were added into the wells. After 48 hours, the cells were lysed and the activity of quinone reductase (NQO1) was assayed by the addition of a reaction mixture containing an NADPH-generating system, menadione and MTT. NQO1 catalyzes the reduction of menadione to menadiol by NADPH, and MTT is reduced nonenzymatically by menadiol, resulting in the formation of a blue color that can then be quantitated as in Prochaska H J, Santamaria A B. "Direct measurement of NAD(P)H:quinone reductase from cells cultured in microtiter wells: a screening assay for anticarcinogenic enzyme inducers." *Anal. Biochem.* 1988; 169:328-336, which is incorporated by reference in its entirety. The reaction was stopped after 5 minutes by adding dicoumarol, a potent inhibitor of NQO1. NQO1 activity and protein content of the lysate were measured in duplicate plates with an optical microtiter plate absorbance reader. The concentration of the extract or compound which doubles the inducer activity is designated as the concentration of doubling (CD). One unit of inducer activity is defined as the amount that, when added to a single microtiter well, doubles the NQO1 specific activity. Sulforaphane and β-naphthoflavone were used as positive controls in each bioassay. Panaxytriol was over 10-fold more potent as an inducer than either protopanxadiol or protopanaxatriol, and it had an average CD of 3.85 μM, or 5,760,000 U/g. For comparison, the reported CD value of sulforaphane is 0.2 μM (188,000,000 U/g), and chlorophyll a was 250 μM (24,600 U/g). FIG. 14 compares the chemoprotective phase II induction curves of a Korean red ginseng extract, SUN GINSENG®, the most potent ginseng extract tested, protopanaxadiol and panaxytriol, and shows the induction of quinone reductase (NQO1) by SUN GINSENG®, protopanaxatriol and panaxytriol. NQO1 inducer activity was assayed as described herein, and is reported here as treated/control at different concentrations of ginseng extract or component per well. Significant cytotoxicity was observed for panaxytriol above 0.5 µg/well and protopanaxadiol above 5 µg/well. (+) Panaxytriol (molecular weight 267), (Δ) Protopanaxatriol (molecular weight 461), (○) Korean red SUN GINSENG® extract. The reductase assay can also be performed as disclosed in PCT Publication No. WO 06/023821, the entire contents of which are hereby incorporated in the instant application.

B. In Vitro Induction of AKR1C Enzymes

Compounds were screened for AKR1C enzyme activity as set forth in Halim, M.; Yee, D. J. and Sames, D. *J. Am. Chem. Soc.* 2008, 129, 14123-14128. "Imaging Induction of Cytoprotective Enzymes in Intact Human Cells: Coumberone, a Metabolic Reporter for Human AKR1C Enzymes Reveals Activation by Panaxytriol, an Active Component of Red Ginseng," hereby incorporated by reference in its entirety. Specifically, coumberone metabolism studies in IMR-32 can be done as follows: Early-passage (<P25) IMR-32 cells were seeded at a density of $4 \times 10^4$ cells/well in 96-well dish. They were then treated with the various inducers or DMSO vehicle (0.5% v/v) control. The concentration of each inducer was varied from 50 nM to 60 µM and the cells were incubated with these for either 24 or 48 hours. 72 hours after seeding, the media was removed and 100 µL of experimental media (DMEM without phenol red supplemented with 100 units/ml penicillin, 100 µg/ml streptomycin, 4 mM L-glutamine and 1% charcoal-dextran treated FBS) was added and incubated for 2 hrs. 100 µl more of the experimental media containing Coumberone (final concentration of 5 µM) was then added. The fluorescence of the cell culture medium was recorded on a plate reader MicroMax 384 connected to a Jobin Yvon Fluorolog by detecting fluorescence at 510 nm upon excitation at 385 nm. The reading was taken every 6 hours for 72 hours. Metabolic conversion rate was obtained by measuring the change in fluorescence per hour for the first 36 hours. The relative increase in metabolic rate was calculated by dividing the metabolic conversion rates of cells incubated with the activator compounds with those incubated with DMSO vehicle. Table 12 lists data for the compounds showing their induction of AKR1C2 and AKR1C3 in human neuroblastoma IMR-32 cells. Fold-induction is the increase metabolic activity of the reporter. The higher the fold induction, the greater the amount of enzymes expressed. 50% toxicity is an estimate and is not an accurate $IC_{50}$ value. The data in rows 13-25 and 31-35 were generated using different batches of IMR-32 cells than the other rows, but the data were reliably reproduced using two different batches of IMR-32 in triplicate. "None" indicates no observed induction.

TABLE 12

| No | Compound | Fold induction of AKR1C2 and AKR1C3 in IMR-32 cells | 50% toxicity in IMR-32 cells |
|---|---|---|---|
| 1 | Panaxytriol | 2-fold at 20 µM | >40 µM |
| 2 | | 2-fold at 15 µM | >40 µM |
| 3 | | 2-fold at 20 µM | >40 µM |
| 4 | | 1.5-fold at 20 µM | >40 µM |

TABLE 12-continued

| No | Compound | Fold induction of AKR1C2 and AKR1C3 in IMR-32 cells | 50% toxicity in IMR-32 cells |
|---|---|---|---|
| 5 | | None | |
| 6 | | None | |
| 7 | | None | |
| 8 | | None | |
| 9 | | None | |
| 10 | | None | ~25 μM |
| 11 | | None | ~35 μM |
| 12 | | None | ~35 μM |
| 13 | | None | ~30 μM |

TABLE 12-continued

| No | Compound | Fold induction of AKR1C2 and AKR1C3 in IMR-32 cells | 50% toxicity in IMR-32 cells |
|---|---|---|---|
| 14 | [structure] | None | ~40 μM |
| 15 | [structure] | None | ~40 μM |
| 16 | [structure] | 2.3 fold induction at 5 μM EC$_{50}$: ~3.5 μM | ~12 μM |
| 17 | [structure] | 1.4 fold induction at ~2.5 μM (statistically very significant induction) | ~5 μM |
| 18 | [structure] | None | ~25 μM |
| 19 | [structure] | None | >40 μM |
| 20 | [structure] | None | ~10 μM |
| 21 | [structure] | 1.4 fold induction at 1 μM (statistically very significant induction) | ~4 μM |

TABLE 12-continued

| No | Compound | Fold induction of AKR1C2 and AKR1C3 in IMR-32 cells | 50% toxicity in IMR-32 cells |
|---|---|---|---|
| 22 | | None | >50 μM |
| 23 | | None | >40 μM |
| 24 | | 1.5 fold induction at 5 μM EC50: ~3.5 μM | ~8 μM |
| 25 | | None | ~32.5 μM |
| 26 | Diketopiperazine | None | |
| 27 | Cribrostatin IV | None | |

TABLE 12-continued
| No | Compound | Fold induction of AKR1C2 and AKR1C3 in IMR-32 cells | 50% toxicity in IMR-32 cells |
|---|---|---|---|
| 28 | 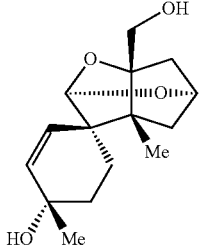 Spirotenuipesine A | None | |
| 29 | 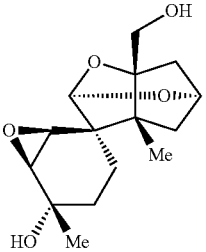 Spirotenuipesine B | None | |
| 30 | 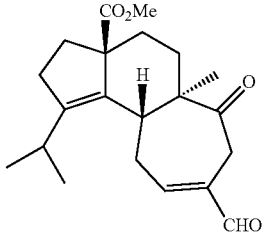 Scabronine G-methyl ester | None | |
| 31 | 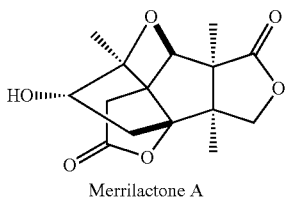 Merrilactone A | None | >40 μM |
| 32 | 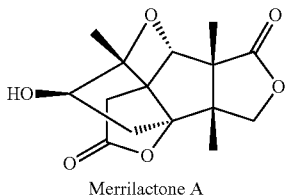 Merrilactone A | None | >40 μM |

TABLE 12-continued

| No | Compound | Fold induction of AKR1C2 and AKR1C3 in IMR-32 cells | 50% toxicity in IMR-32 cells |
|---|---|---|---|
| 33 | rac-11-0-debenzoyltashironin 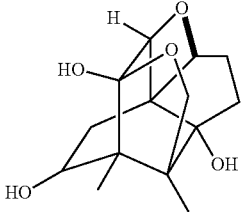 | None | >40 μM |
| 34 | Paecilomycine A 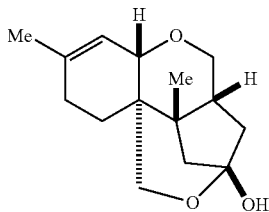 | None | >40 μM |
| 35 | Tricholomalide A 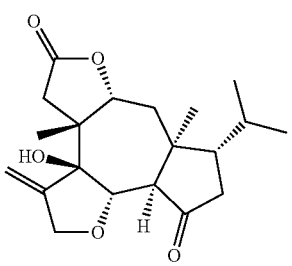 | None | >50 μM |

TABLE 13 also shows chemoprotective Phase-II enzyme induction data for compounds of the invention, using the CCRF-CEM assay described herein and the human neuroblastoma IMR-32 cell line AKR1C2 and AKR1C3 induction assay.

TABLE 13

| Analogs | IC$_{50}$ (μM) CCRF-CEM | Induction of AKR1C2 and AKR1C3* |
|---|---|---|
| 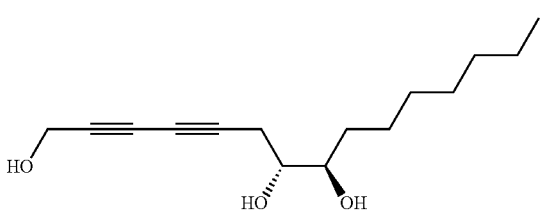 | 5.57 | + |

TABLE 13-continued
| Analogs | IC$_{50}$ (μM) CCRF-CEM | Induction of AKR1C2 and AKR1C3* |
|---|---|---|
| 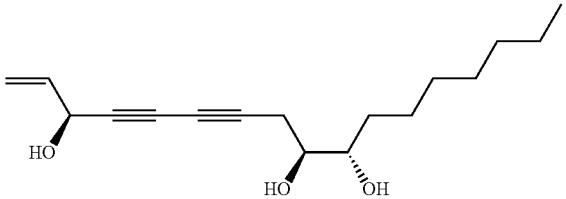 2 | 2.69 | + |
| 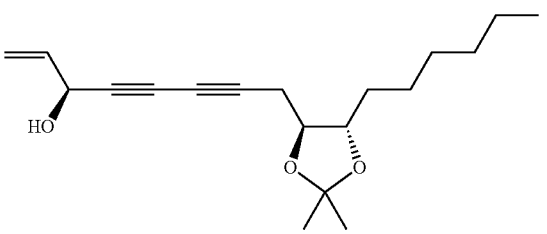 3 | submitted | + |
| 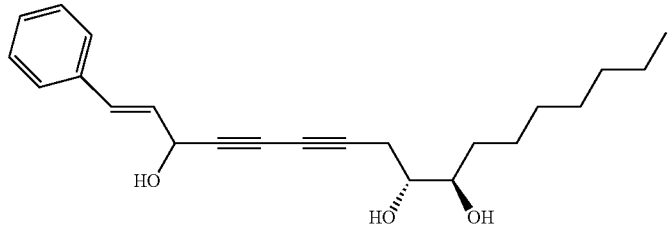 4 | 9.46 | − |
| 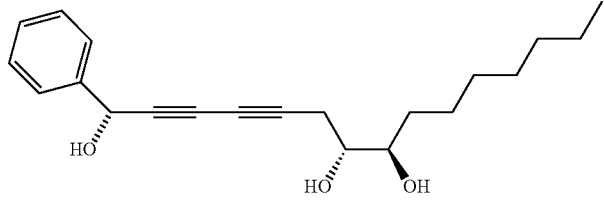 5 | 5.96 | − |
| 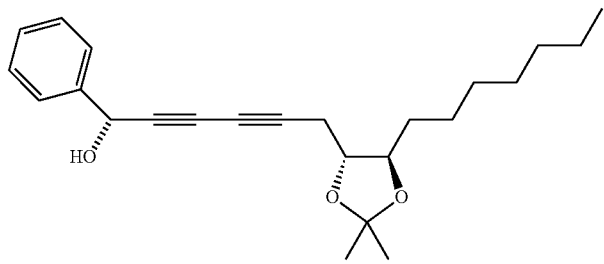 6 | 2.49 | − |

TABLE 13-continued

| Analogs | IC$_{50}$ (μM) CCRF-CEM | Induction of AKR1C2 and AKR1C3* |
|---|---|---|
| 7 | 12.64 | – |
| 8 | 5.25 | – |
| 9 | 4.18 IC$_{50}$ (μM) IMR-32 | – |
| 10 | 35 | – |

TABLE 13-continued

| Analogs | IC$_{50}$ (μM) CCRF-CEM | Induction of AKR1C2 and AKR1C3* |
|---|---|---|
| (structure 11) | 35 | — |
| (structure 12) | 25 | — |

*in human neuroblastoma IMR-32 cells

From these studies, it appears that the diyne is not the sole source of cytotoxicity, as demonstrated by the considerable potency of analogs 8 and 9 against the CCRF-CEM cancer cell line. However the diyne appears to play a role in the induction of phase II chemoprotective enzymes because replacing this moiety results in no observed induction of phase II enzymes (analogs 7-12). Installing bulky groups on the left-hand region also adversely impacts the ability to induce phase II enzymes (analogs 4-6). Furthermore, the enantiomer of panaxytriol and panaxytriol acetonide (2 and 3 respectively) are potently cytotoxic and induce phase II enzymes.

The IMR-32 induction assay was run as follows. Early-passage (<P25) IMR-32 cells were seeded at a density of $4\times10^4$ cells/well in 96-well dish. They were then treated with the various inducers or DMSO vehicle (0.5% v/v) control. The concentration of each inducer was varied from 50 nM to 60 μM and the cells were incubated with these for either 24 or 48 hours. 72 hours after seeding, the media was removed and 100 μL of experimental media (DMEM without phenol red supplemented with 100 units/ml penicillin, 100 μg/ml streptomycin, 4 mM L-glutamine and 1% charcoal-dextran treated FBS) was added and incubated for 2 hrs. 100 μl more of the experimental media containing Coumberone (final concentration of 5 μM) was then added. The fluorescence of the cell culture medium was recorded on a plate reader MicroMax 384 connected to a Jobin Yvon Fluorolog by detecting fluorescence at 510 nm upon excitation at 385 nm. The reading was taken every 6 hours for 72 hours. Metabolic conversion rate was obtained by measuring the change in fluorescence per hour for the first 36 hours. The relative increase in metabolic rate was calculated by dividing the metabolic conversion rates of cells incubated with the activator compounds with those incubated with DMSO vehicle. Citation: Halim, M.; Yee, D. J.; Sames, D. Imaging Induction of Cytoprotective Enzymes in Intact Human Cells: Coumberone, a Metabolic Reporter for Human AKR1C Enzymes Reveals Activation by Panaxytriol, an Active Component of Red Ginseng. *J. Am. Chem. Soc.* 2008, 130, 14123-13128.

5.44 Example 44

Anti-Inflammatory Effect of Compound (D)

Compound (D) shows a mild, slow on-set, anti-inflammatory effect, as seen in FIG. 17, which compares the anti-inflammatory effect of Compound (D), oral acetylsalicylic acid (aspirin), and LIDEX cream against carrageenan-induced paw edema in CD mice. The comparisons are made by comparing the volumes of the inflamed pedis area (induced by a injection of a 1% carageenan solution) at different time points after the initial carageenan injection. 1% Carrageenan (20 μL, i.m., injected directly into the paw of CD mice) was administered at time=0, and each treatment was administered at 24 hours prior to the carrageenan injection, 1 hour prior to the carrageenan injection, and 6 hours after the carrageenan injection. * means P<0.1 and ** means P<0.05.

The present invention is not to be limited in scope by the specific embodiments disclosed in the examples. A number of references have been cited, the entire disclosures of each of which are incorporated herein in their entirety.

What is claimed is:

1. A compound of the Formula

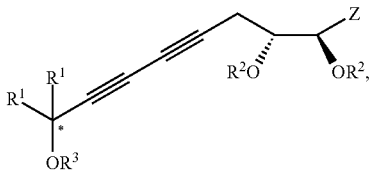

wherein:
each $R^1$ is independently —H;
each $R^2$ is independently —H, —$C_1$-$C_6$ alkyl, or —C(O)— $C_1$-$C_6$ alkyl, or both $R^2$ groups combine to form —C(O)— or —C($R^a$)($R^a$)—, wherein each $R^a$ is independently —H, —$C_1$-$C_6$ alkyl or phenyl;
$R^3$ is —H; and
Z is —$C_1$-$C_{10}$ alkyl;
or a pharmaceutically acceptable salt, solvate or hydrate thereof.

2. The compound of claim 1, wherein the compound is:

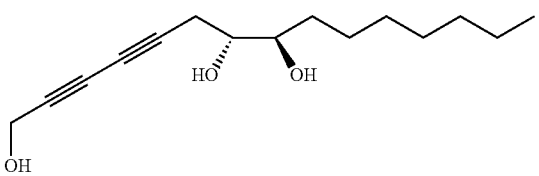 [SMILES: CCCCCCC[C@@H](O)[C@H](O)CC#CC#CCO]

or a pharmaceutically acceptable salt, solvate or hydrate thereof.

3. A method for making Compound (L):

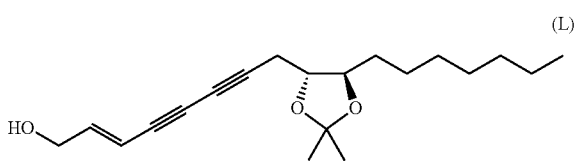 [SMILES: CCCCCCC[C@H]1OC(C)(C)O[C@@H]1CC#CC#C/C=C/CO]

comprising reacting a compound having the structure

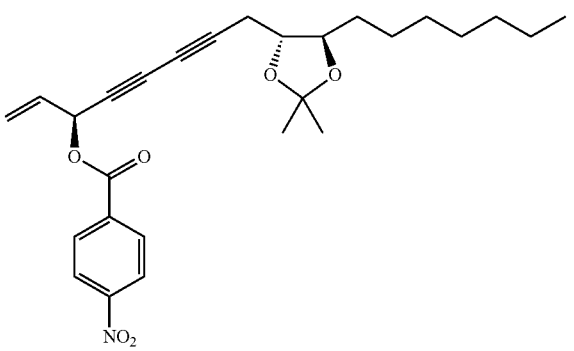 [SMILES: C=C[C@@H](C#CC#CC[C@H]1OC(C)(C)O[C@@H]1CCCCCCC)OC(=O)c1ccc([N+](=O)[O-])cc1]

with a hydroxide ion, under conditions sufficient to produce Compound (L).

4. A composition comprising an effective amount of the compound of claim 1 and at least one of a physiologically acceptable carrier or vehicle, and a drug.

5. The composition of claim 4 wherein the drug is comprised of a member of the group selected from a tubulin-binding drug, a cytotoxic agent drug and an anticancer agent drug and combinations and mixtures thereof.

6. The composition of claim 5, wherein the tubulin-binding drug is selected from the group consisting of allocolchicine, amphethinile, chelidonine, colchicide, colchicine, combrestatin A1, combretastin A4, combretastain A4 phosphate, combrestatin 3, combrestatin 4, cryptophycin, curacin A, deo-dolastatin 10, desoxyepothilone A, desoxyepothilone B, dihydroxy-pentamethoxyflananone, docetaxel, dolastatin 10, dolastatin 15, epidophyllotoxin, epothilone A, epothilone B, epothilone C, epothilone D, etoposide, 9,10-dehydro-desoxyepothilone B, iso-oxazole-dehydelone, fludelone, iso-oxazole-fludelone, griseofulvin, halichondrin B, isocolchicine, lavendustin A, methyl-3,5-diiodo-4-(4'-methoxyphenoxy)benzoate, N-acetylcolchinol, N-acetylcolchinol-O-phosphate, N42-[(4-hydroxyphenypamino]-3-pyridyl]-4-methoxybenzenesulfonamide, nocodazole, paclitaxel, phenstatin, phenylhistin, piceid, podophyllotoxin, resveratrol, rhizoxin, sanguinarine, spongistatin 1, steganacin, paclitaxel, teniposide, thiocolchicine, vincristine, vinblastine, welwistatin, (Z)-2-methoxy-5-[2-(3,4,5-trimethoxyphenyl)vinyl]phenylamine, (Z)-3,5,4'-trimethoxystilbene ($R^3$), 2-aryl-1,8-naphthyridin-4(1H)-one, 2-(4'-methoxyphenyl)-3-(3',4',5'-trimethoxybenzoyl)-6-methoxybenzo[b]thiophene, 2-methoxy estradiol, 2-strylquinazolin-4(3H)-one, 5,6-dihydroindolo(2,1-a)isoquinoline, or 10-deacetylbaccatin III and wherein the anticancer agent drug is selected from the group consisting of 5-fluorouracil, cyclophosphamide, isodehydelone, fludelone, iso-oxazole-fludelone, or paclitaxel.

7. A composition comprising an effective amount of a compound of claim 2 and at least one of a physiologically acceptable carrier or vehicle, and a drug.

8. The composition of claim 7, wherein the drug is comprised of a member of the group selected from a tubulin-binding drug, a cytotoxic agent drug and an anticancer agent drug and combinations and mixtures thereof.

9. The composition of claim 8, wherein the tubulin-binding drug is selected from the group consisting of allocolchicine, amphethinile, chelidonine, colchicide, colchicine, combrestatin A1, combretastin A4, combretastain A4 phosphate, combrestatin 3, combrestatin 4, cryptophycin, curacin A, deo-dolastatin 10, desoxyepothilone A, desoxyepothilone B, dihydroxy-pentamethoxyflananone, docetaxel, dolastatin 10, dolastatin 15, epidophyllotoxin, epothilone A, epothilone B, epothilone C, epothilone D, etoposide, 9,10-dehydro-desoxyepothilone B, iso-oxazole-dehydelone, fludelone, iso-oxazole-fludelone, griseofulvin, halichondrin B, isocolchicine, lavendustin A, methyl-3,5-diiodo-4-(4'-methoxyphenoxy)benzoate, N-acetylcolchinol, N-acetylcolchinol-O-phosphate, N-[2-[(4-hydroxyphenyl)amino]-3-pyridyl]-4-methoxybenzenesulfonamide, nocodazole, paclitaxel, phenstatin, phenylhistin, piceid, podophyllotoxin, resveratrol, rhizoxin, sanguinarine, spongistatin 1, steganacin, paclitaxel, teniposide, thiocolchicine, vincristine, vinblastine, welwistatin, (Z)-2-methoxy-5-[2-(3,4,5-trimethoxyphenyl)vinyl]phenylamine, (Z)-3,5,4'-trimethoxystilbene (R3), 2-aryl-1,8-naphthyridin-4(1H)-one, 2-(4'-methoxyphenyl)-3-(3',4',5'-trimethoxybenzoyl)-6-methoxybenzo[b]thiophene, 2-methoxy estradiol, 2-strylquinazolin-4(3H)-one, 5,6-dihydroindolo(2,1-a)isoquinoline, or 10-deacetylbaccatin III and wherein the anticancer agent drug is selected from the group consisting of 5-fluorouracil, cyclophosphamide, isodehydelone, fludelone, iso-oxazole-fludelone, or paclitaxel.

10. A composition comprising an effective amount of a compound selected from Formulas L and L':

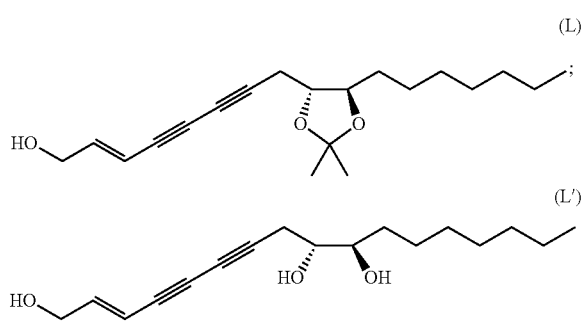

and at least one of a physiologically acceptable carrier or vehicle, and a drug.

11. The composition of claim 10 wherein the drug is comprised of a member of the group selected from a tubulin-binding drug, a cytotoxic agent drug and an anticancer agent drug and combinations and mixtures thereof.

12. A method for inducing a chemoprotective phase II enzyme in a subject; inducing expression of a chemoprotective phase II enzyme in a subject; inducing enzymatic activity of a chemoprotective phase II enzyme; reducing the side effects of a drug; reducing body weight loss side effects of a drug; reducing the side effects of a cancer therapeutic drug or cancer treatment; reducing the side effects of a tubulin-binding drug; reducing a toxic effect of a toxic agent wherein a subject has been or is currently exposed to a drug and is also exposed to the toxic agent; reducing a cytotoxic effect of a cytotoxic agent; reducing a toxic effect of a toxic agent comprising a chemotherapeutic agent; reducing a neurotoxic toxic effect of a neutrotoxic toxic agent; reducing peripheral neuropathy; inducing antioxidant phase-2 enzymes in vivo; comprising administering to an animal or human subject in need thereof an effective amount of a compound of claim 1.

13. The method of claim 12, wherein the chemoprotective phase II enzyme is at least one of a quinone reductase, AKR1C, AKR1C2, AKR1C3, heme oxygenase-1 (HO-1), quinone reductase, NAD(P)H:quinone reductase (NQO1), superoxide dismutase, glutathione peroxidase, nuclear erythroid-2 related factor 2 (Nrf2), or UDP-glucuronosyl transferase 2B7, or a combination or selection thereof.

14. The method of claim 12, wherein the chemoprotective phase II enzyme is induced by the compound binding to an Antioxidant Response Element (ARE).

15. A method for inducing a chemoprotective phase II enzyme in a subject; inducing expression of a chemoprotective phase II enzyme in a subject;
inducing enzymatic activity of a chemoprotective phase II enzyme; reducing the side effects of a drug; reducing body weight loss side effects of a drug; reducing the side effects of a cancer therapeutic drug or cancer treatment; reducing the side effects of a tubulin-binding drug; reducing a toxic effect of a toxic agent wherein a subject has been or is currently exposed to a drug and is also exposed to the toxic agent; reducing a cytotoxic effect of a cytotoxic agent; reducing a toxic effect of a toxic agent comprising a chemotherapeutic agent; reducing a neurotoxic toxic effect of a neutrotoxic toxic agent; reducing peripheral neuropathy; inducing antioxidant phase-2 enzymes in vivo; comprising administering to an animal or human subject in need thereof an effective amount of the compound of claim 2.

16. A method for, treating lung cancer breast cancer, colorectal cancer, prostate cancer, a leukemia, a lymphoma, non-Hodgkin's lymphoma, skin cancer, a brain cancer, a cancer of the central nervous system, ovarian cancer, uterine cancer, stomach cancer, pancreatic cancer, esophageal cancer, kidney cancer, liver cancer, or a head and neck cancer comprising administering to an animal or human subject in need thereof an effective amount of a composition of claim 4.

17. The method of claim 12, wherein the cancer treatment having side effects is radiation therapy.

18. The method of claim 15, wherein the cancer treatment having side effects is radiation treatment.

* * * * *